US012516118B2

(12) United States Patent
Li et al.

(10) Patent No.: US 12,516,118 B2
(45) Date of Patent: Jan. 6, 2026

(54) DOSING FOR TREATMENT WITH ANTI-CD20/ANTI-CD3 BISPECIFIC ANTIBODIES AND ANTI-CD79B ANTIBODY DRUG CONJUGATES

(71) Applicant: Genentech, Inc., South San Francisco, CA (US)

(72) Inventors: Chi-Chung Li, South San Francisco, CA (US); Carol Elaine O'Hear, South San Francisco, CA (US); Stephen James Simko, III, South San Francisco, CA (US); Iris Tranthuyngan To, South San Francisco, CA (US); Klara Totpal, South San Francisco, CA (US); Hong Wang, South San Francisco, CA (US); Michael C. Wei, South San Francisco, CA (US); Shen Yin, South San Francisco, CA (US); Brendan Christian Bender, South San Francisco, CA (US); Xi Chen, South San Francisco, CA (US); Yu-Waye Chu, South San Francisco, CA (US); Maria Hristopoulos, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 1094 days.

(21) Appl. No.: 17/516,979

(22) Filed: Nov. 2, 2021

(65) Prior Publication Data

US 2022/0153842 A1 May 19, 2022

Related U.S. Application Data

(60) Provisional application No. 63/188,695, filed on May 14, 2021, provisional application No. 63/109,781, filed on Nov. 4, 2020.

(51) Int. Cl.

| | |
|---|---|
| ***C07K 16/28*** | (2006.01) |
| ***A61K 47/68*** | (2017.01) |
| ***A61P 35/00*** | (2006.01) |
| ***C07K 16/46*** | (2006.01) |

(52) U.S. Cl.

CPC ...... *C07K 16/2809* (2013.01); *A61K 47/6849* (2017.08); *A61P 35/00* (2018.01); *C07K 16/2887* (2013.01); *C07K 16/468* (2013.01)

(58) Field of Classification Search

CPC ............ C07K 16/2887; C07K 16/2809; C07K 16/2827; C07K 16/2866; C07K 2317/24; C07K 2317/31; C07K 2317/41; A61K 31/573; A61K 2039/507; A61K 2039/545; A61P 35/00

See application file for complete search history.

(56) References Cited

U.S. PATENT DOCUMENTS

| | | | |
|---|---|---|---|
| 5,500,362 | A | 3/1996 | Robinson et al. |
| 5,595,756 | A | 1/1997 | Bally et al. |
| 5,624,821 | A | 4/1997 | Winter et al. |
| 5,648,260 | A | 7/1997 | Winter et al. |
| 5,731,168 | A | 3/1998 | Carter et al. |
| 5,821,337 | A | 10/1998 | Carter et al. |
| 5,869,046 | A | 2/1999 | Presta et al. |
| 6,194,551 | B1 | 2/2001 | Idusogie et al. |
| 6,248,516 | B1 | 6/2001 | Winter et al. |
| 6,455,043 | B1 | 9/2002 | Grillo-Lopez |
| 6,602,684 | B1 | 8/2003 | Umana et al. |
| 6,737,056 | B1 | 5/2004 | Presta |
| 7,332,581 | B2 | 2/2008 | Presta |
| 7,371,826 | B2 | 5/2008 | Presta |
| 7,612,181 | B2 | 11/2009 | Wu et al. |
| 7,682,612 | B1 | 3/2010 | White et al. |
| 7,695,936 | B2 | 4/2010 | Carter et al. |
| 7,799,900 | B2 | 9/2010 | Adams et al. |
| 8,219,149 | B2 | 7/2012 | Lafata et al. |
| 8,258,268 | B2 | 9/2012 | Wu et al. |
| 8,562,992 | B2 | 10/2013 | Adams et al. |
| 8,709,421 | B2 | 4/2014 | Heiss et al. |

(Continued)

FOREIGN PATENT DOCUMENTS

| | | |
|---|---|---|
| CN | 102281902 A | 12/2011 |
| CN | 102369218 A | 3/2012 |

(Continued)

OTHER PUBLICATIONS

Yoon, S et. al. "Managing cytokine release syndrome (CRS) and neurotoxicity with step-up dosing of mosunetuzumab in relapsed/refractory (R/R) B-cell non-Hodgkin lymphoma (NHL)", 2019, Presented at 24th Congress of EHA, PS1094. (Year: 2019).*
Tiwari, A et. al. "Polatuzumab Vedotin Alone or in Combination with Obinutuzumab Synergistically Enhances In-Vitro Cytotoxicity and Cytokine Release Against CD20+/ CD79b+ Burkitt Lymphoma (BL) / Primary Mediastinal Large B Cell Lymphoma (PMBL)", 2017, Blood, 130, 1-3. (Year: 2017).*
Bacac, M et. al. "CD20 Tcb (RG6026), a Novel '2:1' T Cell Bispecific Antibody for the Treatment of B Cell Malignancies", 2016, Blood, 128(22), 1-3. (Year: 2016).*
Engelberts et al., "DuoBody-CD3xCD20 induces potent T-cell-mediated killing of malignant B cells in preclinical models and provides opportunities for subcutaneous dosing," EBioMedicine 52:102625 (Jan. 2020) (13 pages).

(Continued)

*Primary Examiner* — Nelson B Moseley, II
*Assistant Examiner* — Alyssa Rae Stonebraker
(74) *Attorney, Agent, or Firm* — Clark & Elbing LLP; Karen L. Elbing

(57) ABSTRACT

The present invention relates to the treatment of subjects having CD20-positive cell proliferative disorders (e.g., B cell proliferative disorders, such as non-Hodgkin's lymphomas). More specifically, the invention pertains to the treatment of subjects having a CD20-positive cell proliferative disorder (e.g., B cell proliferative disorder) by administering a combination of an anti-CD20/anti-CD3 bispecific antibody and an anti-CD79b antibody drug conjugate.

65 Claims, 20 Drawing Sheets

Specification includes a Sequence Listing.

(56) References Cited

U.S. PATENT DOCUMENTS

| | | | |
|---|---|---|---|
| 8,722,859 B2 | 5/2014 | Miller et al. | |
| 8,895,702 B2 | 11/2014 | Williams et al. | |
| 8,969,526 B2 | 3/2015 | Baehner et al. | |
| 9,011,864 B2 | 4/2015 | Schulz et al. | |
| 9,017,676 B2 | 4/2015 | Lindhofer | |
| 9,308,257 B2 | 4/2016 | Sharma, Sr. et al. | |
| 9,315,567 B2 | 4/2016 | Chang et al. | |
| 9,493,563 B2 | 11/2016 | Blein et al. | |
| 9,587,021 B2 | 3/2017 | Huang et al. | |
| 9,657,102 B2 | 5/2017 | Smith et al. | |
| 10,000,576 B1 | 6/2018 | Weisser et al. | |
| 10,105,391 B2 | 10/2018 | Wu et al. | |
| 10,357,571 B2 | 7/2019 | Williams et al. | |
| 10,561,686 B2 | 2/2020 | Xiao et al. | |
| 11,466,094 B2 | 10/2022 | Chu et al. | |
| 2002/0164328 A1 | 11/2002 | Shinkawa et al. | |
| 2003/0115614 A1 | 6/2003 | Kanda et al. | |
| 2003/0157108 A1 | 8/2003 | Presta | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2005/0014934 A1 | 1/2005 | Hinton et al. | |
| 2005/0095243 A1 | 5/2005 | Chan et al. | |
| 2005/0123546 A1 | 6/2005 | Umana et al. | |
| 2009/0028856 A1* | 1/2009 | Chen | A61P 35/00 435/69.6 |
| 2009/0075279 A1 | 3/2009 | Frantz et al. | |
| 2009/0252683 A1 | 10/2009 | Kischel et al. | |
| 2009/0304719 A1 | 12/2009 | Daugherty et al. | |
| 2010/0015133 A1 | 1/2010 | Igawa et al. | |
| 2010/0150918 A1 | 6/2010 | Kufer et al. | |
| 2010/0331527 A1 | 12/2010 | Davis et al. | |
| 2011/0020322 A1 | 1/2011 | Wilkins et al. | |
| 2011/0123532 A1 | 5/2011 | Gurney et al. | |
| 2011/0178279 A1 | 7/2011 | Williams et al. | |
| 2012/0244577 A1 | 9/2012 | Dixit et al. | |
| 2012/0251531 A1 | 10/2012 | Baehner et al. | |
| 2013/0129723 A1 | 5/2013 | Blankenship et al. | |
| 2013/0165638 A1 | 6/2013 | Hsu et al. | |
| 2013/0171095 A1 | 7/2013 | Bernett et al. | |
| 2013/0266568 A1 | 10/2013 | Brinkmann et al. | |
| 2013/0287774 A1 | 10/2013 | Zugmaier et al. | |
| 2014/0079689 A1 | 3/2014 | Elliott et al. | |
| 2014/0088295 A1 | 3/2014 | Smith et al. | |
| 2014/0112914 A1 | 4/2014 | Nezu et al. | |
| 2014/0170149 A1 | 6/2014 | Neijssen et al. | |
| 2014/0187753 A1 | 7/2014 | Blein et al. | |
| 2014/0302064 A1 | 10/2014 | Moore | |
| 2014/0377270 A1 | 12/2014 | Moore et al. | |
| 2015/0098900 A1 | 4/2015 | Ebens et al. | |
| 2015/0133640 A1 | 5/2015 | Blein et al. | |
| 2015/0166661 A1 | 6/2015 | Chen et al. | |
| 2015/0266966 A1 | 9/2015 | Smith et al. | |
| 2015/0284475 A1 | 10/2015 | Zhou et al. | |
| 2016/0000916 A1 | 1/2016 | Crotts et al. | |
| 2016/0017058 A1 | 1/2016 | Kim et al. | |
| 2016/0075785 A1 | 3/2016 | Ast et al. | |
| 2016/0082120 A1 | 3/2016 | Polson et al. | |
| 2016/0090416 A1 | 3/2016 | Gunde et al. | |
| 2016/0145339 A1 | 5/2016 | Zhou et al. | |
| 2016/0152711 A1 | 6/2016 | Williams et al. | |
| 2016/0159906 A1 | 6/2016 | Sun et al. | |
| 2016/0194399 A1 | 7/2016 | Irving et al. | |
| 2016/0368985 A1 | 12/2016 | Hotzel et al. | |
| 2016/0368994 A1 | 12/2016 | Kelley et al. | |
| 2017/0008971 A1 | 1/2017 | Dennis et al. | |
| 2017/0022274 A1 | 1/2017 | Chang et al. | |
| 2017/0158773 A1 | 6/2017 | Adams et al. | |
| 2017/0204194 A1 | 7/2017 | Chen et al. | |
| 2017/0209573 A1 | 7/2017 | Bacac et al. | |
| 2017/0218074 A1 | 8/2017 | Williams et al. | |
| 2017/0224818 A1 | 8/2017 | Lindhofer et al. | |
| 2017/0267783 A1 | 9/2017 | Nezu et al. | |
| 2018/0057593 A1 | 3/2018 | Dennis | |
| 2018/0117152 A1* | 5/2018 | Lee | C07K 16/30 |
| 2018/0134798 A1* | 5/2018 | Chu | A61P 35/00 |
| 2018/0148508 A1 | 5/2018 | Wang et al. | |
| 2018/0193479 A1 | 7/2018 | Williams et al. | |
| 2020/0129617 A1 | 4/2020 | Brownstein et al. | |
| 2020/0164077 A1 | 5/2020 | Williams et al. | |
| 2020/0199578 A1 | 6/2020 | Short et al. | |
| 2020/0339686 A1 | 10/2020 | Sato et al. | |

FOREIGN PATENT DOCUMENTS

| | | | |
|---|---|---|---|
| CN | 103025759 A | 4/2013 |
| CN | 101675077 B | 9/2013 |
| CN | 104321081 A | 1/2015 |
| CN | 106029696 A | 10/2016 |
| EP | 1870459 A1 | 12/2007 |
| EP | 1923072 A1 | 5/2008 |
| EP | 1870459 A4 | 9/2010 |
| EP | 2482212 A1 | 8/2012 |
| EP | 2578230 A1 | 4/2013 |
| EP | 2647707 A1 | 10/2013 |
| EP | 2647707 A4 | 4/2014 |
| EP | 2769989 A1 | 8/2014 |
| EP | 2840091 A1 | 2/2015 |
| EP | 1870459 B1 | 6/2016 |
| JP | 2008-291036 A | 12/2008 |
| JP | 2009-539413 A | 11/2009 |
| JP | 2013-515509 A | 5/2013 |
| JP | 2013-528569 A | 7/2013 |
| JP | 2013-529084 A | 7/2013 |
| JP | 2015-509951 A | 4/2015 |
| JP | 2015-509952 A | 4/2015 |
| JP | 2018-527887 A | 9/2018 |
| KR | 10-2016-0098464 A | 8/2016 |
| RU | 2539112 C2 | 1/2015 |
| TW | 201508008 A | 3/2015 |
| TW | 201827075 A | 8/2018 |
| WO | WO-91/03493 A1 | 3/1991 |
| WO | WO-92/22653 A1 | 12/1992 |
| WO | WO-94/04679 A1 | 3/1994 |
| WO | WO-94/29351 A2 | 12/1994 |
| WO | WO-96/01126 A1 | 1/1996 |
| WO | WO-96/27011 A1 | 9/1996 |
| WO | WO-97/30087 A1 | 8/1997 |
| WO | WO-98/50431 A2 | 11/1998 |
| WO | WO-98/58964 A1 | 12/1998 |
| WO | WO-98/50431 A3 | 1/1999 |
| WO | WO-99/22764 A1 | 5/1999 |
| WO | WO-99/51642 A1 | 10/1999 |
| WO | WO-00/61739 A1 | 10/2000 |
| WO | WO-01/29246 A1 | 4/2001 |
| WO | WO-02/31140 A1 | 4/2002 |
| WO | WO-03/011878 A2 | 2/2003 |
| WO | WO-03/084570 A1 | 10/2003 |
| WO | WO-03/085107 A1 | 10/2003 |
| WO | WO-03/085119 A1 | 10/2003 |
| WO | WO-2004/056312 A2 | 7/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/083431 A2 | 9/2005 |
| WO | WO-2005/100402 A1 | 10/2005 |
| WO | WO-2006/029879 A2 | 3/2006 |
| WO | WO-2007/005874 A2 | 1/2007 |
| WO | WO-2007/042261 A2 | 4/2007 |
| WO | WO-2007/110205 A2 | 10/2007 |
| WO | WO-2007/146968 A2 | 12/2007 |
| WO | WO-2008/077546 A1 | 7/2008 |
| WO | WO-2008/119566 A2 | 10/2008 |
| WO | WO-2008/119567 A2 | 10/2008 |
| WO | WO-2009/070642 A1 | 6/2009 |
| WO | WO-2009/106321 A1 | 9/2009 |
| WO | WO-2010/057109 A1 | 5/2010 |
| WO | WO-2010/077643 A1 | 7/2010 |
| WO | WO-2010/114940 A1 | 10/2010 |
| WO | WO-2011/028945 A1 | 3/2011 |
| WO | WO-2011/028952 A1 | 3/2011 |
| WO | WO-2011/090754 A1 | 7/2011 |

(56) References Cited

FOREIGN PATENT DOCUMENTS

WO WO-2011/090762 A1 7/2011
WO WO-2011/121110 A1 10/2011
WO WO-2011/131746 A2 10/2011
WO WO-2011/143545 A1 11/2011
WO WO-2012/025525 A1 3/2012
WO WO-2012/058768 A1 5/2012
WO WO-2012/058768 A8 5/2012
WO WO-2012/073985 A1 6/2012
WO WO-2012/075581 A1 6/2012
WO WO-2012/123949 A1 9/2012
WO WO-2012/143524 A2 10/2012
WO WO-2012/158818 A2 11/2012
WO WO-2012/162067 A2 11/2012
WO WO-2013/026831 A1 2/2013
WO WO-2013/128027 A1 9/2013
WO WO-2013/128194 A1 9/2013
WO WO-2014/022540 A1 2/2014
WO WO-2014/028560 A2 2/2014
WO WO-2014/047231 A1 3/2014
WO WO-2014/028560 A3 5/2014
WO WO-2014/083178 A1 6/2014
WO WO-2014/108483 A1 7/2014
WO WO-2014/122251 A2 8/2014
WO WO-2014/141152 A2 9/2014
WO WO-2014/144722 A2 9/2014
WO WO-2014/153002 A1 9/2014
WO WO-2014/122251 A3 10/2014
WO WO-2014/170063 A1 10/2014
WO WO-2014/141152 A3 12/2014
WO WO-2014/191113 A1 12/2014
WO WO-2014/193973 A2 12/2014
WO WO-2014/210064 A1 12/2014
WO WO-2015/006749 A2 1/2015
WO WO-2014/191113 A8 2/2015
WO WO-2015/095392 A1 6/2015
WO WO-2015/143079 A1 9/2015
WO WO-2015/184203 A1 12/2015
WO WO-2015/184207 A1 12/2015
WO WO-2016/014942 A1 1/2016
WO WO-2016/019969 A1 2/2016
WO WO-2016/020065 A1 2/2016
WO WO-2016/036678 A1 3/2016
WO WO-2016/049214 A1 3/2016
WO WO-2016/081490 A1 5/2016
WO WO-2016/090210 A1 6/2016
WO WO-2016/110576 A1 7/2016
WO WO-2016/179003 A1 11/2016
WO WO-2016/191750 A1 12/2016
WO WO-2016/201300 A1 12/2016
WO WO-2016/204966 A1 12/2016
WO WO-2016/205520 A1 12/2016
WO WO-2016/205531 A2 12/2016
WO WO-2017/132279 A1 8/2017
WO WO-2018/093821 A1 5/2018
WO WO-2019/095641 A1 5/2019
WO WO-2020/232169 A1 11/2020

OTHER PUBLICATIONS

Falchi et al., "An Evidence-based Review of Anti-CD20 Antibody-containing Regimens for the Treatment of Patients With Relapsed or Refractory Chronic Lymphocytic Leukemia, Diffuse Large B-cell Lymphoma, or Follicular Lymphoma," Clin Lymphoma Myeloma Leuk. 18(8):508-18.e14 (May 23, 2018) (25 pages).

Xu et al., "Production of bispecific antibodies in 'knobs-into-holes' using a cell-free expression system," *MAbs*. 7(1):231-42 (Nov. 26, 2014) (13 pages).

Yuraszeck et al., "A quantitative systems pharmacology (QSP) model to assess the action of blinatumomab in NHL patients (pts)," Journal of Clinical Oncology 34(15_suppl) Abstract e14511 (May 20, 2016) (3 pages).

"Purified Mouse Anti-Human CD3-epsilon Clone SP34," BD Biosciences, <https://www.bdbiosciences.com/us/reagents/research/antibodies-buffers/immunology-reagents/anti-non-human-primate-antibodies/cell-surface-antigens/purified-mouse-anti-human-cd3-sp34/p/556610>, retrieved on Jan. 4, 2021 (4 pages).

Anderson et al., "G19.4(alpha CD3) × B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. 80(11):2826-34 (1992) (10 pages).

Atwell et al., "Stable heterodimers from remodeling the domain interface of a homodimer using a phage display library," J Mol Biol. 270(1):26-35 (1997).

Baeuerle et al., "Bispecific T-cell engaging antibodies for cancer therapy," Cancer Res. 69(12):4941-4 (2009).

Bortoletto et al., "Optimizing anti-CD3 affinity for effective T cell targeting against tumor cells," Eur J Immunol. 32(11):3102-7 (2002).

Brack et al., "A Bispecific HER2-Targeting FynomAb with Superior Antitumor Activity and Novel Mode of Action," Mol Cancer Ther. 13(8):2030-39 (2014) (11 pages).

Brinkmann et al., "The making of bispecific antibodies," MAbs. 9(2):182-212 (2017).

Brown et al., "Tolerance to single, but not multiple, amino acid replacements in antibody $V_H$ CDR2: a means of minimizing B cell wastage from somatic hypermutation?" J Immunol. 156(9):3285-91 (1996).

Brüggemann et al., "Comparison of the effector functions of human immunoglobulins using a matched set of chimeric antibodies," J Exp Med. 166(5):1351-61 (1987).

Buhmann et al., "Immunotherapy of recurrent B-cell malignancies after allo-SCT with Bi20 (FBTA05), a trifunctional anti-CD3 × anti-CD20 antibody and donor lymphocyte infusion," Bone Marrow Transplant. 43(5):383-97 (2009).

Buhmann et al., "Immunotherapy with FBTA05 (Bi20), a trifunctional bispecific anti-CD3 × anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," J Transl Med. 11:160 (2013) (9 pages).

Carter, "Bispecific human IgG by design," J Immunol Methods. 248(1-2):7-15 (2001).

Choi et al., "Bispecific antibodies engage T cells for antitumor immunotherapy," Expert Opin Biol Ther. 11(7):843-53 (2011).

Chu et al., "Immunotherapy with long-lived anti-CD20 × anti-CD3 bispecific antibodies stimulates potent T cell-mediated killing of human B cell lines and of circuating and lymphoid B cells in monkeys: a potential therapy for B cell lymphomas and lukemias," Blood. 124(21):311 (2014) (1 page).

Clynes et al., "Fc receptors are required in passive and active immunity to melanoma," Proc Natl Acad Sci U S A. 95(2):652-6 (1998).

Cragg et al., "Antibody specificity controls in vivo effector mechanisms of anti-CD20 reagents," Blood. 103(7):2738-43 (2004).

Cragg et al., "Complement-mediated lysis by anti-CD20 mAb correlates with segregation into lipid rafts," Blood. 101(3):1045-52 (2003).

Desnoyers et al., "Tumor-Specific Activation of an EGFR-Targeting Probody Enhances Therapeutic Index," Sci Transl Med. 5(207):207ra144 (2013) (10 pages).

Desnoyers et al., "Tumor-specific activation of an EGFR-targeting probody enhances therapeutic index," Sci Transl Med. 5(207):207ra144 (2013) (2 pages) (Abstract only).

Diefenbach et al., "An individualized risk mitigation approach for safety: experience from the mosunetuzumab (CD20/CD3 bispecific antibody) development program in relation to neurotoxicity risk," 61st ASH Annual Meeting & Exposition, Dec. 7-10, Orlando, Florida, Poster P-4728 (2019) (1 page).

Donaldson et al., "Design and development of masked therapeutic antibodies to limit off-target effects: application to anti-EGFR antibodies," available in PMC Jan. 16, 2013, published in final edited form as: Cancer Biol Ther. 8(22): 2147-52 (2009) (12 pages).

Donaldson et al., "Design and development of masked therapeutic antibodies to limit off-target effects: application to anti-EGFR antibodies," Cancer Biol Ther. 8(22): 2145-50 (2009) (6 pages).

(56) References Cited

OTHER PUBLICATIONS

Drent et al., "A Rational Strategy for Reducing On-Target Off-Tumor Effects of CD38-Chimeric Antigen Receptors by Affinity Optimization," Mol Ther. 25(8):1946-58 (2017).
Duncan et al., "The binding site for C1q on IgG," Nature. 332(6166):738-40 (1988).
Edelman et al., "The covalent structure of an entire gammaG immunoglobulin molecule," Proc Natl Acad Sci U S A. 63(1):78-85 (1969).
Erster et al., "Site-specific targeting of antibody activity in vivo mediated by disease-associated proteases," J Control Release. 161(3): 804-12 (2012) (2 pages) (Abstract only).
Gaston et al., "Intracellular delivery of therapeutic antibodies into specific cells using antibody-peptide fusions," Sci Rep. 9(1):18688 (2019) (12 pages).
Gazzano-Santoro et al., "A non-radioactive complement-dependent cytotoxicity assay for anti-CD20 monoclonal antibody," J Immunol Methods. 202(2):163-71 (1997).
Gonzales et al., "Minimizing the Immunogenicity of Antibodies for Clinical Application," Tumour Biol. 26(1):31-43 (2005) (1 page) (Abstract only).
Guyer et al., "Immunoglobulin binding by mouse intestinal epithelial cell receptors," J Immunol. 117(2):587-93 (1976).
Haile et al., "Soluble CD80 Restores T Cell Activation and Overcomes Tumor Cell Programmed Death Ligand 1-Mediated Immune Suppression," J Immunol. 191(5):2829-36 (2013) (9 pages).
Han et al., "Masked Chimeric Antigen Receptor for Tumor-Specific Activation," Mol Ther. 25(1):274-84 (2017).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of lgG3 antibodies to a human melanoma-associated ganglioside," Proc Natl Acad Sci U S A. 82(5):1499-502 (1985).
Holliger et al., "'Diabodies': small bivalent and bispecific antibody fragments," Proc Natl Acad Sci USA. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).
Hosseini et al., "Mitigating the Risk of Cytokine Release Syndrome in a Phase I Trial of CD20/CD3 Bispecific Antibody Mosunetuzumab In NHL: Impact of Translational System Modeling," NPJ Syst Biol Appl. 6(1):28 (2020) (11 pages).
Hosseini et al., "Systems pharmacology modeling of anti-CD20/CD3 T-cell dependent bispecific antibody and its application to clinical trial design," American Conference on Pharmacometrics 7; Oct. 25; Bellevue, WA. (2016) (1 page).
Huang et al., "In Vivo Deamidation Characterization of Monoclonal Antibody by LC/MS/MS," Anal Chem. 77(5):1432-9 (2005).
Huang et al., "Structural chemistry and therapeutic intervention of protein-protein interactions in immune response, human immunodeficiency virus entry, and apoptosis," Pharmacol Ther. 86(3):201-215 (2000).
Hudson et al., "Engineered antibodies," Nat Med. 9(1):129-34 (2003).
Huehls et al., "Bispecific T-cells engagers for cancer immunotherapy," Immunol Cell Biol. 93(3):290-6 (2015).
Idusogie et al., "Mapping of the C1q Binding Site on Rituxan, A Chimeric Antibody with a Human IgG1 Fc," J Immunol. 164(8):4178-84 (2000).
Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).
Jager et al., "The trifunctional antibody ertumaxomab destroys tumor cells that express low levels of human epidermal growth factor receptor 2," Cancer Res. 69(10):4270-6 (2009).
Junttila et al., "Antitumor Efficacy of a Bispecific Antibody That Targets HER2 and Activates T Cells," Cancer Res. 74(19):5561-71 (2014).
Kanda et al., "Comparison of cell lines for stable production of fucose-negative antibodies with enhanced ADCC," Biotechnol Bioeng. 94(4):680-8 (2006).
Kelley et al., " Thermodynamic Analysis of an Antibody Functional Epitope," Biochemistry. 32(27):6828-35 (1993).
Kiewe et al., "Phase I trial of the trifunctional anti-HER2 × anti-CD3 antibody ertumaxomab in metastatic breast cancer," 2005 ASCO Annual Meeting Proceedings. J Clin Oncol. 23(16S):Abstract 2530 (2005) (1 page).
Kiewe et al., "Phase I trial of the trifunctional anti-HER2 ×× anti-CD3 antibody ertumaxomab in metastatic breast cancer," Clin Cancer Res. 12(10):3085-91 (2006).
Kim et al., "Localization of the site of the murine IgG1 molecule that is involved in binding to the murine intestinal Fc receptor," Eur J Immunol. 24(10):2429-34 (1994).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," mAbs. 4(2):182-97 (2012).
Kortt et al., "Dimeric and trimeric antibodies: high avidity scFvs for cancer targeting," Biomol Eng. 18(3):95-108 (2001) (15 pages).
Law et al., "Expression and characterization of recombinant soluble human CD3 molecules: presentation of antigenic epitopes defined on the native TCR-CD3 complex" Int Immunol 14(4):389-400 (2002).
Leabman et al., "Effects of altered FcγR binding on antibody pharmacokinetics in cynomolgus monkeys," MAbs. 5(6):896-903 (2013) (27 pages).
Lee et al., "Current concepts in the diagnosis and management of cytokine release syndrome," Blood. 124(2):188-95 (2014) (18 pages).
Li et al., "Exposure-response analyses indicate a promising benefit/risk profile of mosunetuzumab in relapsed and refractory non-Hodgkin lymphoma," 61st ASH Annual Meeting & Exposition, Dec. 7-10, 2019, Orlando, Florida. Poster P-1285 (2019).
Li, "Successful QSP modeling in drug development starts with the right questions," American Conference on Pharmacometrics 8, Oct. 16, Fort Lauderdale, FL. (2017) (20 pages).
Lippow et al., "Computational Design of Antibody-Affinity Improvement Beyond in Vivo Maturation," available in PMC Jan. 7, 2010, published in final edited form as: Nat Biotechnol. 25(10):1171-6 (2007) (14 pages).
Liu et al., "Affinity-Tuned ErbB2 or EGFR Chimeric Antigen Receptor T Cells Exhibit an Increased Therapeutic Index against Tumors in Mice," Cancer Res. 75(17):3596-607 (2015) (13 pages).
Liu et al., "Heteroantibody duplexes target cells for lysis by cytotoxic T lymphocytes," Proc Natl Acad Sci U S A. 82(24):8648-52 (1985).
Liu et al., "Improvement in soluble expression levels of a diabody by exchanging expression vectors," Protein Expr Purif. 62(1): 15-20 (2008) (6 pages).
Lord et al., "Structure-based engineering to restore high affinity binding of an isoform-selective anti-TGFβ1 antibody," MAbs. 10(3):444-452 (2018).
Lu et al., "Tetravalent anti-CD20/CD3 bispecific antibody for the treatment of B cell lymphoma," Biochem Biophys Res Commun. 473(4):808-813 (2016) (3 pages) (Abstract only).

(56) References Cited

OTHER PUBLICATIONS

Lum et al., "Targeting T cells with bispecific antibodies for cancer therapy," available in PMC Oct. 8, 2013, published in final edited form as: BioDrugs. 25(6):365-79 (2011) (24 pages).
Mariuzza et al., "The structural basis of antigen-antibody recognition," Annu Rev Biophys Biophys Chem. 16:139-159 (1987) (2 pages) (Abstract only).
Merchant et al., "An efficient route to human bispecific IgG," Nat Biotechnol. 16(7):677-81 (1998).
Metz et al., "Bispecific antibody derivatives with restricted binding functionalities that are activated by proteolytic processing," Protein Eng Des Sel. 25(10):571-80 (2012).
Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
NIH/NCI, "anti-PD-1 fusion protein AMP-224," dated Jul. 10, 2015, accessed Jul. 31, 2019 (1 page).
Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Okazaki et al., "Fucose depletion from human IgG1 oligosaccharide enhances binding enthalpy and association rate between IgG1 and FcgammaRIlla," J Mol Biol. 336(5):1239-49 (2004).
Paino et al., "Reply to Response to "CD20 Positive Cells Are Undetectable in the Majority of Multiple Myeloma Cell Lines and Are Not Associated With a Cancer Stem Cell Phenotype,"" Haematologica. 97(7):1110-1114 (2012) (1 page).
Pessano et al., "The T3/T cell receptor complex: antigenic distinction between the two 20-kd T3 (T3-δand T3-ε) subunits," EMBO J. 4(2):337-44 (1985).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Polu et al., "Probody therapeutics for targeting antibodies to diseased tissue," Expert Opin Biol Ther. 14(8):1049-53 (2014).
Ravetch et al., "Fc receptors," Annu Rev Immunol. 9:457-92 (1991).
Reusch et al., "A tetravalent bispecific TandAb (CD19/CD3), AFM11, efficiently recruits T cells for the potent lysis of CD19(+) tumor cells," MAbs. 7(3):584-604 (2015) (22 pages).
Reusch et al., "Anti-CD3 × anti-epidermal growth factor receptor (EGFR) bispecific antibody redirects T-cell cytolytic activity to EGFR-positive cancers in vitro and in an animal model," Clin Cancer Res. 12(1):183-90 (2006) (9 pages).
Ridgway et al., "'Knobs-into-holes' engineering of antibody $C_H3$ domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Ripka et al., "Two Chinese hamster ovary glycosylation mutants affected in the conversion of GDP-mannose to GDP-fucose," Arch Biochem Biophys. 249(2):533-45 (1986).
Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).
Salmerón et al., "A conformational epitope expressed upon association of CD3-epsilon with either CD3-delta or CD3-gamma is the main target for recognition by anti-CD3 monoclonal antibodies," J Immunol. 147(9): 3047-52 (1991) (2 pages) (Abstract only).
Saphire et al., "Crystal structure of a neutralizing human IgG against HIV-1: a template for vaccine design," Science. 293(5532):1155-9 (2001).
Schuster et al., "Immunotherapy with the trifunctional anti-CD20 × anti-CD3 antibody FBTA05 (Lymphomun) in paediatric high-risk patients with recurrent CD20-positive B cell malignancies," Br J Haematol. 169:90-102 (2015) (13 pages).
Seimetz et al., "Development and approval of the trifunctional antibody catumaxomab (anti-EpCAM × anti-CD3) as a targeted cancer immunotherapy," Cancer Treat Rev. 36(6):458-67 (2010).
Sen et al., "Use of Anti-CD3 × Anti-HER2/neu Bispecific Antibody for Redirecting Cytotoxicity of Activated T Cells Toward HER2/neu+ Tumors," J Hematother Stem Cell Res. 10(2):247-60 (2001).
Shalaby et al., "Bispecific HER2 × CD3 antibodies enhance T-cell cytotoxicity in vitro and localize to HER2-overexpressing xenografts in nude mice," Clin Immunol Immunopathol. 74(2):185-92 (1995).
Shen et al., "Preparation and characterization for bispecific antibodies of anti-CD3 × anti-idiotype to B cell lymphocytic leukemia," J Tongji Med Univ. 19(3):166-9 (1999) (4 pages).
Shi et al., "Margin-Infiltrating $CD20^+$ B Cells Display an Atypical Memory Phenotype and Correlate with Favorable Prognosis in Hepatocellular Carcinoma," Clin Cancer Res. 19(21):5994-6005 (2013).
Shields et al., "High resolution mapping of the binding site on human IgG1 for FcγRI, FcγRII, FcγRIII, and FcRn and design of IgG1 variants with improved binding to the FcγR," J Biol Chem. 276(9):6591-604 (2001).
Somasundaram et al., "Will Engineered T Cells Expressing CD20 scFv Eradicate Melanoma?" Mol Ther. 19(4):638-40 (2011).
Sondermann et al., "The 3.2-A crystal structure of the human IgG1 Fc fragment-FcγRIII complex," Nature. 406(6793):267-73 (2000).
Spiess et al., "Alternative molecular formats and therapeutic applications for bispecific antibodies," Mol Immunol. 67(2 pt A):95-106 (2015).
Spiess et al., "Bispecific antibodies with natural architecture produced by co-culture of bacteria expressing two distinct half-antibodies," Nat Biotechnol. 31(8):753-8 (2013) (7 pages).
Stanglmaier et al., "Bi20 (FBTA05), a novel trifunctional bispecific antibody (anti-CD20 × anti-CD3), mediates efficient killing of B-cell lymphoma cells even with very low CD20 expression levels," Int J Cancer. 123(5):1181-9 (2008).
Stein et al., "Novel and Emerging Drugs for Acute Myeloid Leukemia," available in PMC May 22, 2014, published in final edited form as: Curr Cancer Drug Targets. 12(5):522-530 (2012) (19 pages).
Stieglmaier et al., "Utilizing the BiTE (bispecific T-cell engager) platform for immunotherapy of cancer," Expert Opin Biol Ther. 15(8):1093-9 (2015) (8 pages).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Wakefield et al., "Addition of a C-terminal extension sequence to transforming growth factor-beta 1 interferes with biosynthetic processing and abolishes biological activity," Growth Factors. 5(3):243-53 (1991) (2 pages) (Abstract only).
Wark et al., "Latest technologies for the enhancement of antibody affinity," Adv Drug Deliv Rev. 58(5-6):657-70 (2006).
Weidle et al., "The Intriguing Options of Multispecific Antibody Formats for Treatment of Cancer," Cancer Genomics Proteomics. 10(1):1-18 (2013) (18 pages).
Wells et al., "Reaching for high-hanging fruit in drug discovery at protein-protein interfaces," Nature. 450(7172):1001-9 (2007).
Westin et al., "Safety and activity of PD1 blockade by pidilizumab in combination with rituximab in patients with relapsed follicular lymphoma: a single group, open-label, phase 2 trial," Lancet Oncol. 15(1):69-77 (2014).
Wright et al., "Effect of glycosylation on antibody function: implications for genetic engineering," Trends Biotechnol. 15(1):26-32 (1997).

(56) References Cited

OTHER PUBLICATIONS

Wu et al., "Humanization of a Murine Monoclonal Antibody by Simultaneous Optimization of Framework and CDR Residues," J Mol Biol. 294(1):151-162 (1999).
Wuellner et al., "Bispecific CD3/HER2 Targeting FynomAb Induces Redirected T Cell-Mediated Cytolysis with High Potency and Enhanced Tumor Selectivity," Antibodies. 4(4):426-440 (2015) (15 pages).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. 87(5):614-22 (2004).
Yan et al., "Succinimide Formation at Asn 55 in the Complementarity Determining Region of a Recombinant Monoclonal Antibody IgG1 Heavy Chain," J Pharm Sci. 98(10):3509-21 (2009).
Yang et al., "Generation and characterization of a target-selectively activated antibody against epidermal growth factor receptor with enhanced anti-tumor potency," MAbs. 7(2):440-50 (2015).
Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).
Zhu et al., "Identification of heavy chain residues in a humanized anti-CD3 antibody important for efficient antigen binding and T cell activation," J Immunol. 155(4):1903-10 (1995).
Budde et al., "Mosunetuzumab, a Full-Length Bispecific CD20/CD3 Antibody, Displays Clinical Activity in Relapsed/Refractory B-Cell Non-Hodgkin Lymphoma (NHL): Interim Safety and Efficacy Results from a Phase 1 Study," Blood. 132(Supplement 1):399 (2018) (6 pages).
Goebeler et al., "Bispecific T-cell Engager (BiTE) Antibody Construct Blinatumomab for the Treatment of Patients With Relapsed/Refractory Non-Hodgkin Lymphoma: Final Results From a Phase I Study," J Clin Oncol. 34(10):1104-11 (2016).
Hernandez et al., "Pharmacodynamic Effects and Immune Correlates of Response to the CD20/CD3 Bispecific Antibody Mosunetuzumab in Relapsed or Refractory Non-Hodgkin Lymphoma," Blood. 134(Supplement 1):1585 (2019) (4 pages).
Li et al., "Exposure-response analyses indicate a promising benefit/risk profile of mosunetuzumab in relapsed and refractory non-Hodgkin lymphoma," Blood. 134(Supplement 1):1285 (2019) (8 pages).
Olszewski et al., "401 Single-agent mosunetuzumab is a promising safe and efficacious chemotherapy-free regimen for elderly/unfit patients with previously untreated diffuse large B-cell lymphoma," 62nd American Society of Hematology (ASH) Annual Meeting and Exposition, December 5-8, Oral Abstract, <https://ash.confex.com/ash/2020/webprogram/Paper136255.html>, retrieved on Apr. 21, 2022 (2020) (4 pages).
International Search Report and Written Opinion for International Application No. PCT/US2021/057714, mailed Mar. 21, 2022 (20 pages).
Auerbach et al., "Angiogenesis assays: problems and pitfalls," Cancer Metastasis Rev. 19(1-2):167-72 (2000).
Bartlett et al., "610 Mosunetuzumab Monotherapy Demonstrates Durable Efficacy with a Manageable Safety Profile in Patients with Relapsed/Refractory Follicular Lymphoma Who Received greater than or equal to 2 Prior Therapies: Updated Results from a Pivotal Phase II Study." American Society of Hematology (ASH) Annual Meeting and Exposition, Dec. 10-13, 2022 (3 pages).
Beans, Carolyn, "Targeting metastasis to halt cancer's spread," PNAS. 115(50):12539-43 (Dec. 1, 2018).
Choi et al, "Reference values of hematology, biochemistry, and blood type in cynomolgus monkeys from cambodia origin," Lab Anim Res. 32(1):46-55 (2016).
Curigliano et al., "Safety and Tolerability of Phosphatidylinositol-3-Kinase (PI3K) Inhibitors in Oncology," Drug Safety. 42:247-62 (Jan. 16, 2019).
Dornan et al., "Therapeutic potential of an anti-CD79b antibody-drug conjugate, anti-CD79b-vc-MMAE, for the treatment of non-Hodgkin lymphoma," Blood. 114(13):2721-9 (2009).
Gravanis et al., "The changing world of cancer drug development: the regulatory bodies' perspective," Chin Clin Oncol. 3(2):22 (2014) (5 pages).
Gura, T. "Systems for identifying new drugs are often faulty," Science. 278(5340):1041-2 (1997).
Hait, William, "Anticancer drug development: the grand challenges," Nature Reviews/Drug Discovery. 9(4):253-4 (2010).
Harris et al., "The World Health Organization Classification of Neoplasms of the Hematopoietic and Lymphoid Tissues: Report of the Clinical Advisory Committee Meeting—Airlie House, Virginia, Nov. 1997," The Hematology Journal. 1:53-66 (2000).
Heppner et al., "Tumor heterogeneity: biological implications and therapeutic consequences," Cancer Metastasis Reviews. 2(1):5-23 (1983).
Jain, "Barriers to drug delivery in solid tumors," Sci Am. 271(1):58-65 (1994).
Shao et al., "Distinguishing Hairy Cell Leukemia Variant from Hairy Cell Leukemia: Development and Validation of Diagnostic Criteria," available in PMC Aug. 30, 2017, published in final edited form as: Leuk Res. 37(4):401-9 (2013) (22 pages).
Sporn et al., "Chemoprevention of cancer," Carcinogenesis. 21(3):525-30 (2000).
International Preliminary Report on Patentability for International Patent Application No. PCT/US2021/057714, dated May 8, 2023 (8 pages).
Office Action and Search Report for Taiwanese Patent Application No. 110140844 dated Apr. 6, 2023. (8 pages).
Audino et al., "Polatuzumab Vedotin, an Antibody-Drug Conjugate Targeting CD79b, Is a Highly Active Agent Against Burkitt Lymphoma and Primary Mediastinal B-Cell Lymphoma," Blood. 134(Supplement 1):3963 (2019) (5 pages).
Forero-Torres et al., "Polatuzumab Vedotin Combined with Obinutuzumab, Cyclophosphamide, Doxorubicin, and Prednisone (G-CHP) for Patients with Previously Untreated Diffuse Large B-Cell Lymphoma (DLBCL): Preliminary Results of a Phase Ib/II Dose-Escalation Study," Blood. 128(22):1856 (2016) (2 pages).
"History of Changes for Study: NCT02500407: A Safety, Efficacy and Pharmacokinetic Study of BTCT4465A (Mosunetuzumab) as a Single Agent and Combined With Atezolizumab in Non-Hodgkin's Lymphoma (NHL) and Chronic Lymphocytic Leukemia (CLL) ," ClinicalTrials.gov, last updated Mar. 17, 2022, retrieved Jul. 17, 2023, from <https://classic.clinicaltrials.gov/ct2/history/NCT02500407?V_74=View#StudyPageTop> (10 pages).
Beans, Carolyn, "Targeting metastasis to halt cancer's spread," PNAS. 115(50):12539-43 (Dec. 11, 2018).
Choi et al., "Reference values of hematology, biochemistry, and blood type in cynomolgus monkeys from cambodia origin," Lab Anim Res. 32(1):46-55 (Mar. 2016).
Gura, "Systems for identifying new drugs are often faulty," Science. 278(5340):1041-2 (1997).
Olszewski et al., "Mosunetuzumab and Polatuzumab Vedotin Demonstrates Preliminary Efficacy in Elderly Unfit/Frail Patients with Previously Untreated Diffuse Large B-Cell Lymphoma," Blood, 142 (Supplement 1): 855 (2023) (3 pages) (Abstract Only).
Trneny et al., "A phase II multicenter study of the anti-CD19 antibody drug conjugate coltuximab ravtansine (SAR3419) in patients with relapsed or refractory diffuse large B-cell lymphoma previously treated with rituximab-based immunotherapy," Haematologica, 103(8):1351-8, 2018.
Wolska-Washer et al., "Safety and Tolerability of Antibody-Drug Conjugates in Cancer" Drug Safety. 42:295-314 (Jan. 16, 2019).
Wang, et al., "Fixed Duration Mosunetuzumab Plus Polatuzumab Vedotin Has Promising Efficacy and a Manageable Safety Profile in Patients with BTKi Relapsed/Refractory Mantle Cell Lymphoma: Initial Results from a Phase Ib/II Study," Blood, 142 (Supplement 1): 734 (2023) (3 pages) (Abstract Only).
Office Action and Search Report for Tawianese Patent Application No. 110140844 dated Apr. 6, 2023. (8 pages).
Budde et al., "Mosunetuzumab with polatuzumab vedotin in relapsed or refractory aggressive large B cell lymphoma: a phase 1b/2 trial," Nature Medicine. 30(1):229-39 (Jan. 2024) (30 pages).

(56) References Cited

OTHER PUBLICATIONS

Budde et al., “Single-Agent Mosunetuzumab Shows Durable Complete Responses in Patients with Relapsed or Refractory B-Cell Lymphomas: Phase I Dose-Escalation Study,” J Clin Oncol 40(5):481-95 (Dec. 2021).
Cleveland Clinic, “Non-Hodgkin Lymphoma,” <https://my.clevelandclinic.org/health/diseases/15662-non-hodgkin-lymphoma>, accessed online Jul. 29, 2024 (15 pages).
FDA label, “POLIVY™ (polatuzumab vedotin-piiq) for injection, for intravenous use Initial U.S. Approval: 2019” <https://www.accessdata.fda.gov/drugsatfda_docs/label/2019/761121s000lbl.pdf>, dated Jun. 2019 (19 pages).
Kawasaki et al., “Revealing the Synergistic Potential of Mosunetuzumab Plus Polatuzumab Vedotin through CD20 Upregulation,” Blood. 144(Supplement 1):4171-2 (Nov. 2024) (Abstract only) (2 pages).
World Health Organization, “International Nonproprietary Names for Pharmaceutical Substances (INN),” WHO Drug Information. 31(2):241-383 (2017).

* cited by examiner

FIG.: Condition:
2A Vehicle + PBMCs
2B 5 mg/kg CD20 TDB + no PBMCs
2C 0.5 mg/kg CD20 TDB + PBMCs
2D 1 mg/kg CD20 TDB + PBMCs
2E 5 mg/kg CD20 TBD + PBMCs Tumor Volume (mm³) on linear scale
1600
1200
800
400
0
0
10
20
30
Day
Individual animal
Reference fit
Group fit FIG.: Condition:
2F anti-CD79b-MC-vc-PAB-MMAE + no PBMCs
2G anti-CD79b-MC-vc-PAB-MMAE + PBMCs
2H anti-CD79b-MC-vc-PAB-MMAE + 0.5 mg/kg CD20 TDB + PBMCs
2I anti-CD79b-MC-vc-PAB-MMAE + 1 mg/kg CD20 TDB +PBMCs Tumor Volume (mm³) on linear scale
1600
1200
800
400
0
0
10
20
30
Day
Individual animal
Reference fit
Group fit

FIG. 10

| MedDRA Preferred Term | A1 1/2/9 mg (N=7) | A2 1/2/20 mg (N=3) | A3 1/2/40 mg (N=6) | A4 1/2/60/30 mg (N=6) | Overall (N=22) |
|---|---|---|---|---|---|
| Total number of patients with at least one adverse event | 5 (71.4%) | 2 (66.7%) | 6 ( 100%) | 5 (83.3%) | 18 (81.8%) |
| Total number of events | 21 | 17 | 36 | 34 | 108 |
| Fatigue | 0 | 1 (33.3%) | 4 (66.7%) | 3 (50.0%) | 8 (36.4%) |
| Neutrophil count decreased | 3 (42.9%) | 0 | 0 | 3 (50.0%) | 6 (27.3%) |
| Diarrhoea | 1 (14.3%) | 0 | 1 (16.7%) | 2 (33.3%) | 4 (18.2%) |
| Nausea | 1 (14.3%) | 1 (33.3%) | 1 (16.7%) | 1 (16.7%) | 4 (18.2%) |
| Pruritus | 1 (14.3%) | 1 (33.3%) | 1 (16.7%) | 1 (16.7%) | 4 (18.2%) |
| Pyrexia | 1 (14.3%) | 1 (33.3%) | 0 | 2 (33.3%) | 4 (18.2%) |
| Vomiting | 0 | 1 (33.3%) | 1 (16.7%) | 1 (16.7%) | 3 (13.6%) |
| Anaemia | 1 (14.3%) | 1 (33.3%) | 0 | 0 | 2 ( 9.1%) |
| Bone pain | 0 | 0 | 1 (16.7%) | 1 (16.7%) | 2 ( 9.1%) |
| Cellulitis | 0 | 0 | 1 (16.7%) | 1 (16.7%) | 2 ( 9.1%) |
| Constipation | 1 (14.3%) | 0 | 0 | 1 (16.7%) | 2 ( 9.1%) |
| Cytokine release syndrome | 1 (14.3%) | 1 (33.3%) | 0 | 0 | 2 ( 9.1%) |
| Decreased appetite | 0 | 0 | 1 (16.7%) | 1 (16.7%) | 2 ( 9.1%) |
| Headache | 0 | 1 (33.3%) | 1 (16.7%) | 0 | 2 ( 9.1%) |
| Hypomagnesaemia | 1 (14.3%) | 1 (33.3%) | 0 | 0 | 2 ( 9.1%) |
| Hypophosphataemia | 0 | 1 (33.3%) | 1 (16.7%) | 0 | 2 ( 9.1%) |
| Pain of skin | 0 | 0 | 1 (16.7%) | 1 (16.7%) | 2 ( 9.1%) |
| Tumour pain | 0 | 0 | 1 (16.7%) | 1 (16.7%) | 2 ( 9.1%) |
| White blood cell count decreased | 2 (28.6%) | 0 | 0 | 0 | 2 ( 9.1%) |

FIG. 10 (continued)

| | | | | | |
|---|---|---|---|---|---|
| Abdominal pain | 0 | 0 | 1 (16.7%) | 0 | 1 ( 4.5%) |
| Activated partial thromboplastin time prolonged | 0 | 0 | 1 (16.7%) | 0 | 1 ( 4.5%) |
| Alanine aminotransferase | 0 | 1 (33.3%) | 0 | 0 | 1 ( 4.5%) |
| Alopecia | 1 (14.3%) | 0 | 0 | 0 | 1 ( 4.5%) |
| Anosmia | 0 | 0 | 0 | 1 (16.7%) | 1 ( 4.5%) |
| Aspartate aminotransferase increased | 0 | 1 (33.3%) | 0 | 0 | 1 ( 4.5%) |
| Atrial fibrillation | 0 | 0 | 1 (16.7%) | 0 | 1 ( 4.5%) |
| Blood alkaline phosphatase increased | 1 (14.3%) | 0 | 0 | 0 | 1 ( 4.5%) |
| C-reactive protein increased | 0 | 0 | 1 (16.7%) | 0 | 1 ( 4.5%) |
| Chills | 1 (14.3%) | 0 | 0 | 0 | 1 ( 4.5%) |
| Cough | 1 (14.3%) | 0 | 0 | 0 | 1 ( 4.5%) |
| Dry eye | 0 | 0 | 1 (16.7%) | 0 | 1 ( 4.5%) |
| Dry mouth | 0 | 0 | 1 (16.7%) | 0 | 1 ( 4.5%) |
| Dry skin | 0 | 0 | 0 | 1 (16.7%) | 1 ( 4.5%) |
| Dyspnoea | 0 | 0 | 0 | 1 (16.7%) | 1 ( 4.5%) |
| Erythema | 0 | 0 | 1 (16.7%) | 0 | 1 ( 4.5%) |
| Face oedema | 0 | 0 | 0 | 1 (16.7%) | 1 ( 4.5%) |
| Feeling hot | 0 | 0 | 1 (16.7%) | 0 | 1 ( 4.5%) |
| Fungal skin infection | 0 | 0 | 0 | 1 (16.7%) | 1 ( 4.5%) |
| Hyperglycaemia | 0 | 0 | 1 (16.7%) | 0 | 1 ( 4.5%) |
| Hyponatraemia | 0 | 1 (33.3%) | 0 | 0 | 1 ( 4.5%) |
| Infusion related reaction | 0 | 0 | 0 | 1 (16.7%) | 1 ( 4.5%) |
| Insomnia | 0 | 0 | 0 | 1 (16.7%) | 1 ( 4.5%) |
| Lacrimation increased | 1 (14.3%) | 0 | 0 | 0 | 1 ( 4.5%) |
| Lethargy | 0 | 1 (33.3%) | 0 | 0 | 1 ( 4.5%) |
| Lymphoedema | 0 | 0 | 1 (16.7%) | 0 | 1 ( 4.5%) |
| Malaise | 0 | 0 | 0 | 1 (16.7%) | 1 ( 4.5%) |
| Muscle spasms | 0 | 0 | 1 (16.7%) | 0 | 1 ( 4.5%) |

FIG. 10 (continued)

| | | | | | |
|---|---|---|---|---|---|
| Neutropenia | 0 | 0 | 1 (16.7%) | 0 | 1 ( 4.5%) |
| No coding available | 0 | 0 | 1 (16.7%) | 0 | 1 ( 4.5%) |
| Oedema peripheral | 0 | 0 | 1 (16.7%) | 0 | 1 ( 4.5%) |
| Pain in extremity | 1 (14.3%) | 0 | 0 | 0 | 1 ( 4.5%) |
| Platelet count decreased | 0 | 1 (33.3%) | 0 | 0 | 1 ( 4.5%) |
| Pleural effusion | 0 | 0 | 0 | 1 (16.7%) | 1 ( 4.5%) |
| Pneumonia | 0 | 0 | 1 (16.7%) | 0 | 1 ( 4.5%) |
| Productive cough | 0 | 0 | 1 (16.7%) | 0 | 1 ( 4.5%) |
| Rash erythematous | 0 | 0 | 1 (16.7%) | 0 | 1 ( 4.5%) |
| Rash maculo-papular | 0 | 1 (33.3%) | 0 | 0 | 1 ( 4.5%) |
| Rash pustular | 1 (14.3%) | 0 | 0 | 0 | 1 ( 4.5%) |
| Red blood cell sedimentation rate increased | 0 | 0 | 1 (16.7%) | 0 | 1 ( 4.5%) |
| Skin burning sensation | 0 | 0 | 0 | 1 (16.7%) | 1 ( 4.5%) |
| Skin exfoliation | 0 | 0 | 0 | 1 (16.7%) | 1 ( 4.5%) |

Data Cutoff Date: 09JUN2020

FIG. 11

| MedDRA Preferred Term | A1 1/2/9 mg (N=7) | A2 1/2/20 mg (N=3) | A3 1/2/40 mg (N=6) | A4 1/2/60/30 mg (N=6) | Overall (N=22) |
|---|---|---|---|---|---|
| Total number of patients with at least one adverse event | 6 (85.7%) | 2 (66.7%) | 6 ( 100%) | 5 (83.3%) | 19 (86.4%) |
| Total number of events | 20 | 15 | 34 | 40 | 109 |
| Fatigue | 0 | 1 (33.3%) | 4 (66.7%) | 3 (50.0%) | 8 (36.4%) |
| Neutrophil count decreased | 3 (42.9%) | 0 | 1 (16.7%) | 3 (50.0%) | 7 (31.8%) |
| Nausea | 2 (28.6%) | 1 (33.3%) | 2 (33.3%) | 1 (16.7%) | 6 (27.3%) |
| Diarrhoea | 0 | 0 | 2 (33.3%) | 2 (33.3%) | 4 (18.2%) |
| Peripheral sensory neuropathy | 1 (14.3%) | 0 | 1 (16.7%) | 2 (33.3%) | 4 (18.2%) |
| Constipation | 1 (14.3%) | 0 | 0 | 2 (33.3%) | 3 (13.6%) |
| Decreased appetite | 0 | 0 | 1 (16.7%) | 2 (33.3%) | 3 (13.6%) |
| Neuropathy peripheral | 1 (14.3%) | 1 (33.3%) | 1 (16.7%) | 0 | 3 (13.6%) |
| Vomiting | 0 | 1 (33.3%) | 1 (16.7%) | 1 (16.7%) | 3 (13.6%) |
| Anaemia | 1 (14.3%) | 1 (33.3%) | 0 | 0 | 2 ( 9.1%) |
| Cellulitis | 0 | 0 | 1 (16.7%) | 1 (16.7%) | 2 ( 9.1%) |
| Dyspnoea | 1 (14.3%) | 0 | 0 | 1 (16.7%) | 2 ( 9.1%) |
| Hypomagnesaemia | 1 (14.3%) | 1 (33.3%) | 0 | 0 | 2 ( 9.1%) |
| Pruritus | 1 (14.3%) | 1 (33.3%) | 0 | 0 | 2 ( 9.1%) |
| Pyrexia | 1 (14.3%) | 0 | 0 | 1 (16.7%) | 2 ( 9.1%) |

FIG. 11 (continued)

| | | | | | |
|---|---|---|---|---|---|
| Rash maculo-papular | 0 | 1 (33.3%) | 1 (16.7%) | 0 | 2 ( 9.1%) |
| White blood cell count decreased | 2 (28.6%) | 0 | 0 | 0 | 2 ( 9.1%) |
| Abdominal distension | 0 | 0 | 0 | 1 (16.7%) | 1 ( 4.5%) |
| Abdominal pain | 0 | 0 | 1 (16.7%) | 0 | 1 ( 4.5%) |
| Activated partial thromboplastin time prolonged | 0 | 0 | 1 (16.7%) | 0 | 1 ( 4.5%) |
| Alanine aminotransferase | 0 | 1 (33.3%) | 0 | 0 | 1 ( 4.5%) |
| Anosmia | 0 | 0 | 0 | 1 (16.7%) | 1 ( 4.5%) |
| Aspartate aminotransferase increased | 0 | 1 (33.3%) | 0 | 0 | 1 ( 4.5%) |
| Atrial fibrillation | 0 | 0 | 1 (16.7%) | 0 | 1 ( 4.5%) |
| Blood alkaline phosphatase increased | 1 (14.3%) | 0 | 0 | 0 | 1 ( 4.5%) |
| Bone pain | 0 | 0 | 0 | 1 (16.7%) | 1 ( 4.5%) |
| C-reactive protein increased | 0 | 0 | 1 (16.7%) | 0 | 1 ( 4.5%) |
| Cough | 1 (14.3%) | 0 | 0 | 0 | 1 ( 4.5%) |
| Dizziness | 0 | 0 | 0 | 1 (16.7%) | 1 ( 4.5%) |
| Dry mouth | 0 | 0 | 1 (16.7%) | 0 | 1 ( 4.5%) |
| Dry skin | 0 | 0 | 0 | 1 (16.7%) | 1 ( 4.5%) |
| Dyspepsia | 0 | 0 | 0 | 1 (16.7%) | 1 ( 4.5%) |
| Fungal skin infection | 0 | 0 | 0 | 1 (16.7%) | 1 ( 4.5%) |
| Headache | 0 | 0 | 1 (16.7%) | 0 | 1 ( 4.5%) |
| Hyperglycaemia | 0 | 0 | 1 (16.7%) | 0 | 1 ( 4.5%) |
| Hypocalcaemia | 0 | 0 | 1 (16.7%) | 0 | 1 ( 4.5%) |
| Hyponatraemia | 0 | 1 (33.3%) | 0 | 0 | 1 ( 4.5%) |
| Hypophosphataemia | 0 | 1 (33.3%) | 0 | 0 | 1 ( 4.5%) |
| Infusion related reaction | 0 | 0 | 0 | 1 (16.7%) | 1 ( 4.5%) |
| Insomnia | 0 | 0 | 0 | 1 (16.7%) | 1 ( 4.5%) |
| Lethargy | 0 | 1 (33.3%) | 0 | 0 | 1 ( 4.5%) |
| Lymphoedema | 0 | 0 | 1 (16.7%) | 0 | 1 ( 4.5%) |
| Malaise | 0 | 0 | 0 | 1 (16.7%) | 1 ( 4.5%) |
| Muscle spasms | 0 | 0 | 1 (16.7%) | 0 | 1 ( 4.5%) |

FIG. 11 (continued)

| | | | | | |
|---|---|---|---|---|---|
| Muscle strain | 0 | 0 | 0 | 1 (16.7%) | 1 ( 4.5%) |
| Neutropenia | 0 | 0 | 1 (16.7%) | 0 | 1 ( 4.5%) |
| No coding available | 0 | 0 | 1 (16.7%) | 0 | 1 ( 4.5%) |
| Pain in extremity | 1 (14.3%) | 0 | 0 | 0 | 1 ( 4.5%) |
| Pain of skin | 0 | 0 | 1 (16.7%) | 0 | 1 ( 4.5%) |
| Paraesthesia oral | 0 | 0 | 0 | 1 (16.7%) | 1 ( 4.5%) |
| Platelet count decreased | 0 | 1 (33.3%) | 0 | 0 | 1 ( 4.5%) |
| Pneumonia | 0 | 0 | 1 (16.7%) | 0 | 1 ( 4.5%) |
| Pneumonitis | 1 (14.3%) | 0 | 0 | 0 | 1 ( 4.5%) |
| Productive cough | 0 | 0 | 1 (16.7%) | 0 | 1 ( 4.5%) |
| Red blood cell sedimentation rate increased | 0 | 0 | 1 (16.7%) | 0 | 1 ( 4.5%) |
| Skin exfoliation | 0 | 0 | 0 | 1 (16.7%) | 1 ( 4.5%) |
| Urinary tract infection | 0 | 0 | 0 | 1 (16.7%) | 1 ( 4.5%) |

Data Cutoff Date: 09JUN2020

SEQUENCE LISTING

```
<160> NUMBER OF SEQ ID NOS: 86

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Ser Tyr Asn Met His
1               5                   10


<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Ala Ile Tyr Pro Gly Asn Gly Asp Thr Ser Tyr Asn Gln Lys Phe Lys
1               5                   10                  15

Gly


<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Val Val Tyr Tyr Ser Asn Ser Tyr Trp Tyr Phe Asp Val
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Arg Ala Ser Ser Ser Val Ser Tyr Met His
1 5 10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Pro Ser Asn Leu Ala Ser
1 5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Trp Ser Phe Asn Pro Pro Thr
1 5

<210> SEQ ID NO 7
<211> LENGTH: 122
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Thr Ser Tyr
20 25 30

Asn Met His Trp Val Arg Gln Ala Pro Gly Lys Gly Leu Glu Trp Val
35 40 45

Gly Ala Ile Tyr Pro Gly Asn Gly Asp Thr Ser Tyr Asn Gln Lys Phe
50 55 60

Lys Gly Arg Phe Thr Ile Ser Val Asp Lys Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Val Tyr Tyr Ser Asn Ser Tyr Trp Tyr Phe Asp Val Trp
100 105 110

Gly Gln Gly Thr Leu Val Thr Val Ser Ser
115 120

<210> SEQ ID NO 8
<211> LENGTH: 106
<212> TYPE: PRT
<213> ORGANISM: Artificial Sequence
<220> FEATURE:

<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys
            100                 105

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 10
<211> LENGTH: 14
<212> TYPE: PRT
<213> ORGANISM: Artificial Sequence
<220> FEATURE:
<223> OTHER INFORMATION: Synthetic Construct

<400> SEQUENCE: 10

Trp Val Arg Gln Ala Pro Gly Lys Gly Leu Glu Trp Val Gly
1               5                   10

<210> SEQ ID NO 11
<211> LENGTH: 32
<212> TYPE: PRT
<213> ORGANISM: Artificial Sequence
<220> FEATURE:
<223> OTHER INFORMATION: Synthetic Construct

<400> SEQUENCE: 11

Arg Phe Thr Ile Ser Val Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Gly Gln Gly Thr Leu Val Thr Val Ser Ser
1 5 10

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Trp Tyr Gln Gln Lys Pro Gly Lys Ala Pro Lys Pro Leu Ile Tyr
1 5 10 15

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct

<400> SEQUENCE: 15

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Phe Gly Gln Gly Thr Lys Val Glu Ile Lys
1 5 10

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Asn Tyr Tyr Ile His
1 5

<210> SEQ ID NO 18
<211> LENGTH: 17
<212> TYPE: PRT

<213> ORGANISM: Artificial Sequence
<220> FEATURE:
<223> OTHER INFORMATION: Synthetic Construct

<400> SEQUENCE: 18

Trp Ile Tyr Pro Gly Asp Gly Asn Thr Lys Tyr Asn Glu Lys Phe Lys
1 5 10 15

Gly

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Asp Ser Tyr Ser Asn Tyr Tyr Phe Asp Tyr
1 5 10

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Lys Ser Ser Gln Ser Leu Leu Asn Ser Arg Thr Arg Lys Asn Tyr Leu
1 5 10 15

Ala

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Trp Ala Ser Thr Arg Glu Ser
1 5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Thr Gln Ser Phe Ile Leu Arg Thr
1 5

<210> SEQ ID NO 23
<211> LENGTH: 119
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr

```
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115


<210> SEQ ID NO 24
<211> LENGTH: 112
<212> TYPE: PRT
<213> ORGANISM: Artificial Sequence
<220> FEATURE:
<223> OTHER INFORMATION: Synthetic Construct

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110


<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30


<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Trp Val Arg Gln Ala Pro Gly Gln Gly Leu Glu Trp Ile Gly
1               5                   10
```

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

```
Arg Ala Thr Leu Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30
```

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

```
Trp Gly Gln Gly Thr Leu Val Thr Val Ser Ser
1               5                   10
```

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

```
Trp Tyr Gln Gln Lys Pro Gly Gln Pro Pro Lys Leu Leu Ile Tyr
1               5                   10                  15
```

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 32
<211> LENGTH: 10
<212> TYPE: PRT

-continued

<213> ORGANISM: Artificial Sequence
<220> FEATURE:
<223> OTHER INFORMATION: Synthetic Construct

<400> SEQUENCE: 32

Phe Gly Gln Gly Thr Lys Val Glu Ile Lys
1 5 10

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65
<211> LENGTH: 10
<212> TYPE: PRT

<213> ORGANISM: Artificial Sequence
<220> FEATURE:
<223> OTHER INFORMATION: Synthetic Construct

<400> SEQUENCE: 65

Gly Tyr Thr Phe Ser Ser Tyr Trp Ile Glu
1 5 10

<210> SEQ ID NO 66
<211> LENGTH: 18
<212> TYPE: PRT
<213> ORGANISM: Artificial Sequence
<220> FEATURE:
<223> OTHER INFORMATION: Synthetic Construct

<400> SEQUENCE: 66

Gly Glu Ile Leu Pro Gly Gly Gly Asp Thr Asn Tyr Asn Glu Ile Phe
1 5 10 15

Lys Gly

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Thr Arg Arg Val Pro Ile Arg Leu Asp Tyr
1 5 10

<210> SEQ ID NO 68
<211> LENGTH: 15
<212> TYPE: PRT
<213> ORGANISM: Artificial Sequence
<220> FEATURE:
<223> OTHER INFORMATION: Synthetic Construct

<400> SEQUENCE: 68

Lys Ala Ser Gln Ser Val Asp Tyr Glu Gly Asp Ser Phe Leu Asn
1 5 10 15

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Ala Ala Ser Asn Leu Glu Ser
1 5

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Gln Gln Ser Asn Glu Asp Pro Leu Thr
1 5

<210> SEQ ID NO 71
<211> LENGTH: 117

<212> TYPE: PRT
<213> ORGANISM: Artificial Sequence
<220> FEATURE:
<223> OTHER INFORMATION: Synthetic Construct

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115
```

<210> SEQ ID NO 72
<211> LENGTH: 112
<212> TYPE: PRT
<213> ORGANISM: Artificial Sequence
<220> FEATURE:
<223> OTHER INFORMATION: Synthetic Construct

<400> SEQUENCE: 72

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110
```

<210> SEQ ID NO 73
<211> LENGTH: 25
<212> TYPE: PRT
<213> ORGANISM: Artificial Sequence
<220> FEATURE:
<223> OTHER INFORMATION: Synthetic Construct

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 74
<211> LENGTH: 13
<212> TYPE: PRT
<213> ORGANISM: Artificial Sequence
<220> FEATURE:
<223> OTHER INFORMATION: Synthetic Construct

<400> SEQUENCE: 74

Trp Val Arg Gln Ala Pro Gly Lys Gly Leu Glu Trp Ile
1 5 10

<210> SEQ ID NO 75
<211> LENGTH: 30
<212> TYPE: PRT
<213> ORGANISM: Artificial Sequence
<220> FEATURE:
<223> OTHER INFORMATION: Synthetic Construct

<400> SEQUENCE: 75

Arg Ala Thr Phe Ser Ala Asp Thr Ser Lys Asn Thr Ala Tyr Leu Gln
1 5 10 15

Met Asn Ser Leu Arg Ala Glu Asp Thr Ala Val Tyr Tyr Cys
20 25 30

<210> SEQ ID NO 76
<211> LENGTH: 11
<212> TYPE: PRT
<213> ORGANISM: Artificial Sequence
<220> FEATURE:
<223> OTHER INFORMATION: Synthetic Construct

<400> SEQUENCE: 76

Trp Gly Gln Gly Thr Leu Val Thr Val Ser Ser
1 5 10

<210> SEQ ID NO 77
<211> LENGTH: 23
<212> TYPE: PRT
<213> ORGANISM: Artificial Sequence
<220> FEATURE:
<223> OTHER INFORMATION: Synthetic Construct

<400> SEQUENCE: 77

Asp Ile Gln Leu Thr Gln Ser Pro Ser Ser Leu Ser Ala Ser Val Gly
1 5 10 15

Asp Arg Val Thr Ile Thr Cys
20

<210> SEQ ID NO 78
<211> LENGTH: 15
<212> TYPE: PRT
<213> ORGANISM: Artificial Sequence
<220> FEATURE:
<223> OTHER INFORMATION: Synthetic Construct

<400> SEQUENCE: 78

Trp Tyr Gln Gln Lys Pro Gly Lys Ala Pro Lys Leu Leu Ile Tyr
1 5 10 15

<210> SEQ ID NO 79
<211> LENGTH: 32
<212> TYPE: PRT
<213> ORGANISM: Artificial Sequence
<220> FEATURE:
<223> OTHER INFORMATION: Synthetic Construct

<400> SEQUENCE: 79

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 80
<211> LENGTH: 11
<212> TYPE: PRT
<213> ORGANISM: Artificial Sequence
<220> FEATURE:
<223> OTHER INFORMATION: Synthetic Construct

<400> SEQUENCE: 80

Phe Gly Gln Gly Thr Lys Val Glu Ile Lys Arg
1 5 10

<210> SEQ ID NO 81
<211> LENGTH: 447
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Ser Ser Tyr
20 25 30

Trp Ile Glu Trp Val Arg Gln Ala Pro Gly Lys Gly Leu Glu Trp Ile
35 40 45

Gly Glu Ile Leu Pro Gly Gly Gly Asp Thr Asn Tyr Asn Glu Ile Phe
50 55 60

Lys Gly Arg Ala Thr Phe Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Thr Arg Arg Val Pro Ile Arg Leu Asp Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu

```
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 82
<211> LENGTH: 218
<212> TYPE: PRT
<213> ORGANISM: Artificial Sequence
<220> FEATURE:
<223> OTHER INFORMATION: Synthetic Construct

<400> SEQUENCE: 82

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
```

180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 83
<211> LENGTH: 449
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Tyr Ile His Trp Val Arg Gln Ala Pro Gly Gln Gly Leu Glu Trp Ile
35 40 45

Gly Trp Ile Tyr Pro Gly Asp Gly Asn Thr Lys Tyr Asn Glu Lys Phe
50 55 60

Lys Gly Arg Ala Thr Leu Thr Ala Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Asp Ser Tyr Ser Asn Tyr Tyr Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys

-continued

```
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 84
<211> LENGTH: 219
<212> TYPE: PRT
<213> ORGANISM: Artificial Sequence
<220> FEATURE:
<223> OTHER INFORMATION: Synthetic Construct

<400> SEQUENCE: 84

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 85
```

<211> LENGTH: 452
<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Thr Ser Tyr
20 25 30

Asn Met His Trp Val Arg Gln Ala Pro Gly Lys Gly Leu Glu Trp Val
35 40 45

Gly Ala Ile Tyr Pro Gly Asn Gly Asp Thr Ser Tyr Asn Gln Lys Phe
50 55 60

Lys Gly Arg Phe Thr Ile Ser Val Asp Lys Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Val Tyr Tyr Ser Asn Ser Tyr Trp Tyr Phe Asp Val Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser
210 215 220

Cys Asp Lys Thr His Thr Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Gly Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Trp Cys Leu Val Lys Gly Phe Tyr Pro Ser Asp Ile Ala Val
370 375 380

-continued

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 86
<211> LENGTH: 213
<212> TYPE: PRT
<213> ORGANISM: Artificial Sequence
<220> FEATURE:
<223> OTHER INFORMATION: Synthetic Construct

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

DOSING FOR TREATMENT WITH ANTI-CD20/ANTI-CD3 BISPECIFIC ANTIBODIES AND ANTI-CD79B ANTIBODY DRUG CONJUGATES

CROSS-REFERENCE TO RELATED APPLICATIONS

This application claims benefit of priority to U.S. Provisional Application No. 63/109,781, filed on Nov. 4, 2020 and U.S. Provisional Application No. 63/188,695, filed on May 14, 2021, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 28, 2021, is named 50474-227003_Sequence_Listing_10_28_21_ST25 and is 36,330 bytes in size.

FIELD OF THE INVENTION

The present invention relates to the treatment of B cell proliferative disorders. More specifically, the invention concerns the specific treatment of human subjects having a CD20-positive cell proliferative disorder (e.g., a B cell proliferative disorder) using anti-cluster of differentiation 20 (CD20)/anti-cluster of differentiation 3 (CD3) bispecific antibodies in combination with anti-cluster of differentiation 79b (CD79b) antibody drug conjugates.

BACKGROUND

Cancers are characterized by the uncontrolled growth of cell subpopulations. Cancers are the leading cause of death in the developed world and the second leading cause of death in developing countries, with over 14 million new cancer cases diagnosed and over eight million cancer deaths occurring each year. As the elderly population has grown, the incidence of cancer has concurrently risen, as the probability of developing cancer is more than two-fold higher after the age of seventy. Cancer care thus represents a significant and ever-increasing societal burden.

Hematologic cancers, in particular, are the second leading cause of cancer-related deaths. Hematologic cancers include B cell proliferative disorders, such as non-Hodgkin's lymphoma (NHL) (e.g., diffuse-large B cell lymphoma (DLBCL), follicular lymphoma (FL), and mantle cell lymphoma (MCL)), which advances quickly and is fatal if untreated. Although treatment with the monoclonal anti-CD20 antibody rituximab has resulted in fewer relapsed DLBCL patients, it has become increasing challenging to treat those patients with relapsed or refractory DLBCL. For such patients, alternative or secondary treatment modalities, such as bispecific antibody-based immunotherapies, may be particularly efficacious. Bispecific antibodies are capable of simultaneously binding cell surface antigens on cytotoxic cells (e.g., T cells, via binding to CD3) and cancer cells (e.g., B cells, via binding to CD20), with the intent that the bound cytotoxic cell will destroy the bound cancer cell. Antibody drug conjugates are capable of binding to cell-surface epitopes (e.g., targeting CD79b) to promote internalization of the bound drug conjugate for targeted delivery of cytotoxic agents. However, such antibody-based and antibody-drug-conjugate-based immunotherapies may be limited by unwanted effects, including cytokine-driven toxicities (e.g., cytokine release syndrome (CRS)), infusion-related reactions (IRRs), severe tumor lysis syndrome (TLS), and hepatotoxicities.

Thus, there is an unmet need in the field for the development of efficacious methods of combination dosing using therapeutic bispecific antibodies (e.g., anti-CD20/anti-CD3 bispecific antibodies) and antibody drug conjugates (e.g., anti-CD79b antibody drug conjugates) for the treatment of B cell proliferative disorders that achieve a more favorable benefit-risk profile.

SUMMARY OF THE INVENTION

The present invention provides methods of treating a subject having a CD20-positive cell proliferative disorder (e.g., a B cell proliferative disorder (e.g., an NHL, e.g., a DLBCL, an FL, or an MCL)) by administering a combination of an anti-CD79b antibody drug conjugate and a bispecific antibody that binds to CD20 and CD3 in a multi-cycle dosing regimen involving a fractionated, escalating dose of the bispecific antibody in the first dosing cycle.

In one aspect, the invention features a method of treating a subject having a CD20-positive cell proliferative disorder (e.g., a B cell proliferative disorder) comprising administering to the subject an anti-CD79b antibody drug conjugate and a bispecific antibody that binds to CD20 and CD3 in a dosing regimen comprising at least a first dosing cycle and a second dosing cycle, wherein: (a) the first dosing cycle comprises a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; and (b) the second dosing cycle comprises a single dose (C2D1) of the bispecific antibody, wherein the C2D1 of the bispecific antibody is equal to or greater than the C1D3.

In some embodiments, the C1D1 of the bispecific antibody is about 1 mg, the C1D2 of the bispecific antibody is about 2 mg, and the C1 D3 of the bispecific antibody is about 9 mg. In some embodiments, the C2D1 of the bispecific antibody is about 9 mg.

In some embodiments, the C1D1 of the bispecific antibody is about 1 mg, the C1D2 of the bispecific antibody is about 2 mg, and the C1 D3 of the bispecific antibody is about 13.5 mg. In some embodiments, the C2D1 of the bispecific antibody is about 13.5 mg.

In some embodiments, the C1D1 of the bispecific antibody is about 1 mg, the C1D2 of the bispecific antibody is about 2 mg, and the C1 D3 of the bispecific antibody is about 20 mg. In some embodiments, the C2D1 of the bispecific antibody is about 20 mg.

In some embodiments, the C1D1 of the bispecific antibody is about 1 mg, the C1D2 of the bispecific antibody is about 2 mg, and the C1 D3 of the bispecific antibody is about 40 mg. In some embodiments, wherein the C2D1 of the bispecific antibody is about 40 mg.

In some embodiments, the first dosing cycle comprises a single dose C1D1 of the anti-CD79b antibody drug conjugate. In some embodiments, the single dose C1D1 of the anti-CD79b antibody drug conjugate is from about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some embodiments, the single dose C1D1 of the anti-CD79b antibody drug conjugate is about 1.8 mg/kg. In some embodiments, the second dosing cycle comprises a single dose C2D1 of the anti-CD79b antibody drug conjugate. In some embodiments, the single dose C2D1 of the anti-CD79b antibody drug conjugate is from about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some embodiments, the single dose C2D1 of the anti-CD79b antibody drug conjugate is about 1.8 mg/kg.

In some embodiments, the C1D1 of the bispecific antibody, the C1D2 of the bispecific antibody, and the C1D3 of the bispecific antibody are administered to the subject on or about Days 1, 8, and 15, respectively, of the first dosing cycle. In some embodiments, the C2D1 of the bispecific antibody is administered to the subject on Day 1 of the second dosing cycle. In some embodiments, the C1D1 of the anti-CD79b antibody drug conjugate is administered to the subject on Day 1 of the first dosing cycle and/or the C2D1 of the anti-CD79b antibody drug conjugate is administered to the subject on Day 1 of the second dosing cycle. In some embodiments, the first and second dosing cycles are 21-day dosing cycles. In some embodiments, the dosing regimen comprises one or more additional dosing cycles. In some embodiments, the dosing regimen comprises four to 15 additional dosing cycles (e.g., from four to ten additional dosing cycles (e.g., four additional dosing cycles, five additional dosing cycles, six additional dosing cycles, seven additional dosing cycles, eight additional dosing cycles, nine additional dosing cycles, or ten additional dosing cycles) or from 11-15 additional dosing cycles (e.g., 11 additional dosing cycles, 12 additional dosing cycles, 13 additional dosing cycles, 14 additional dosing cycles, or 15 additional dosing cycles)). In particular embodiments, the dosing regimen comprises four additional dosing cycles. In some embodiments, the additional dosing cycles are 21-day dosing cycles.

In some embodiments, one or more of the additional dosing cycles comprise an additional single dose of the bispecific antibody and an additional single dose of the anti-CD79b antibody drug conjugate. In some embodiments, the additional single dose of the anti-CD79b antibody drug conjugate is equivalent in amount to the C2D1 of the anti-CD79b antibody drug conjugate. In some embodiments, the additional single dose of the anti-CD79b antibody drug conjugate is administered to the subject on Day 1 of each additional dosing cycle comprising an additional dose of the anti-CD79b antibody drug conjugate. In some embodiments, one or more of the additional dosing cycles comprise an additional single dose of the bispecific antibody and do not comprise administration of the anti-CD79b antibody drug conjugate. In some embodiments, the additional single dose of the bispecific antibody is equivalent in amount to the C2D1 of the bispecific antibody. In some embodiments, the additional single dose of the bispecific antibody is administered to the subject on Day 1 of each additional dosing cycle comprising an additional dose of the bispecific antibody. In some embodiments, the dosing regimen comprises six or more additional dosing cycles, wherein each of the six or more additional dosing cycles comprises a single dose of the bispecific antibody, and wherein no more than four of the six or more additional dosing cycles comprises administration of the anti-CD79b antibody drug conjugate.

In another aspect, the invention features a method of treating a subject having a CD20-positive cell proliferative disorder (e.g., a B cell proliferative disorder) comprising administering to the subject an anti-CD79b antibody drug conjugate and a bispecific antibody that binds to CD20 and CD3 in a dosing regimen comprising at least a first dosing cycle and a second dosing cycle, wherein: (a) the first dosing cycle comprises: (i) a single dose (C1D1) of the anti-CD79b antibody drug conjugate; and (ii) a first dose (C1D1) of the bispecific antibody and a second dose (C1D2) of the bispecific antibody, wherein the C1D1 and the C1D2 of the bispecific antibody are each administered to the subject after the C1D1 of the anti-CD79b antibody drug conjugate, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), and the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); and (b) the second dosing cycle comprises: (i) a single dose (C2D1) of the anti-CD79b antibody drug conjugate; and (ii) a single dose (C2D1) of the bispecific antibody, wherein the C2D1 of the bispecific antibody is greater than or equal to the C1D2. In some embodiments, the C1D1 of the bispecific antibody is about 1 mg and the C1D2 of the bispecific antibody is about 2 mg. In some embodiments, the C2D1 of the bispecific antibody is about 9 mg, about 13.5 mg, about 20 mg, about 40 mg, about 45 mg, or about 60 mg.

In some embodiments, the first dosing cycle comprises a single dose C1D1 of the anti-CD79b antibody drug conjugate. In some embodiments, the single dose C1D1 of the anti-CD79b antibody drug conjugate is from about 0.5 mg/kg to about 10 mg/kg. In some embodiments, the single dose C1D1 of the anti-CD79b antibody drug conjugate is about 1.8 mg/kg. In some embodiments, the second dosing cycle comprises a single dose C2D1 of the anti-CD79b antibody drug conjugate. In some embodiments, the single dose C2D1 of the anti-CD79b antibody drug conjugate is from about 0.5 mg/kg to about 10 mg/kg. In some embodiments, the single dose C2D1 of the anti-CD79b antibody drug conjugate is about 1.8 mg/kg.

In some embodiments, the C1D1 of the bispecific antibody and the C1D2 of the bispecific antibody are administered to the subject on or about Days 8 and 15, respectively, of the first dosing cycle. In some embodiments, the C2D1 of the bispecific antibody is administered to the subject on Day 1 of the second dosing cycle. In some embodiments, the C1D1 of the anti-CD79b antibody drug conjugate is administered to the subject on Day 1 of the first dosing cycle and the C2D1 of the anti-CD79b antibody drug conjugate is administered to the subject on Day 1 of the second dosing cycle. In some embodiments, the first and second dosing cycles are 21-day dosing cycles.

In some embodiments, the dosing regimen comprises one or more additional dosing cycles. In some embodiments, the dosing regimen comprises four to 15 additional dosing cycles (e.g., from four to ten additional dosing cycles (e.g., four additional dosing cycles, five additional dosing cycles, six additional dosing cycles, seven additional dosing cycles, eight additional dosing cycles, nine additional dosing cycles, or ten additional dosing cycles) or from 11-15 additional dosing cycles (e.g., 11 additional dosing cycles, 12 additional dosing cycles, 13 additional dosing cycles, 14 additional dosing cycles, or 15 additional dosing cycles)). In particular embodiments, the dosing regimen comprises four additional dosing cycles. In some embodiments, the additional dosing cycles are 21-day dosing cycles. In some embodiments, one or more of the additional dosing cycles comprise an additional single dose of the bispecific antibody and an additional single dose of the anti-CD79b antibody drug conjugate. In some embodiments, the additional single dose of the anti-CD79b antibody drug conjugate is equivalent in amount to the C2D1 of the anti-CD79b antibody drug conjugate. In some embodiments, the additional single dose of the anti-CD79b antibody drug conjugate is administered to the subject on Day 1 of each additional dosing cycle comprising an additional dose of the anti-CD79b antibody drug conjugate. In some embodiments, one or more of the additional dosing cycles comprise an additional single dose of the bispecific antibody and do not comprise administration of the anti-CD79b antibody drug conjugate. In some embodiments, the additional single dose of the bispecific antibody is equivalent in amount to the C2D1 of the bispecific antibody. In some embodiments, the additional single dose of the bispecific antibody is administered to the subject on Day 1 of each additional dosing cycle comprising an additional dose of the bispecific antibody. In some embodiments, the dosing regimen comprises six or more additional dosing cycles, wherein each of the six or more additional dosing cycles comprises a single dose of the bispecific antibody, and wherein no more than four of the six or more additional dosing cycles comprises administration of the anti-CD79b antibody drug conjugate.

In yet another aspect, the invention features a method of treating a subject having a CD20-positive cell proliferative disorder (e.g., a B cell proliferative disorder) comprising administering to the subject an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

In some embodiments, the C1D3 and C2D1-C8D1 of the bispecific antibody are about equivalent in amount. In some embodiments, the C1D1-C6D1 of the anti-CD79b antibody drug conjugate are about equivalent in amount.

In yet another aspect, the invention features a method of treating a subject having a CD20-positive cell proliferative disorder (e.g., a B cell proliferative disorder) comprising administering to the subject an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein the single dose C2D1 is about equivalent in amount to the C1D3 and each single dose C3D1-C8D1 of the bispecific antibody is less than the C1D3. In some embodiments, each single dose C3D1-C8D1 of the bispecific antibody is between about 10 mg and about 45 mg (e.g., between about 10 mg and about 40 mg, between about 10 mg and about 35 mg, between about 15 mg and about 45 mg, between about 20 mg and about 45 mg, or between about 25 mg and about 45 mg; e.g., about 30 mg).

In some embodiments, each of the C1D1-C6D1 of the anti-CD79b antibody drug conjugate is from about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some embodiments, each of the C1D1-C6D1 of the anti-CD79b antibody drug conjugate is about 1.8 mg/kg.

In some embodiments, the C1D1 of the bispecific antibody, the C1D2 of the bispecific antibody, and the C1D3 of the bispecific antibody are administered to the subject on or about Days 1, 8, and 15, respectively, of the first dosing cycle. In some embodiments, the C1D1-C8D1 of the bispecific antibody is administered to the subject on Day 1 of each dosing cycle. In some embodiments, the C1D1-C6D1 of the anti-CD79b antibody drug conjugate is administered to the subject on Day 1 of each dosing cycle. In some embodiments, each dosing cycle is a 21-day dosing cycle.

In yet another aspect, the invention provides a method of treating a subject having a CD20-positive cell proliferative disorder (e.g., a B cell proliferative disorder) comprising administering to the subject an anti-CD79b antibody drug conjugate and a bispecific antibody that binds to CD20 and CD3 in a dosing regimen comprising eight or more dosing cycles, wherein: (a) the first dosing cycle comprises a first dose (C1D1) of the bispecific antibody and a second dose (C1D2) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 is about 9 mg, about 13.5 mg, about 20 mg, about 40 mg, about 45 mg, or about 60 mg; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1 D3.

In some embodiments, the C1D3 and C2D1-C8D1 of the bispecific antibody are about equivalent in amount.

In some embodiments, the C2D1-C6D1 of the anti-CD79b antibody drug conjugate are about equivalent in amount. In some embodiments, each of the C2D1-C6D1 of the anti-CD79b antibody drug conjugate is from about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some embodiments, each of the C2D1-C6D1 of the anti-CD79b antibody drug conjugate is about 1.8 mg/kg.

In some embodiments, the C1D1 of the bispecific antibody, the C1D2 of the bispecific antibody, and the C1D3 of the bispecific antibody are administered to the subject on or about Days 1, 8, and 15, respectively, of the first dosing cycle. In some embodiments, the C1D1 and C2D1-C8D1 of the bispecific antibody are administered to the subject on Day 1 of each dosing cycle. In some embodiments, the C2D1-C6D1 of the anti-CD79b antibody drug conjugate are administered to the subject on Day 1 of each dosing cycle. In some embodiments, each dosing cycle is a 21-day dosing cycle.

In another aspect, the invention provides a method of treating a subject having a CD20-positive cell proliferative disorder (e.g., a B cell proliferative disorder) comprising administering to the subject an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) and a second dose (C1D2) of the bispecific antibody, wherein the C1 D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), and the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); and (ii) a single dose (C1D1) of the anti-CD79b antibody drug conjugate; (b) the second dosing cycle comprises: (i) a single dose (C2D1) of the bispecific antibody, wherein the C2D1 of the bispecific antibody is about 9 mg, about 13.5 mg, about 20 mg, about 40 mg, about 45 mg, or about 60 mg; and (ii) a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is greater than the C1D2.

In some embodiments, the C2D1-C8D1 of the bispecific antibody are about equivalent in amount. In some embodiments, the C1D1-C6D1 of the anti-CD79b antibody drug conjugate are about equivalent in amount. In some embodiments, each of the C1D1-C6D1 of the anti-CD79b antibody drug conjugate is from about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some embodiments, each of the C1D1-C6D1 of the anti-CD79b antibody drug conjugate is about 1.8 mg/kg. In some embodiments, the C1D1 of the bispecific antibody is administered after the C1D1 of the anti-CD79b antibody drug conjugate. In some embodiments, the C1D1 of the bispecific antibody is administered about seven days after the C1 D1 of the anti-CD79b antibody drug conjugate.

In some embodiments, the C1D1 of the bispecific antibody and the C1D2 of the bispecific antibody are administered to the subject on or about Days 8 and 15, respectively, of the first dosing cycle. In some embodiments, the C2D1-C8D1 of the bispecific antibody are administered to the subject on Day 1 of each dosing cycle. In some embodiments, the C1D1-C6D1 of the anti-CD79b antibody drug conjugate are administered to the subject on Day 1 of each dosing cycle. In some embodiments, each dosing cycle is a 21-day dosing cycle. In some embodiments, the dosing regimen comprises one or more additional dosing cycles comprising a single dose of the bispecific antibody. In some embodiments, the dosing regimen comprises from one to nine additional dosing cycles comprising a single dose of the bispecific antibody. In some embodiments, each of the additional dosing cycles does not comprise administration of the anti-CD79b antibody drug conjugate. In some embodiments, each of the additional dosing cycles is a 21-day dosing cycle.

In some embodiments, the bispecific antibody and the anti-CD79b antibody drug conjugate have a synergistic effect in a mouse NSG:human WSU-DLCL2 model system when compared to either the bispecific antibody or the anti-CD79b antibody drug conjugate alone.

In some embodiments of any of the above aspects, the method further comprises administering to the subject one or more additional therapeutic agents. In some embodiments, the one or more additional therapeutic agents is a corticosteroid or an IL-R6 antagonist. In some embodiments, the IL-R6 antagonist is tocilizumab. In some embodiments, the tocilizumab is administered intravenously to the subject as a single dose of about 8 mg/kg, and wherein the single dose does not exceed 800 mg. In some embodiments, the one or more additional therapeutic agents is a corticosteroid. In some embodiments, the corticosteroid is dexamethasone, prednisone, or methylprednisolone. In some embodiments, the one or more additional therapeutic agents comprise one or more chemotherapeutic agents. In some embodiments, the one or more chemotherapeutic agents comprise cyclophosphamide or doxorubicin.

In another aspect, the invention provides a method of reducing the rate of cytokine release syndrome in a population of subjects having a CD20-positive cell proliferative disorder (e.g., a B cell proliferative disorder) who are administered an anti-CD79b antibody drug conjugate and a bispecific antibody that binds to CD20 and CD3, wherein the method comprises administering to one or more subjects of the population an anti-CD79b antibody drug conjugate and a bispecific antibody that binds to CD20 and CD3 according to the method of any one the embodiments described herein.

In another aspect, the invention provides method of reducing the rate of cytokine release syndrome in a population of subjects having a CD20-positive cell proliferative disorder (e.g., a B cell proliferative disorder) who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising at least a first dosing cycle and a second dosing cycle, wherein: (a) the first dosing cycle comprises a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; and (b) the second dosing cycle comprises a single dose (C2D1) of the bispecific antibody, wherein the C2D1 of the bispecific antibody is equal to or greater than the C1D3, wherein the rate of adverse events is reduced in the population of subjects compared to a reference population of subjects to whom no anti-CD79b antibody drug conjugate has been administered.

In a further aspect, the invention provides a method of reducing the rate of cytokine release syndrome in a population of subjects having a CD20-positive cell proliferative disorder (e.g., a B cell proliferative disorder) who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising at least a first dosing cycle and a second dosing cycle, wherein: (a) the first dosing cycle comprises: (i) a single dose (C1D1) of the anti-CD79b antibody drug conjugate; and (ii) a first dose (C1D1) of the bispecific antibody and a second dose (C1D2) of the bispecific antibody, wherein the C1D1 and the C1D2 of the bispecific antibody are each administered to the subject after the C1D1 of the anti-CD79b antibody drug conjugate, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), and the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); and (b) the second dosing cycle comprises: (i) a single dose (C2D1) of the anti-CD79b antibody drug conjugate; and (ii) a single dose (C2D1) of the bispecific antibody, wherein the C2D1 of the bispecific antibody is greater than or equal to the C1D2 of the bispecific antibody, wherein the rate of adverse events is reduced in the population of subjects compared to a reference population of subjects to whom no anti-CD79b antibody drug conjugate has been administered.

In yet another aspect, the invention provides a method of reducing the rate of cytokine release syndrome in a population of subjects having a CD20-positive cell proliferative disorder (e.g., a B cell proliferative disorder) who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1 D3, and wherein the rate of adverse events is reduced in the population of subjects compared to a reference population of subjects to whom no anti-CD79b antibody drug conjugate has been administered.

In yet another aspect, the invention provides a method of reducing the rate of cytokine release syndrome in a population of subjects having a CD20-positive cell proliferative disorder (e.g., a B cell proliferative disorder) who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein the single dose C2D1 is about equivalent in amount to the C1D3 and each single dose C3D1-C8D1 of the bispecific antibody is less than the C1D3, and wherein the rate of adverse events is reduced in the population of subjects compared to a reference population of 5 subjects to whom no anti-CD79b antibody drug conjugate has been administered. In some embodiments, each single dose C3D1-C8D1 of the bispecific antibody is between about 10 mg and about 45 mg (e.g., between about 10 mg and about 40 mg, between about 10 mg and about 35 mg, between about 15 mg and about 45 mg, between about 20 mg and about 45 mg, or between about 25 mg and about 45 mg; e.g., about 30 mg).

In yet a further aspect, the invention provides a method of reducing the rate of cytokine release syndrome in a population of subjects having a CD20-positive cell proliferative disorder (e.g., a B cell proliferative disorder) who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein: (a) the first dosing cycle comprises a first dose (C1D1) of the bispecific antibody and a second dose (C1D2) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 is about 9 mg, about 13.5 mg, about 20 mg, about 40 mg, about 45 mg, or about 60 mg; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D2, and wherein the rate of adverse events is reduced in the population of subjects compared to a reference population of subjects to whom no anti-CD79b antibody drug conjugate has been administered.

In another aspect, the invention provides a method of reducing the rate of cytokine release syndrome in a population of subjects having a CD20-positive cell proliferative disorder (e.g., a B cell proliferative disorder) who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) and a second dose (C1D2) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), and the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); and (ii) a single dose (C1D1) of the anti-CD79b antibody drug conjugate; (b) the second dosing cycle comprises: (i) a single dose (C2D1) of the bispecific antibody, wherein the C2D1 of the bispecific antibody is about 9 mg, about 13.5 mg, about 20 mg, about 40 mg, about 45 mg, or about 60 mg; and (ii) a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1 D2, and wherein the rate of adverse events is reduced in the population of subjects compared to a reference population of subjects to whom no anti-CD79b antibody drug conjugate has been administered.

In some embodiments, the rate of the cytokine release syndrome in the population of subjects is less than or equal to about 20% (e.g., less than or equal to about 18%, less than or equal to about 15%, less than or equal to about 14%, less than or equal to about 13%, less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 20%, less than or equal to about 1%; e.g., between about 0% to about 20%, between about 1% to about 20%, between about 5% to about 20%, between about 10% to about 20%, between about 15% to about 20%, between about 0% to about 5%, between about 1% to about 5%, between about 1% to about 10%, between about 5% to about 10%, between about 10% to about 15%, or between about 5% to about 15%; e.g., about 20%, about 15%, about 10%, about 7%, about 5%, about 4%, about 3%, about 20%, about 1%, or about 0%). In some embodiments, the rate of cytokine release syndrome in the population of subjects is less than or equal to about 10% (e.g., less than or equal to about 9%, less than or equal to about 8%, less than or equal to about 7%, less than or equal to about 6%, less than or equal to about 5%, less than or equal to about 4%, less than or equal to about 3%, less than or equal to about 20%, or less than or equal to about 1%; e.g. between about 0.1% to about 10%, between about 0.5% and about 10%, between about 1% and about 10%, between about 1% and about 7%, between about 1% and about 5%, between about 1% and about 3%, or between about 5% and about 10%; e.g., about 10%, about 7%, about 5%, about 4%, about 3%, about 20%, about 1%, or about 0%). In some embodiments, the rate of cytokine release syndrome in the population of subjects is less than or equal to about 5% (e.g., from about 1% to about 5%, from about 2% to about 5%, from about 3% to about 5%, from about 4% to about 5%, from about 0% to about 4%, from about 1% to about 4%, from about 2% to about 4%, from about 3% to about 4%, from about 0% to about 3%, from about 1% to about 3%, from about 2% to about 3%, from about 0% to about 2%, from about 1% to about 2%, or from about 0% to about 1%; e.g., about 5%, about 4%, about 3%, about 2%, about 1%, or about 0%). In some embodiments, the rate of cytokine release syndrome in the population of subjects is less than or equal to about 3%. In some embodiments, the rate of cytokine release syndrome having a grade of 2 or greater (as defined by the American Society for Transplantation and Cellular Therapy, 2019; ASTCT) is less than or equal to about 20% (e.g., less than or equal to about 18%, less than or equal to about 15%, less than or equal to about 14%, less than or equal to about 13%, less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 20%, less than or equal to about 1%; e.g., between about 0% to about 20%, between about 1% to about 20%, between about 5% to about 20%, between about 10% to about 20%, between about 15% to about 20%, between about 0% to about 5%, between about 1% to about 5%, between about 1% to about 10%, between about 5% to about 10%, between about 10% to about 15%, or between about 5% to about 15%; e.g., about 20%, about 15%, about 10%, about 7%, about 5%, about 4%, about 3%, about 20%, about 1%, or about 0%). In some embodiments, the rate of cytokine release syndrome having a grade of 2 or greater (as defined by the ASTCT) is less than or equal to about 5% (e.g., from about 1% to about 5%, from about 20% to about 5%, from about 3% to about 5%, from about 4% to about 5%, from about 0% to about 4%, from about 1% to about 4%, from about 20% to about 4%, from about 3% to about 4%, from about 0% to about 3%, from about 1% to about 3%, from about 20% to about 3%, from about 0% to about 20%, from about 1% to about 20%, or from about 0% to about 1%; e.g., about 5%, about 4%, about 3%, about 20%, about 1%, or about 0%). In some embodiments, the rate of cytokine release syndrome having a grade of 2 or greater (as defined by the ASTCT) is about 0%.

In some embodiments, the CD20-positive cell proliferative disorder is a B cell proliferative disorder. In some embodiments, the B cell proliferative disorder is a non-Hodgkin's lymphoma (NHL), a chronic lymphoid leukemia (CLL), or a central nervous system lymphoma (CNSL). In some embodiments, the NHL is a diffuse-large B cell lymphoma (DLBCL), a follicular lymphoma (FL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, is a marginal zone lymphoma, a Burkitt lymphoma, a lymphoplasmacytic lymphoma. In some embodiments, the NHL is a relapsed or refractory NHL. In some embodiments, the NHL is a FL. In some embodiments, the NHL is a DLBCL. In some embodiments, the NHL is an MCL. In some embodiments, the DLBCL is a relapsed or refractory DLBCL. In some embodiments, the DLBCL is a Richter's transformation. In some embodiments, the FL is a relapsed or refractory FL. In some embodiments, the FL is a transformed FL.

In some embodiments, the MCL is a relapsed or refractory MCL. In some embodiments, the B cell proliferative disorder is relapsed and/or refractory.

In some embodiments of any of the above aspects, the anti-CD79b antibody drug conjugate is polatuzumab vedotin or anti-CD79b-MC-vc-PAB-MMAE. In some embodiments, the anti-CD79b antibody drug conjugate is polatuzumab vedotin.

In some embodiments of any of the above aspects, the bispecific antibody comprises an anti-CD20 arm comprising a first binding domain comprising the following six hypervariable regions (HVRs):(a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSN- SYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some embodiments, the bispecific antibody comprises an anti-CD20 arm comprising a first binding domain comprising (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b). In some embodiments, the first binding domain comprises a VH domain comprising an amino acid sequence of SEQ ID NO: 7 and a VL domain comprising an amino acid sequence of SEQ ID NO: 8.

In some embodiments of any of the above aspects, the bispecific antibody comprises an anti-CD3 arm comprising a second binding domain comprising the following six HVRs: (a) an HVR-H1 comprising the amino acid sequence of NYYIH (SEQ ID NO: 17); (b) an HVR-H2 comprising the amino acid sequence of WIYPGDGNTKYNEKFKG (SEQ ID NO: 18); (c) an HVR-H3 comprising the amino acid sequence of DSYSNYYFDY (SEQ ID NO: 19); (d) an HVR-L1 comprising the amino acid sequence of KSSQSLLNSRTRKNYLA (SEQ ID NO: 20); (e) an HVR-L2 comprising the amino acid sequence of WASTRES (SEQ ID NO: 21); and (f) an HVR-L3 comprising the amino acid sequence of TQSFILRT (SEQ ID NO: 22). In some embodiments, the bispecific antibody comprises an anti-CD3 arm comprising a second binding domain comprising (a) a VH domain comprising an amino acid sequence having at least 95% sequence identity to the amino acid sequence of SEQ ID NO: 23; (b) a VL domain comprising an amino acid sequence having at least 95% sequence identity to the amino acid sequence of SEQ ID NO: 24; or (c) a VH domain as in (a) and a VL domain as in (b). In some embodiments, the second binding domain comprises a VH domain comprising an amino acid sequence of SEQ ID NO: 23 and a VL domain comprising an amino acid sequence of SEQ ID NO: 24.

In some embodiments, the bispecific antibody comprises (a) an anti-CD20 arm comprising (i) a heavy chain comprising an amino acid sequence having at least 95% sequence identity to the amino acid sequence of SEQ ID NO: 85, and (ii) a light chain comprising an amino acid sequence having at least 95% sequence identity to the amino acid sequence of SEQ ID NO: 86; and (b) an anti-CD3 arm comprising (i) a heavy chain comprising an amino acid sequence having at least 95% sequence identity to the amino acid sequence of SEQ ID NO: 83, and (ii) a light chain comprising an amino acid sequence having at least 95% sequence identity to the amino acid sequence of SEQ ID NO: 84. In some antibodies, (a) the anti-CD20 arm comprises a heavy chain comprising an amino acid sequence of SEQ ID NO: 85 and a light chain comprising an amino acid sequence of SEQ ID NO: 86, and (b) the anti-CD3 arm comprises a heavy chain comprising an amino acid sequence of SEQ ID NO: 83 and a light chain comprising an amino acid sequence of SEQ ID NO: 84.

In some embodiments of any of the above aspects, the bispecific antibody is a humanized antibody. In some embodiments, the bispecific antibody is a chimeric antibody. In some embodiments, the bispecific antibody is an antibody fragment that binds CD20 and CD3. In some embodiments, the antibody fragment is selected from the group consisting of Fab, Fab'-SH, Fv, scFv, and $(Fab')_2$ fragments. In some embodiments, the bispecific antibody is a full-length antibody. In some embodiments, the bispecific antibody is an IgG antibody. In some embodiments, the IgG antibody is an IgG1 antibody. In some embodiments, the IgG antibody comprises a mutation at amino acid residue N297 (EU numbering) that results in the absence of glycosylation. In some embodiments, the mutation at amino acid residue N297 is a substitution mutation. In some embodiments, the mutation at amino acid residue N297 reduces effector function of the Fc region. In some embodiments, the mutation is an N297G or N297A mutation. In some embodiments, the bispecific antibody comprises a mutation in the Fc region that reduces effector function. In some embodiments, the mutation is a substitution mutation. In some embodiments, the substitution mutation is at amino acid residue L234, L235, D265, and/or P329 (EU numbering). In some embodiments, the substitution mutation is selected from the group consisting of L234A, L235A, D265A, and P329G.

In some embodiments of any of the above aspects, the bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some embodiments, at least one of the one or more heavy chain constant domains is paired with another heavy chain constant domain. In some embodiments, the $CH3_1$ and $CH3_2$domains each comprise a protuberance or cavity, and wherein the protuberance or cavity in the $CH3_1$ domain is positionable in the cavity or protuberance, respectively, in the $CH3_2$ domain. In some embodiments, the $CH3_1$ and $CH3_2$ domains meet at an interface between the protuberance and cavity. In some embodiments, the $CH2_1$ and $CH2_2$ domains each comprise a protuberance or cavity, and wherein the protuberance or cavity in the $CH2_1$ domain is positionable in the cavity or protuberance, respectively, in the $CH2_2$domain. In some embodiments, the $CH2_1$ and $CH2_2$domains meet at an interface between said protuberance and cavity.

In some embodiments the anti-CD20 arm of the bispecific antibody further comprises T366W and N297G substitution mutations (EU numbering). In some embodiments, the anti-CD3 arm of the bispecific antibody further comprises T366S, L368A, Y407V, and N297G substitution mutations (EU numbering). In some embodiments, (a) the anti-CD20 arm further comprises T366W and N297G substitution mutations and (b) the anti-CD3 arm further comprises T366S, L368A, Y407V, and N297G substitution mutations (EU numbering).

In another aspect, the invention provides a method of treating a subject having a NHL comprising administering to the subject polatuzumab vedotin and mosunetuzumab in a dosing regimen comprising at least a first dosing cycle and a second dosing cycle, wherein: (a) the first dosing cycle comprises a first dose (C1D1) of the mosunetuzumab, a second dose (C1D2) of the mosunetuzumab, and a third dose (C1D3) of the mosunetuzumab, wherein the C1D1 of the mosunetuzumab is about 1 mg, the C1D2 of the mosunetuzumab is about 2 mg, and the C1D3 of the mosunetuzumab is about 9 mg, about 13.5 mg, about 20 mg, about 40 mg, about 45 mg, or about 60 mg; and (b) the second dosing cycle comprises a single dose (C2D1) of the mosunetuzumab, wherein the C2D1 of the mosunetuzumab is equal to or greater than the C1D3.

In yet another aspect, the invention provides a method of treating a subject having a NHL (e.g., a relapsed and/or refractory NHL) comprising administering to the subject polatuzumab vedotin and mosunetuzumab in a dosing regimen comprising at least a first dosing cycle and a second dosing cycle, wherein: (a) the first dosing cycle comprises: (i) a single dose (C1D1) of the polatuzumab vedotin; and (ii) a first dose (C1D1) of the mosunetuzumab and a second dose (C1D2) of the mosunetuzumab, wherein the C1D1 and the C1D2 of the mosunetuzumab are each administered to the subject after the C1D1 of the polatuzumab vedotin, wherein the C1D1 of the mosunetuzumab is about 1 mg, and the C1D2 of the mosunetuzumab is about 2 mg; and (b) the second dosing cycle comprises: (i) a single dose (C2D1) of the polatuzumab vedotin; and (ii) a single dose (C2D1) of the mosunetuzumab, wherein the C2D1 of the mosunetuzumab is about 9 mg, about 13.5 mg, about 20 mg, about 40 mg, about 45 mg, or about 60 mg, and the C1D1 and C2D2 of the polatuzumab vedotin are each about 1.8 mg/kg.

In a further aspect, the invention provides a method of treating a subject having a NHL (e.g., a relapsed and/or refractory NHL) comprising administering to the subject polatuzumab vedotin and mosunetuzumab in a dosing regimen comprising eight or more dosing cycles, wherein: (a) the first dosing cycle comprises: (i) a first dose (C1D1) of the mosunetuzumab, a second dose (C1D2) of the mosunetuzumab, and a third dose (C1D3) of the mosunetuzumab, wherein the C1 D1 of the mosunetuzumab is about 1 mg, the C1D2 of the mosunetuzumab is about 2 mg, and the C1D3 of the mosunetuzumab is about 9 mg, about 13.5 mg, about 20 mg, about 40 mg, about 45 mg, or about 60 mg; and (ii) a single dose (C1D1) of the polatuzumab vedotin; (b) the second dosing cycle comprises a single dose (C2D1) of the mosunetuzumab and a single dose (C2D1) of the polatuzumab vedotin; (c) the third dosing cycle comprises a single dose (C3D1) of the mosunetuzumab and a single dose (C3D1) of the polatuzumab vedotin; (d) the fourth dosing cycle comprises a single dose (C4D1) of the mosunetuzumab and a single dose (C4D1) of the polatuzumab vedotin; (e) the fifth dosing cycle comprises a single dose (C5D1) of the mosunetuzumab and a single dose (C5D1) of the polatuzumab vedotin; (f) the sixth dosing cycle comprises a single dose (C6D1) of the mosunetuzumab and a single dose (C6D1) of the polatuzumab vedotin; (g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C2D1-C8D1 of the mosunetuzumab is about equal or less than to the C1D3 and each single dose C1D1-C6D1 of the polatuzumab vedotin is about 1.8 mg/kg.

In yet another aspect, the invention provides a method of treating a subject having a NHL (e.g., a relapsed and/or refractory NHL) comprising administering to the subject polatuzumab vedotin and mosunetuzumab in a dosing regimen comprising eight or more dosing cycles, wherein: (a) the first dosing cycle comprises a first dose (C1D1) of the mosunetuzumab, a second dose (C1D2) of the mosunetuzumab, and a third dose of the mosunetuzumab, wherein the C1D1 of the mosunetuzumab is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 is about 9 mg, about 13.5 mg, about 20 mg, about 40 mg, about 45 mg, or about 60 mg; (b) the second dosing cycle comprises a single dose (C2D1) of the mosunetuzumab and a single dose (C2D1) of the polatuzumab vedotin; (c) the third dosing cycle comprises a single dose (C3D1) of the mosunetuzumab and a single dose (C3D1) of the polatuzumab vedotin; (d) the fourth dosing cycle comprises a single dose (C4D1) of the mosunetuzumab and a single dose (C4D1) of the polatuzumab vedotin; (e) the fifth dosing cycle comprises a single dose (C5D1) of the mosunetuzumab and a single dose (C5D1) of the polatuzumab vedotin; (f) the sixth dosing cycle comprises a single dose (C6D1) of the mosunetuzumab and a single dose (C6D1) of the polatuzumab vedotin; (g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C2D1-C8D1 of the mosunetuzumab is about equal to or less than the C1D3 and each single dose C2D1-C6D1 of the polatuzumab vedotin is about 1.8 mg/kg.

In yet a further aspect, the invention provides a method of treating a subject having a NHL comprising administering to the subject polatuzumab vedotin and mosunetuzumab in a dosing regimen comprising eight or more dosing cycles, wherein: (a) the first dosing cycle comprises: (i) a first dose (C1D1) and a second dose (C1D2) of the mosunetuzumab, wherein the C1D1 of the mosunetuzumab is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), and the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); and (ii) a single dose (C1D1) of the polatuzumab vedotin; (b) the second dosing cycle comprises: (i) a single dose (C2D1) of the mosunetuzumab, wherein the C2D1 of the mosunetuzumab is about 9 mg, about 13.5 mg, about 20 mg, about 40 mg, about 45 mg, or about 60 mg; and (ii) a single dose (C2D1) of the polatuzumab vedotin; (c) the third dosing cycle comprises a single dose (C3D1) of the mosunetuzumab and a single dose (C3D1) of the polatuzumab vedotin; (d) the fourth dosing cycle comprises a single dose (C4D1) of the mosunetuzumab and a single dose (C4D1) of the polatuzumab vedotin; (e) the fifth dosing cycle comprises a single dose (C5D1) of the mosunetuzumab and a single dose (C5D1) of the polatuzumab vedotin; (f) the sixth dosing cycle comprises a single dose (C6D1) of the mosunetuzumab and a single dose (C6D1) of the polatuzumab vedotin; (g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C2D1-C8D1 of the mosunetuzumab is about equal to or less than the C1D3 and each single dose C1D1-C6D1 of the polatuzumab vedotin is about 1.8 mg/kg.

In some embodiments, the NHL is an aggressive NHL (e.g., de novo DLBCL, transformed FL, or Grade 3b FL). In some embodiments, the NHL is a DLBCL. In some embodiments, the NHL is a R/R MCL.

In one aspect, the invention provides a method of treating a population of subjects having a CD20-positive cell proliferative disorder comprising administering to the subjects an anti-CD79b antibody drug conjugate and a bispecific antibody that binds to CD20 and CD3 in a dosing regimen comprising at least a first dosing cycle and a second dosing cycle, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg (e.g., between about 0.05 mg to about 2 mg, between about 0.1 mg to about 2 mg, between about 0.5 mg to about 2 mg, between about 0.5 mg to about 1.5 mg, between about 0.8 mg to about 1.2 mg, between about 0.5 mg to about 1 mg, or between about 1 mg to about 2 mg, e.g., about 0.5 mg, about 0.8 mg, about 0.9 mg, about 1 mg, about 1.1 mg, about 1.2 mg, about 1.5 mg, or about 2 mg), the C1D2 of the bispecific antibody is between about 0.05 mg to about 5 mg (e.g., between about 0.1 mg to about 5 mg, between about 0.1 mg to about 4 mg, between about 0.1 mg to about 3 mg, between about 0.5 mg to about 3 mg, between about 1 mg to about 3 mg, between about 1.5 mg to about 2.5 mg, between about 1.8 mg to about 2.2 mg, between about 3 mg to about 5 mg, between about 2 mg to about 4 mg, or between about 1 mg to about 5 mg; e.g., about 0.5 mg, about 1 mg, about 1.5 mg, about 1.8 mg, about 1.9 mg, about 2 mg, about 2.1 mg, about 2.2 mg, about 2.5 mg, about 3 mg, about 4 mg, or about 5 mg), and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises: (i) a single dose (C2D1) of the bispecific antibody, wherein the C2D1 of the bispecific antibody is about equivalent in amount to the C1D3; and (ii) a single dose (C2D1) of the anti-CD79b antibody drug conjugate, wherein the C1D1 of the anti-CD79b antibody drug conjugate and the C2D1 of the anti-CD79b antibody drug conjugate are each about 1.8 mg/kg.

In another aspect, the invention provides a method of treating a population of subjects having a CD20-positive cell proliferative disorder comprising administering to the subjects an anti-CD79b antibody drug conjugate and a bispecific antibody that binds to CD20 and CD3 in a dosing regimen comprising at least a first dosing cycle and a second dosing cycle, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is about 1 mg, the C1D2 of the bispecific antibody is about 2 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises: (i) a single dose (C2D1) of the bispecific antibody, wherein the C2D1 of the bispecific antibody is about equivalent in amount to the C1D3; and (ii) a single dose (C1D1) of the anti-CD79b antibody drug conjugate, wherein the C1D1 of the anti-CD79b antibody drug conjugate and the C2D1 of the anti-CD79b antibody drug conjugate are each about 1.8 mg/kg.

In another aspect, the invention provides a method of treating a population of subjects having a CD20-positive cell proliferative disorder comprising administering to the subjects an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg (e.g., between about 0.05 mg to about 2 mg, between about 0.1 mg to about 2 mg, between about 0.5 mg to about 2 mg, between about 0.5 mg to about 1.5 mg, between about 0.8 mg to about 1.2 mg, between about 0.5 mg to about 1 mg, or between about 1 mg to about 2 mg, e.g., about 0.5 mg, about 0.8 mg, about 0.9 mg, about 1 mg, about 1.1 mg, about 1.2 mg, about 1.5 mg, or about 2 mg), the C1D2 of the bispecific antibody is between about 0.05 mg to about 5 mg (e.g., between about 0.1 mg to about 5 mg, between about 0.1 mg to about 4 mg, between about 0.1 mg to about 3 mg, between about 0.5 mg to about 3 mg, between about 1 mg to about 3 mg, between about 1.5 mg to about 2.5 mg, between about 3 mg to about 5 mg, between about 2 mg to about 4 mg, or between about 1 mg to about 5 mg; e.g., about 0.5 mg, about 1 mg, about 1.5 mg, about 1.8 mg, about 1.9 mg, about 2 mg, about 2.1 mg, about 2.2 mg, about 2.5 mg, about 3 mg, about 4 mg, or about 5 mg), and the C1D3 of the bispecific antibody is about 9 mg, about 13.5 mg, about 20 mg, or about 40 mg; and (ii) a single dose (C1D1) of the anti-CD79b antibody drug conjugate; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody about equivalent in amount to the C1D3, and wherein each single dose C1D1-C6D1 of the anti-CD79b antibody drug conjugate is about 1.8 mg/kg.

In another aspect, the invention provides a method of treating a population of subjects having a CD20-positive cell proliferative disorder comprising administering to the subjects an anti-CD79b antibody drug conjugate and a bispecific antibody that binds to CD20 and CD3 in a dosing regimen comprising eight or more dosing cycles, wherein: (a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, or about 40 mg; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is about equivalent in amount to the C1D3, and wherein each single dose C1D1-C6D1 of the anti-CD79b antibody drug conjugate is about 1.8 mg/kg.

In some embodiments, the CD20-positive cell proliferative disorder is an NHL. In some embodiments, the overall response rate is at least 55% (e.g., at least 60%, at least 65%, at least 70%, at least 75%, at least 80%, at least 85%, at least 90%, or at least 95%; e.g., between 55% and 100%, between 55% and 90%, between 55% and 80%, between 55% and 70%, between 55% and 65%, between 55% and 60%, between 60% and 65%, between 60% and 70%, between 60% and 90%, or between 70% and 90%; e.g., about 55%, about 60%, about 65%, about 66%, about 67%, about 68%, about 69%, about 70%, about 75%, about 80%, about 85%, about 90%, or about 95%). In some embodiments, the overall response rate is at least 65%. In some embodiments, the complete response rate is at least 45% (e.g., at least 50%, at least 55%, at least 60%, at least 65%, at least 70%, at least 80%, at least 85%, at least 90%, or at least 95%; e.g., between 45% and 100%, between 45% and 80%, between 45% and 60%, between 45% and 55%, between 45% and 50%, between 50% and 55%, between 50% and 65%, between 50% and 70%, between 60% and 70%, or between 70% and 90%; e.g., about 45%, about 50%, about 53%, about 54%, about 55%, about 56%, about 57 about 60%, about 65%, about 70%, about 75%, about 80%, about 85%, about 90%, or about 95%). In some embodiments, the complete response rate is at least 55%.

In some embodiments, the CD20-positive cell proliferative disorder is an aggressive NHL (e.g., de novo DLBCL, transformed FL, or Grade 3b FL). In some embodiments, the overall response rate is at least 50% (e.g., at least 55%, at least 60%, at least 65%, at least 70%, at least 75%, at least 80%, at least 85%, at least 90%, or at least 95%; e.g., between 50% and 100%, between 50% and 80%, between 50% and 60%, between 50% and 55%, between 55% and 60%, between 55% and 65%, between 50% and 70%, between 60% and 70%, or between 70% and 90%; e.g., about 50%, about 55%, about 60%, about 61%, about 62%, about 63%, about 64%, about 65%, about 70%, about 75%, about 80%, about 85%, about 90%, or about 95%). In some embodiments, the overall response rate is at least 60%. In some embodiments, the complete response rate is at least 35% (e.g., at least 40%, at least 45%, at least 50%, at least 55%, at least 60%, at least 70%, at least 80%, or at least 90%; e.g., between 35% and 100%, between 35% and 80%, between 35% and 60%, between 35% and 55%, between 35% and 50%, between 35% and 45%, between 40% and 60%, between 45% and 50%, between 45% and 55%, between 45% and 60%, or between 50% and 70%; e.g., about 35%, about 40%, about 45%, about 46%, about 47%, about 48%, about 49%, about 50%, about 55%, about 60%, about 70%, about 80%, about 90%, or about 95%). In some embodiments, the complete response rate is at least 45%.

In some embodiments, the CD20-positive cell proliferative disorder is an NHL, and wherein the subjects of the population are post-CAR-T subjects (e.g., patients who were treated with CAR-T therapy at least 30 days prior to administration of the first study treatment (e.g., anti-CD20/anti-CD3 bispecific antibody and/or anti-CD79b antibody drug conjugate; e.g., mosunetuzumab and/or polatuzumab vedotin)). In some embodiments, the overall response rate is at least 50% (e.g., at least 55%, at least 60%, at least 65%, at least 70%, at least 80%, at least 85%, at least 90%, or at least 95%; e.g., between 50% and 100%, between 50% and 80%, between 50% and 60%, between 50% and 55%, between 55% and 60%, between 55% and 65%, between 50% and 70%, between 60% and 70%, or between 70% and 90%; e.g., about 50%, about 55%, about 56%, about 57%, about 58%, about 59%, about 60%, about 65%, about 70%, about 75%, about 80%, about 85%, about 90%, or about 95%). In some embodiments, the overall response rate is at least 55%. In some embodiments, the complete response rate is at least 20% (e.g., at least 25%, at least 30%, at least 35%, at least 40%, at least 50%, at least 60%, at least 70%, or at least 90%; e.g., between 20% and 100%, between 20% and 80%, between 20% and 60%, between 20% and 40%, between 20% and 30%, between 20% and 25%, between 25% and 30%, between 25% and 35%, between 25% and 50%, between 30% and 60%, or between 50% and 70%; e.g., about 20%, about 25%, about 26%, about 27%, about 28%, about 29%, about 30%, about 31%, about 35%, about 50%, about 60%, about 70%, about 80%, about 90%, about 95%). In some embodiments, the complete response rate is at least 25%.

In some embodiments, the CD20-positive cell proliferative disorder is an FL. In some embodiments, the overall response rate is at least 80% (e.g., at least 85%, at least 90%, at least 95%, at least 97%, at least 98%, or at least 99%; e.g., between 80% and 100%, between 80% and 95%, between 80% and 90%, between 80% and 85%, between 85% and 95%, between 90% and 100%, or between 95% and 100%; e.g., about 80%, about 85%, about 90%, about 91%, about 92% about 93%, about 94%, about 95%, about 96%, about 97%, about 98%, about 99%, or about 100%). In some embodiments, the overall response rate is at least 90%. In some embodiments, the complete response rate is at least 80% (e.g., at least 85%, at least 90%, at least 95%, at least 97%, at least 98%, or at least 99%; e.g., between 80% and 100%, between 80% and 95%, between 80% and 90%, between 80% and 85%, between 85% and 95%, between 90% and 100%, or between 95% and 100%; e.g., about 80%, about 85%, about 90%, about 91%, about 92%, about 93%, about 94%, about 95%, about 96%, about 97%, about 98%, about 99%, or about 100%). In some embodiments, the complete response rate is at least 90%.

In some embodiments, the bispecific antibody is mosunetuzumab. In some embodiments, the anti-CD79b antibody drug conjugate is polatuzumab vedotin.

In some embodiments of any of the above aspects, the subject is a human.

BRIEF DESCRIPTION OF THE DRAWINGS

FIG. 3A depicts the Dose-Finding Phase of the Phase Ib study. FIG. 3B depicts the Single-Arm Expansion Phase of the Phase II study. FIG. 3C depicts the Gated Randomized Expansion Phase of the Phase II study. 2L+=second line or later; approx.=approximately; BR=bendamustine plus rituximab; DLBCL=diffuse large B-cell lymphoma; FL=follicular lymphoma; Pola=polatuzumab vedotin; R=randomization; R/R=relapsed or refractory.

FIG. 10 is a table reporting frequency of all adverse events related to mosunetuzumab in 22 safety-evaluable patients in a study of combination treatment of mosunetuzumab with polatuzumab vedotin. Dosages reported in top row of table reflect C1D1, C1D2, and C1D3 doses of mosunetuzumab.

FIG. 11 is a table reporting frequency of all adverse events related to polatuzumab vedotin in 22 safety-evaluable patients in a study of combination treatment of mosunetuzumab with polatuzumab vedotin. Dosages reported in top row of table reflect C1D1, C1D2, and C1D3 doses of mosunetuzumab.

FIG. 12A and FIG. 12B depict levels of IFNγ in culture supernatant from cultured PBMCs from two healthy donors (HD-1 and HD-2), respectively, and FIG. 12C and FIG. 12D depict levels of TNFα in culture supernatant from cultured PBMCs from HD-1 and HD-2, respectively. Purified PBMCs from two healthy donors (HD-1 and HD-2) were treated with 100 ng/mL of anti-CD20/CD3 bispecific antibody and another test article as indicated. Polatuzumab vedotin, polatuzumab antibody or gD-vcMMAE was in μg/mL concentration, while free MMAE was in nM concentration, as labeled. Assays were performed in duplicate; mean cytokine levels were shown.

DETAILED DESCRIPTION OF THE INVENTION

I. General Techniques

Figure 1:
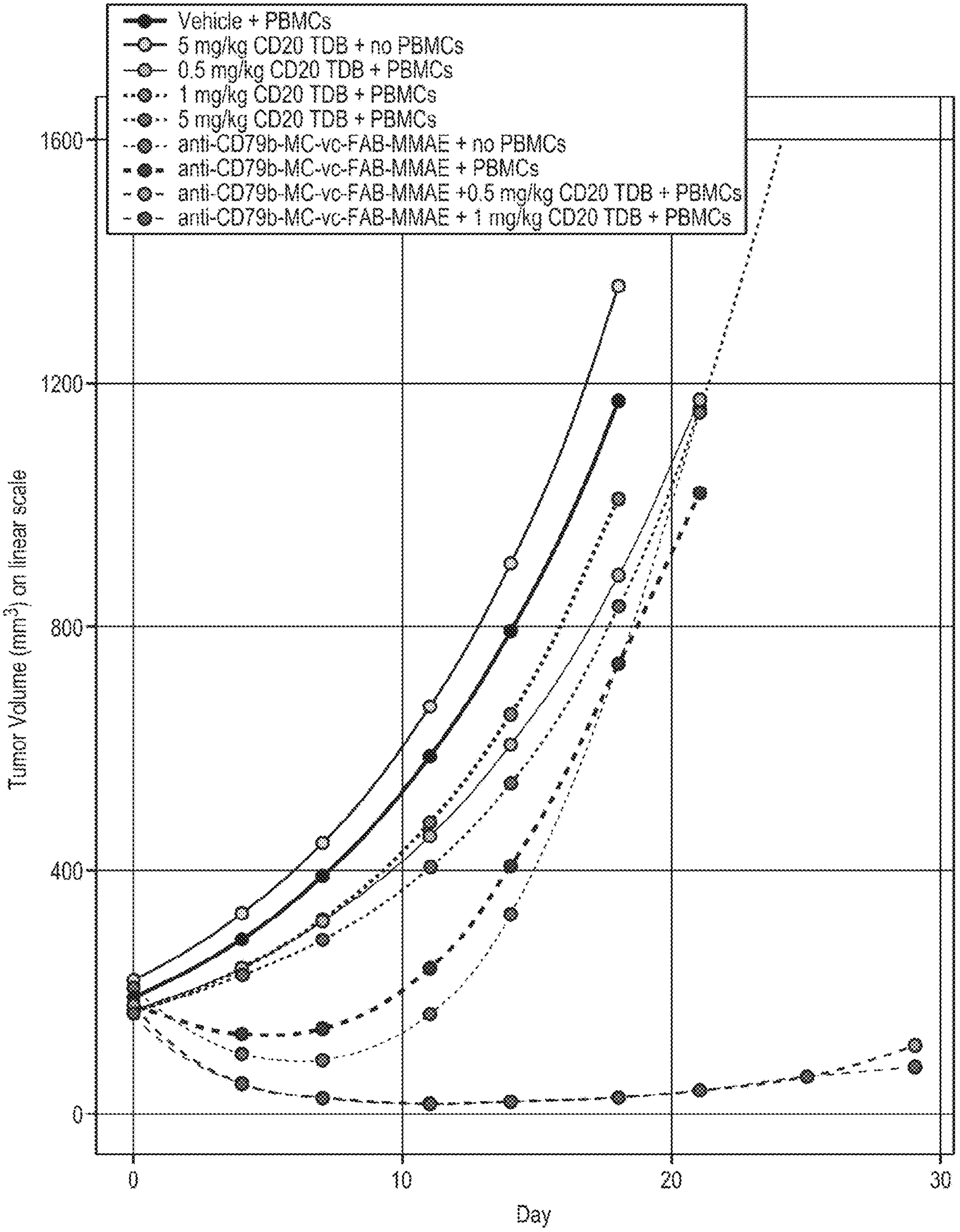
FIG. 1 is a graph showing the combination efficacy of anti-CD20/anti-CD3 T cell-dependent bispecific (TDB) antibody (CD20 TDB)+/−anti-CD79b (SN8v28)-MC-vc-PAB-MMAE (anti-CD79b-MC-v-PAB-MMAE) against WSU-DLCL2 B-cell lymphoma cells, in NSG mice supplemented with human peripheral blood mononuclear cells (PBMCs). Starting from top-left-most to bottom-right-most, the order of the lines are 5 mg/kg CD20 TDB+no PBMCs, vehicle+PBMCs, 1 mg/kg CD20 TDB+PBMCs, 0.5 mg/kg CD20 TDB+PBMCs, 5 mg/kg CD20 TDB+PBMCs, anti-CD79b-MC-v-PAB-MMAE+PBMCs, anti-CD79b-MC-v-PAB-MMAE+no PBMCs, anti-CD79b-MC-v-PAB-MMAE+0.5 mg/kg CD20 TDB+PBMCs, and anti-CD79b-MC-v-PAB-MMAE+1 mg/kg CD20 TDB+PBMCs.
Figures 2A, 2B, 2C, 2D, 2E:
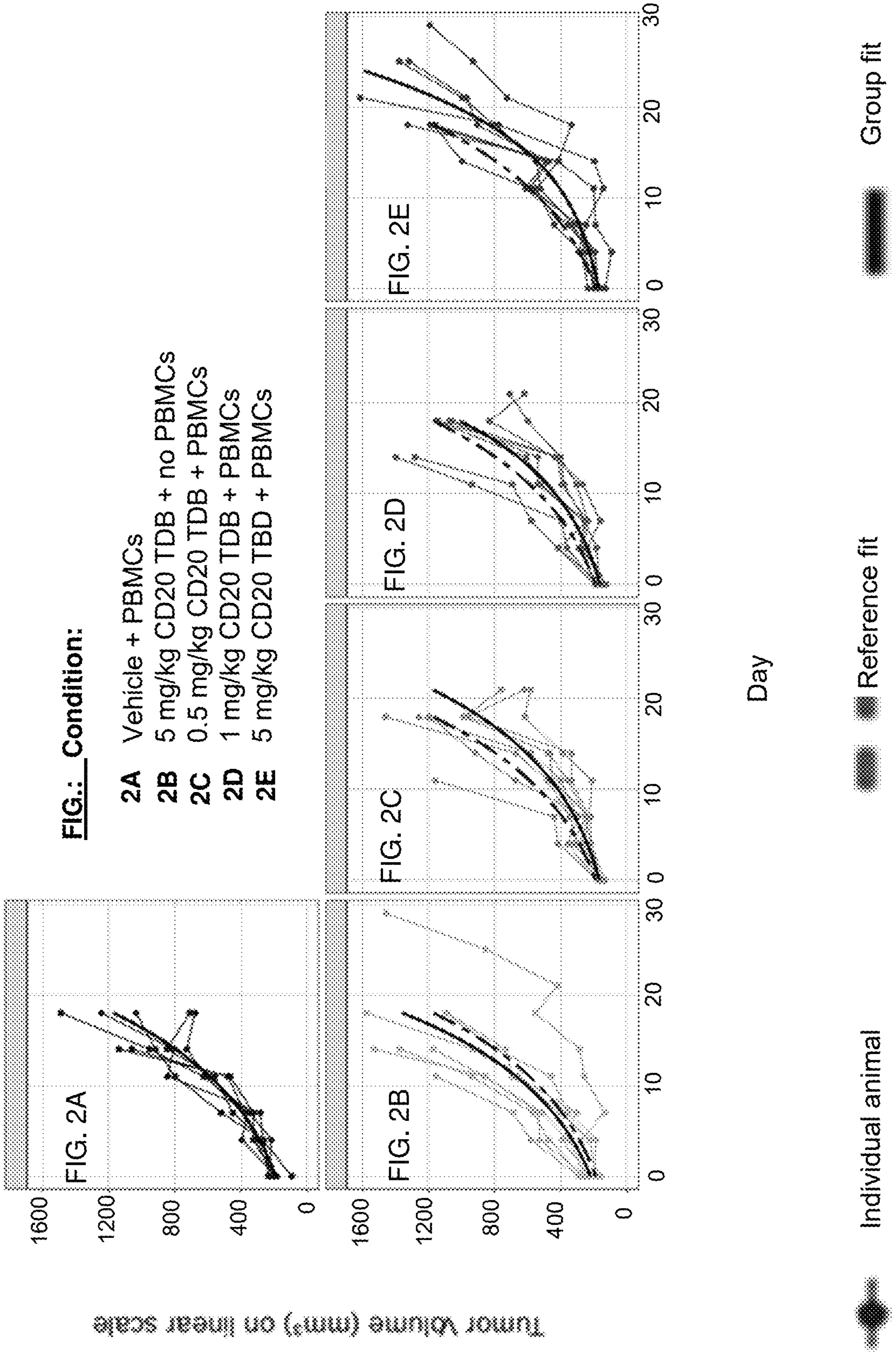
FIG. 2A-FIG. 2I are a series of graphs showing tumor volume change over time for individual mice treated as described in Example 1. In particular, Panel 1 (FIG. 2A) corresponds to vehicle+PBMCs; Panel 2 (FIG. 2B) corresponds to 5 mg/kg CD20 TDB+no PBMCs; Panel 3 (FIG. 2C) corresponds to 0.5 mg/kg CD20 TDB+PBMCs; Panel 4 (FIG. 2D) corresponds to 1 mg/kg CD20 TDB+PBMCs; Panel 5 (FIG. 2E) corresponds to 5 mg/kg CD20 TDB+PBMCs; Panel 6 (FIG. 2F) corresponds to anti-CD79b-MC-v-PAB-MMAE+no PBMCs; Panel 7 (FIG. 2G) corresponds to anti-CD79b-MC-v-PAB-MMAE+PBMCs; Panel 8 (FIG. 2H) corresponds to anti-CD79b-MC-v-PAB-MMAE+0.5 mg/kg CD20 TDB+PBMCs; and Panel 9 (FIG. 2I) corresponds to anti-CD79b-MC-v-PAB-MMAE+1 mg/kg CD20 TDB+PBMCs. The dashed line in Panels 2-9 (FIG. 2B-FIG. 2I) refers to the reference fit (of vehicle+PBMCs in Panel 1). The solid black line in Panels 2-9 (FIG. 2B-FIG. 2I) refers to the fit of the data with each respective Panel.
Figures 2F, 2G, 2H, 2I:
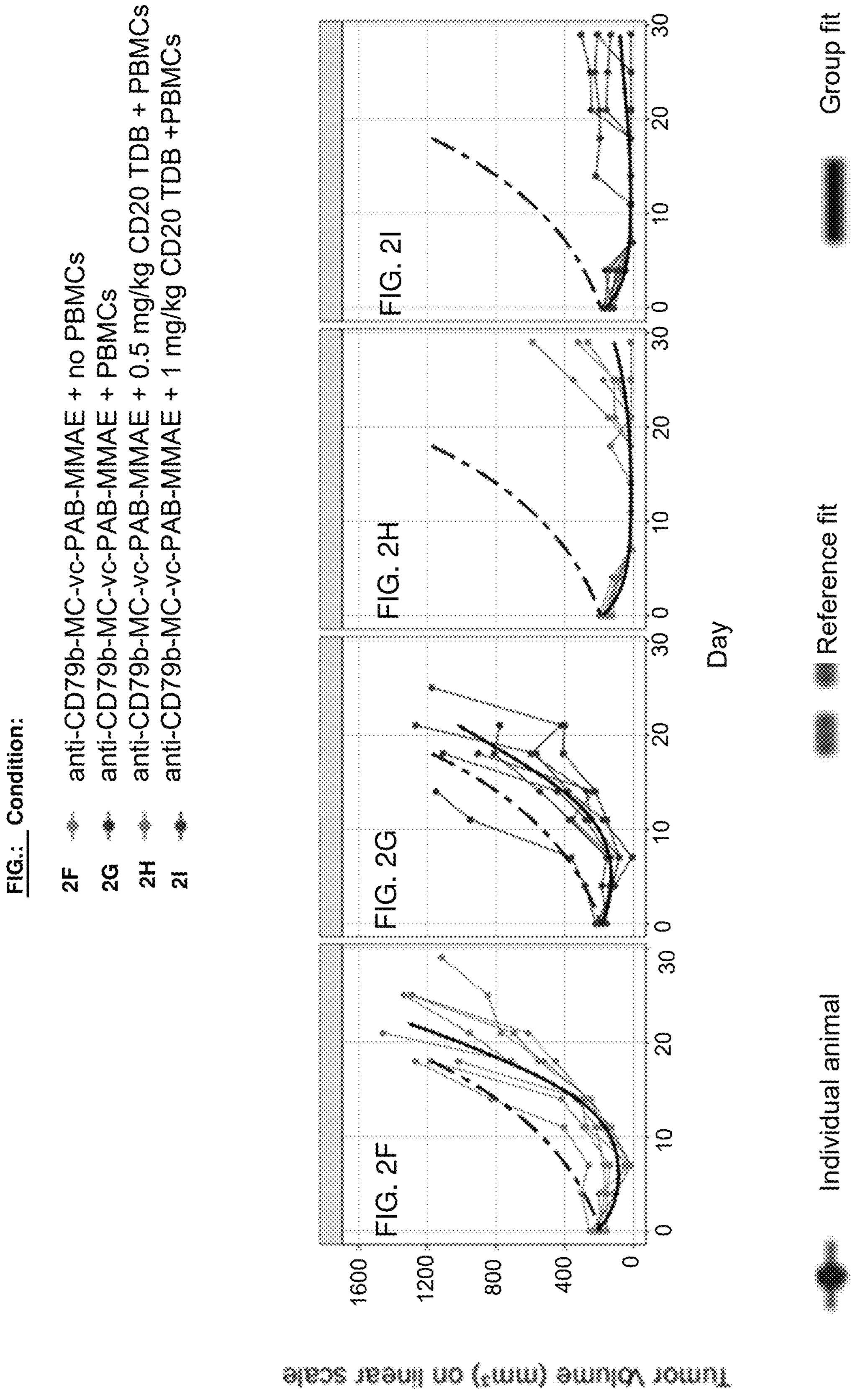

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al., eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, *A Laboratory Manual*, and Animal Cell Culture (R. I. *Freshney, ed.* (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); *Introduction to Cell and Tissue Culture* (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

The "amount," "level," or "expression level," used herein interchangeably, of a biomarker is a detectable level in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). Expression levels can be measured by methods known to one skilled in the art and also disclosed herein.

The presence and/or expression level/amount of various biomarkers described herein in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (e.g., Serum ELISA), biochemical enzymatic activity assays, in situ hybridization, fluorescence in situ hybridization (FISH), Southern analysis, Northern analysis, whole genome sequencing, massively parallel DNA sequencing (e.g., next-generation sequencing), NANOSTRING®, polymerase chain reaction (PCR) including quantitative real time PCR (qRT-PCR) and other amplification type detection methods, such as, for example, branched DNA, SISBA, TMA and the like, RNA-seq, microarray analysis, gene expression profiling, and/or serial analysis of gene expression ("SAGE"), as well as any one of the wide variety of assays that can be performed by protein, gene, and/or tissue array analysis. Multiplexed immunoassays such as those available from Rules Based Medicine or Meso Scale Discovery ("MSD") may also be used.

The terms "cancer" and "cancerous" refer to or describe the physiological condition in mammals that is typically characterized by unregulated cell growth. Examples of cancer include, but are not limited to, hematologic cancers, such as mature B cell cancers, such as non-Hodgkin's lymphoma (NHL), which may be relapsed and/or refractory NHL, e.g., diffuse large B cell lymphoma (DLBCL), which may be relapsed and/or refractory DLBCL, follicular lymphoma (FL), which may be relapsed and/or refractory FL and/or transformed FL, and mantle cell lymphoma (MCL), which may be relapsed and/or refractory MCL. DLBCL includes Richter's Transformation, germinal-center B cell-like (GCB) DLBCL, and activated B cell-like DLBCL. Other specific examples of cancer include acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, heavy chain diseases, a heavy chain disease, γ heavy chain disease, p heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, primary mediastinal (thymic) large B cell lymphoma (PMLBCL), intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and Burkitt lymphoma, and B cell lymphoma, unclassifiable, with features intermediate between DLBCL and classical Hodgkin's lymphoma. Further examples of cancer include, but are not limited to, carcinoma, lymphoma, blastoma, sarcoma, and leukemia or lymphoid malignancies, including B cell lymphomas. More particular examples of such cancers include, but are not limited to, multiple myeloma (MM); low grade/follicular NHL; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; AIDS-related lymphoma; and acute lymphoblastic leukemia (ALL); chronic myeloblastic leukemia; and post-transplant lymphoproliferative disorder (PTLD). In some embodiments, NHLs may include aggressive NHLs, including de novo DLBCL, transformed FL, and Grade 3b FL.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder," and "tumor" are not mutually exclusive as referred to herein.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In another embodiment, the cell proliferative disorder is a tumor.

The terms "B cell proliferative disorder" or "B cell malignancy" refer to disorders that are associated with some degree of abnormal B cell proliferation and include, for example, lymphomas, leukemias, myelomas, and myelodysplastic syndromes. In one embodiment, the B cell proliferative disorder is a lymphoma, such as non-Hodgkin's lymphoma (NHL), including, for example, relapsed and/or refractory NHL, DLBCL (e.g., relapsed or refractory DLBCL), FL (e.g., relapsed or refractory FL or transformed FL), or MCL (e.g., relapsed or refractory MCL). In another embodiment, the B cell proliferative disorder is a leukemia, such as chronic lymphocytic leukemia (CLL). In yet another embodiment, the B cell proliferative disorder is a central nervous system lymphoma (CNSL).

As used herein, "treatment" (and grammatical variations thereof, such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the invention can delay development of a disease or to slow the progression of a disease.

As used herein, "administering" is meant a method of giving a dosage of a compound (e.g., an anti-CD79b antibody drug conjugate and/or an anti-CD20/anti-CD3 bispecific antibody) or a composition (e.g., a pharmaceutical composition, e.g., a pharmaceutical composition including an anti-CD79b antibody drug conjugate and/or an anti-CD20/anti-CD3 bispecific antibody) to a subject. The compounds and/or compositions utilized in the methods described herein can be administered, for example, intravenously (e.g., by intravenous infusion), subcutaneously, intramuscularly, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subconjunctivally, intravesicularily, mucosally, intrapericardially, intraumbilically, intraocularly, orally, topically, locally, by inhalation, by injection, by infusion, by continuous infusion, by localized perfusion bathing target cells directly, by catheter, by lavage, in creams, or in lipid compositions. The method of administration can vary depending on various factors (e.g., the compound or composition being administered and the severity of the condition, disease, or disorder being treated).

A "fixed" or "flat" dose of a therapeutic agent (e.g., an anti-CD79b antibody drug conjugate and/or an anti-CD20/anti-CD3 bispecific antibody) herein refers to a dose that is administered to a subject without regard for the weight or body surface area (BSA) of the subject. The fixed or flat dose is therefore not provided as a mg/kg dose or a mg/m2 dose, but rather as an absolute amount of the therapeutic agent (e.g., mg).

A "subject," "patient," or an "individual" is a mammal. Mammals include, but are not limited to, primates (e.g., humans and non-human primates such as monkeys), domesticated animals (e.g., cows, sheep, cats, dogs, and horses), rabbits, and rodents (e.g., mice and rats). In certain embodiments, the subject, patient, or individual is a human.

A "post-CAR-T subject" or "post-CAR-T patient" is a subject or patient who has been previously treated with CAR-T (chimeric antigen receptor T-cell) therapy. Typically, the subject or patient has also undergone a minimum waiting period prior to administration of a subsequent non-CAR-T treatment. In some embodiments, the post-CAR-T subject or patient received the CAR-T therapy at least 30 days prior to the first administration of the non-CAR-T treatment. In some embodiments, the non-CAR-T treatment is an anti-CD20/anti-CD3 bispecific antibody (e.g., mosunetuzumab), an anti-CD79b antibody drug conjugate (e.g., polatuzumab vedotin), or a combination thereof.

As used herein, "complete response" or "CR" refers to disappearance of all target lesions (i.e., all evidence of disease).

As used herein, "partial response" or "PR" refers to at least a 30% decrease in the sum of the longest diameters (SLD) of target lesions, taking as reference the baseline SLD, or at least a 50% decrease in the product of the diameters (SPD) of target lesions, taking as reference the baseline SPD.

As used herein, "objective response rate" (ORR) refers to the sum of complete response (CR) rate and partial response (PR) rate.

As used herein, "duration of objective response" (DOR) is defined as the time from the first occurrence of a documented objective response to disease progression, or death from any cause within 30 days of the last dose of a treatment, whichever occurs first.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

An "effective response" of a subject or a subject's "responsiveness" to treatment with a medicament and similar wording refers to the clinical or therapeutic benefit imparted to a subject as risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

A subject who "does not have an effective response" to treatment refers to a subject who does not have any one of extending survival (including overall survival and progression free survival); resulting in an objective response (including a complete response or a partial response); or improving signs or symptoms of cancer.

As used herein, "survival" refers to the subject remaining alive, and includes overall survival as well as progression-free survival.

As used herein, "overall survival" (OS) refers to the percentage of subjects in a group who are alive after a particular duration of time, e.g., 1 year or 5 years from the time of diagnosis or treatment.

As used herein, "progression-free survival" (PFS) refers to the length of time during and after treatment during which the disease being treated does not worsen. Progression-free survival may include the amount of time subjects have experienced a complete response or a partial response, as well as the amount of time subjects have experienced stable disease.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD, or at least a 50% increase in the SPD of target legions, taking as reference the smallest SPD, recorded since the treatment started or the presence of one or more new lesions.

As used herein, "delaying progression" of a disorder or disease means to defer, hinder, slow, retard, stabilize, and/or postpone development of the disease or disorder (e.g., a CD20-positive cell proliferative disorder (e.g., a B cell proliferative disorder, e.g., NHL (e.g., DLBCL, FL, or MCL))). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20%, 30%, 40%, 50%, 60%, 70%, 75%, 80%, 85%, 90%, 95%, or greater. In certain embodiments, reduce or inhibit can refer to the reduction or inhibition of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the fractionated, dose-escalation dosing regimen of the invention relative to treatment with an anti-CD20/anti-CD3 bispecific antibody using an non-fractioned dosing regimen. In other embodiments, reduce or inhibit can refer to effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

As used herein, the term "reducing or inhibiting cancer relapse" means to reduce or inhibit tumor or cancer relapse, or tumor or cancer progression.

By "extending survival" is meant increasing overall or progression-free survival in a treated subject relative to an untreated subject (e.g., relative to a subject not treated with the medicament), or relative to a subject who does not express a biomarker at the designated level, and/or relative to a subject treated with an approved anti-tumor agent. An objective response refers to a measurable response, including complete response or partial response.

The term "protein," as used herein, refers to any native protein from any vertebrate source, including mammals such as primates (e.g., humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include, but are not limited to Fv, Fab, Fab', Fab'-SH, $F(ab')_2$; diabodies; linear antibodies; single-chain antibody molecules (e.g., scFv); and multispecific antibodies formed from antibody fragments.

The terms "full-length antibody," "intact antibody," and "whole antibody" are used herein interchangeably to refer to an antibody having a structure substantially similar to a native antibody structure or having heavy chains that contain an Fc region as defined herein.

By "binding domain" is meant a part of a compound or a molecule that specifically binds to a target epitope, antigen, ligand, or receptor. Binding domains include, but are not limited to antibodies (e.g., monoclonal, polyclonal, recombinant, humanized, and chimeric antibodies), antibody fragments or portions thereof (e.g., Fab fragments, $Fab'_2$, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

The "class" of an antibody refers to the type of constant domain or constant region possessed by its heavy chain.

There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term IgG "isotype" or "subclass" as used herein is meant any of the subclasses of immunoglobulins defined by the chemical and antigenic characteristics of their constant regions. "Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "humanized" antibody refers to a chimeric antibody comprising amino acid residues from non-human HVRs and amino acid residues from human FRs. In certain embodiments, a humanized antibody may comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy, Alan R. Liss*, p. 77 (1985); Boerner et al., *J. Immunol.,* 147(1):86-95 (1991). See also van Dijk and van de Winkel, *Curr. Opin. Pharmacol.,* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nad. Acad. Sci. USA,* 103:3557-3562 (2006) regarding human antibodies generated via a human B-cell hybridoma technology. The term "chimeric" antibody refers to an antibody in which a portion of the heavy and/or light chain is derived from a particular source or species, while the remainder of the heavy and/or light chain is derived from a different source or species.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al., *Kuby Immunology,* $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of mmunologicalInterest,* 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al., *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent. In certain embodiments, an immunoconjugate is an antibody drug conjugate. In certain embodiments, an antibody drug conjugate is an anti-CD79b antibody drug conjugate, such as polatuzumab vedotin, anti-CD79b-MC-vc-PAB-MMAE, or an anti-CD79b antibody drug conjugate described in any one of U.S. Pat. No. 8,088,378 and/or US 2014/0030280.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (A), based on the amino acid sequence of its constant domain.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (Ko) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Ko) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, or e.g., from $10^{-9}$ M to $10^{-13}$ M). In certain embodiments, an anti-CD20 antibody binds to an epitope of CD20 that is conserved among CD20 from different species.

The terms "anti-CD20/anti-CD3 bispecific antibody," "bispecific anti-CD20/anti-CD3 antibody," and "antibody that binds to CD20 and CD3," or variants thereof, refer to a multispecific antibody (e.g., a bispecific antibody) that is capable of binding to CD20 and CD3 with sufficient affinity such that the antibody is useful as a diagnostic and/or therapeutic agent in targeting CD20 and/or CD3. In one embodiment, the extent of binding of an anti-CD20/anti-CD3 bispecific antibody to an unrelated, non-CD3 protein and/or non-CD20 protein is less than about 10% of the binding of the antibody to CD3 and/or CD20 as measured, e.g., by a radioimmunoassay (RIA). In certain embodiments, an antibody that binds to CD20 and CD3 has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, or e.g., from $10^{-9}$ M to $10^{-13}$ M). In certain embodiments, an anti-CD20/anti-CD3 bispecific antibody binds to an epitope of CD3 that is conserved among CD3 from different species and/or an epitope of CD20 that is conserved among CD20 from different species. In some instances, the anti-CD20/anti-CD3 bispecific antibody is mosunetuzumab (also known as BTCT4465A or RG 7828), as defined by International Nonproprietary Names for Pharmaceutical Substances (INN) List 117 (WHO Drug Information, Vol. 31, No. 2, 2017, p. 304-305).

As used herein, the term "binds," "specifically binds to," or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, for example, by a radioimmunoassay (RIA). In certain embodiments, an antibody that specifically binds to a target has a dissociation constant ($K_D$) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding. The term as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower, or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low Ko value. In one embodiment, the term "specific binding" refers to binding where a molecule binds to a particular polypeptide or epitope on a particular polypeptide without substantially binding to any other polypeptide or polypeptide epitope.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "chemotherapeutic agent" refers to a compound useful in the treatment of cancer, such as a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a marginal zone lymphoma (MZL)) or a relapsed or refractory CLL). Examples of chemotherapeutic agents include EGFR inhibitors (including small molecule inhibitors (e.g., erlotinib (TARCEVA®, Genentech/OSI Pharm.); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine)); a tyrosine kinase inhibitor (e.g., an EGFR inhibitor; a small molecule HER2 tyrosine kinase inhibitor such as TAK165 (Takeda); CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; PKI-166 (Novartis); pan-HER inhibitors such as canertinib (CI-1033; Pharmacia); Raf-1 inhibitors such as antisense agent ISIS-5132 (ISIS Pharmaceuticals) which inhibit Raf-1 signaling; non-HER-targeted tyrosine kinase inhibitors such as imatinib mesylate (GLEEVEC®, Glaxo SmithKline); multi-targeted tyrosine kinase inhibitors such as sunitinib (SUTENT®, Pfizer); VEGF receptor tyrosine kinase inhibitors such as vatalanib (PTK787/ZK222584, Novartis/Schering AG); MAPK extracellular regulated kinase I inhibitor CI-1040 (Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino) phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®)); proteasome inhibitors such as bortezomib (VELCADE®, Millennium Pharm.); disulfiram; epigallocatechin gallate; salinosporamide A; carfilzomib; 17-AAG (geldanamycin); radicicol; lactate dehydrogenase A (LDH-A); fulvestrant (FASLODEX®, AstraZeneca); letrozole (FEMARA®, Novartis), finasunate (VATALANIB®, Novartis); oxaliplatin (ELOXATIN®, Sanofi); 5-FU (5-fluorouracil); leucovorin; lonafamib (SCH 66336); sorafenib (NEXAVAR®, Bayer Labs); AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1 and calicheamicin ω1); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, cactinomycin, carabicin, caminomycin, carzinophilin, chromomycinis, dactinomycin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; chloranmbucil; GEMZAR® (gemcitabine); 6-thioguanine; mercaptopurine; methotrexate; etoposide (VP-16); ifosfamide; mitoxantrone; novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids, prodrugs, and derivatives of any of the above.

Chemotherapeutic agents also include (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstibestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; (ix) growth inhibitory agents including vincas (e.g., vincristine and vinblastine), NAVELBINE® (vinorelbine), taxanes (e.g., paclitaxel, nab-paclitaxel, and docetaxel), topoisomerase II inhibitors (e.g., doxorubicin, epirubicin, daunorubicin, etoposide, and bleomycin), and DNA alkylating agents (e.g., tamoxigen, dacarbazine, mechlorethamine, cisplatin, methotrexate, 5-fluorouracil, and ara-C); and (x) pharmaceutically acceptable salts, acids, prodrugs, and derivatives of any of the above.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis, with a result being to restore or enhance T-cell function (e.g., proliferation, cytokine production, and/or target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates, or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen-binding fragments thereof, immunoadhesins, fusion proteins, oligopeptides, and other molecules that decrease, block, inhibit, abrogate, or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific embodiment, a PD-1 binding antagonist is MDX-1106 (nivolumab). In another specific embodiment, a PD-1 binding antagonist is MK-3475 (pembrolizumab, previously known as lambrolizumab). In another specific embodiment, a PD-1 binding antagonist is AMP-224. In another embodiment, a PD-1 antagonist antibody is MEDI-0680 (AMP-514), PDR001 (spartalizumab), REGN2810 (cemiplimab), BGB-108, prolgolimab, camrelizumab, sintilimab, tislelizumab, or toripalimab.

The term "PD-L1 binding antagonist" refers to a molecule that decreases, blocks, inhibits, abrogates, or interferes with signal transduction resulting from the interaction of PD-L1 with either one or more of its binding partners, such as PD-1 or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen-binding fragments thereof, immunoadhesins, fusion proteins, oligopeptides, and other molecules that decrease, block, inhibit, abrogate, or interfere with signal transduction resulting from the interaction of PD-L1 with one or more of its binding partners, such as PD-1 or B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific embodiment, the anti-PD-L1 antibody is atezolizumab (CAS Registry Number: 1422185-06-5), also known as MPDL3280A. In another specific embodiment, the anti-PD-L1 antibody is MDX-1105. In still another specific aspect, the anti-PD-L1 antibody is MED14736.

As used herein, the term "atezolizumab" refers to anti-PD-L1 antagonist antibody having the International Non-proprietary Names for Pharmaceutical Substances (INN) List 112 (WHO Drug Information, Vol. 28, No. 4, 2014, p. 488), or the CAS Registry Number 1380723-44-3.

The term "PD-L2 binding antagonist" refers to a molecule that decreases, blocks, inhibits, abrogates, or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen-binding fragments thereof, immunoadhesins, fusion proteins, oligopeptides, and other molecules that decrease, block, inhibit, abrogate, or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some instances, a PD-L2 binding antagonist is an immunoadhesin.

The term "cluster of differentiation 3" or "CD3," as used herein, refers to any native CD3 from any vertebrate source, including mammals such as primates (e.g., humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The term "cluster of differentiation 20" or "CD20," as used herein, refers to any native CD20 from any vertebrate source, including mammals such as primates (e.g., humans) and rodents (e.g., mice and rats), unless otherwise indicated. The term encompasses "full-length," unprocessed CD20, as well as any form of CD20 that results from processing in the cell. The term also encompasses naturally occurring variants of CD20, including, for example, splice variants or allelic variants. CD20 includes, for example, human CD20 protein (see, e.g., NCBI RefSeq Nos. NP_068769.2 and NP_690605.1), which is 297 amino acids in length and may be generated, for example, from variant mRNA transcripts that lack a portion of the 5' UTR (see, e.g., NCBI RefSeq No. NM_021950.3) or longer variant mRNA transcripts (see, e.g., NCBI RefSeq No. NM_152866.2).

The term "cluster of differentiation 79b" or "CD79b," as used herein, refers to any native CD79b from any vertebrate source, including mammals such as primates (e.g., humans) and rodents (e.g., mice and rats), unless otherwise indicated. The term encompasses "full-length," unprocessed CD79b, as well as any form of CD79b that results from processing in the cell. The term also encompasses naturally occurring variants of CD79b, including, for example, splice variants or allelic variants. CD79b includes, for example, human CD79b protein (NCBI RefSeq No. NP_000617), which is 229 amino acids in length.

The terms "anti-CD79b antibody" and "an antibody that binds to CD79b" refer to an antibody that is capable of binding CD79b with sufficient affinity such that the antibody is useful as a diagnostic and/or therapeutic agent in targeting CD79b. In one embodiment, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (Ko) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, or e.g., from $10^{-9}$ M to $10^{-13}$ M). In certain embodiments, an anti-CD79b antibody binds to an epitope of CD79b that is conserved among CD79b from different species.

The term "cytotoxic agent" as used herein refers to a substance that inhibits or prevents a cellular function and/or causes cell death or destruction. Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu); chemotherapeutic agents or drugs (e.g., methotrexate, adriamicin, or *vinca* alkaloids (vincristine, vinblastine, or etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of a compound, for example, an anti-CD79b antibody drug conjugate and/or an anti-CD20/anti-CD3 bispecific antibody or a composition (e.g., pharmaceutical composition) thereof, is at least the minimum amount required to achieve the desired therapeutic result, such as a measurable improvement of a particular disorder (e.g., a CD20-positive cell proliferative disorder (e.g., a B cell proliferative disorder, e.g., NHL (e.g., DLBCL, FL, or MCL))). An effective amount herein may vary according to factors such as the disease state, age, sex, and weight of the subject, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, the term "cytokine release syndrome" (abbreviated as "CRS") refers to an increase in the levels of cytokines, particularly tumor necrosis factor alpha (TNF-α), interferon gamma (IFN-γ), interleukin-6 (IL-6), interleukin-10 (IL-10), interleukin-2 (IL-2) and/or interleukin-8 (IL-8), in the blood of a subject during or shortly after administration of a therapeutic agent, resulting in adverse symptoms. In some instances, e.g., after the administration of CAR-T cells, CRS can also occur only later, e.g., several days after administration upon expansion of the CAR-T cells. The incidence and severity typically decrease with subsequent infusions. Symptoms may range from symptomatic discomfort to fatal events, and may include fever, chills, dizziness, hypertension, hypotension, dyspnea, restlessness, sweating, flushing, skin rash, tachycardia, tachypnoea, headache, tumor pain, nausea, vomiting and/or organ failure. A skilled artisan should recognize that CRS can be graded by a number of different published CRS grading systems, including, but not limited to, those outlined in the American Society for Transplantation and Cellular Therapy (ASTCT) Consensus Grading Criteria (Lee et al., *Biology of Blood and Marrow Transplantation.* 25(4): 625-638, 2019), the National Cancer Institute (NCI) Common Terminology Criteria for Adverse Events (CTCAE) v4.03, the NCI CTCAE v5.0, and the Lee Criteria (Lee et al., *Blood.* 2014. 124: 188-195). Unless otherwise specified, CRS grading herein follows the ASTCT Consensus Grading Criteria.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, a "week" is 7 days ±2 days.

III. Therapeutic Methods

The methods provided herein benefit patients by providing methods of treating CD20-positive disorders while achieving a more favorable benefit-risk profile. Thus, provided herein are methods for treating a subject having a CD20-positive cell proliferative disorder (e.g., a B cell proliferative disorder (e.g., non-Hodgkin's lymphoma (NHL) (e.g., a relapsed and/or refractory NHL, a diffuse-large B cell lymphoma (DLBCL) (e.g., a relapsed and/or refractory DLBCL), a follicular lymphoma (FL) (e.g., a relapsed and/or refractory FL or a transformed FL), or a mantle cell lymphoma (MCL) (e.g., a relapsed and/or refractory MCL)), a chronic lymphoid leukemia (CLL), or a central nervous system lymphoma (CNSL))) by administering a combination of an anti-CD79b antibody drug conjugate and a bispecific antibody that binds to CD20 and CD3 in a multi-cycle dosing regimen involving a fractionated, escalating dose of the bispecific antibody in the first dosing cycle. In particular, double-step fractionation provided by the methods described herein can be an effective safety mitigation strategy for a dose-escalation dosing regimen of an anti-CD20/anti-CD3 bispecific antibody. Furthermore, the T-cell recruiting anti-CD20/anti-CD3 bispecific antibody can facilitate recognition of tumor cells by T cells, while the anti-CD79b ADC can induce tumor-cell killing, which can lead to release of tumor-specific neo-antigens that may elicit additional anti-tumor adaptive immune responses. Each agent targets a different cell surface antigen (CD20, CD79b), which can mitigate against antigen-loss escape mechanisms of resistance to a single agent. The methods provided herein can reduce or inhibit unwanted treatment effects, which include cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or hepatotoxicities. In particular, the methods provided herein can reduce potential exacerbation of overlapping toxicities of the two antibodies, including toxicities associated with the combination not previously identified with single-agent treatment and/or for more severe or more frequent toxicities than that observed with the individual agents.

A. Therapeutic Methods for Dosing of the Anti-CD20/Anti-CD3 Bispecific Antibody and Anti-CD79b ADC The invention provides methods for treating a subject having a CD20-positive cell proliferative disorder (e.g., a B cell proliferative disorder (e.g., non-Hodgkin's lymphoma (NHL) (e.g., a relapsed and/or refractory NHL, a diffuse-large B cell lymphoma (DLBCL) (e.g., a relapsed and/or refractory DLBCL), a follicular lymphoma (FL) (e.g., a relapsed and/or refractory FL or a transformed FL), or a mantle cell lymphoma (MCL) (e.g., a relapsed or refractory MCL)), a chronic lymphoid leukemia (CLL), or a central nervous system lymphoma (CNSL))) that includes administering to the subject an anti-CD79b antibody drug conjugate and/or an anti-CD20/anti-CD3 bispecific antibody, e.g., in a fractionated, dose-escalation dosing regimen. In some instances, the present methods are used for treating a subject having relapsed and/or refractory NHL (e.g., an aggressive NHL (e.g., a relapsed and/or refractory DLBCL, a relapsed and/or refractory FL, or a relapsed and/or refractory MCL)). In some instances, the subject has relapsed to one or more (e.g., one, two, three, or more) prior therapies (e.g., one or more prior systemic therapies, e.g., one or more prior systemic chemotherapies (e.g., one or more prior systemic therapies involving administration of anthracycline), one or more prior stem cell therapies, or one or more prior CAR-T cell therapies) after having a documented history of response (e.g., a complete response or a partial response) of at least 6 months in duration from completion of the therapy. In some instances, the subject is refractory to any prior therapy, (e.g., has had no response to the prior therapy, or progression within 6 months of completion of the last dose of therapy). Thus, in some embodiments, the present dosing regimen is a second line therapy. In some embodiments, the present dosing regimen is a third line therapy. In some embodiments, the subject has a transformed FL, which is a refractory to standard therapies for transformed FL. In some embodiments, the FL is a Graded FL (e.g., a Grade 1, 2, 3a, or 3b FL).

In some instances, the invention involves treating a subject having a CD20-positive cell proliferative disorder (e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL)) by administering to the subject a bispecific antibody that binds to CD20 and CD3 in a dosing regimen including at least a first dosing cycle and a second dosing cycle, wherein: (a) the first dosing cycle includes a first dose (C1D1), a second dose (C1D2), and a third dose (C1D3) of the bispecific antibody, wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 is about 9 mg, about 13.5 mg, about 20 mg, about 40 mg, about 45 mg, or about 60 mg; and (b) the second dosing cycle includes a single dose (C2D1) of the bispecific antibody, wherein the C2D1 is greater than or equal to the C1D3.

Methods for treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL), include administering to the subject a bispecific antibody that binds to CD20 and CD3 in a dosing regimen including at least a first dosing cycle and a second dosing cycle, wherein: (a) the first dosing cycle includes a first dose (C1D1), a second dose (C1D2), and a third dose (C1D3) of the bispecific antibody, wherein the C1D3 is greater than or equal to the C1D2 and C1D1, and the C1 D2 is greater than or equal to the C1D1, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 is about 9 mg, about 13.5 mg, about 20 mg, about 40 mg, about 45 mg, or about 60 mg; and (b) the second dosing cycle includes a single dose (C2D1) of the bispecific antibody, wherein the C2D1 is greater than or equal to the C1D3 and is about 9 mg, about 13.5 mg, about 20 mg, about 40 mg, about 45 mg, or about 60 mg.

In some instances, (a) the C1D1 is between about 0.02 mg to about 5 mg, the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 is about 9 mg, about 13.5 mg, about 20 mg, about 40 mg, about 45 mg, or about 60 mg, and (b) the C2D1 is greater than or equal to C1D3. In some instances, (a) the C1D1 is about 1 mg, the C1D2 is about 2 mg, and the C1D3 is about 9 mg, and (b) the C2D1 is greater than or equal to C1D3. In some instances, (a) the C1D1 is about 1 mg, the C1D2 is about 2 mg, and the C1D3 is about 9 mg, and (b) the C2D1 is about 9 mg. In some instances, (a) the C1D1 is about 1 mg, the C1D2 is about 2 mg, and the C1D3 is about 13.5 mg, and (b) the C2D1 is greater than or equal to C1 D3. In some instances, (a) the C1D1 is about 1 mg, the C1D2 is about 2 mg, and the C1D3 is about 13.5 mg, and (b) the C2D1 is about 13.5 mg. In some instances, (a) the C1D1 is about 1 mg, the C1D2 is about 2 mg, and the C1D3 is about 20 mg, and (b) the C2D1 is greater than or equal to C1D3. In some instances, (a) the C1D1 is about 1 mg, the C1D2 is about 2 mg, and the C1D3 is about 20 mg, and (b) the C2D1 is about 20 mg. In other instances, (a) the C1D1 is about 1 mg, the C1D2 is about 2 mg, and the C1 D3 is about 40 mg, and (b) the C2D1 is greater than or equal to C1D3. In some instances, (a) the C1D1 is about 1 mg, the C1D2 is about 2 mg, and the C1D3 is about 40 mg, and (b) the C2D1 is about 40 mg. In other instances, (a) the C1D1 is about 1 mg, the C1 D2 is about 2 mg, and the C1D3 is about 60 mg, and (b) the C2D1 is greater than or equal to C1D3. In some instances, (a) the C1D1 is about 1 mg, the C1D2 is about 2 mg, and the C1D3 is about 60 mg, and (b) the C2D1 is about 60 mg. In other instances, (a) the C1D1 is about 5 mg, the C1D2 is about 15 mg, and the C1D3 is about 45 mg, and (b) the C2D1 is about 45 mg. In some instances, (a) the C1D1 is about 5 mg, the C1D2 is about 45 mg, and the C1D3 is about 45 mg, and (b) the C2D1 is about 45 mg.

In some instances of the methods described above, the first dosing cycle includes administering to the subject a single dose C1D1 of the anti-CD79b ADC. In some instances, the single dose C1D1 of the anti-CD79b ADC is between about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some instances, the single dose C1D1 of the anti-CD79b ADC is about 1.8 mg/kg. In some instances, the second dosing cycle may include administering to the subject a single dose C2D1 of the anti-CD79b ADC. In some instances, the single dose C2D1 of the anti-CD79b ADC is between about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some instances, the single dose C2D1 of the anti-CD79b ADC is about 1.8 mg/kg.

In some instances, the methods described herein may include a first dosing cycle of 14 to 28 days (e.g., 14 days, 15 days, 16 days, 17 days, 18 days, 19 days, 20 days, 21 days, 22 days, 23 days, 24 days, 25 days, 26 days, 27 days, or 28 days). In some instances, the length of the first dosing cycle is about three weeks or 21 days. In some instances, the methods may include administering to the subject the C1D1 of the bispecific antibody, the C1D2 of the bispecific antibody, and the C1D3 of the bispecific antibody on or about Days 1, 8, and 15, respectively (e.g., Day 1±3 days, Day 8±3 days, and Day 15+3 days, respectively), of the first dosing cycle.

In some instances, the methods described herein may include a second dosing cycle of 14 to 28 days (e.g., 14 days, 15 days, 16 days, 17 days, 18 days, 19 days, 20 days, 21 days, 22 days, 23 days, 24 days, 25 days, 26 days, 27 days, or 28 days). In some instances, the length of the second dosing cycle is about three weeks or 21 days. In some instances, the methods may include administering to the subject the C2D1 of the bispecific antibody on or about Day 1 (e.g., Day 1±3 days) of the second dosing cycle.

In some instances, the methods described above may include one or more additional dosing cycles (e.g., in addition to the first and second dosing cycles). In some instances, the dosing regimen includes 1 to 15 additional dosing cycles (e.g., 1, 2, 3, 4, 5, 6, 7, 8, 9, 10, 11, 12, 13, 14, or 15 additional dosing cycles; i.e., the dosing regimen includes one or more of additional dosing cycle(s) C3, C4, C5, C6, C7, C8, C9, C10, C11, C12, C13, C14, C15, C16, and C17). In some instances, the dosing regimen includes 6 to 15 additional dosing cycles (e.g., 6, 7, 8, 9, 10, 11, 12, 13, 14, or 15 additional cycles). In some instances, the length of each of the one or more additional dosing cycles is 7 days, 14 days, 21 days, or 28 days (e.g., 7±3 days, 14±3 days, 21±3 days, or 28±3 days, respectively). In some instances, the length of each of the one or more additional dosing cycles is three weeks or 21 days. In some instances, each of the one or more additional dosing cycles comprises an additional single dose of the bispecific antibody and an additional single dose of the anti-CD79b ADC. In some instances, each additional single dose of the anti-CD79b ADC is equivalent in amount to the C2D1 of the bispecific antibody. In some instances, the provided methods include administering to the subject the additional single doses of the anti-CD79b ADC on or about Day 1 of each of the one or more additional dosing cycles. In some instances, the each of the additional dosing cycles only include an additional single dose of the bispecific antibody, and not an additional dose of the anti-CD79b ADC. In some instances, each additional single dose of the bispecific antibody is equivalent in amount to the C2D1 of the bispecific antibody. In some instances, the provided methods include administering to the subject the additional single doses of the bispecific antibody on or about Day 1 of each of the one or more additional dosing cycles. In some instances, the dosing regimen described above may include six or more additional dosing cycles, wherein each of the six or more additional dosing cycles include an additional single dose of the bispecific antibody, and where no more than four of the six or more additional dosing cycles include an additional single dose of the anti-CD79b ADC.

The invention additionally provides methods for treating a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) by administering to the subject an anti-CD79b ADC and a bispecific antibody that binds to CD20 and CD3 in a dosing regimen including at least a first dosing cycle and a second dosing cycle, wherein: (a)(i) the first dosing cycle includes a first dose (C1D1) of the anti-CD79 ADC; (a)(ii) the first dosing cycle includes a first dose (C1D1) and a second dose (C1D2) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); (b)(i) the second dosing cycle includes a single dose (C2D1) of the anti-CD79b ADC; and (b)(ii) the second dosing cycle includes a single dose (C2D1) of the bispecific antibody, wherein the C2D1 of the bispecific antibody is greater than or equal to the C1D2 of the bispecific antibody.

The invention also provides methods for treating a subject having a CD20-positive cell proliferative disorder, e.g., a B cell proliferative disorder (e.g., an NHL (e.g., a relapsed and/or refractory NHL, a DLBCL (e.g., relapsed and/or refractory DLBCL), a FL (e.g., a relapsed and/or refractory FL or a transformed FL), or an MCL (e.g., a relapsed and/or refractory MCL)), a CLL, or a CNSL) including administering to the subject an anti-CD79b ADC and a bispecific antibody that binds to CD20 and CD3 in a dosing regimen including at least a first dosing cycle and a second dosing cycle, wherein: (a)(i) the first dosing cycle includes a first dose (C1D1) of the anti-CD79b ADC; (a)(ii) the first dosing cycle includes a first dose (C1D1) of the bispecific antibody, a second dose (C1D2) of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); (b)(i) the second dosing cycle includes a single dose (C2D1) of the anti-CD79b ADC; and (b)(ii) the second dosing cycle includes a single dose (C2D1) of the bispecific antibody, wherein the C2D1 of the bispecific antibody is greater than or equal to the C1D2 of the bispecific antibody and is about 9 mg, about 13.5 mg, about 20 mg, about 45 mg, or about 60 mg.

In some instances, for example, (a) the C1 D1 of the bispecific antibody is between about 0.02 mg to about 5 mg and the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and (b) the C2D1 of the bispecific antibody is greater than or equal to the C1D2 of the bispecific antibody. In some instances, (a) the C1D1 of the bispecific antibody is about 1 mg and the C1D2 of the bispecific antibody is about 2 mg, and (b) the C2D1 of the bispecific antibody is greater than or equal to the C1D2 of the bispecific antibody. In some instances, (a) the C1D1 of the bispecific antibody is about 1 mg and the C1D2 of the bispecific antibody is about 2 mg, and (b) the C2D1 of the bispecific antibody is about 9 mg. In some instances, (a) the C1D1 of the bispecific antibody is about 1 mg and the C1D2 of the bispecific antibody is about 2 mg, and (b) the C2D1 of the bispecific antibody is about 13.5 mg. In some instances, (a) the C1D1 of the bispecific antibody is about 1 mg and the C1D2 of the bispecific antibody is about 2 mg, and (b) the C2D1 of the bispecific antibody is about 20 mg. In some instances, (a) the C1 D1 of the bispecific antibody is about 1 mg and the C1D2 of the bispecific antibody is about 2 mg, and (b) the C2D1 of the bispecific antibody is about 40 mg. In other instances, (a) the C1D1 is about 1 mg and the C1D2 is about 2 mg, and (b) the C2D1 is greater than or equal to C1D3. In some instances, (a) the C1D1 is about 1 mg and the C1D2 is about 2 mg, and (b) the C2D1 is about 60 mg. In other instances, (a) the C1D1 is about 5 mg and the C1 D2 is about 15 mg, and (b) the C2D1 is about 45 mg. In some instances, (a) the C1D1 is about 5 mg and the C1 D2 is about 45 mg, and (b) the C2D1 is about 45 mg.

In any of the above instances, the dosing regimen may include a first dosing cycle and a second dosing cycle, wherein: (a) the first dosing cycle includes a C1D1 and a C1D2 of the bispecific antibody, and (b) the second dosing cycle includes a C2D1 of the bispecific antibody. In any of the above instances, the dosing regimen may include at least a first dosing cycle and a second dosing cycle, wherein: (a) the first dosing cycle includes a C1D1 and a C1D2 of the bispecific antibody, and (b) the second dosing cycle includes a C2D1 of the bispecific antibody.

In some instances of the methods described above, the first dosing cycle may include administering to the subject a single dose C1D1 of the anti-CD79b ADC. In some instances, the single dose C1 D1 of the anti-CD79b ADC is between about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some instances, the single dose C1D1 of the anti-CD79b ADC is about 1.8 mg/kg. In some instances, the second dosing cycle may include administering to the subject a single dose C2D1 of the anti-CD79b ADC. In some instances, the single dose C2D1 of the anti-CD79b ADC is between about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some instances, the single dose C2D1 of the anti-CD79b ADC is about 1.8 mg/kg.

In some instances, the methods described above may include a first dosing cycle of 14 to 28 days (e.g., 14 days, 15 days, 16 days, 17 days, 18 days, 19 days, 20 days, 21 days, 22 days, 23 days, 24 days, 25 days, 26 days, 27 days, or 28 days). In some instances, the length of the first dosing cycle is about three weeks or 21 days. In some instances, the methods may include administering to the subject the C1D1 of the bispecific antibody and the C1D2 of the bispecific antibody on or about Days 8 and 15, respectively (e.g., Day 8±3 days and Day 15±3 days, respectively), of the first dosing cycle.

In some instances, the methods described above may include a second dosing cycle of 14 to 28 days (e.g., 14 days, 15 days, 16 days, 17 days, 18 days, 19 days, 20 days, 21 days, 22 days, 23 days, 24 days, 25 days, 26 days, 27 days, or 28 days). In some instances, the length of the second dosing cycle is about three weeks or 21 days. In some instances, the methods may include administering to the subject the C2D1 of the bispecific antibody on or about Day 1 (e.g., Day 1±3 days) of the second dosing cycle.

In some instances, the methods described above may include one or more additional dosing cycles. In some instances, the dosing regimen includes 1 to 15 additional dosing cycles (e.g., 1, 2, 3, 4, 5, 6, 7, 8, 9, 10, 11, 12, 13, 14, or 15 additional dosing cycles; i.e., the dosing regimen includes one or more of additional dosing cycle(s) C3, C4, C5, C6, C7, C8, C9, C10, C11, C12, C13, C14, C15, C16, and C17). In some instances, the dosing regimen includes 6 to 15 additional dosing cycles (e.g., 6, 7, 8, 9, 10, 11, 12, 13, 14, or 15 additional cycles). In some instances, the length of each of the one or more additional dosing cycles is 7 days, 14 days, 21 days, or 28 days (e.g., 7±3 days, 14±3 days, 21±3 days, or 28±3 days, respectively). In some instances, the length of each of the one or more additional dosing cycles is three weeks or 21 days. In some instances, each of the one or more additional dosing cycles comprises an additional single dose of the bispecific antibody and an additional single dose of the anti-CD79b ADC. In some instances, each additional single dose of the anti-CD79b ADC is equivalent in amount to the C2D1 of the bispecific antibody. In some instances, the provided methods include administering to the subject the additional single doses of the anti-CD79b ADC on or about Day 1 of each of the one or more additional dosing cycles. In some instances, the each of the additional dosing cycles only include an additional single dose of the bispecific antibody, and not an additional dose of the anti-CD79b ADC. In some instances, each additional single dose of the bispecific antibody is equivalent in amount to the C2D1 of the bispecific antibody. In some instances, the provided methods include administering to the subject the additional single doses of the bispecific antibody on or about Day 1 of each of the one or more additional dosing cycles. In some instances, the dosing regimen described above may include six or more additional dosing cycles, wherein each of the six or more additional dosing cycles include an additional single dose of the bispecific antibody, and where no more than four of the six or more additional dosing cycles include an additional single dose of the anti-CD79b ADC.

The invention additionally provides methods for treating a subject having a CD20-positive cell proliferative disorder, e.g., B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subject an anti-CD79b ADC and a bispecific antibody that binds to CD20 and CD3 in a dosing regimen including eight or more dosing cycles, wherein: (a)(i) the first dosing cycle includes a first dose (C1D1), a second dose (C1D2), and a third dose (C1D3) of the bispecific antibody, wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1 D3 is about 9 mg, about 13.5 mg, about 20 mg, about 40 mg, about 45 mg, or about 60 mg; (a)(ii) the first dosing cycle includes a single dose (C1D1) of the anti-CD79b ADC; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1, C3D1, C4D1, C5D1, C6D1, C7D1, and C8D1 of the bispecific antibody are each greater than or equal to the C1D3 of the bispecific antibody.

The invention also provides methods for treating a subject having a CD20-positive cell proliferative disorder, e.g., a B cell proliferative disorder (e.g., an NHL (e.g., a DLBCL (e.g., relapsed and/or refractory DLBCL), a FL (e.g., a relapsed and/or refractory FL or a transformed FL), or an MCL (e.g., a relapsed or refractory MCL)), a CLL, or a CNSL) including administering to the subject a bispecific antibody that binds to CD20 and CD3 in a dosing regimen including at least eight or more dosing cycles, wherein: (a)(i) the first dosing cycle includes a first dose (C1D1), a second dose (C1D2), and a third dose (C1D3) of the bispecific antibody, the C1D3 of the bispecific antibody is greater than or equal to the C1D2 and C1D1 of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1 D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; (a)(ii) the first dosing cycle includes a single dose (C1D1) of the anti-CD79b ADC; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1, C3D1, C4D1, C5D1, C6D1, C7D1, and C8D1 of the bispecific antibody are each greater than or equal to the C1D3 of the bispecific antibody and are each about 9 mg, about 13.5 mg, about 20 mg, about 40 mg, about 45 mg, or about 60 mg.

In some instances, the C1 D3 and C2D1-C8D1 of the bispecific antibody are about equivalent in amount. In some instances, the C1D1-C6D1 of the anti-CD79b ADC are about equivalent in amount.

The invention additionally provides methods for treating a subject having a CD20-positive cell proliferative disorder, e.g., B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subject an anti-CD79b ADC and a bispecific antibody that binds to CD20 and CD3 in a dosing regimen including eight or more dosing cycles, wherein: (a)(i) the first dosing cycle includes a first dose (C1D1), a second dose (C1D2), and a third dose (C1D3) of the bispecific antibody, wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1 D3 is about 9 mg, about 13.5 mg, about 20 mg, about 40 mg, about 45 mg, or about 60 mg; (a)(ii) the first dosing cycle includes a single dose (C1D1) of the anti-CD79b ADC; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C1 D3 and the C2D1 are about equivalent in amount, and the C3D1, C4D1, C5D1, C6D1, C7D1, and C8D1 of the bispecific antibody are each less than the C1D3 of the bispecific antibody.

The invention also provides methods for treating a subject having a CD20-positive cell proliferative disorder, e.g., a B cell proliferative disorder (e.g., an NHL (e.g., a DLBCL (e.g., relapsed and/or refractory DLBCL), a FL (e.g., a relapsed and/or refractory FL or a transformed FL), or an MCL (e.g., a relapsed or refractory MCL)), a CLL, or a CNSL) including administering to the subject a bispecific antibody that binds to CD20 and CD3 in a dosing regimen including at least eight or more dosing cycles, wherein: (a)(i) the first dosing cycle includes a first dose (C1D1), a second dose (C1D2), and a third dose (C1D3) of the bispecific antibody, the C1D3 of the bispecific antibody is greater than or equal to the C1D2 and C1D1 of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1 D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; (a)(ii) the first dosing cycle includes a single dose (C1D1) of the anti-CD79b ADC; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C3D1 and the C2D1 are about equivalent in amount, and the C3D1, C4D1, C5D1, C6D1, C7D1, and C8D1 of the bispecific antibody are each less than the C1D3 of the bispecific antibody and are each between about 10 mg and about 45 mg (e.g., between about 10 mg and about 40 mg, between about 10 mg and about 35 mg, between about 15 mg and about 45 mg, between about 20 mg and about 45 mg, or between about 25 mg and about 45 mg; e.g., about 30 mg). In some instances, each of the C3D1-C8D1 are about 30 mg.

In some instances, in the methods described above, each single dose C1D1-C6D1 of the anti-CD79b ADC is between about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some instances, each single dose C1D1-C6D1 of the anti-CD79b ADC is about 1.8 mg/kg.

In some instances, the methods described above may include a first dosing cycle of 14 to 28 days (e.g., 14 days, 15 days, 16 days, 17 days, 18 days, 19 days, 20 days, 21 days, 22 days, 23 days, 24 days, 25 days, 26 days, 27 days, or 28 days). In some instances, the length of the first dosing cycle is about three weeks or 21 days. In some instances, the methods may include administering to the subject the C1D1 of the bispecific antibody, the C1D2 of the bispecific antibody, and the C1D3 of the bispecific antibody on or about Days 1, 8, and 15, respectively (e.g., Day 1±3 days, Day 8±3 days, and Day 15+3 days, respectively), of the first dosing cycle. In some instances, each single dose C1D1-C8D1 of the bispecific antibodies is administered to the subject on Day 1 (e.g., Day 1±3 days) of each dosing cycle.

In some instances, each single dose C1D1-C6D1 of the anti-CD79b ADC is administered to the subject on Day 1 (e.g., Day 1±3 days) of each dosing cycle. In some instances, the length of each of the one or more additional dosing cycles is 7 days, 14 days, 21 days, or 28 days (e.g., 7±3 days, 14±3 days, 21±3 days, or 28±3 days, respectively). In some instances, the length of each of the one or more additional dosing cycles is three weeks or 21 days.

The invention additionally provides methods for treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subject an anti-CD79b ADC and a bispecific antibody that binds to CD20 and CD3 in a dosing regimen including eight or more dosing cycles, wherein: (a) the first dosing cycle includes a first dose (C1D1), a second dose (C1D2), and a third dose (C1D3) of the bispecific antibody, wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1 D3 is about 9 mg, about 13.5 mg, about 20 mg, about 40 mg, about 45 mg, or about 60 mg; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1, C3D1, C4D1, C5D1, C6D1, C7D1, and C8D1 of the bispecific antibody are each greater than or equal to the C1D3 of the bispecific antibody.

The invention also provides methods for treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) including administering to the subject a bispecific antibody that binds to CD20 and CD3 in a dosing regimen including at least eight or more dosing cycles, wherein: (a) the first dosing cycle includes a first dose (C1D1), a second dose (C1D2), and a third dose (C1D3) of the bispecific antibody, the C1D3 of the bispecific antibody is greater than or equal to the C1D2 and C1D1 of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1, C3D1, C4D1, C5D1, C6D1, C7D1, and C8D1 of the bispecific antibody are each greater than or equal to the C1D3 of the bispecific antibody and are each about 9 mg, about 13.5 mg, about 20 mg, about 40 mg, about 45 mg, or about 60 mg.

In some instances, the C1 D3 and C2D1-C8D1 of the bispecific antibody are about equivalent in amount. In some instances, the C2D1-C6D1 of the anti-CD79b ADC are about equivalent in amount.

In some instances, in the methods described above, each single dose C2D1-C6D1 of the anti-CD79b ADC is between about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some instances, each single dose C2D1-C6D1 of the anti-CD79b ADC is about 1.8 mg/kg.

In some instances, the methods described above may include a first dosing cycle of three weeks or 21 days. In some instances, the methods may include administering to the subject the C1D1 of the bispecific antibody, the C1D2 of the bispecific antibody, and the C1D3 of the bispecific antibody on or about Days 1, 8, and 15, respectively, of the first dosing cycle. In some instances, each single dose C1D1-C8D1 of the bispecific antibodies is administered to the subject on Day 1 of each dosing cycle. In some instances, each single dose C2D1-C6D1 of the anti-CD79b ADC is administered to the subject on Day 1 of each dosing cycle. In some instances, the length of each of the one or more additional dosing cycles is 7 days, 14 days, 21 days, or 28 days (e.g., 7±3 days, 14±3 days, 21±3 days, or 28±3 days, respectively). In some instances, the length of each of the one or more additional dosing cycles is three weeks or 21 days.

The invention additionally provides methods for treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) including administering to the subject an anti-CD79b ADC and a bispecific antibody that binds to CD20 and CD3 in a dosing regimen including eight or more dosing cycles, wherein: (a)(i) the first dosing cycle includes a first dose (C1D1) and a second dose (C1D2) of the bispecific antibody, wherein the C1D1 of the bispecific antibody is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 of the bispecific antibody is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); (a)(ii) the first dosing cycle includes a first dose (C1D1) of the anti-CD79 ADC; (b)(i) the second dosing cycle includes a single dose (C2D1) of the anti-CD79b ADC; (b)(ii) the second dosing cycle includes a single dose (C2D1) of the bispecific antibody, wherein the C2D1 of the bispecific antibody is greater than or equal to the C1D3 of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody. In some instances, the C2D1, C3D1, C4D1, C5D1, C6D1, C7D1, and C8D1 of the bispecific antibody are each greater than C1D2 of the bispecific antibody.

The invention also provides methods for treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subject an anti-CD79b ADC and a bispecific antibody that binds to CD20 and CD3 in a dosing regimen including at least a first dosing cycle and a second dosing cycle, wherein: (a)(i) the first dosing cycle includes a first dose (C1D1) of the bispecific antibody, a second dose (C1D2) of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); (a)(ii) the first dosing cycle includes a first dose (C1D1) of the anti-CD79b ADC; (b)(i) the second dosing cycle includes a single dose (C2D1) of the anti-CD79b ADC; and (b)(ii) the second dosing cycle includes a single dose (C2D1) of the bispecific antibody, wherein the C2D1 is about 9 mg, about 13.5 mg, about 20 mg, about 40 mg, about 45 mg, or about 60 mg; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1 of the bispecific antibody is greater than or equal to the C1D2 of the bispecific antibody, wherein the C3D1, C4D1, C5D1, C6D1, C7D1, and C8D1 of the bispecific antibody are each greater than the C1D2 of the bispecific antibody and are each about 9 mg, about 13.5 mg, about 20 mg, about 45 mg, or about 60 mg.

In some instances, the C2D1-C8D1 of the bispecific antibody are about equivalent in amount. In some instances, the C1D1-C6D1 of the anti-CD79b ADC are about equivalent in amount.

In some instances, each single dose C1D1-C6D1 of the anti-CD79b ADC is between about 0.5 mg/kg to about 10 mg/kg (e.g., between about 0.5 mg/kg to about 9 mg/kg, between about 0.5 mg/kg to about 8 mg/kg, between about 0.5 mg/kg to about 7 mg/kg, between about 0.5 mg/kg to about 6 mg/kg, between about 0.5 mg/kg to about 5 mg/kg, between about 0.5 mg/kg to about 4 mg/kg, between about 0.5 mg/kg to about 3 mg/kg, between about 0.5 mg/kg to about 2 mg/kg, between about 0.75 mg/kg to about 10 mg/kg, between about 1 mg/kg to about 10 mg/kg, between about 1.5 mg/kg to about 10 mg/kg, between about 1 mg/kg to about 5 mg/kg, between about 1 mg/kg to about 3 mg/kg, between about 1.5 mg/kg to about 2.5 mg/kg, between about 1.5 mg/kg to about 2 mg/kg, or about 1.8 mg/kg). In some instances, each single dose C1D1-C6D1 of the anti-CD79b ADC is about 1.8 mg/kg.

In some instances, the C1 D1 of the bispecific drug may be administered to the subject after the C1D1 of the anti-CD79b ADC. In some instances, the C1D1 of the bispecific drug may be administered to the subject about one week or about 7 days (e.g., 7±3 days) after the C1D1 of the anti-CD79b ADC.

In some instances, the methods may include administering to the subject the C1D1 of the bispecific antibody and the C1D2 of the bispecific antibody on or about Days 8 and 15, respectively (e.g., Day 8±3 days and Day 15±3 days, respectively), of the first dosing cycle. In some instances, each single dose C2D1-C8D1 of the bispecific antibodies is administered to the subject on Day 1 (e.g., Day 1+3 days) of each dosing cycle. In some instances, each single dose C1 D1-C6D1 of the anti-CD79b ADC is administered to the subject on Day 1 (e.g., Day 1±3 days) of each dosing cycle. In some instances, the length of each of the one or more additional dosing cycles is 7 days, 14 days, 21 days, or 28 days (e.g., 7±3 days, 14±3 days, 21±3 days, or 28±3 days, respectively). In some instances, the length of each of the one or more additional dosing cycles is three weeks or 21 days.

In some instances, the methods described above may include a dosing regimen in which each of one or more additional dosing cycles include a single dose of the bispecific antibody. In some instances, the dosing regimen may include one to nine additional dosing cycles, wherein each additional dosing cycle does not include the administration of the anti-CD79b ADC to the subject. In some instances, the length of each of the one or more additional dosing cycles is 7 days, 14 days, 21 days, or 28 days (e.g., 7±3 days, 14±3 days, 21±3 days, or 28±3 days, respectively). In some instances, the length of each of the one or more additional dosing cycles is three weeks or 21 days.

In the methods provided above, the anti-CD79b antibody drug conjugate includes anti-CD79b-MC-vc-PAB-MMAE, the anti-CD79b antibody drug conjugate described in any one of U.S. Pat. No. 8,088,378 and/or US 2014/0030280, or polatuzumab vedotin. In some instances, the anti-CD79b ADC is polatuzumab vedotin. In some instances, the bispecific anti-CD20/anti-CD3 antibody and the anti-CD79b ADC exhibit a synergistic effect in a mouse NSG:human WSU-DLCL2 model system (see, e.g., WO 2013/059944) when compared to either the bispecific antibody or the anti-CD79b antibody drug conjugate alone. WSU-DLCL2 is a human DLBCL cell line isolated from the pleural effusion of a 41-year-old Caucasian male (Leibnitz Institute-DSMZ, Cat. #ACC 575). NSG mice can be obtained from Jackson Labs (The Jackson Laboratory; stock no. 005557).

In some instances, the methods described above include administering the anti-CD79b ADC and the bispecific anti-CD20/anti-CD3 antibody with a further chemotherapy agent and/or an antibody-drug conjugate (ADC). In some instances, the bispecific anti-CD20/anti-CD3 antibody is co-administered with one or more additional chemotherapy agents selected from cyclophosphamide and doxorubicin. In some instances, the bispecific anti-CD20/anti-CD3 antibody is co-administered with an ADC. In some instances, the bispecific anti-CD20/anti-CD3 antibody is co-administered with CHOP, wherein vincristine is replaced with an ADC.

In some instances, the methods described above include administering the anti-CD79b ADC and the bispecific anti-CD20/anti-CD3 antibody with a corticosteroid. In some instances, the corticosteroid is dexamethasone (CAS #: 50-02-2), prednisone (CAS #: 53-03-2), or methylprednisolone (CAS #: 83-43-2).

Any of the methods of the invention described herein may be useful for treating CD20-positive cell proliferative disorders, e.g., B cell proliferative disorders/malignancies. In particular, B cell proliferative disorders amenable to treatment with a bispecific anti-CD20/anti-CD3 antibody in accordance with the methods described herein include, without limitation, non-Hodgkin's lymphoma (NHL), including diffuse large B cell lymphoma (DLBCL), which may be relapsed or refractory DLBCL, as well as other cancers including germinal-center B cell-like (GCB) diffuse large B cell lymphoma (DLBCL), activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, heavy chain diseases, a heavy chain disease, γ heavy chain disease, p heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, primary mediastinal (thymic) large B cell lymphoma (PMLBCL), intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and Burkitt lymphoma, and B cell lymphoma, unclassifiable, with features intermediate between DLBCL and classical Hodgkin's lymphoma. Further examples of B cell proliferative disorders include, but are not limited to, multiple myeloma (MM); low grade/follicular NHL; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; AIDS-related lymphoma; and acute lymphoblastic leukemia (ALL); chronic myeloblastic leukemia; and post-transplant lymphoproliferative disorder (PTLD). In particular instances, the B cell proliferative disorder may be an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL). In some instances, the NHL is an aggressive NHL (e.g., de novo DLBCL, transformed FL, or Grade 3b FL). In some instances, the NHL is a DLBCL. In some instances, the NHL is a R/R MCL.

Any of the methods of the invention described herein may be useful for treating a population of subjects having a CD20-positive cell proliferative disorder. In some instances, the invention provides methods for treating a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subjects an anti-CD79b antibody drug conjugate and a bispecific antibody that binds to CD20 and CD3 in a dosing regimen comprising at least a first dosing cycle and a second dosing cycle, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg (e.g., between about 0.05 mg to about 2 mg, between about 0.1 mg to about 2 mg, between about 0.5 mg to about 2 mg, between about 0.5 mg to about 1.5 mg, between about 0.8 mg to about 1.2 mg, between about 0.5 mg to about 1 mg, or between about 1 mg to about 2 mg, e.g., about 0.5 mg, about 0.8 mg, about 0.9 mg, about 1 mg, about 1.1 mg, about 1.2 mg, about 1.5 mg, or about 2 mg), the C1D2 of the bispecific antibody is between about 0.05 mg to about 5 mg (e.g., between about 0.1 mg to about 5 mg, between about 0.1 mg to about 4 mg, between about 0.1 mg to about 3 mg, between about 0.5 mg to about 3 mg, between about 1 mg to about 3 mg, between about 1.5 mg to about 2.5 mg, between about 1.8 mg to about 2.2 mg, between about 3 mg to about 5 mg, between about 2 mg to about 4 mg, or between about 1 mg to about 5 mg; e.g., about 0.5 mg, about 1 mg, about 1.5 mg, about 1.8 mg, about 1.9 mg, about 2 mg, about 2.1 mg, about 2.2 mg, about 2.5 mg, about 3 mg, about 4 mg, or about 5 mg), and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises: (i) a single dose (C2D1) of the bispecific antibody, wherein the C2D1 of the bispecific antibody is about equivalent in amount to the C1D3; and (ii) a single dose (C2D1) of the anti-CD79b antibody drug conjugate, wherein the C1D1 of the anti-CD79b antibody drug conjugate and the C2D1 of the anti-CD79b antibody drug conjugate are each about 1.8 mg/kg.

The invention also provides methods for treating a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subjects an anti-CD79b antibody drug conjugate and a bispecific antibody that binds to CD20 and CD3 in a dosing regimen comprising at least a first dosing cycle and a second dosing cycle, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is about 1 mg, the C1D2 of the bispecific antibody is about 2 mg, and the C1 D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises: (i) a single dose (C2D1) of the bispecific antibody, wherein the C2D1 of the bispecific antibody is about equivalent in amount to the C1D3; and (ii) a single dose (C1D1) of the anti-CD79b antibody drug conjugate, wherein the C1D1 of the anti-CD79b antibody drug conjugate and the C2D1 of the anti-CD79b antibody drug conjugate are each about 1.8 mg/kg.

The invention also provides methods for treating a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subjects an anti-CD79b antibody drug conjugate and a bispecific antibody that binds to CD20 and CD3 in a dosing regimen comprising eight or more dosing cycles, wherein: (a) the first dosing cycle comprises: (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg (e.g., between about 0.05 mg to about 2 mg, between about 0.1 mg to about 2 mg, between about 0.5 mg to about 2 mg, between about 0.5 mg to about 1.5 mg, between about 0.8 mg to about 1.2 mg, between about 0.5 mg to about 1 mg, or between about 1 mg to about 2 mg, e.g., about 0.5 mg, about 0.8 mg, about 0.9 mg, about 1 mg, about 1.1 mg, about 1.2 mg, about 1.5 mg, or about 2 mg), the C1D2 of the bispecific antibody is between about 0.05 mg to about 5 mg (e.g., between about 0.1 mg to about 5 mg, between about 0.1 mg to about 4 mg, between about 0.1 mg to about 3 mg, between about 0.5 mg to about 3 mg, between about 1 mg to about 3 mg, between about 1.5 mg to about 2.5 mg, between about 3 mg to about 5 mg, between about 2 mg to about 4 mg, or between about 1 mg to about 5 mg; e.g., about 0.5 mg, about 1 mg, about 1.5 mg, about 1.8 mg, about 1.9 mg, about 2 mg, about 2.1 mg, about 2.2 mg, about 2.5 mg, about 3 mg, about 4 mg, or about 5 mg), and the C1D3 of the bispecific antibody is about 9 mg, about 13.5 mg, about 20 mg, or about 40 mg; and (ii) a single dose (C1D1) of the anti-CD79b antibody drug conjugate; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody about equivalent in amount to the C1D3, and wherein each single dose C1D1-C6D1 of the anti-CD79b antibody drug conjugate is about 1.8 mg/kg.

The invention further provides methods for treating a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to the subjects an anti-CD79b antibody drug conjugate and a bispecific antibody that binds to CD20 and CD3 in a dosing regimen comprising eight or more dosing cycles, wherein: (a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, or about 40 mg; (b) the second dosing cycle comprises a single dose (C2D1) of the bispecific antibody and a single dose (C2D1) of the anti-CD79b antibody drug conjugate; (c) the third dosing cycle comprises a single dose (C3D1) of the bispecific antibody and a single dose (C3D1) of the anti-CD79b antibody drug conjugate; (d) the fourth dosing cycle comprises a single dose (C4D1) of the bispecific antibody and a single dose (C4D1) of the anti-CD79b antibody drug conjugate; (e) the fifth dosing cycle comprises a single dose (C5D1) of the bispecific antibody and a single dose (C5D1) of the anti-CD79b antibody drug conjugate; (f) the sixth dosing cycle comprises a single dose (C6D1) of the bispecific antibody and a single dose (C6D1) of the anti-CD79b antibody drug conjugate; (g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is about equivalent in amount to the C1D3, and wherein each single dose C1D1-C6D1 of the anti-CD79b antibody drug conjugate is about 1.8 mg/kg.

In some embodiments, the CD20-positive cell proliferative disorder is an NHL. In some embodiments, the overall response rate is at least 55% (e.g., at least 60%, at least 65%, at least 70%, at least 75%, at least 80%, at least 85%, at least 90%, or at least 95%; e.g., between 55% and 100%, between 55% and 90%, between 55% and 80%, between 55% and 70%, between 55% and 65%, between 55% and 60%, between 60% and 65%, between 60% and 70%, between 60% and 90%, or between 70% and 90%; e.g., about 55%, about 60%, about 65%, about 66%, about 67%, about 68%, about 69%, about 70%, about 75%, about 80%, about 85%, about 90%, or about 95%). In some embodiments, the overall response rate is at least 65%. In some embodiments, the complete response rate is at least 45% (e.g., at least 50%, at least 55%, at least 60%, at least 65%, at least 70%, at least 80%, at least 85%, at least 90%, or at least 95%; e.g., between 45% and 100%, between 45% and 80%, between 45% and 60%, between 45% and 55%, between 45% and 50%, between 50% and 55%, between 50% and 65%, between 50% and 70%, between 60% and 70%, or between 70% and 90%; e.g., about 45%, about 50%, about 53%, about 54%, about 55%, about 56%, about 57%, about 60%, about 65%, about 70%, about 75%, about 80%, about 85%, about 90%, or about 95%). In some embodiments, the complete response rate is at least 55%.

In some embodiments, the CD20-positive cell proliferative disorder is an aggressive NHL (e.g., de novo DLBCL, transformed FL, or Grade 3b FL). In some embodiments, the overall response rate is at least 50% (e.g., at least 55%, at least 60%, at least 65%, at least 70%, at least 75%, at least 80%, at least 85%, at least 90%, or at least 95%; e.g., between 50% and 100%, between 50% and 80%, between 50% and 60%, between 50% and 55%, between 55% and 60%, between 55% and 65%, between 50% and 70%, between 60% and 70%, or between 70% and 90%; e.g., about 50%, about 55%, about 60%, about 61%, about 62%, about 63%, about 64%, about 65%, about 70%, about 75%, about 80%, about 85%, about 90%, or about 95%). In some embodiments, the overall response rate is at least 60%. In some embodiments, the complete response rate is at least 35% (e.g., at least 40%, at least 45%, at least 50%, at least 55%, at least 60%, at least 70%, at least 80%, or at least 90%; e.g., between 35% and 100%, between 35% and 80%, between 35% and 60%, between 35% and 55%, between 35% and 50%, between 35% and 45%, between 40% and 60%, between 45% and 50%, between 45% and 55%, between 45% and 60%, or between 50% and 70%; e.g., about 35%, about 40%, about 45%, about 46%, about 47%, about 48%, about 49%, about 50%, about 55%, about 60%, about 70%, about 80%, about 90%, or about 95%). In some embodiments, the complete response rate is at least 45%.

In some embodiments, the CD20-positive cell proliferative disorder is an NHL, and wherein the subjects of the population are post-CAR-T subjects (e.g., patients who were treated with CAR-T therapy at least 30 days prior to administration of the first study treatment (e.g., anti-CD20/anti-CD3 bispecific antibody and/or anti-CD79b antibody drug conjugate; e.g., mosunetuzumab and/or polatuzumab vedotin)). In some embodiments, the overall response rate is at least 50% (e.g., at least 55%, at least 60%, at least 65%, at least 70%, at least 80%, at least 85%, at least 90%, or at least 95%; e.g., between 50% and 100%, between 50% and 80%, between 50% and 60%, between 50% and 55%, between 55% and 60%, between 55% and 65%, between 50% and 70%, between 60% and 70%, or between 70% and 90%; e.g., about 50%, about 55%, about 56%, about 57%, about 58%, about 59%, about 60%, about 65%, about 70%, about 75%, about 80%, about 85%, about 90%, or about 95%). In some embodiments, the overall response rate is at least 55%. In some embodiments, the complete response rate is at least 20% (e.g., at least 25%, at least 30%, at least 35%, at least 40%, at least 50%, at least 60%, at least 70%, or at least 90%; e.g., between 20% and 100%, between 20% and 80%, between 20% and 60%, between 20% and 40%, between 20% and 30%, between 20% and 25%, between 25% and 30%, between 25% and 35%, between 25% and 50%, between 30% and 60%, or between 50% and 70%; e.g., about 20%, about 25%, about 26%, about 27%, about 28%, about 29%, about 30%, about 31%, about 35%, about 50%, about 60%, about 70%, about 80%, about 90%, or about 95%). In some embodiments, the complete response rate is at least 25%.

In some embodiments, the CD20-positive cell proliferative disorder is an FL. In some embodiments, the overall response rate is at least 80% (e.g., at least 85%, at least 90%, at least 95%, at least 97%, at least 98%, or at least 99%; e.g., between 80% and 100%, between 80% and 95%, between 80% and 90%, between 80% and 85%, between 85% and 95%, between 90% and 100%, or between 95% and 100%; e.g., about 80%, about 85%, about 90%, about 91%, about 92% about 93%, about 94%, about 95%, about 96%, about 97%, about 98%, about 99%, or about 100%). In some embodiments, the overall response rate is at least 90%. In some embodiments, the complete response rate is at least 80% (e.g., at least 85%, at least 90%, at least 95%, at least 97%, at least 98%, or at least 99%; e.g., between 80% and 100%, between 80% and 95%, between 80% and 90%, between 80% and 85%, between 85% and 95%, between 90% and 100%, or between 95% and 100%; e.g., about 80%, about 85%, about 90%, about 91%, about 92%, about 93%, about 94%, about 95%, about 96%, about 97%, about 98%, about 99%, or about 100%). In some embodiments, the complete response rate is at least 90%.

In some instances, the bispecific antibody is mosunetuzumab. In some instances, the anti-CD79b antibody drug conjugate is polatuzumab vedotin.

The methods described herein may result in an improved benefit-risk profile for subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) being treated with an anti-CD20/anti-CD3 bispecific antibody. In some instances, treatment using the methods described herein that result in administering the anti-CD20/anti-CD3 bispecific antibody in the context of a fractionated, dose-escalation dosing regimen results in a reduction (e.g., by 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater; e.g., between 20% and 100%, between 20% and 90%, between 20% and 80%, between 20% and 70%, between 20% and 60%, between 20% and 50%, between 20% and 40%, between 20% and 30%, between 40% and 100%, between 60% and 100%, between 80% and 100%, between 30% and 70%, between 40% and 60%, between 30% and 50%, between 50% and 80%, or between 90% and 100%; e.g., about 20%, about 25%, about 30%, about 35%, about 40%, about 45%, about 50%, about 55%, about 60%, about 65%, about 70%, about 75%, about 80%, about 85%, about 90%, about 95%, about 97%, about 99%, or about 100%) or complete inhibition (100% reduction) of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the fractionated, dose-escalation dosing regimen of the invention relative to treatment with an anti-CD20/anti-CD3 bispecific antibody using an non-fractioned dosing regimen.

B. Therapeutic Methods for Reducing the Rate of CRS

The methods and uses described herein may be used to reduce the rate and/or severity of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) who are administered an anti-CD79b ADC and a bispecific anti-CD20/anti-CD3 antibody.

The invention provides methods for reducing the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) including administering to one or more subjects of the population an anti-CD79b ADC and a bispecific antibody that binds to CD20 and CD3 in a dosing regimen including at least a first dosing cycle and a second dosing cycle, compared to a population of subjects to whom no anti-CD79b ADC has been administered, wherein: (a) the first dosing cycle includes a first dose (C1D1), a second dose (C1D2), and a third dose (C1D3) of the bispecific antibody, the C1D3 is greater than or equal to the C1 D2 and C1D1, and the C1D2 is greater than or equal to the C1D1, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 is about 9 mg, about 13.5 mg, about 20 mg, about 40 mg, about 45 mg, or about 60 mg; and (b) the second dosing cycle includes a single dose (C2D1) of the bispecific antibody, wherein the C2D1 is greater than or equal to the C1D3 and is about 9 mg, about 13.5 mg, about 20 mg, about 40 mg, about 45 mg, or about 60 mg.

The invention provides methods for reducing the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) including administering to one or more subjects of the population an anti-CD79b ADC and a bispecific antibody that binds to CD20 and CD3 in a dosing regimen including at least a first dosing cycle and a second dosing cycle, compared to a population of subjects to whom no anti-CD79b ADC has been administered, wherein: (a)(i) the first dosing cycle includes a first dose (C1D1) of the anti-CD79b ADC; (a)(ii) the first dosing cycle includes a first dose (C1D1) of the bispecific antibody, a second dose (C1D2) of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); (b)(i) the second dosing cycle includes a single dose (C2D1) of the anti-CD79b ADC; and (b)(ii) the second dosing cycle includes a single dose (C2D1) of the bispecific antibody, wherein the C2D1 of the bispecific antibody is about 9 mg, about 13.5 mg, about 20 mg, about 40 mg, about 45 mg, or about 60 mg.

The invention provides methods for reducing the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) including administering to one or more subjects of the population an anti-CD79b ADC and a bispecific antibody that binds to CD20 and CD3 in a dosing regimen including eight or more dosing cycles, compared to a population of subjects to whom no anti-CD79b ADC has been administered, wherein: (a)(i) the first dosing cycle includes a first dose (C1D1), a second dose (C1D2), and a third dose (C1D3) of the bispecific antibody, the C1D3 of the bispecific antibody is greater than or equal to the C1D2 and C1D1 of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, or about 45 mg; (a)(ii) the first dosing cycle includes a single dose (C1D1) of the anti-CD79b ADC; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1, C3D1, C4D1, C5D1, C6D1, C7D1, and C8D1 of the bispecific antibody are each greater than or equal to the C1D3 of the bispecific antibody and are each about 9 mg, about 13.5 mg, about 20 mg, about 45 mg, or about 60 mg.

The invention provides methods for reducing the rate of cytokine release syndrome in a population of subjects having a CD20-positive cell proliferative disorder, e.g., a B cell proliferative 5 disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) including administering to one or more subjects of the population an anti-CD79b ADC and a bispecific antibody that binds to CD20 and CD3 in a dosing regimen including eight or more dosing cycles, compared to a population of subjects to whom no anti-CD79b ADC has been administered, wherein: (a) the first dosing cycle includes a first dose (C1D1), a second dose (C1D2), and a third dose (C1D3) of the bispecific antibody, the C1D3 of the bispecific antibody is greater than or equal to the C1D2 and C1D1 of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg), and the C1D3 of the bispecific antibody is about 9 mg, about 13.5 mg, about 20 mg, about 40 mg, about 45 mg, or about 60 mg; (b) the second dosing cycle includes a single dose (C2D1) of the anti-CD79b ADC and a single dose (C2D1) of the bispecific antibody; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1, C3D1, C4D1, C5D1, C6D1, C7D1, and C8D1 of the bispecific antibody are each greater than or equal to the C1D3 of the bispecific antibody and are each about 9 mg, about 13.5 mg, about 20 mg, about 40 mg, about 45 mg, or about 60 mg.

The invention provides methods for reducing the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) including administering to one or more subjects of the population an anti-CD79b ADC and a bispecific antibody that binds to CD20 and CD3 in a dosing regimen including eight or more dosing cycles, compared to a population of subjects to whom no anti-CD79b ADC has been administered, wherein: (a)(i) the first dosing cycle includes a first dose (C1D1) of the bispecific antibody, a second dose (C1D2) of the bispecific antibody, and the C1D2 of the bispecific antibody is greater than or equal to the C1D1 of the bispecific antibody, and wherein the C1D1 is between about 0.02 mg to about 5.0 mg (e.g., about 0.05 mg to about 5 mg, about 0.1 mg to about 5.0 mg, about 0.5 mg to about 5.0 mg, about 1 mg to about 5.0 mg, about 2 mg to about 5.0 mg, about 3 mg to about 5.0 mg, about 0.05 mg to about 4.0 mg, about 0.05 mg to about 3.0 mg, about 0.05 mg to about 2.0 mg, about 0.1 mg to about 2.0 mg, about 0.5 mg to about 2.0 mg, about 2 mg to about 4.0 mg, about 1 mg to about 3.0 mg, about 1 mg, about 2 mg, or about 5 mg), the C1D2 is between about 0.05 mg to about 10.0 mg (e.g., about 0.1 mg to about 10.0 mg, about 0.5 mg to about 10.0 mg, 1 mg to about 10.0 mg, about 2 mg to about 3.0 mg, about 5 mg to about 10.0 mg, about 8 mg to about 10.0 mg, about 0.5 mg to about 7.0 mg, about 0.5 mg to about 5.0 mg, about 1 mg to about 5.0 mg, about 1 mg to about 3.0 mg, about 3 mg to about 8.0 mg, about 1 mg, about 2 mg, or about 5 mg) or between about 10 mg to about 60 mg (e.g., about 10 mg to about 50 mg, about 10 mg to about 40 mg, about 10 mg to about 30 mg, about 10 mg to about 20 mg, about 10 mg to about 15 mg, about 20 mg to about 50 mg, about 30 mg to about 50 mg, about 40 mg to about 50 mg, about 45 mg to about 50 mg, about 13 mg to about 17 mg, about 43 mg to about 48 mg, about 15 mg to about 35 mg, about 25 mg to about 45 mg, about 15 mg, about 30 mg, or about 45 mg); (a)(ii) the first dosing cycle includes a first dose (C1D1) of the anti-CD79b ADC; (b)(i) the second dosing cycle includes a single dose (C2D1) of the anti-CD79b ADC; and (b)(ii) the second dosing cycle includes a single dose (C2D1) of the bispecific antibody, wherein the C2D1 is about 9 mg, about 13.5 mg, about 20 mg, about 40 mg, about 45 mg, or about 60 mg; (c) the third dosing cycle includes a single dose (C3D1) of the anti-CD79b ADC and a single dose (C3D1) of the bispecific antibody; (d) the fourth dosing cycle includes a single dose (C4D1) of the anti-CD79b ADC and a single dose (C4D1) of the bispecific antibody; (e) the fifth dosing cycle includes a single dose (C5D1) of the anti-CD79b ADC and a single dose (C5D1) of the bispecific antibody; (f) the sixth dosing cycle includes a single dose (C6D1) of the anti-CD79b ADC and a single dose (C6D1) of the bispecific antibody; (g) the seventh dosing cycle includes a single dose (C7D1) of the anti-CD79b ADC and a single dose (C7D1) of the bispecific antibody; and (h) the eighth dosing cycle includes a single dose (C8D1) of the anti-CD79b ADC and a single dose (C8D1) of the bispecific antibody, wherein the C2D1 of the bispecific antibody is greater than or equal to the C1D2 of the bispecific antibody, wherein the C3D1, C4D1, C5D1, C6D1, C7D1, and C8D1 of the bispecific antibody are each greater than the C1D2 of the bispecific antibody and are each about 9 mg, about 13.5 mg, about 20 mg, about 40 mg, about 45 mg, or about 60 mg.

The methods described herein may be used to reduce the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) who are administered a bispecific anti-CD20/anti-CD3 antibody. In some instances the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) who are administered an anti-CD79b ADC and a bispecific anti-CD20/anti-CD3 antibody may be lower than the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) who are administered a bispecific anti-CD20/anti-CD3 antibody but who are not administered an anti-CD79b ADC. In some instances, the rate of the rate of cytokine release syndrome in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) who are administered an anti-CD79b ADC and a bispecific anti-CD20/anti-CD3 antibody may be less than or equal to about 20% (e.g., less than or equal to about 19%, less than or equal to about 18%, less than or equal to about 17%, less than or equal to about 16%, less than or equal to about 15%, less than or equal to about 14%, less than or equal to about 13%, less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 20%, or less than or equal to about 1%; e.g., between about 0% to about 20%, between about 1% to about 20%, between about 5% to about 20%, between about 10% to about 20%, between about 15% to about 20%, between about 0% to about 5%, between about 1% to about 5%, between about 1% to about 10%, between about 5% to about 10%, between about 10% to about 15%, or between about 5% to about 15%; e.g., about 20%, about 15%, about 10%, about 7%, about 5%, about 4%, about 3%, about 20%, about 1%, or about 0%). In some other instances, the rate of the rate of cytokine release syndrome having a grade of 2 or greater as defined by the ASTCT in a population of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) who are administered an anti-CD79b ADC and a bispecific anti-CD20/anti-CD3 antibody may be less than or equal to about 20% (e.g., less than or equal to about 19%, less than or equal to about 18%, less than or equal to about 17%, less than or equal to about 16%, less than or equal to about 15%, less than or equal to about 14%, less than or equal to about 13%, less than or equal to about 12$^{0}$/, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, or less than or equal to about 1%; e.g., between about 0% to about 20%, between about 1% to about 20%, between about 5% to about 20%, between about 10% to about 20%, between about 15% to about 20%, between about 0% to about 5%, between about 1% to about 5%, between about 1% to about 10%, between about 5% to about 10%, between about 10% to about 15%, or between about 5% to about 15%; e.g., about 20%, about 15%, about 10%, about 7%, about 5%, about 4%, about 3%, about 20%, about 1%, or about 0%).

Any of the methods described herein may involve monitoring a subject for cytokine release syndrome (CRS), e.g., a CRS event following commencement of any of the methods described above. Current clinical management focuses on treating the individual signs and symptoms, providing supportive care, and attempting to dampen the inflammatory response using a high dose of corticosteroids. However, this approach is not always successful, especially in the case of late intervention. The CRS grading criteria used by the methods described herein are published by the American Society for Transplantation and Cellular Therapy (ASTCT) to define mild, moderate, severe, or life-threatening CRS and harmonize reporting across clinical trials to allow rapid recognition and treatment of CRS (Lee et al., *Biology of Blood and Marrow Transplantation.* 25(4): 625-638, 2019). The ASTCT criteria is intended to be objective, easy to apply, and more accurately categorize the severity of CRS. This revised CRS grading system is shown in Table 1 below.

TABLE 1

CRS Grading System

| | CRS Parameter | | | |
|---|---|---|---|---|
| | Grade 1 | Grade 2 | Grade 3 | Grade 4 |
| Fever | Temperature ≤38° C. | Temperature ≤38° C. | Temperature ≤38° C. with | Temperature ≤38° C. |
| Hypotension | None | Not requiring vasopressors | Requiring a vasopressor with or without vasopressin and/or | Requiring multiple vasopressors (excluding vasopressin) |
| Hypoxia | None | Requiring low-glow nasal cannula or blow-by | Requiring high-flow nasal cannula, facemask, nonrebreather mask or Venturi mask | Requiring positive pressure (e.g., CPAP, BiPAP, intubation and mechanical ventilation) |

ASTCT = American Society for Transplantation and Cellular Therapy;
BiPAP = bilevel positive airway pressure;
CPAP = continuous positive airway pressure;
CRS = cytokine release syndrome;
CTCAE = Common Terminology Criteria for Adverse Events.

Fever is defined as a temperature ≥38° C. not attributable to any other cause. In subjects who have CRS then receive antipyretic or anticytokine therapy such as tocilizumab or steroids, fever is no longer required to grade subsequent CRS severity. In this case, CRS grading is determined by hypotension and/or hypoxia.

CRS grade is determined by the more severe event, hypotension or hypoxia not attributable to any other cause. For example, a subject with temperature of 39.5° C., hypotension requiring 1 vasopressor, and hypoxia requiring low-flow nasal cannula is classified as Grade 3 CRS.

Low-flow nasal cannula is defined as oxygen delivered at ≤6 L/minute. Low flow also includes blow-by oxygen delivery, sometimes used in pediatrics. High-flow nasal cannula is defined as oxygen delivered at >6 L/minute.

CRS is associated with elevations in a wide array of cytokines, including marked elevations in IFNγ, IL-6, and TNF-α levels. Emerging evidence implicates IL-6, in particular, as a central mediator in CRS. IL-6 is a proinflammatory, multi-functional cytokine produced by a variety of cell types, which has been shown to be involved in a diverse array of physiological processes, including T cell activation. Regardless of the inciting agent, CRS is associated with high IL-6 levels (Nagorsen et al., *Cytokine.* 25(1): 31-5, 2004; Lee et al., *Blood.* 124(2): 188-95, 2014); Doesegger et al., *Clin. Transl. Immunology.* 4(7): e39, 2015), and IL-6 correlates with the severity of CRS, with subjects who experience a grade 4 or 5 CRS event having much higher IL-6 levels compared to subjects who do not experience CRS or experience milder CRS (grades 0-3) (Chen et al., *J. Immunol. Methods.* 434:1-8, 2016).

Therefore, blocking the inflammatory action of IL-6 using an agent that inhibits IL-6-mediated signaling to manage CRS observed in subjects during the double-step fractionated, dose-escalation dosing regimen is an alternative to steroid treatment that would not be expected to negatively impact T cell function or diminish the efficacy or clinical benefit of anti-CD20/anti-CD3 bispecific antibody therapy in the treatment of CD20-positive cell proliferative disorders, e.g., B cell proliferative disorders.

Tocilizumab (ACTEMRA®/RoACTEMRA®) is a recombinant, humanized, anti-human monoclonal antibody directed against soluble and membrane-bound IL-6R, which inhibits IL-6-mediated signaling (see, e.g., WO 1992/019579, which is incorporated herein by reference in its entirety).

If the subject has a cytokine release syndrome (CRS) event following administration of the bispecific antibody, the method may further involve administering to the subject an effective amount of an interleukin-6 receptor (IL-6R) antagonist (e.g., an anti-IL-6R antibody, e.g., tocilizumab (ACTEMRA®/RoACTEMRA®)) to manage the event. In some instances, tocilizumab is administered intravenously to the subject as a single dose of about 8 mg/kg, but does not exceed 800 mg per single dose. Other anti-IL-6R antibodies that could be used instead of, or in combination with, tocilizumab include sarilumab, vobarilizumab (ALX-0061), satralizumab (SA-237), and variants thereof. In some instances, tocilizumab may be administered to patients being treated with the bispecific antibody (e.g., TDB) as a prophylactic measure (i.e., before and/or in the absence of CRS symptoms).

If the subject has a CRS event that does not resolve or worsens within 24 hours of administering the IL-6R antagonist to treat the symptoms of the CRS event, and the method may further comprise administering to the subject one or more additional doses of the IL-6R antagonist (e.g., an anti-IL-6R antibody, e.g., tocilizumab) to manage the CRS event. The subject may be administered a corticosteroid, such as methylprednisolone or dexamethasone if CRS event is not managed through administration of the IL-6R antagonist.

Management of the CRS events may be tailored based on the Stage of the CRS and the presence of comorbidities. For example, if the subject has a Grade 2 cytokine release syndrome (CRS) event in the absence of comorbidities or in the presence of minimal comorbidities following administration of the bispecific antibody, the method may further include treating the symptoms of the Grade 2 CRS event while suspending treatment with the bispecific antibody. If the Grade 2 CRS event then resolves to a Grade ≤1 CRS event for at least three consecutive days, the method may further include resuming treatment with the bispecific antibody without altering the dose. On the other hand, if the Grade 2 CRS event does not resolve or worsens to a Grade a 3 CRS event within 24 hours of treating the symptoms of the Grade 2 CRS event, the method may further involve administering to the subject an effective amount of an interleukin-6 receptor (IL-6R) antagonist (e.g., an anti-IL-6R antibody, e.g., tocilizumab (ACTEMRA®/RoACTEMRA®)) to manage the Grade 2 or Grade a 3 CRS event. In some instances, tocilizumab is administered intravenously to the subject as a single dose of about 8 mg/kg. Other anti-IL-6R antibodies that could be used instead of, or in combination with, tocilizumab include sarilumab, vobarilizumab (ALX-0061), satralizumab (SA-237), and variants thereof.

If the subject has a Grade 2, 3, or 4 CRS event in the presence of extensive comorbidities following administration of the bispecific antibody, the method may further include methods understood in the art to mitigate the CRS event, such as administering to the subject a first dose of an IL-6R antagonist (e.g., an anti-IL-6R antibody, e.g., tocilizumab (ACTEMRA®/RoACTEMRA®)) to manage the CRS event while suspending treatment with the bispecific antibody. Other anti-IL-6R antibodies that could be used instead of, or in combination with, tocilizumab include sarilumab, vobarilizumab (ALX-0061), satralizumab (SA-237), and variants thereof. In some instances, the method further includes administering to the subject an effective amount of a corticosteroid, such as methylprednisolone or dexamethasone.

In some instances, the bispecific antibody is administered subcutaneously to the subject. In this embodiment, the bispecific antibody can be administered at a dose of between about 0.5 mg to about 40 mg. Alternatively, in this embodiment, the bispecific antibody can be administered at a dose of between 40 mg to about 60 mg. In some embodiments, the bispecific antibody is administered at a dose of between about 1.0 to about 20 mg, between about 1.0 to about 10 mg, or between about 1.0 to about 5 mg. In other embodiments, the bispecific antibody is administered at a dose of between about 50 mg to about 60 mg, between about 40 mg to about 50 mg, between about 45 mg to about 55 mg, between about 55 mg to about 60 mg. In one embodiment, the bispecific antibody is administered in a dose of about 1.6 mg. In another embodiment, the bispecific antibody is administered in a dose of about 5 mg. In one embodiment, the bispecific antibody is administered at a dose of about 15 mg. In another embodiment, the bispecific antibody is administered at a dose of about 45 mg. In yet another embodiment, the bispecific antibody is administered in a dose of about 60 mg. Subsequent doses can be administered in amounts equal to the initial subcutaneous dose.

IV. Therapeutic Agents for Use in the Methods of the Invention

Exemplary anti-CD79b antibody drug conjugates and anti-CD20/anti-CD3 bispecific antibodies for treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), a CLL, or a CNSL) in accordance with the methods of the invention are described herein.

A. Anti-CD79b Antibody Drug Conjugates

Anti-CD79b antibody drug conjugates useful in the methods described herein (e.g., for treating a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) include any of the anti-CD79b antibody drug conjugates described in U.S. Pat. No. 8,088,378, which is incorporated herein by reference in its entirety. In some instances, the anti-CD79b antibody drug conjugate includes an anti-CD79b binding domain comprising at least one, two, three, four, five, or six hypervariable regions (HVRs) selected from (a) an HVR-H1 comprising the amino acid sequence of SEQ ID NO: 65; (b) an HVR-H2 comprising the amino acid sequence of SEQ ID NO: 66; (c) an HVR-H3 comprising the amino acid sequence of SEQ ID NO: 67; (d) an HVR-L1 comprising the amino acid sequence of SEQ ID NO: 68; (e) an HVR-L2 comprising the amino acid sequence of SEQ ID NO: 69; and (f) an HVR-L3 comprising the amino acid sequence of SEQ ID NO: 70. In some instances, the anti-CD79b antibody drug conjugate includes an anti-CD79b binding domain comprising all six of the following HVRs: (a) an HVR-H1 comprising the amino acid sequence of GYTFSSYWIE (SEQ ID NO: 65); (b) an HVR-H2 comprising the amino acid sequence of GEILPGGGDTNYNEIFKG (SEQ ID NO: 66); (c) an HVR-H3 comprising the amino acid sequence of TRRVPIRLDY (SEQ ID NO: 67); (d) an HVR-L1 comprising the amino acid sequence of KASQSVDYEGDSFLN (SEQ ID NO: 68); (e) an HVR-L2 comprising the amino acid sequence of AASNLES (SEQ ID NO: 69); and (f) an HVR-L3 comprising the amino acid sequence of QQSNEDPLT (SEQ ID NO: 70). In some instances, the anti-CD79b antibody drug conjugate comprises at least one (e.g., 1, 2, 3, or 4) of heavy chain framework regions FR-H1, FR-H2, FR-H3, and FR-H4 comprising the sequences of SEQ ID NOs: 73-76, respectively, and/or at least one (e.g., 1, 2, 3, or 4) of the light chain framework regions FR-L1, FR-L2, FR-L3, and FR-L4 comprising the sequences of SEQ ID NOs: 77-80, respectively. In some instances, the anti-CD79b antibody drug conjugate comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 71; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 72; or (c) a VH domain as in (a) and a VL domain as in (b). Accordingly, in some instances, the first binding domain comprises a VH domain comprising an amino acid sequence of SEQ ID NO: 71 and a VL domain comprising an amino acid sequence of SEQ ID NO: 72.

The sequences of the anti-CD79b antibody, polatuzumab vedotin, are summarized in Table 2 below.

TABLE 2

Sequence IDs for anti-CD79b antibody of polatuzumab vedotin

| Heavy Chain | | Light Chain | |
|---|---|---|---|
| SEQ ID NO: | Description | SEQ ID NO: | Description |
| 65 | HVR-H1 | 68 | HVR-L1 |
| 66 | HVR-H2 | 69 | HVR-L2 |
| 67 | HVR-H3 | 70 | HVR-L3 |
| 71 | VH | 72 | VL |
| 81 | Heavy Chain | 82 | Light Chain |

In some instances, the anti-CD79b antibody is linked to a toxin such as monomethyl auristatin E (MMAE, i.e., vedotin). In some instances, the anti-CD79b antibody drug conjugate is polatuzumab vedotin (immunoglobulin G1-kappa auristatin E conjugate, anti-[*Homo sapiens* CD79b (immunoglobulin-associated CD79 beta)], humanized monoclonal antibody conjugated to auristatin E; gamma1 heavy chain (1-447) [humanized VH (*Homo sapiens* IGHV3-23*04 (76.50%)-(IGHD)-IGHJ4*01) [8.8.10](1-117) -*Homo sapiens* IGHG1*03 (CH1 R120>K (214)(118-215), hinge (216-230), CH2 (231-340), CH3 (341-445), CHS (446-447)) (118-447)], (220-218')-disulfide with kappa light chain (1'-218') [humanized V-KAPPA (*Homo sapiens* IGKV1-39*01 (85.90%) -IGKJ1*01) [10.3.9](1'-111') -*Homo sapiens* IGKC*01 (112-218')]; dimer (226-226":229-229")-bisdisulfide; conjugated, on an average of 3 to 4 cysteinyl, to monomethylauristatin E (MMAE), via a cleavable maleimidocaproyl-valyl-citrullinyl-p-aminobenzyloxycarbonyl (mc-val-cit-PABC) type linker; also known as RG-7596, or RO5541077-000)), as defined by International Nonproprietary Names for Pharmaceutical Substances (INN) List 110 (WHO Drug Information, Vol. 27, No. 4, 2016, p. 443). Polatuzumab vedotin is also referred to as IUPHAR/BPS Number 8404, the KEGG Number D10761, or the CAS Registry Number 1313206-42-6. Polatuzumab vedotin-piiq is also interchangeably referred to as "polatuzumab vedotin-piiq", "huMA79bv28-MC-vc-PAB-MMAE", or "DCDS4501A." In some embodiments, the anti-CD79b antibody (e.g., the anti-CD79b ADC) comprises a heavy chain sequence of SEQ ID NO: 81 and a light chain sequence of SEQ ID NO: 82.

In some instances, the anti-CD79b antibody drug conjugate comprises the formula:

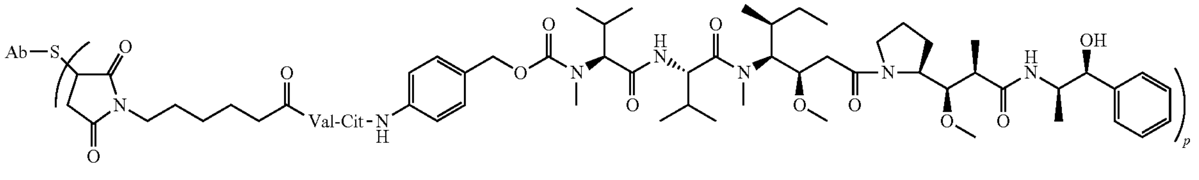

wherein Ab is an anti-CD79b antibody comprising (i) a hypervariable region-H1 (HVR-H1) that comprises the amino acid sequence of SEQ ID NO: 65; (ii) an HVR-H2 comprising the amino acid sequence of SEQ ID NO: 66; (iii) an HVR-H3 comprising the amino acid sequence of SEQ ID NO: 67; (iv) an HVR-L1 comprising the amino acid sequence of SEQ ID NO: 68; (v) an HVR-L2 comprising the amino acid sequence of SEQ ID NO: 69; and (vi) an HVR-L3 comprising the amino acid sequence of SEQ ID NO: 70, and wherein p is between 1 and 8.

In some embodiments, the antibody drug conjugate comprises an anti-CD79b antibody comprising (a) a VH domain comprising at least one, at least two, or all three VH HVR sequences selected from (i) HVR-H1 comprising the amino acid sequence of SEQ ID NO: 65, (ii) HVR-H2 comprising the amino acid sequence of SEQ ID NO: 66, and (iii) HVR-H3 comprising an amino acid sequence selected from SEQ ID NO: 67; and (b) a VL domain comprising at least one, at least two, or all three VL HVR sequences selected from (i) HVR-L1 comprising an amino acid sequence of SEQ ID NO: 68, (ii) HVR-L2 comprising the amino acid sequence of SEQ ID NO: 69, and (iii) HVR-L3 comprising the amino acid sequence of SEQ ID NO: 70. In some embodiments, the antibody drug conjugate comprises an anti-CD79b antibody that comprises at least one of: (i) HVR-H3 comprising the amino acid sequence of SEQ ID NO: 67, and/or (ii) HVR-L1 comprising the amino acid sequence of SEQ ID NO: 68. In some embodiments, the antibody drug conjugate comprises an anti-CD79b antibody that comprises (a) HVR-H1 comprising the amino acid sequence of SEQ ID NO: 65; (b) HVR-H2 comprising the amino acid sequence of SEQ ID NO: 66; (c) HVR-H3 comprising the amino acid sequence of SEQ ID NO: 67; (d) HVR-L1 comprising an amino acid sequence of SEQ ID NO: 68; (e) HVR-L2 comprising the amino acid sequence of SEQ ID NO: 69; and (f) HVR-L3 comprising the amino acid sequence of SEQ ID NO: 70.

In some embodiments, the antibody drug conjugate comprises at least one of: HVR-H3 comprising the amino acid sequence of SEQ ID NO: 67 and/or HVR-L1 comprising an amino acid sequence of SEQ ID NO: 68. In some embodiments, the antibody drug conjugate comprises an anti-CD79b antibody that comprises (a) HVR-H1 comprising the amino acid sequence of SEQ ID NO: 65; (b) HVR-H2 comprising the amino acid sequence of SEQ ID NO: 66; (c) HVR-H3 comprising the amino acid sequence of SEQ ID NO: 67; (d) HVR-L1 comprising the amino acid sequence of SEQ ID NO: 68; (e) HVR-L2 comprising the amino acid sequence of SEQ ID NO: 69; and (f) HVR-L3 comprising the amino acid sequence of SEQ ID NO: 70.

In some embodiments, the anti-CD79b antibody drug conjugate comprises a humanized anti-CD79b antibody. In some embodiments, an anti-CD79b antibody comprises HVRs as in any of the embodiments provided herein, and further comprises a human acceptor framework, e.g., a human immunoglobulin framework or a human consensus framework. In some embodiments, the human acceptor framework is the human VL kappa 1 (VLKI) framework and/or the VH framework VHIII. In some embodiments, a humanized anti-CD79b antibody comprises (a) HVR-H1 comprising the amino acid sequence of SEQ ID NO: 65; (b) HVR-H2 comprising the amino acid sequence of SEQ ID NO: 66; (c) HVR-H3 comprising the amino acid sequence of SEQ ID NO: 67; (d) HVR-L1 comprising an amino acid sequence of SEQ ID NO: 68; (e) HVR-L2 comprising the amino acid sequence of SEQ ID NO: 69; and (f) HVR-L3 comprising the amino acid sequence of SEQ ID NO: 70. In some embodiments, a humanized anti-CD79b antibody comprises (a) HVR-H1 comprising the amino acid sequence of SEQ ID NO: 65; (b) HVR-H2 comprising the amino acid sequence of SEQ ID NO: 66; (c) HVR-H3 comprising the amino acid sequence of SEQ ID NO: 67; (d) HVR-L1 comprising the amino acid sequence of SEQ ID NO: 68; (e) HVR-L2 comprising the amino acid sequence of SEQ ID NO: 69; and (f) HVR-L3 comprising the amino acid sequence of SEQ ID NO: 70.

In some embodiments, the antibody drug conjugate (e.g., the anti-CD79b antibody drug conjugate) comprises an anti-CD79 antibody comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 71. In some embodiments, a VH sequence having at least 90%, 91%, 92%, 93%, 94%, 95%, 96%, 97%, 98%, or 99% identity to the amino acid sequence of SEQ ID NO: 71 contains substitutions (e.g., conservative substitutions), insertions, or deletions relative to the reference sequence, but an anti-CD79b antibody drug conjugate comprising that sequence retains the ability to bind to CD79b. In some embodiments, a total of 1 to 10 amino acids have been substituted, inserted and/or deleted in SEQ ID NO: 71. In some embodiments, a total of 1 to 5 amino acids have been substituted, inserted and/or deleted in SEQ ID NO: 71. In some embodiments, substitutions, insertions, or deletions occur in regions outside the HVRs (i.e., in the FRs, e.g., SEQ ID NOs: 73-76). In some embodiments, the antibody drug conjugate (e.g., the anti-CD79b antibody drug conjugate) comprises the VH sequence of SEQ ID NO: 71, including posttranslational modifications of that sequence. In some embodiments, the VH comprises one, two or three HVRs selected from: (a) HVR-H1 comprising the amino acid sequence of SEQ ID NO: 65, (b) HVR-H2 comprising the amino acid sequence of SEQ ID NO: 66, and (c) HVR-H3 comprising the amino acid sequence of SEQ ID NO: 67.

In some embodiments, the antibody drug conjugate (e.g., the anti-CD79b antibody drug conjugate) comprises an anti-CD79b antibody that comprises a light chain variable domain (VL) having at least 90%, 91%, 92%, 93%, 94%, 95%, 96%, 97%, 98%, 99%, or 100% sequence identity to the amino acid sequence of SEQ ID NO: 72. In certain embodiments, a VL sequence having at least 90%, 91%, 92%, 93%, 94%, 95%, 96%, 97%, 98%, or 99% identity to the amino acid sequence of SEQ ID NO: 72 contains substitutions (e.g., conservative substitutions), insertions, or deletions relative to the reference sequence, but an anti-CD79b antibody drug conjugate comprising that sequence retains the ability to bind to CD79b. In certain embodiments, a total of 1 to 10 amino acids have been substituted, inserted and/or deleted in SEQ ID NO: 72. In certain embodiments, a total of 1 to 5 amino acids have been substituted, inserted and/or deleted in SEQ ID NO: 72. In certain embodiments, the substitutions, insertions, or deletions occur in regions outside the HVRs (i.e., in the FRs, e.g., SEQ ID NOs: 77-80). In some embodiments, the anti-CD79b antibody drug conjugate comprises an anti-CD79b antibody that comprises the VL sequence of SEQ ID NO: 72, including post-translational modifications of that sequence. In some embodiments, the VL comprises one, two or three HVRs selected from (a) HVR-L1 comprising an amino acid sequence of SEQ ID NO: 68; (b) HVR-L2 comprising the amino acid sequence of SEQ ID NO: 69; and (c) HVR-L3 comprising the amino acid sequence of SEQ ID NO: 70. In some embodiments, the VL comprises one, two or three HVRs selected from (a) HVR-L1 comprising the amino acid sequence of SEQ ID NO: 68; (b) HVR-L2 comprising the amino acid sequence of SEQ ID NO: 69; and (c) HVR-L3 comprising the amino acid sequence of SEQ ID NO: 70.

In some embodiments, the antibody drug conjugate (e.g., the anti-CD79b antibody drug conjugate) comprises an anti-CD79b antibody that comprises VH as in any of the embodiments provided herein, and a VL as in any of the embodiments provided herein. In some embodiments, the antibody drug conjugate comprises an anti-CD79b antibody that comprises the VH and VL sequences in SEQ ID NO: 71 and SEQ ID NO: 72, respectively, including post-translational modifications of those sequences.

In some embodiments, the antibody drug conjugate (e.g., anti-CD79b antibody drug conjugate) comprises an anti-CD79b antibody that binds to the same epitope as an anti-CD79b antibody described herein. For example, in some embodiments, the antibody drug conjugate (e.g., anti-CD79b antibody drug conjugate) comprises an anti-CD79b antibody that binds to the same epitope as an anti-CD79b antibody comprising a VH sequence of SEQ ID NO: 71 and a VL sequence of SEQ ID NO: 72.

In some embodiments, the antibody drug conjugate comprises an anti-CD79b antibody that is a monoclonal antibody, a chimeric antibody, humanized antibody, or human antibody. In some embodiments, antibody drug conjugate comprises an antigen-binding fragment of an anti-CD79b antibody described herein, e.g., a Fv, Fab, Fab', scFv, diabody, or $F(ab')_2$ fragment. In some embodiments, the antibody drug conjugate comprises a substantially full length anti-CD79b antibody, e.g., an $IgG_1$ antibody or other antibody class or isotype as described elsewhere herein. Anti-CD79b antibody drug conjugates may be produced using recombinant methods and compositions, for example, as described in U.S. Pat. No. 4,816,567.

In some instances, the anti-CD79b antibody drug conjugates according to any of the embodiments described above may incorporate any of the features, singly or in combination, as described in Section C below.

B. Anti-CD20/Anti-CD3 Bispecific Antibodies

Bispecific antibodies that bind to CD20 and CD3 (i.e., anti-CD20/anti-CD3 antibodies) useful in the methods described herein (e.g., for treating a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) include bispecific antibodies having an anti-CD3 binding domain and at least one anti-CD20 binding domain (e.g., having one anti-CD20 binding domain (e.g., mosunetuzumab)).

In some instances, the bispecific antibody includes an anti-CD20 arm having a first binding domain comprising at least one, two, three, four, five, or six hypervariable regions (HVRs) selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some instances, the bispecific antibody includes an anti-CD20 arm having a first binding domain comprising all six of the following HVRs: (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 9-12, respectively, and/or at least one (e.g., 1, 2, 3, or 4) of the light chain framework regions FR-L1, FR-L2, FR-L3, and FR-L4 comprising the sequences of SEQ ID NOs: 13-16, respectively. In some instances, the bispecific antibody comprises an anti-CD20 arm comprising a first binding domain comprising (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b). Accordingly, in some instances, the first binding domain comprises a VH domain comprising an amino acid sequence of SEQ ID NO: 7 and a VL domain comprising an amino acid sequence of SEQ ID NO: 8.

In some instances, the bispecific antibody includes an anti-CD3 arm having a second binding domain comprising at least one, two, three, four, five, or six HVRs selected from (a) an HVR-H1 comprising the amino acid sequence of NYYIH (SEQ ID NO: 17); (b) an HVR-H2 comprising the amino acid sequence of WIYPGDGNTKYNEKFKG (SEQ ID NO: 18); (c) an HVR-H3 comprising the amino acid sequence of DSYSNYYFDY (SEQ ID NO: 19); (d) an HVR-L1 comprising the amino acid sequence of KSSQSLLNSRTRKNYLA (SEQ ID NO: 20); (e) an HVR-L2 comprising the amino acid sequence of WASTRES (SEQ ID NO: 21); and (f) an HVR-L3 comprising the amino acid sequence of TQSFILRT (SEQ ID NO: 22). In some instances, the bispecific antibody includes an anti-CD3 arm having a second binding domain comprising all six of the following HVRs: (a) an HVR-H1 comprising the amino acid sequence of NYYIH (SEQ ID NO: 17); (b) an HVR-H2 comprising the amino acid sequence of WIYPGDGNTKYNEKFKG (SEQ ID NO: 18); (c) an HVR-H3 comprising the amino acid sequence of DSYSNYYFDY (SEQ ID NO: 19); (d) an HVR-L1 comprising the amino acid sequence of KSSQSLLNSRTRKNYLA (SEQ ID NO: 20); (e) an HVR-L2 comprising the amino acid sequence of WASTRES (SEQ ID NO: 21); and (f) an HVR-L3 comprising the amino acid sequence of TQSFILRT (SEQ ID NO: 22). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, the bispecific antibody comprises an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 23; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 24; or (c) a VH domain as in (a) and a VL domain as in (b). Accordingly, in some instances, the second binding domain comprises a VH domain comprising an amino acid sequence of SEQ ID NO: 23 and a VL domain comprising an amino acid sequence of SEQ ID NO: 24.

In some instances, the bispecific antibody includes (1) an anti-CD20 arm having a first binding domain comprising at least one, two, three, four, five, or six HVRs selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6); and (2) an anti-CD3 arm having a second binding domain comprising at least one, two, three, four, five, or six HVRs selected from (a) an HVR-H1 comprising the amino acid sequence of NYYIH (SEQ ID NO: 17); (b) an HVR-H2 comprising the amino acid sequence of WIYPGDGNTKYNEKFKG (SEQ ID NO: 18); (c) an HVR-H3 comprising the amino acid sequence of DSYSNYYFDY (SEQ ID NO: 19); (d) an HVR-L1 comprising the amino acid sequence of KSSQSLLNSRTRKNYLA (SEQ ID NO: 20); (e) an HVR-L2 comprising the amino acid sequence of WASTRES (SEQ ID NO: 21); and (f) an HVR-L3 comprising the amino acid sequence of TQSFILRT (SEQ ID NO: 22). In some instances, the bispecific antibody includes (1) an anti-CD20 arm having a first binding domain comprising all six of the following HVRs: (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6); and (2) an anti-CD3 arm having a second binding domain comprising all six of the following HVRs: (a) an HVR-H1 comprising the amino acid sequence of NYYIH (SEQ ID NO: 17); (b) an HVR-H2 comprising the amino acid sequence of WIYPGDGNTKYNEKFKG (SEQ ID NO: 18); (c) an HVR-H3 comprising the amino acid sequence of DSYSNYYFDY (SEQ ID NO: 19); (d) an HVR-L1 comprising the amino acid sequence of KSSQSLLNSRTRKNYLA (SEQ ID NO: 20); (e) an HVR-L2 comprising the amino acid sequence of WASTRES (SEQ ID NO: 21); and (f) an HVR-L3 comprising the amino acid sequence of TQSFILRT (SEQ ID NO: 22). In some instances, the anti-CD20/anti-CD3 bispecific antibody comprises (1) at least one (e.g., 1, 2, 3, or 4) of heavy chain framework regions FR-H1, FR-H2, FR-H3, and FR-H4 comprising the sequences of SEQ ID NOs: 9-12, respectively, and/or at least one (e.g., 1, 2, 3, or 4) of the light chain framework regions FR-L1, FR-L2, FR-L3, and FR-L4 comprising the sequences of SEQ ID NOs: 13-16, respectively, and (2) at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, the anti-CD20/anti-CD3 bispecific antibody comprises (1) an anti-CD20 arm comprising a first binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b), and (2) an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 23; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 24; or (c) a VH domain as in (a) and a VL domain as in (b). In some instances, the anti-CD20/anti-CD3 bispecific antibody comprises (1) a first binding domain comprising a VH domain comprising an amino acid sequence of SEQ ID NO: 7 and a VL domain comprising an amino acid sequence of SEQ ID NO: 8 and (2) a second binding domain comprising a VH domain comprising an amino acid sequence of SEQ ID NO: 23 and a VL domain comprising an amino acid sequence of SEQ ID NO: 24.

In some instances, the bispecific antibody is an IgG antibody, e.g., an $IgG_1$ antibody. In some instances, the IgG antibody comprises a mutation at amino acid residue N297 (EU numbering) that results in the absence of glycosylation. In some instances, the mutation at amino acid residue N297 is a substitution mutation. In some instances, the mutation at amino acid residue N297 reduces effector function of the Fc region. In some instances, the mutation is an N297G or N297A mutation. In some instances, the bispecific antibody comprises a mutation in the Fc region that reduces effector function. In some instances, the mutation is a substitution mutation, e.g., a substitution mutation at amino acid residue L234, L235, D265, and/or P329 (EU numbering). In particular instances, the substitution mutation is selected from the group consisting of L234A, L235A, D265A, and P329G.

In some embodiments the anti-CD20 arm of the anti-CD20/anti-CD3 bispecific antibody further comprises T366W and N297G substitution mutations (EU numbering). In some embodiments, the anti-CD3 arm of the anti-CD20/anti-CD3 bispecific antibody further comprises T366S, L368A, Y407V, and N297G substitution mutations (EU numbering). In some embodiments, (a) the anti-CD20 arm further comprises T366W and N297G substitution mutations and (b) the anti-CD3 arm further comprises T366S, L368A, Y407V, and N297G substitution mutations (EU numbering).

Anti-CD20/anti-CD3 bispecific antibodies useful in the methods of the present invention include any of the anti-CD20/anti-CD3 bispecific antibodies described in International Patent Publication No. WO 2015/09539, which is incorporated herein by reference in its entirety. In some instances, the anti-CD20/anti-CD3 bispecific antibody is mosunetuzumab (also known as BTCT4465A or RG 7828), as defined by International Nonproprietary Names for Pharmaceutical Substances (INN) List 117 (WHO Drug Information, Vol. 31, No. 2, 2017, p. 304-305). In some embodiments, the anti-CD20/anti-CD3 bispecific antibody comprises (1) an anti-CD20 arm comprising a first binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 85; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 86; or (c) a heavy chain as in (a) and a light chain as in (b), and (2) an anti-CD3 arm comprising a second binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 83; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 84; or (c) a heavy chain as in (a) and a light chain as in (b). In some embodiments, the anti-CD20/anti-CD3 bispecific antibody comprises (1) an anti-CD20 arm comprising a first binding domain comprising a heavy chain comprising an amino acid sequence of SEQ ID NO: 85 and a light chain comprising an amino acid sequence of SEQ ID NO: 86 and (2) an anti-CD3 arm comprising a second binding domain comprising a heavy chain comprising an amino acid sequence of SEQ ID NO: 83 and a light chain comprising an amino acid sequence of SEQ ID NO: 84.

The amino acid sequences comprising mosunetuzumab are summarized in Table 3 below.

TABLE 3

Sequence IDs for mosunetuzumab

| CD3 Arm | | CD20 Arm | |
|---|---|---|---|
| SEQ ID NO: | Description | SEQ ID NO: | Description |
| 17 | CD3 HVR-H1 | 1 | CD20 HVR-H1 |
| 18 | CD3 HVR-H2 | 2 | CD20 HVR-H2 |
| 19 | CD3 HVR-H3 | 3 | CD20 HVR-H3 |
| 20 | CD3 HVR-L1 | 4 | CD20 HVR-L1 |
| 21 | CD3 HVR-L2 | 5 | CD20 HVR-L2 |
| 22 | CD3 HVR-L3 | 6 | CD20 HVR-L3 |
| 23 | CD3 VH | 7 | CD20 VH |
| 24 | CD3 VL | 8 | CD20 VL |
| 83 | CD3 heavy chain | 85 | CD20 heavy chain |
| 84 | CD3 light chain | 86 | CD20 light chain |

The anti-CD20/anti-CD3 bispecific antibody may be produced using recombinant methods and compositions, for example, as described in U.S. Pat. No. 4,816,567.

In some instances, the anti-CD20/anti-CD3 bispecific antibody according to any of the embodiments described above may incorporate any of the features, singly or in combination, as described in Section C below.

C. Antibody Formats and Properties

1. Antibody Affinity

In certain instances, an anti-CD79b antibody drug conjugate and/or an anti-CD20/anti-CD3 bispecific antibody has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, or e.g., from $10^{-9}$ M to $10^{-13}$ M).

In one instance, Ko is measured by a radiolabeled antigen binding assay (RIA). In one instance, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μL/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another instance, Ko is measured using a BIACORE® surface plasmon resonance assay. For example, an assay using a BIACORE®-2000 or a BIACORE®-3000 (BIAcore, Inc., Piscataway, NJ) is performed at 25° C. with immobilized antigen CM5 chips at ~10 response units (RU). In one instance, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μL/min. Association rates ($k_{on}$) and dissociation rates ($k_{off}$) are calculated using a simple one-to-one *Langmuir* binding model (BIACORE® Evaluation Software version 3.2) by simultaneously fitting the association and dissociation sensorgrams. The equilibrium dissociation constant (Ko) is calculated as the ratio $k_{off}/k_{on}$. See, for example, Chen et al., J. Mol. Biol. 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain instances, an anti-CD79b antibody drug conjugate and/or an anti-CD20/anti-CD3 bispecific antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al., *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain instances, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein. 3. Chimeric and Humanized Antibodies In certain instances, an anti-CD79b antibody drug conjugate and/or an anti-CD20/anti-CD3 bispecific antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain instances, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some instances, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include, but are not limited to: framework regions selected using the "best-fit" method (see, e.g., Sims et al., *J. Immunol.* 151:2296 (1993)); framework regions derived from the consensus sequence of human antibodies of a particular subgroup of light or heavy chain variable regions (see, e.g., Carter et al., *Proc. Natd. Acad. Sci. USA,* 89:4285 (1992); and Presta et al., *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271: 22611-22618 (1996)).

4. Human Antibodies

In certain instances, an anti-CD79b antibody (e.g., as part of an anti-CD79b antibody drug conjugate) and/or an anti-CD20/anti-CD3 bispecific antibody is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing $HUM_{AB}$® technology; U.S. Pat. No. 7,041,870 describing K-M MOUSES technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4)265-268 (2006) (describing human-human hybridomas). Human hybridoma technology (Trioma technology) is also described in Vollmers and Brandlein, *Histology and Histopathology,* 20(3) 927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Anti-CD79b antibody drug conjugates and/or anti-CD20/anti-CD3 bispecific antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

Anti-CD79b antibodies and/or anti-CD20/anti-CD3 bispecific antibodies or antibody fragments isolated from human antibody libraries are considered human antibodies or human antibody fragments herein.

6. Antibody Variants

In certain instances, amino acid sequence variants of anti-CD79b antibodies (or antibody drug conjugates thereof) and/or anti-CD20/anti-CD3 bispecific antibodies of the invention are contemplated. As described in detail herein, anti-TIGIT antagonist antibodies, PD-1 axis binding antagonist antibodies (e.g., anti-PD-L1 antagonist antibodies), and/or anti-VEGF antibodies may be optimized based on desired structural and functional properties. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain instances, anti-CD79b antibody and/or anti-CD20/anti-CD3 bispecific antibody variants having one or more amino acid substitutions are provided. Sites of interest for substitutional mutagenesis include the HVRs and FRs. Conservative substitutions are shown in Table 4 under the heading of "preferred substitutions." More substantial changes are provided in Table 4 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 4

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, lie;

(2) neutral hydrophilic: Cys, Ser, Thr, Asn, Gin;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity)

relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, NJ, (2001).) In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain instances of the variant VH and VL sequences provided above, each HVR either is unaltered, or includes no more than one, two, or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain instances, anti-CD79b antibody drug conjugates and/or anti-CD20/anti-CD3 bispecific antibodies of the invention can be altered to increase or decrease the extent to which the antibody is glycosylated. Addition or deletion of glycosylation sites to anti-CD79b antibody drug conjugates and/or anti-CD20/anti-CD3 bispecific antibodies of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 1526-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention are made in order to create antibody variants with certain improved properties.

In one instance, anti-CD79b antibody drug conjugate and/or anti-CD20/anti-CD3 bispecific antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., U.S. Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249:533-545 (1986); U.S. Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.,* 94(4):680-688 (2006); and WO 2003/085107).

In view of the above, in some instances, the methods of the invention involve administering to the subject in the context of a fractionated, dose-escalation dosing regimen an anti-CD79b antibody drug conjugate and/or an anti-CD20/anti-CD3 bispecific antibody variant that comprises an aglycosylation site mutation. In some instances, the aglycosylation site mutation reduces effector function of the antibody. In some instances, the aglycosylation site mutation is a substitution mutation. In some instances, the antibody comprises a substitution mutation in the Fc region that reduces effector function. In some instances, the substitution mutation is at amino acid residue N297, L234, L235, and/or D265 (EU numbering). In some instances, the substitution mutation is selected from the group consisting of N297G, N297A, L234A, L235A, D265A, and P329G. In some instances, the substitution mutation is at amino acid residue N297. In a preferred instance, the substitution mutation is N297A.

Anti-CD79b antibody drug conjugate and/or anti-CD20/anti-CD3 bispecific antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and U.S. 2005/0123546. Antibody variants with at least one galactose residue in the oligosaccharide attached to the Fc region are also provided. Such antibody variants may have improved CDC function. Such antibody variants are described, e.g., in WO 1997/30087, WO 1998/58964, and WO 1999/22764.

c. Fc Region Variants

In certain instances, one or more amino acid modifications are introduced into the Fc region of an anti-CD79b antibody drug conjugate and/or an anti-CD20/anti-CD3 bispecific antibody of the invention, thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain instances, the invention contemplates an anti-CD79b antibody drug conjugate and/or an anti-CD20/anti-CD3 bispecific antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII, and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al., *Proc. Nat Acad. Sci. USA* 83:7059-7063 (1986)) and Hellstrom, I et al., *Proc. Natl Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (PROMEGA®, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl Acad. Sci. USA* 95: 652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro 5 et al., *J. Immunol. Methods* 202:163 (1996); Cragg, M. S. et al., *Blood.* 101:1045-1052 (2003); and Cragg, M. S. and M. J. Glennie Blood. 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain instances, the proline at position 329 of a wild-type human Fc region in the antibody is substituted with glycine or arginine or an amino acid residue large enough to destroy the proline sandwich within the Fc/Fc.gamma receptor interface that is formed between the proline 329 of the Fc and tryptophan residues Trp87 and Trp110 of FcγRIII (Sondermann et al., *Nature* 406, 267-273 (20 Jul. 2000)). In certain instances, the antibody comprises at least one further amino acid substitution. In one instance, the further amino acid substitution is S228P, E233P, L234A, L235A, L235E, N297A, N297D, or P331S, and still in another instance the at least one further amino acid substitution is L234A and L235A of the human IgG1 Fc region or S228P and L235E of the human IgG4 Fc region (see e.g., US 2012/0251531), and still in another instance the at least one further amino acid substitution is L234A and L235A and P329G of the human $IgG_1$ Fc region.

Certain antibody variants with improved or diminished binding to FcRs are described. See, e.g., U.S. Pat. No. 6,737,056; WO 2004/056312, and Shields et al., *J. Biol. Chem.* 9(2): 6591-6604 (2001).

In certain instance, an antibody variant comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some aspects, the anti-CD79b antibody drug conjugate and/or anti-CD20/anti-CD3 bispecific antibody comprises an Fc region comprising an N297G mutation (EU numbering).

In some instances, the anti-CD79b antibody drug conjugate and/or anti-CD20/anti-CD3 bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some instances, the $CH3_1$ and $CH3_2$ domains meet at an interface between said protuberance and cavity. In some instances, the $CH2_1$ and $CH2_2$ domains each comprise a protuberance or cavity, and wherein the protuberance or cavity in the $CH2_1$ domain is positionable in the cavity or protuberance, respectively, in the $CH2_2$domain. In other instances, the $CH2_1$ and $CH2_2$ domains meet at an interface between said protuberance and cavity. In some instances, the anti-CD79b antibody drug conjugate and/or anti-CD20/anti-CD3 bispecific antibody is an IgG1 antibody.

d. Cysteine Engineered Antibody Variants

In certain instances, it is desirable to create cysteine engineered anti-CD79b antibody drug conjugates and/or anti-CD20/anti-CD3 bispecific antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate or antibody drug conjugate, as described further herein. In certain instances, any one or more of the following residues are substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

e. Antibody Derivatives

In certain instances, an anti-CD79b antibody drug conjugate and/or an anti-CD20/anti-CD3 bispecific antibody provided herein is further modified to contain additional nonproteinaceous moieties that are known in the art and readily available. The moieties suitable for derivatization of the antibody include, but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and nonproteinaceous moiety that may be selectively heated by exposure to radiation are provided. In one instance, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

f. Recombinant Production Methods

Anti-CD79b antibody drug conjugates and/or anti-CD20/anti-CD3 bispecific antibodies of the invention may be produced using recombinant methods and compositions, for example, as described in U.S. Pat. No. 4,816,567, which is incorporated herein by reference in its entirety.

For recombinant production of an anti-CD79b antibody drug conjugate and/or an anti-CD20/anti-CD3 bispecific antibody, nucleic acid encoding an antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR® CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, NJ), pp. 255-268 (2003).

g. Immunoconjugates

The invention also provides immunoconjugates or antibody drug conjugates comprising an anti-CD79b antibody and/or an anti-CD20/anti-CD3 bispecific antibody of the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some instances, an immunoconjugate is an antibody-drug conjugate (ADC) in which an antibody is conjugated to one or more drugs, including but not limited to an auristatin such as monomethylauristatin drug moieties DE and DF (MMAE (vedotin) and MMAF) (see U.S. Pat. Nos. 5,635,483, 5,780,588, 7,498,298, and 8,088,378); a maytansinoid (see U.S. Pat. Nos. 5,208,020, 5,416,064, and European Patent EP 0 425 235 B1); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises anti-CD79b antibody or an anti-CD20/anti-CD3 bispecific antibody conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica* charanda inhibitor, curcin, crotin, *Sapaonaria officinalis* inhibitor, gelonin, mitogellin, restrictocin, phenomycin, enomycin, and the tricothecenes.

In another instance, an immunoconjugate comprises an anti-CD79b antibody and/or an anti-CD20/anti-CD3 bispecific antibody conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{153}$Re, $^{153}$Re, $^{212}$Bi, $^{32}$P, $^{212}$Pb and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-i4-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker, or disulfide-containing linker (Chari et al., *Cancer Res.* 52:127-131 (1992); U.S. Pat. No. 5,208,020) may be used.

The immunoconjugates or ADCs herein expressly contemplate, but are not limited to, such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

Alternatively, any of the antibodies described herein (e.g., an anti-CD20/anti-CD3 bispecific antibody) can be a naked antibody.

D. Additional Therapeutic Agents

In some instances, the methods described herein include administering the bispecific anti-CD20/anti-CD3 antibody and the anti-CD79b ADC with an additional therapeutic agent (e.g., a further chemotherapy agent and/or an antibody-drug conjugate (ADC)). In some instances, the bispecific anti-CD20/anti-CD3 antibody and the anti-CD79b ADC are co-administered with one or more additional chemotherapy agents selected from cyclophosphamide and doxorubicin. In some instances, the bispecific anti-CD20/anti-CD3 antibody and the anti-CD79b ADC are co-administered with a corticosteroid. In some instances, the corticosteroid is dexamethasone (CAS #: 50-02-2), prednisone (CAS #: 53-03-2), or methylprednisolone (CAS #: 83-43-2). In some instances, the bispecific anti-CD20/anti-CD3 antibody and the anti-CD79b ADC are co-administered with CHOP, wherein vincristine is replaced with an ADC. In some instances, the bispecific anti-CD20/anti-CD3 antibody and the anti-CD79b ADC are co-administered an anti-CD19 antibody drug conjugate, an anti-CD22 antibody drug conjugate, an anti-CD45 antibody drug conjugate, and an anti-CD32 antibody drug conjugate.

In some instances, the additional therapeutic agent is a biological modifier. In one instance, the bispecific anti-CD20/anti-CD3 antibody and the anti-CD79b ADC are co-administered with one or more biological modifiers selected from a BCL-2 inhibitor (such as GDC-0199/ABT-199), lenalidomide (REVLIMID®), pomalidomide, thalidomide, a PI3K-delta inhibitor (such as idelalisib (ZYDELIG®; CAS #: 936563-96-1)), a PI3K inhibitor (such as taselisib (CAS #: 1282512-48-4), copanlisib (CAS #: 1032568-63-0), duvelisib (CAS #: 1201438-56-3), alpelisib (CAS #: 1217486-61-7), and umbralisib (CAS #: 1532533-67-7)), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some of the methods described herein, the dosing regimen may include administration of one or more additional therapeutic agents. In such instances, the method may include administration of one or more additional therapeutic agents in the context of the dosing regimen. For example, in a particular instance, the bispecific anti-CD20/anti-CD3 antibody and anti-CD79b antibody drug conjugate can be co-administered with obinutuzumab (GAZYVA®) or tocilizumab (ACTEMRA®/RoACTEMRA®), wherein the subject is first administered with obinutuzumab (GAZYVA®) or tocilizumab (ACTEMRA®/RoACTEMRA®) and then separately administered with the bispecific anti-CD20/anti-CD3 antibody (e.g., the subject is pre-treated with obinutuzumab (GAZYVA®) or tocilizumab (ACTEMRA®/RoACTEMRA®)). In some embodiments, the one or more additional therapeutic agents may reduce the rate or the severity of cytokine release syndrome (CRS). In some embodiments, the one or more additional therapeutic agents may prevent symptoms associated with CRS. In particular embodiments, the additional therapeutic agent used to reduce the rate or severity of CRS or prevent symptoms associated with CRS is a corticosteroid (e.g., dexamethasone or methylprednisolone) or an IL-R6 antagonist (e.g., tocilizumab, sarilumab, vobarilizumab (ALX-0061), satralizumab (SA-237), and variants thereof).

In some instances, the PD-1 binding antagonist is an anti-PD-1 antibody. A variety of anti-PD-1 antibodies can be utilized in the methods and uses disclosed herein. In any of the instances herein, the PD-1 antibody can bind to a human PD-1 or a variant thereof. In some instances, the anti-PD-1 antibody is a monoclonal antibody. In some instances, the anti-PD-1 antibody is an antibody fragment selected from the group consisting of Fab, Fab', Fab'-SH, Fv, scFv, and $(Fab')_2$ fragments. In some instances, the anti-PD-1 antibody is a humanized antibody. In other instances, the anti-PD-1 antibody is a human antibody. Exemplary anti-PD-1 antagonist antibodies include nivolumab, pembrolizumab, MEDI-0680, PDR001 (spartalizumab), REGN2810 (cemiplimab), BGB-108, prolgolimab, camrelizumab, sintilimab, tislelizumab, toripalimab, dostarlimab, retifanlimab, sasanlimab, penpulimab, CS1003, HLX10, SCT-110A, zimberelimab, balstilimab, genolimzumab, BI 754091, cetrelimab, YBL-006, BAT1306, HX008, budigalimab, CX-188, JTX-4014, 609A, Sym021, LZM009, F520, SG001, AM0001, ENUM 244C8, ENUM 388D4, STI-1110, AK-103, and hAb21. In some instances, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO 2006/121168. In some instances, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA®, is an anti-PD-1 antibody described in WO 2009/114335. In some instances, the anti-PD-1 antibody is MEDI-0680 (AMP-514; AstraZeneca). MEDI-0680 is a humanized IgG4 anti-PD-i antibody. In some instances, the anti-PD-1 antibody is PDR001 (CAS Registry No. 1859072-53-9; Novartis). PDR001 is a humanized IgG4 anti-PD-1 antibody that blocks the binding of PD-L1 and PD-L2 to PD-1. In some instances, the anti-PD-1 antibody is REGN2810 (Regeneron). REGN2810 is a human anti-PD-1 antibody. In some instances, the anti-PD-1 antibody is BGB-108 (BeiGene). In some instances, the anti-PD-1 antibody is BGB-A317 (BeiGene). In some instances, the anti-PD-1 antibody is JS-001 (Shanghai Junshi). JS-001 is a humanized anti-PD-1 antibody. In some instances, the anti-PD-1 antibody is STI-A1110 (Sorrento). STI-A1110 is a human anti-PD-1 antibody. In some instances, the anti-PD-1 antibody is INCSHR-1210 (Incyte). INCSHR-1210 is a human $IgG_4$ anti-PD-1 antibody. In some instances, the anti-PD-1 antibody is PF-06801591 (Pfizer). In some instances, the anti-PD-1 antibody is TSR-042 (also known as ANB011; Tesaro/AnaptysBio). In some instances, the anti-PD-1 antibody is AM0001 (ARMO Biosciences). In some instances, the anti-PD-1 antibody is ENUM 244C8 (Enumeral Biomedical Holdings). ENUM 244C8 is an anti-PD-1 antibody that inhibits PD-1 function without blocking binding of PD-L1 to PD-1. In some instances, the anti-PD-1 antibody is ENUM 388D4 (Enumeral Biomedical Holdings). ENUM 388D4 is an anti-PD-1 antibody that competitively inhibits binding of PD-L1 to PD-1. In some instances, the anti-PD-1 antibody comprises the six HVR sequences (e.g., the three heavy chain HVRs and the three light chain HVRs) and/or the heavy chain variable domain and light chain variable domain from an anti-PD-1 antibody described in WO 2015/112800, WO 2015/112805, WO 2015/112900, US 20150210769, WO2016/089873, WO 2015/035606, WO 2015/085847, WO 2014/206107, WO 2012/145493, U.S. Pat. No. 9,205,148, WO 2015/119930, WO 2015/119923, WO 2016/032927, WO 2014/179664, WO 2016/106160, and WO 2014/194302.

In other instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In other instances, the PD-1 binding antagonist is AMP-224. AMP-224, also known as B7-DCIg, is a PD-L2-Fc fusion soluble receptor described in PCT Pub. Nos. WO 2010/027827 and WO 2011/066342.

In some instances, the PD-L1 binding antagonist is an anti-PD-L1 antibody. A variety of anti-PD-L1 antibodies are contemplated and described herein. In any of the instances herein, the isolated anti-PD-L1 antibody can bind to a human PD-L1, for example a human PD-L1 as shown in UniProtKB/Swiss-Prot Accession No. Q9NZQ7-1, or a variant thereof. In some instances, the anti-PD-L1 antibody is capable of inhibiting binding between PD-L1 and PD-1 and/or between PD-L1 and B7-1. In some instances, the anti-PD-L1 antibody is a monoclonal antibody. In some instances, the anti-PD-L1 antibody is an antibody fragment selected from the group consisting of Fab, Fab'-SH, Fv, scFv, and $(Fab')_2$ fragments. In some instances, the anti-PD-L1 antibody is a humanized antibody. In some instances, the anti-PD-L1 antibody is a human antibody. Exemplary anti-PD-L1 antibodies include atezolizumab, MDX-1105, MED4736 (durvalumab), MSB0010718C (avelumab), SHR-1316, CS1001, envafolimab, TQB2450, ZKAB001, LP-002, CX-072, IMC-001, KL-A167, APL-502, cosibelimab, lodapolimab, FAZ053, TG-1501, BGB-A333, BCD-135, AK-106, LDP, GR1405, HLX20, MSB2311, RC98, PDL-GEX, KD036, KY1003, YBL-007, HS-636, LY3300054 (Eli Lilly), STI-A1014 (Sorrento), and KN035 (Suzhou Alphamab). In some instances, the anti-PD-L1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some instances, the anti-PD-L1 antibody is CX-072 (CytomX Therapeutics). In some instances, the anti-PD-L1 antibody comprises the six HVR sequences (e.g., the three heavy chain HVRs and the three light chain HVRs) and/or the heavy chain variable domain and light chain variable domain from an anti-PD-L1 antibody described in US 20160108123, WO 2016/000619, WO 2012/145493, U.S. Pat. No. 9,205,148, WO 2013/181634, or WO 2016/061142. Examples of anti-PD-L1 antibodies useful in the methods of this invention and methods of making them are described in International Patent Application Publication No. WO 2010/077634 and U.S. Pat. No. 8,217,149, each of which is incorporated herein by reference in its entirety.

In other instances, the PD-L2 binding antagonist is an anti-PD-L2 antibody (e.g., a human, a humanized, or a chimeric anti-PD-L2 antibody). In some instances, the PD-L2 binding antagonist is an immunoadhesin.

In some instances, the bispecific anti-CD20/anti-CD3 antibody and the anti-CD79b ADC are co-administered with one or more chemotherapy agents. In one instance, the bispecific anti-CD20/anti-CD3 antibody and the anti-CD79b ADC are co-administered with CHOP. In one instance, the bispecific anti-CD20/anti-CD3 antibody and the anti-CD79b ADC are co-administered with an ADC. In one instance, the bispecific anti-CD20/anti-CD3 antibody and the anti-CD79b ADC are co-administered with CHOP, wherein vincristine is replaced with an ADC. In one instance, the bispecific anti-CD20/anti-CD3 antibody and the anti-CD79b ADC are co-administered with an ADC selected from an anti-CD19 antibody drug conjugate, an anti-CD22 antibody drug conjugate, an anti-CD45 antibody drug conjugate, and an anti-CD32 drug conjugate.

In some instances, the bispecific anti-CD20/anti-CD3 antibody and the anti-CD79b ADC are co-administered with one or more biological modifiers selected from a BCL-2 inhibitor (such as GDC-0199/ABT-199), lenalidomide (REVLIMID®), pomalidomide, thalidomide, a PI3K-delta inhibitor (such as idelalisib (ZYDELIG®; CAS #: 936563-96-1)), a PI3K inhibitor (such as taselisib (CAS #: 1282512-48-4), copanlisib (CAS #: 1032568-63-0), duvelisib (CAS #: 1201438-56-3), alpelisib (CAS #: 1217486-61-7), and umbralisib (CAS #: 1532533-67-7)), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody and the anti-CD79b ADC are co-administered with one or more chemotherapy agents and one or more biological modifiers selected from a BCL-2 inhibitor (such as GDC-0199/ABT-199), lenalidomide (REVLIMID®), pomalidomide, thalidomide, a PI3K-delta inhibitor (such as idelalisib (ZYDELIG®; CAS #: 936563-96-1)), a PI3K inhibitor (such as taselisib (CAS #: 1282512-48-4), copanlisib (CAS #: 1032568-63-0), duvelisib (CAS #: 1201438-56-3), alpelisib (CAS #: 1217486-61-7), and umbralisib (CAS #: 1532533-67-7)), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody and the anti-CD79b ADC are co-administered with one or more biological modifiers selected from a BCL-2 inhibitor (such as GDC-0199/ABT-199), lenalidomide (REVLIMID®), pomalidomide, thalidomide, a PI3K-delta inhibitor (such as idelalisib (ZYDELIG®; CAS #: 936563-96-1)), a PI3K inhibitor (such as taselisib (CAS #: 1282512-48-4), 5 copanlisib (CAS #: 1032568-63-0), duvelisib (CAS #: 1201438-56-3), alpelisib (CAS #: 1217486-61-7), and umbralisib (CAS #: 1532533-67-7)), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody and the anti-CD79b ADC are co-administered with obinutuzumab and one or more chemotherapy agents. In one instance, the bispecific anti-CD20/anti-CD3 antibody is co-administered with obinutuzumab and CHOP. In one instance, the bispecific anti-CD20/anti-CD3 antibody is co-administered with obinutuzumab and an ADC. In one instance, the bispecific anti-CD20/anti-CD3 antibody is co-administered with obinutuzumab and CHOP, wherein vincristine is replaced with an ADC. In one instance, the bispecific anti-CD20/anti-CD3 antibody is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate. In one instance, the bispecific anti-CD20/anti-CD3 antibody is co-administered with obinutuzumab and one or more biological modifiers selected from a BCL-2 inhibitor (such as GDC-0199/ABT-199), lenalidomide (REVLIMID®), pomalidomide, thalidomide, a PI3K-delta inhibitor (such as idelalisib (ZYDELIG®; CAS #: 936563-96-1)), a PI3K inhibitor (such as taselisib (CAS #: 1282512-48-4), copanlisib (CAS #: 1032568-63-0), duvelisib (CAS #: 1201438-56-3), alpelisib (CAS #: 1217486-61-7), and umbralisib (CAS #: 1532533-67-7)), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances the bispecific anti-CD20/anti-CD3 antibody and the anti-CD79b ADC are co-administered with obinutuzumab and one or more biological modifiers selected from a BCL-2 inhibitor (such as GDC-0199/ABT-199), lenalidomide (REVLIMID®), pomalidomide, thalidomide, a PI3K-delta inhibitor (such as idelalisib (ZYDELIG®; CAS #: 936563-96-1)), a PI3K inhibitor (such as taselisib (CAS #: 1282512-48-4), copanlisib (CAS #: 1032568-63-0), duvelisib (CAS #: 1201438-56-3), alpelisib (CAS #: 1217486-61-7), and umbralisib (CAS #: 1532533-67-7)), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the additional therapy comprises a BCL-2 inhibitor. In one embodiment, the BCL-2 inhibitor is 4-(4-{[2-(4-chlorophenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin-5-yloxy)benzamide and salts thereof. In one instance, the BCL-2 inhibitor is venetoclax (CAS #: 1257044-40-8).

In some instances, the additional therapy comprises a phosphoinositide 3-kinase (PI3K) inhibitor. In one instance, the PI3K inhibitor inhibits delta isoform of PI3K (i.e., P1105). In some instances, the PI3K inhibitor is 5-Fluoro-3-phenyl-2-[(1S)-1-(7H-purin-6-ylamino)propyl]-4(3H)-quinazolinone and salts thereof. In some instances, the PI3K inhibitor is idelalisib (CAS #: 870281-82-6). In one instance, the PI3K inhibitor inhibits alpha and delta isoforms of PI3K. In some instances, the PI3K inhibitor is 2-{3-[2-(1-Isopropyl-3-methyl-1H-1,2-4-triazol-5-yl)-5,6-dihydrobenzo[f] imidazo[1,2-d][1,4]oxazepin-9-yl]-1H-pyrazol-1-yl}-2-methylpropanamide and salts thereof. In some instance, the PI3K inhibitor is taselisib (CAS #: 1282512-48-4). In some instances, the PI3K inhibitor is 2-amino-N-[2,3-dihydro-7-methoxy-8-[3-(4-morpholinyl)propoxy]imidazo[1,2-c]quinazolin-5-yl]-5-pyrimidinecarboxamide and salts thereof. In some instance, the PI3K inhibitor is copanlisib (CAS #: 1032568-63-0). In some instances, the PI3K inhibitor is 8-chloro-2-phenyl-3-[(1S)-1-(9H-purin-6-ylamino)ethyl]-1 (2H)-isoquinolinone and salts thereof. In some instance, the PI3K inhibitor is duvelisib (CAS #: 1201438-56-3). In some instances, the PI3K inhibitor is (2S)-$N^1$-[4-methyl-5-[2-(2,2,2-trifluoro-1,1-dimethylethyl)-4-pyridinyl]-2-thiazolyl]-1,2-pyrrolidinedicarboxamide and salts thereof. In some instance, the PI3K inhibitor is alpelisib (CAS #: 1217486-61-7). In some instances, the PI3K inhibitor is 2-[(1S)-1-[4-amino-3-[3-fluoro-4-(1-methylethoxy)phenyl]-1H-pyrazolo[3,4-d]pyrimidin-1-yl]ethyl]-6-fluoro-3-(3-fluorophenyl)-4H-1-benzopyran-4-one and salts thereof. In some instance, the PI3K inhibitor is umbralisib (CAS #: 1532533-67-7).

In a further aspect of the invention, the additional therapy comprises a Bruton's tyrosine kinase (BTK) inhibitor. In one instance, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one and salts thereof. In one instance, the BTK inhibitor is ibrutinib (CAS #: 936563-96-1). In some instances, the BTK inhibitor is (7S)-4,5,6,7-tetrahydro-7-[1-(1-oxo-2-propen-1-yl)-4-piperidinyl]-2-(4-phenoxyphenyl)-pyrazolo[1,5-a]pyrimidine-3-carboxamide and salts thereof. In some instances, the BTK inhibitor is zanubrutimib (CAS #: 1691249-45-2). In some instances, the BTK inhibitor is 4-[8-amino-3-[(2S)-1-(1-oxo-2-butyn-1-yl)-2-pyrrolidinyl]imidazo[1,5-a]pyrazin-1-yl]-N-2-pyridinyl-benzamide and salts thereof. In some instances, the BTK inhibitor is acalabrutinib (CAS #: 1420477-60-6).

In some instances, the additional therapy comprises thalidomide or a derivative thereof. In one instance, the thalidomide or a derivative thereof is (RS)-3-(4-Amino-1-oxo-1,3-dihydro-2H-isoindol-2-yl)piperidine-2,6-dione and salts thereof. In one instance, the thalidomide or a derivative thereof is lenalidomide (CAS #: 191732-72-6).

In instances for which the methods described herein involve a combination therapy, such as a particular combination therapy noted above, the combination therapy encompasses the administration of the bispecific anti-CD20/anti-CD3 antibody and the anti-CD79b ADC with one or more additional therapeutic agents, and such co-administration may be combined administration (where two or more therapeutic agents are included in the same or separate formulations) or separate administration, in which case, the administration of the anti-CD20/anti-CD3 bispecific antibody and anti-CD79b ADC can occur prior to, simultaneously, and/or following, administration of the additional therapeutic agent or agents. In one embodiment, the administration of the anti-CD20/anti-CD3 bispecific antibody and anti-CD79b ADC and administration of an additional therapeutic agent or exposure to radiotherapy can occur within about one month, or within about one, two or three weeks, or within about one, two, three, four, five, or six days, of each other. In a particular instance, the bispecific anti-CD20/anti-CD3 antibody and the anti-CD79b ADC can be co-administered with obinutuzumab (GAZYVA®), wherein the subject is first administered with obinutuzumab (GAZYVA®) and then separately administered with the bispecific anti-CD20/anti-CD3 antibody (e.g., the subject is pre-treated with obinutuzumab (GAZYVA®)). In another particular instance, the bispecific anti-CD20/anti-CD3 antibody and the anti-CD79b ADC can be co-administered with tocilizumab (ACTEMRA®/RoACTEMRA®), wherein the subject is first administered with tocilizumab (ACTEMRA®/RoACTEMRA®) and then separately administered with the bispecific anti-CD20/anti-CD3 antibody (e.g., the subject is pre-treated with tocilizumab (ACTEMRA®/RoACTEMRA®)).

The methods described herein may result in an improved benefit-risk profile for subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), a CLL, or a CNSL) being treated with an anti-CD20/anti-CD3 bispecific antibody and anti-CD79b ADC. In some instances, treatment using the methods described herein that result in administering the anti-CD20/anti-CD3 bispecific antibody and anti-CD79b ADC in the context of a fractionated, dose-escalation dosing regimen results in a reduction (e.g., by 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater) or complete inhibition (100% reduction) of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or hepatotoxicities, following treatment with an anti-CD20/anti-CD3 bispecific antibody and anti-CD79b ADC using the fractionated, dose-escalation dosing regimen of the invention relative to treatment with an anti-CD20/anti-CD3 bispecific antibody and anti-CD79b ADC using an non-fractioned dosing regimen.

The methods may involve administering the anti-CD20/anti-CD3 bispecific antibody and anti-CD79b ADC (and/or any additional therapeutic agent) by any suitable means, including parenteral, intrapulmonary, and intranasal, and, if desired for local treatment, intralesional administration. Parenteral infusions include intravenous, subcutaneous, intramuscular, intraarterial, and intraperitoneal administration routes. In some embodiments, the anti-CD20/anti-CD3 bispecific antibody and anti-CD79b ADC are administered by intravenous infusion. In other instances, the anti-CD20/anti-CD3 bispecific antibody and anti-CD79b ADC are administered subcutaneously. In yet other instances, the anti-CD20/anti-CD3 bispecific antibody is administered subcutaneously and the anti-CD79b ADC is administered by intravenous infusion. In some instances, the anti-CD20/anti-CD3 bispecific antibody and anti-CD79b ADC administered by intravenous injection exhibit a less toxic response (i.e., fewer unwanted effects) in a subject than the same anti-CD20/anti-CD3 bispecific antibody and anti-CD79b ADC administered by subcutaneous injection. In some instances, a less toxic response in a subject is observed when the anti-CD20/anti-CD3 bispecific antibody is administered subcutaneously while the anti-CD79b ADC is intravenously administered in a subject than the same anti-CD20/anti-CD3 bispecific antibody and anti-CD79b ADC administered by intravenous injection.

For all the methods described herein, the anti-CD20/anti-CD3 bispecific antibody and anti-CD79b ADC would be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The anti-CD20/anti-CD3 bispecific antibody and anti-CD79b ADC need not be, but is optionally formulated with, one or more agents currently used to prevent or treat the disorder in question. The effective amount of such other agents depends on the amount of the anti-CD20/anti-CD3 bispecific antibody and anti-CD79b ADC present in the formulation, the type of disorder or treatment, and other factors discussed above. The anti-CD20/anti-CD3 bispecific antibody and anti-CD79b ADC may be suitably administered to the subject over a series of treatments.

In some instances, additional therapeutic agents useful in the present invention include therapeutic antibodies, such as alemtuzumab (CAMPATH®), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (BEXXAR®, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, tafasitamab, talizumab, tefibazumab, tocilizumab, toralizumab, tucotuzumab celmoleukin, tucusituzumab, umavizumab, urtoxazumab, ustekinumab, visilizumab, and briakinumab.

V. Pharmaceutical Compositions and Formulations

Any of the anti-CD79b antibody drug conjugates, anti-CD20/anti-CD3 bispecific antibodies, and/or additional therapeutic agents described herein can be used in pharmaceutical compositions and formulations. Pharmaceutical compositions and formulations of an anti-CD79b antibody drug conjugate, an anti-CD20/anti-CD3 bispecific antibody, and/or one or more additional therapeutic agents (e.g., one or more chemotherapeutic agents) can be prepared by can be prepared by mixing one or more agents having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

VI. Kits and Articles of Manufacture

In another aspect of the invention, a kit or an article of manufacture containing materials useful for the treatment, prevention, and/or diagnosis of the disorders described above is provided. The kit or article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an anti-CD79b antibody drug conjugate or an anti-CD20/anti-CD3 bispecific antibody. The label or package insert indicates that the composition is used for treating the condition of choice (e.g., a CD20-positive cell proliferative disorder, e.g., a B cell proliferative disorder (e.g., an NHL (e.g., a relapsed and/or refractory NHL, a DLBCL (e.g., a relapsed and/or refractory DLBCL), an FL (e.g., a relapsed and/or refractory FL or a transformed FL), or an MCL (e.g., a relapsed or refractory MCL)), a CLL, or a CNSL)) and further includes information related to at least one of the dosing regimens described herein. The kit or article of manufacture may comprise a container with a composition contained therein, wherein the composition comprises an anti-CD20/anti-CD3 bispecific antibody described herein (e.g., mosunetuzumab) or an anti-CD79b antibody drug conjugated described herein (e.g., polatuzumab vedotin). Alternatively, the kit or article of manufacture may comprise (a) a first container with a composition contained therein, wherein the composition comprises an anti-CD20/anti-CD3 bispecific antibody described herein, an anti-CD79b antibody drug conjugated described herein, or both an anti-CD20/anti-CD3 bispecific antibody and an anti-CD79b antibody drug conjugated; and/or (b) a second container with a composition contained therein, wherein the composition comprises an additional therapeutic agent (e.g., a further cytotoxic or otherwise therapeutic agent). Alternatively, or additionally, the kit or article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

VII. Embodiments

Some embodiments of the technology described herein can be defined according to any of the following numbered embodiments:

1. A method of treating a subject having a CD20-positive cell proliferative disorder comprising administering to the subject an anti-CD79b antibody drug conjugate and a bispecific antibody that binds to CD20 and CD3 in a dosing regimen comprising at least a first dosing cycle and a second dosing cycle, wherein:

(a) the first dosing cycle comprises a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (b) the second dosing cycle comprises a single dose (C2D1) of the bispecific antibody, wherein the C2D1 of the bispecific antibody is equal to or greater than the C1D3.

2. A bispecific antibody that binds to CD20 and CD3 for use in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising at least a first dosing cycle and a second dosing cycle, wherein:

(a) the first dosing cycle comprises a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (b) the second dosing cycle comprises a single dose (C2D1) of the bispecific antibody, wherein the C2D1 of the bispecific antibody is equal to or greater than the C1D3.

3. Use of a bispecific antibody that binds to CD20 and CD3 in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising at least a first dosing cycle and a second dosing cycle, wherein:

(a) the first dosing cycle comprises a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (b) the second dosing cycle comprises a single dose (C2D1) of the bispecific antibody, wherein the C2D1 of the bispecific antibody is equal to or greater than the C1D3.

4. Use of a bispecific antibody that binds to CD20 and CD3 in the manufacture of a medicament in combination with an anti-CD79b antibody drug conjugate for treating a subject having a CD20-positive cell proliferative disorder, wherein the bispecific antibody and the anti-CD79b antibody drug conjugate are formulated for administration to the subject in a dosing regimen comprising at least a first dosing cycle and a second dosing cycle, wherein:

(a) the first dosing cycle comprises a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (b) the second dosing cycle comprises a single dose (C2D1) of the bispecific antibody, wherein the C2D1 of the bispecific antibody is equal to or greater than the C1D3.

5. The method, bispecific antibody for use, or use of any one of embodiments 1-4, wherein the C1D1 of the bispecific antibody is about 1 mg, the C1D2 of the bispecific antibody is about 2 mg, and the C1D3 of the bispecific antibody is about 9 mg.

6. The method, bispecific antibody for use, or use of embodiment 5, wherein the C2D1 of the bispecific antibody is about 9 mg.

7. The method, bispecific antibody for use, or use of any one of embodiments 1-4, wherein the C1D1 of the bispecific antibody is about 1 mg, the C1D2 of the bispecific antibody is about 2 mg, and the C1D3 of the bispecific antibody is about 13.5 mg.

8. The method, bispecific antibody for use, or use of embodiment 7, wherein the C2D1 of the bispecific antibody is about 13.5 mg.

9. The method, bispecific antibody for use, or use of any one of embodiments 1-4, wherein the C1D1 of the bispecific antibody is about 1 mg, the C1D2 of the bispecific antibody is about 2 mg, and the C1D3 of the bispecific antibody is about 20 mg.

10. The method, bispecific antibody for use, or use of embodiment 9, wherein the C2D1 of the bispecific antibody is about 20 mg.

11. The method, bispecific antibody for use, or use of any one of embodiments 1-4, wherein the C1D1 of the bispecific antibody is about 1 mg, the C1D2 of the bispecific antibody is about 2 mg, and the C1D3 of the bispecific antibody is about 40 mg.

12. The method, bispecific antibody for use, or use of embodiment 8, wherein the C2D1 of the bispecific antibody is about 40 mg.

13. The method, bispecific antibody for use, or use of any one of embodiments 1-4, wherein the C1D1 of the bispecific antibody is about 5 mg, the C1D2 of the bispecific antibody is about 15 mg, and the C1D3 of the bispecific antibody is about 45 mg.

14. The method, bispecific antibody for use, or use of embodiment 13, wherein the C2D1 of the bispecific antibody is about 45 mg.

15. The method, bispecific antibody for use, or use of any one of embodiments 1-4, wherein the C1D1 of the bispecific antibody is about 5 mg, the C1D2 of the bispecific antibody is about 45 mg, and the C1D3 of the bispecific antibody is about 45 mg.

16. The method, bispecific antibody for use, or use of embodiment 15, wherein the C2D1 of the bispecific antibody is about 45 mg.

17. The method, bispecific antibody for use, or use of any one of embodiments 1-4, wherein the C1D1 of the bispecific antibody is about 1 mg, the C1D2 of the bispecific antibody is about 2 mg, and the C1D3 of the bispecific antibody is about 60 mg.

18. The method, bispecific antibody for use, or use of embodiment 14, wherein the C2D1 of the bispecific antibody is about 60 mg.

19. The method, bispecific antibody for use, or use of any one of embodiments 1-18, wherein the first dosing cycle comprises a single dose C1D1 of the anti-CD79b antibody drug conjugate.

20. The method, bispecific antibody for use, or use of embodiment 19, wherein the single dose C1D1 of the anti-CD79b antibody drug conjugate is from about 0.5 mg/kg to about 10 mg/kg.

21. The method, bispecific antibody for use, or use of embodiment 20, wherein the single dose C1D1 of the anti-CD79b antibody drug conjugate is about 1.8 mg/kg.

22. The method, bispecific antibody for use, or use of any one of embodiments 1-21, wherein the second dosing cycle comprises a single dose C2D1 of the anti-CD79b antibody drug conjugate.

23. The method, bispecific antibody for use, or use of embodiment 22, wherein the single dose C2D1 of the anti-CD79b antibody drug conjugate is from about 0.5 mg/kg to about 10 mg/kg.

24. The method, bispecific antibody for use, or use of embodiment 23, wherein the single dose C2D1 of the anti-CD79b antibody drug conjugate is about 1.8 mg/kg.

25. The method, bispecific antibody for use, or use of any one of embodiments 1-24, wherein the C1D1 of the bispecific antibody, the C1D2 of the bispecific antibody, and the C1D3 of the bispecific antibody are administered or are to be administered to the subject on or about Days 1, 8, and 15, respectively, of the first dosing cycle.

26. The method, bispecific antibody for use, or use of any one of embodiments 1-19, wherein the C2D1 of the bispecific antibody is administered or is to be administered to the subject on Day 1 of the second dosing cycle.

27. The method, bispecific antibody for use, or use of any one of embodiments 1-26, wherein the C1D1 of the anti-CD79b antibody drug conjugate is administered or is to be administered to the subject on Day 1 of the first dosing cycle and/or the C2D1 of the anti-CD79b antibody drug conjugate is administered or is to be administered to the subject on Day 1 of the second dosing cycle.

28. The method, bispecific antibody for use, or use of any one of embodiments 1-27, wherein the first and second dosing cycles are 21-day dosing cycles.

29. The method, bispecific antibody for use, or use of any one of embodiments 1-28, wherein the dosing regimen comprises one or more additional dosing cycles.

30. The method, bispecific antibody for use, or use of embodiment 29, wherein the dosing regimen comprises four to 15 additional dosing cycles.

31. The method, bispecific antibody for use, or use of embodiment 29 or 30, wherein the additional dosing cycles are 21-day dosing cycles.

32. The method, bispecific antibody for use, or use of any one of embodiments 29-31, wherein one or more of the additional dosing cycles comprise an additional single dose of the bispecific antibody and an additional single dose of the anti-CD79b antibody drug conjugate.

33. The method, bispecific antibody for use, or use of embodiment 32, wherein the additional single dose of the anti-CD79b antibody drug conjugate is equivalent in amount to the C2D1 of the anti-CD79b antibody drug conjugate.

34. The method, bispecific antibody for use, or use of embodiment 32 or 33, wherein the additional single dose of the anti-CD79b antibody drug conjugate is administered or is to be administered to the subject on Day 1 of each additional dosing cycle comprising an additional dose of the anti-CD79b antibody drug conjugate.

35. The method, bispecific antibody for use, or use of any one of embodiments 29-34, wherein one or more of the additional dosing cycles comprise an additional single dose of the bispecific antibody and do not comprise administration of the anti-CD79b antibody drug conjugate.

36. The method, bispecific antibody for use, or use of any one of embodiments 32-35, wherein the additional single dose of the bispecific antibody is equivalent in amount to the C2D1 of the bispecific antibody.

37. The method, bispecific antibody for use, or use of any one of embodiments 32-35, wherein the additional single dose of the bispecific antibody is less than the C2D1 of the bispecific antibody.

38. The method, bispecific antibody for use, or use of any one of embodiments 32-37, wherein the additional single dose of the bispecific antibody is administered or is to be administered to the subject on Day 1 of each additional dosing cycle comprising an additional dose of the bispecific antibody.

39. The method, bispecific antibody for use, or use of any one of embodiments 29-38, wherein the dosing regimen comprises six or more additional dosing cycles, wherein each of the six or more additional dosing cycles comprises a single dose of the bispecific antibody, and wherein no more than four of the six or more additional dosing cycles comprises administration of the anti-CD79b antibody drug conjugate.

40. The method, bispecific antibody for use, or use of any one of embodiments 29-38, wherein the dosing regimen comprises four or more additional dosing cycles, wherein each of the four or more additional dosing cycles comprises a single dose of the bispecific antibody, and wherein no more than four of the four or more additional dosing cycles comprises administration of the anti-CD79b antibody drug conjugate.

41. A method of treating a subject having a CD20-positive cell proliferative disorder comprising administering to the subject an anti-CD79b antibody drug conjugate and a bispecific antibody that binds to CD20 and CD3 in a dosing regimen comprising eight or more dosing cycles, wherein:

(a) the first dosing cycle comprises:
   (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and
   (ii) a single dose (C1D1) of the anti-CD79b antibody drug conjugate;
(b) the second dosing cycle comprises a single dose (C2D1) of the bispecific antibody and a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

42. A bispecific antibody that binds to CD20 and CD3 for use in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:
  (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and
  (ii) a single dose (C1D1) of the anti-CD79b antibody drug conjugate;
(b) the second dosing cycle comprises a single dose (C2D1) of the bispecific antibody and a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

43. Use of a bispecific antibody that binds to CD20 and CD3 in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:
  (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and
  (ii) a single dose (C1D1) of the anti-CD79b antibody drug conjugate;
(b) the second dosing cycle comprises a single dose (C2D1) of the bispecific antibody and a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

44. Use of a bispecific antibody that binds to CD20 and CD3 in the manufacture of a medicament in combination with an anti-CD79b antibody drug conjugate for treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:
  (i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and
  (ii) a single dose (C1D1) of the anti-CD79b antibody drug conjugate;
(b) the second dosing cycle comprises a single dose (C2D1) of the bispecific antibody and a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

45. The method, bispecific antibody for use, or use of any one of embodiments 41-44, wherein the C1D3 and C2D1-C8D1 of the bispecific antibody are about equivalent in amount.

46. A method of treating a subject having a CD20-positive cell proliferative disorder comprising administering to the subject an anti-CD79b antibody drug conjugate and a bispecific antibody that binds to CD20 and CD3 in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or less than the C1D3.

47. A bispecific antibody that binds to CD20 and CD3 for use in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or less than the C1D3.

48. Use of a bispecific antibody that binds to CD20 and CD3 in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or less than the C1D3.

49. Use of a bispecific antibody that binds to CD20 and CD3 in the manufacture of a medicament in combination with an anti-CD79b antibody drug conjugate for treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or less than the C1D3.

50. The method, bispecific antibody for use, or use of any one of embodiments 46-49, wherein the C1D3 and C2D1 of the bispecific antibody are about equivalent in amount and each of the C3D1-C8D1 of the bispecific antibody is less than the C1 D3.

51. The method, bispecific antibody for use, or use of any one of embodiments 46-50, wherein each of the C3D1-C8D1 of the bispecific antibody is about half of the C1D3.

52. The method, bispecific antibody for use, or use of any one of embodiments 41-51, wherein the C1D1-C6D1 of the anti-CD79b antibody drug conjugate are about equivalent in amount.

53. The method, bispecific antibody for use, or use of embodiment 52, wherein each of the C1D1-C6D1 of the anti-CD79b antibody drug conjugate is from about 0.5 mg/kg to about 10 mg/kg.

54. The method, bispecific antibody for use, or use of embodiment 53, wherein each of the C1D1-C6D1 of the anti-CD79b antibody drug conjugate is about 1.8 mg/kg.

55. The method, bispecific antibody for use, or use of any one of embodiments 41-54, wherein the C1D1 of the bispecific antibody, the C1D2 of the bispecific antibody, and the C1D3 of the bispecific antibody are administered or are to be administered to the subject on or about Days 1, 8, and 15, respectively, of the first dosing cycle.

56. The method, bispecific antibody for use, or use of any one of embodiments 41-55, wherein the C1D1-C8D1 of the bispecific antibody is administered or is to be administered to the subject on Day 1 of each dosing cycle.

57. The method, bispecific antibody for use, or use of any one of embodiments 41-56, wherein the C1D1-C6D1 of the anti-CD79b antibody drug conjugate is administered or is to be administered to the subject on Day 1 of each dosing cycle.

58. The method, bispecific antibody for use, or use of any one of embodiments 41-57, wherein each dosing cycle is a 21-day dosing cycle.

59. A method of treating a subject having a CD20-positive cell proliferative disorder comprising administering to the subject an anti-CD79b antibody drug conjugate and a bispecific antibody that binds to CD20 and CD3 in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

60. A bispecific antibody that binds to CD20 and CD3 for use in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

61. Use of a bispecific antibody that binds to CD20 and CD3 in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

62. Use of a bispecific antibody that binds to CD20 and CD3 in the manufacture of a medicament in combination with an anti-CD79b antibody drug conjugate for treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3.

63. The method, bispecific antibody for use, or use of any one of any one of embodiments 59-62, wherein the C1D3 and C2D1-C8D1 of the bispecific antibody are about equivalent in amount.

64. A method of treating a subject having a CD20-positive cell proliferative disorder comprising administering to the subject an anti-CD79b antibody drug conjugate and a bispecific antibody that binds to CD20 and CD3 in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein the C2D1 of the bispecific antibody is equivalent in amount to the C1 D3 and each of the C3D1-C8D1 is less than the C1D3.

65. A bispecific antibody that binds to CD20 and CD3 for use in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein the C2D1 of the bispecific antibody is equivalent in amount to the C1 D3 and each of the C3D1-C8D1 is less than the C1D3.

66. Use of a bispecific antibody that binds to CD20 and CD3 in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein the C2D1 of the bispecific antibody is equivalent in amount to the C1 D3 and each of the C3D1-C8D1 is less than the C1D3.

67. Use of a bispecific antibody that binds to CD20 and CD3 in the manufacture of a medicament in combination with an anti-CD79b antibody drug conjugate for treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;

(b) the second dosing cycle comprises a single dose (C2D1) of the bispecific antibody and a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate, wherein the C2D1 of the bispecific antibody is equivalent in amount to the C1 D3 and each of the C3D1-C8D1 is less than the C1D3.

68. The method, bispecific antibody for use, or use of any one of embodiments 59-67, wherein the C2D1-C6D1 of the anti-CD79b antibody drug conjugate are about equivalent in amount.

69. The method, bispecific antibody for use, or use of any one of embodiments 59-68, wherein each of the C2D1-C6D1 of the anti-CD79b antibody drug conjugate is from about 0.5 mg/kg to about 10 mg/kg.

70. The method, bispecific antibody for use, or use of embodiment 69, wherein each of the C2D1-C6D1 of the anti-CD79b antibody drug conjugate is about 1.8 mg/kg.

71. The method, bispecific antibody for use, or use of any one of embodiments 59-70, wherein the C1D1 of the bispecific antibody, the C1D2 of the bispecific antibody, and the C1D3 of the bispecific antibody are administered or are to be administered to the subject on or about Days 1, 8, and 15, respectively, of the first dosing cycle.

72. The method, bispecific antibody for use, or use of any one of embodiments 59-71, wherein the C1D1 and C2D1-C8D1 of the bispecific antibody are administered or are to be administered to the subject on Day 1 of each dosing cycle.

73. The method, bispecific antibody for use, or use of any one of embodiments 59-72, wherein the C2D1-C6D1 of the anti-CD79b antibody drug conjugate are administered or are to be administered to the subject on Day 1 of each dosing cycle.

74. The method, bispecific antibody for use, or use of any one of embodiments 59-73, wherein each dosing cycle is a 21-day dosing cycle.

75. The method, bispecific antibody for use, or use of any one of embodiments 41-74, wherein the dosing regimen comprises one or more additional dosing cycles comprising a single dose of the bispecific antibody.

76. The method, bispecific antibody for use, or use of embodiment 75, wherein the dosing regimen comprises from one to nine additional dosing cycles comprising a single dose of the bispecific antibody.

77. The method, bispecific antibody for use, or use of embodiment 75 or 76, wherein each of the additional dosing cycles does not comprise administration of the anti-CD79b antibody drug conjugate.

78. The method, bispecific antibody for use, or use of any one of embodiments 75-77, wherein each of the additional dosing cycles is a 21-day dosing cycle.

79. The method, bispecific antibody for use, or use of any one of embodiments 1-78, wherein the bispecific antibody and the anti-CD79b antibody drug conjugate have a synergistic effect in a mouse NSG:human WSU-DLCL2 model system when compared to either the bispecific antibody or the anti-CD79b antibody drug conjugate alone.

80. The method, bispecific antibody for use, or use of any one of embodiments 1-79, wherein the method further comprises administering to the subject one or more additional therapeutic agents.

81. The method, bispecific antibody for use, or use of embodiment 80, wherein the one or more additional therapeutic agents is a corticosteroid or an IL-R6 antagonist.

82. The method, bispecific antibody for use, or use of embodiment 81, wherein the IL-R6 antagonist is tocilizumab.

83. The method, bispecific antibody for use, or use of embodiment 82, wherein tocilizumab is administered intravenously to the subject as a single dose of about 8 mg/kg, and wherein the single dose does not exceed 800 mg.

84. The method, bispecific antibody for use, or use of embodiment 81, wherein the one or more additional therapeutic agents is a corticosteroid.

85. The method, bispecific antibody for use, or use of embodiment 84, wherein the corticosteroid is dexamethasone, prednisone, or methylprednisolone.

86. The method, bispecific antibody for use, or use of embodiment 80, wherein the one or more additional therapeutic agents comprise one or more chemotherapeutic agents.

87. The method, bispecific antibody for use, or use of embodiment 86, wherein the one or more chemotherapeutic agents comprise cyclophosphamide or doxorubicin.

88. A method of reducing the rate of cytokine release syndrome in a population of subjects having a CD20-positive cell proliferative disorder who are administered an anti-CD79b antibody drug conjugate and a bispecific antibody that binds to CD20 and CD3, wherein the method comprises administering to one or more subjects of the population an anti-CD79b antibody drug conjugate and a bispecific antibody that binds to CD20 and CD3 according to the method, bispecific antibody for use, or use of any one of embodiments 1-87.

89. A bispecific antibody that binds to CD20 and CD3 for use in combination with an anti-CD79b antibody drug conjugate in reducing the rate of cytokine release syndrome in a population of subjects having a CD20-positive cell proliferative disorder, wherein the bispecific antibody and the anti-CD79b antibody drug conjugate are formulated for administration to one or more subjects of the population according to the method, bispecific antibody for use, or use of any one of embodiments 1-87.

90. Use of a bispecific antibody that binds to CD20 and CD3 in combination with an anti-CD79b antibody drug conjugate in reducing the rate of cytokine release syndrome in a population of subjects having a CD20-positive cell proliferative disorder, wherein the bispecific antibody and the anti-CD79b antibody drug conjugate are formulated for administration to one or more subjects of the population according to the method, bispecific antibody for use, or use of any one of embodiments 1-87.

91. Use of a bispecific antibody that binds to CD20 and CD3 in the manufacture of a medicament in combination with an anti-CD79b antibody drug conjugate for reducing the rate of cytokine release syndrome in a population of subjects having a CD20-positive cell proliferative disorder, wherein the bispecific antibody and the anti-CD79b antibody drug conjugate are formulated for administration to one or more subjects of the population according to the method, bispecific antibody for use, or use of any one of embodiments 1-87.

92. A method of reducing the rate of cytokine release syndrome in a population of subjects having a CD20-positive cell proliferative disorder who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising at least a first dosing cycle and a second dosing cycle, wherein:

(a) the first dosing cycle comprises a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (b) the second dosing cycle comprises a single dose (C2D1) of the bispecific antibody, wherein the C2D1 of the bispecific antibody is equal to or greater than the C1D3, wherein the rate of cytokine release syndrome is reduced in the population of subjects compared to a reference population of subjects to whom no anti-CD79b antibody drug conjugate has been administered.

93. A method of reducing the rate of cytokine release syndrome in a population of subjects having a CD20-positive cell proliferative disorder who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is equal to or greater than the C1D3, and wherein the rate of cytokine release syndrome is reduced in the population of subjects compared to a reference population of subjects to whom no anti-CD79b antibody drug conjugate has been administered.

94. A method of reducing the rate of cytokine release syndrome in a population of subjects having a CD20-positive cell proliferative disorder who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 5.0 mg, the C1D2 of the bispecific antibody is between about 0.05 mg to about 60 mg, and the C1 D3 of the bispecific antibody is about 9 mg, about 13.5 mg, about 20 mg, about 40 mg, about 45 mg, or about 60 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate,
wherein the single dose C2D1 of the bispecific antibody is equivalent in amount to the C1D3 and each single dose C3D1-C8D1 of the bispecific antibody is less than the C1D3, and wherein the rate of cytokine release syndrome is reduced in the population of subjects compared to a reference population of subjects to whom no anti-CD79b antibody drug conjugate has been administered.

95. A method of reducing the rate of cytokine release syndrome in a population of subjects having a CD20-positive cell proliferative disorder who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein:
(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;
(b) the second dosing cycle comprises a single dose (C2D1) of the bispecific antibody and a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate,
wherein each single dose C2D1-C8D1 of the bispecific antibody is equal to or greater than the C1D3, and wherein the rate of cytokine release syndrome is reduced in the population of subjects compared to a reference population of subjects to whom no anti-CD79b antibody drug conjugate has been administered.

96. A method of reducing the rate of cytokine release syndrome in a population of subjects having a CD20-positive cell proliferative disorder who are administered an anti-CD79b antibody drug conjugate and a bispecific antibody that binds to CD20 and CD3, the method comprising administering to one or more subjects of the population an anti-CD79b antibody drug conjugate and a bispecific antibody that binds to CD20 and CD3 in a dosing regimen comprising eight or more dosing cycles, wherein:
(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, about 40 mg, about 45 mg, or about 60 mg;
(b) the second dosing cycle comprises a single dose (C2D1) of the bispecific antibody and a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate,
wherein the single dose C2D1 of the bispecific antibody is equivalent in amount to the C1D3 and each single dose C3D1-C8D1 of the bispecific antibody is less than the C1D3, and wherein the rate of cytokine release syndrome is reduced in the population of subjects compared to a reference population of subjects to whom no anti-CD79b antibody drug conjugate has been administered.

97. The method, bispecific antibody for use, or use of any one of embodiments 88-96, wherein the population of subjects exhibits cytokine release syndrome after administering the bispecific antibody, wherein the rate of the cytokine release syndrome in the population of subjects is less than or equal to about 20%.

98. The method, bispecific antibody for use, or use of embodiment 97, wherein the rate of cytokine release syndrome in the population of subjects is less than or equal to about 10%.

99. The method, bispecific antibody for use, or use of embodiment 98, wherein the rate of cytokine release syndrome in the population of subjects is less than or equal to about 5%, 100. The method, bispecific antibody for use, or use of embodiment 99, wherein the rate of cytokine release syndrome in the population of subjects is less than or equal to about 3%.

101. The method, bispecific antibody for use, or use of any one of embodiments 88-100, wherein the rate of cytokine release syndrome having a grade of 2 or greater (as defined by the American Society for Transplantation and Cellular Therapy, 2019; ASTCT) is less than or equal to about 20%,
102. The method, bispecific antibody for use, or use of embodiment 101, wherein the rate of cytokine release syndrome having a grade of 2 or greater (as defined by the ASTCT) is less than or equal to about 5%.
103. The method, bispecific antibody for use, or use of embodiment 102, wherein the rate of cytokine release syndrome having a grade of 2 or greater (as defined by the ASTCT) is about 0%.
104. The method, bispecific antibody for use, or use of any one of embodiments 1-103, wherein the CD20-positive cell proliferative disorder is a B cell proliferative disorder.
105. The method, bispecific antibody for use, or use of embodiment 104, wherein the B cell proliferative disorder is a non-Hodgkin's lymphoma (NHL), a chronic lymphoid leukemia (CLL), or a central nervous system lymphoma (CNSL).
106. The method, bispecific antibody for use, or use of embodiment 105, wherein the NHL is a diffuse-large B cell lymphoma (DLBCL), a follicular lymphoma (FL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma.
107. The method, bispecific antibody for use, or use of embodiment 105, wherein the NHL is a relapsed or refractory NHL.
108. The method, bispecific antibody for use, or use of embodiment 106, wherein the NHL is a DLBCL.
109. The method, bispecific antibody for use, or use of embodiment 108, wherein the DLBCL is a relapsed or refractory DLBCL.
110. The method, bispecific antibody for use, or use of embodiment 108, wherein the DLBCL is a Richter's transformation.
111. The method, bispecific antibody for use, or use of embodiment 106, wherein the NHL is an FL.
112. The method, bispecific antibody for use, or use of embodiment 111, wherein the FL is a relapsed or refractory FL.
113. The method, bispecific antibody for use, or use of embodiment 111, wherein the FL is a transformed FL.
114. The method, bispecific antibody for use, or use of embodiment 106, wherein the NHL is an MCL.
115. The method, bispecific antibody for use, or use of embodiment 114, wherein the MCL is a relapsed or refractory MCL.
116. The method, bispecific antibody for use, or use of embodiment 104, wherein the B cell proliferative disorder is relapsed and/or refractory.
117. The method, bispecific antibody for use, or use of any one of embodiments 1-116, wherein the anti-CD79b antibody drug conjugate is polatuzumab vedotin or anti-CD79b-MC-vc-PAB-MMAE.
118. The method, bispecific antibody for use, or use of embodiment 117, wherein the anti-CD79b antibody drug conjugate is polatuzumab vedotin.
119. The method, bispecific antibody for use, or use of any one of embodiments 1-118, wherein the bispecific antibody comprises an anti-CD20 arm comprising a first binding domain comprising the following six hypervariable regions (HVRs):

(SEQ ID NO: 1)
(a) an HVR-H1 comprising the amino acid sequence of GYTFTSYNMH;

(SEQ ID NO: 2)
(b) an HVR-H2 comprising the amino acid sequence of AIYPGNGDTSYNQKFKG;

(SEQ ID NO: 3)
(c) an HVR-H3 comprising the amino acid sequence of VVYYSNSYWYFDV;

(SEQ ID NO: 4)
(d) an HVR-L1 comprising the amino acid sequence of RASSSVSYMH;

(SEQ ID NO: 5)
(e) an HVR-L2 comprising the amino acid sequence of APSNLAS;

and (SEQ ID NO: 6)
(f) an HVR-L3 comprising the amino acid sequence of QQWSFNPPT.

120. The method, bispecific antibody for use, or use of any one of embodiments 1-119, wherein the bispecific antibody comprises an anti-CD20 arm comprising a first binding domain comprising (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b).
121. The method, bispecific antibody for use, or use of embodiment 120, wherein the first binding domain comprises a VH domain comprising an amino acid sequence of SEQ ID NO: 7 and a VL domain comprising an amino acid sequence of SEQ ID NO: 8.
122. The method, bispecific antibody for use, or use of any one of embodiments 1-121 wherein the bispecific antibody comprises an anti-CD3 arm comprising a second binding domain comprising the following six HVRs:

(SEQ ID NO: 17)
(a) an HVR-H1 comprising the amino acid sequence of NYYIH;

(SEQ ID NO: 18)
(b) an HVR-H2 comprising the amino acid sequence of WIYPGDGNTKYNEKFKG;

(SEQ ID NO: 19)
(c) an HVR-H3 comprising the amino acid sequence of DSYSNYYFDY;

-continued (SEQ ID NO: 20)
(d) an HVR-L1 comprising the amino acid sequence of KSSQSLLNSRTRKNYLA;

(SEQ ID NO: 21)
(e) an HVR-L2 comprising the amino acid sequence of WASTRES;
and (SEQ ID NO: 22)
(f) an HVR-L3 comprising the amino acid sequence of TQSFILRT.

123. The method, bispecific antibody for use, or use of any one of embodiments 1-122, wherein the bispecific antibody comprises an anti-CD3 arm comprising a second binding domain comprising (a) a VH domain comprising an amino acid sequence having at least 95% sequence identity to the amino acid sequence of SEQ ID NO: 23; (b) a VL domain comprising an amino acid sequence having at least 95% sequence identity to the amino acid sequence of SEQ ID NO: 24; or (c) a VH domain as in (a) and a VL domain as in (b).

124. The method, bispecific antibody for use, or use of embodiment 123, wherein the second binding domain comprises a VH domain comprising an amino acid sequence of SEQ ID NO: 23 and a VL domain comprising an amino acid sequence of SEQ ID NO: 24.

125. The method, bispecific antibody for use, or use of any one of embodiments 1-124, wherein the bispecific antibody comprises (a) an anti-CD20 arm comprising (i) a heavy chain comprising an amino acid sequence having at least 95% sequence identity to the amino acid sequence of SEQ ID NO: 85, and (ii) a light chain comprising an amino acid sequence having at least 95% sequence identity to the amino acid sequence of SEQ ID NO: 86; and (b) an anti-CD3 arm comprising (i) a heavy chain comprising an amino acid sequence having at least 95% sequence identity to the amino acid sequence of SEQ ID NO: 83, and (ii) a light chain comprising an amino acid sequence having at least 95% sequence identity to the amino acid sequence of SEQ ID NO: 84.

126. The method, bispecific antibody for use, or use of embodiment 125, wherein (a) the anti-CD20 arm comprises a heavy chain comprising an amino acid sequence of SEQ ID NO: 85 and a light chain comprising an amino acid sequence of SEQ ID NO: 86, and (b) the anti-CD3 arm comprises a heavy chain comprising an amino acid sequence of SEQ ID NO: 83 and a light chain comprising an amino acid sequence of SEQ ID NO: 84.

127. The method, bispecific antibody for use, or use of any one of embodiments 1-126, wherein the bispecific antibody is mosunetuzumab.

128. The method, bispecific antibody for use, or use of any one of embodiments 1-127, wherein the bispecific antibody is a humanized antibody.

129. The method, bispecific antibody for use, or use of any one of embodiments 1-127, wherein the bispecific antibody is a chimeric antibody.

130. The method, bispecific antibody for use, or use of any one of embodiments 1-129, wherein the bispecific antibody is an antibody fragment that binds CD20 and CD3.

131. The method, bispecific antibody for use, or use of embodiment 130, wherein the antibody fragment is selected from the group consisting of Fab, Fab'-SH, Fv, scFv, and $(Fab')_2$ fragments.

132. The method, bispecific antibody for use, or use of any one of embodiments 1-131, wherein the bispecific antibody is a full-length antibody.

133. The method, bispecific antibody for use, or use of any one of embodiments 1-129 and 132, wherein the bispecific antibody is an IgG antibody.

134. The method, bispecific antibody for use, or use of embodiment 133, wherein the IgG antibody is an $IgG_1$ antibody.

135. The method, bispecific antibody for use, or use of embodiment 133 or 134, wherein the IgG antibody comprises a mutation at amino acid residue N297 (EU numbering) that results in the absence of glycosylation.

136. The method, bispecific antibody for use, or use of embodiment 135, wherein the mutation at amino acid residue N297 is a substitution mutation.

137. The method, bispecific antibody for use, or use of embodiment 135 or 136, wherein the mutation at amino acid residue N297 reduces effector function of the Fc region.

138. The method, bispecific antibody for use, or use of any one of embodiments 135-137, wherein the mutation is an N297G or N297A mutation.

139. The method, bispecific antibody for use, or use of any one of embodiments 134-138, wherein the bispecific antibody comprises a mutation in the Fc region that reduces effector function.

140. The method, bispecific antibody for use, or use of embodiment 139, wherein the mutation is a substitution mutation.

141. The method, bispecific antibody for use, or use of embodiment 140, wherein the substitution mutation is at amino acid residue 1234, 1235, D265, and/or P329 (EU numbering).

142. The method, bispecific antibody for use, or use of embodiment 141, wherein the substitution mutation is selected from the group consisting of L234A, L235A, D265A, and P329G.

143. The method, bispecific antibody for use, or use of any one of embodiments 1-129 and 132-142, wherein the bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain.

144. The method, bispecific antibody for use, or use of embodiment 143, wherein at least one of the one or more heavy chain constant domains is paired with another heavy chain constant domain.

145. The method, bispecific antibody for use, or use of embodiment 142 or 144, wherein the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain.

146. The method, bispecific antibody for use, or use of embodiment 145, wherein the $CH3_1$ and $CH3_2$domains meet at an interface between the protuberance and cavity.

147. The method, bispecific antibody for use, or use of any one of embodiments 143-146, wherein the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain.

148. The method, bispecific antibody for use, or use of embodiment 147, wherein the $CH2_1$ and $CH2_2$domains meet at an interface between said protuberance and cavity.

149. The method, bispecific antibody for use, or use of embodiment 120 or 121, wherein the anti-CD20 arm further comprises T366W and N297G substitution mutations (EU numbering).

150. The method, bispecific antibody for use, or use of embodiment 123 or 124, wherein the anti-CD3 arm further comprises T366S, L368A, Y407V, and N297G substitution mutations (EU numbering).

151. The method, bispecific antibody for use, or use of embodiment 125 or 126, wherein (a) the anti-CD20 arm further comprises T366W and N297G substitution mutations and (b) the anti-CD3 arm further comprises T366S, L368A, Y407V, and N297G substitution mutations (EU numbering).

152. The method, bispecific antibody for use, or use of any one of embodiments 1-151, wherein the anti-CD79b antibody drug conjugate comprises an anti-CD79b antibody comprising the following six HVRs:

```
                                        (SEQ ID NO: 65)
(a) an HVR-H1 comprising the amino acid sequence of

GYTFSSYWIE;

                                        (SEQ ID NO: 66)
(b) an HVR-H2 comprising the amino acid sequence of

GEILPGGGDTNYNEIFKG;

                                        (SEQ ID NO: 67)
(c) an HVR-H3 comprising the amino acid sequence of

TRRVPIRLDY;

                                        (SEQ ID NO: 68)
(d) an HVR-L1 comprising the amino acid sequence of

KASQSVDYEGDSFLN;

                                        (SEQ ID NO: 69)
(e) an HVR-L2 comprising the amino acid sequence of

AASNLES;
and

                                        (SEQ ID NO: 70)
(f) an HVR-L3 comprising the amino acid sequence of

QQSNEDPLT.
```

153. The method, bispecific antibody for use, or use of any one of embodiments 1-152, wherein the anti-CD79b antibody drug conjugate comprises an anti-CD79b antibody comprising (a) a VH domain comprising an amino acid sequence having at least 95% sequence identity to the amino acid sequence of SEQ ID NO: 71; (b) a VL domain comprising an amino acid sequence having at least 95% sequence identity to the amino acid sequence of SEQ ID NO: 72; or (c) a VH domain as in (a) and a VL domain as in (b).

154. The method, bispecific antibody for use, or use of embodiment 153, wherein anti-CD79b antibody comprises a VH domain comprising an amino acid sequence of SEQ ID NO: 71 and a VL domain comprising an amino acid sequence of SEQ ID NO: 72.

155. The method, bispecific antibody for use, or use of any one of embodiments 1-154, wherein the anti-CD79b antibody drug conjugate comprises an anti-CD79b antibody comprising (a) a heavy chain comprising an amino acid sequence having at least 95% sequence identity to the amino acid sequence of SEQ ID NO: 81; and (b) a light chain comprising an amino acid sequence having at least 95% sequence identity to the amino acid sequence of SEQ ID NO: 82.

156. The method, bispecific antibody for use, or use of embodiment 155, wherein anti-CD79b antibody comprises a heavy chain comprising an amino acid sequence of SEQ ID NO: 81 and a light chain comprising an amino acid sequence of SEQ ID NO: 82.

157. A method of treating a subject having an NHL comprising administering to the subject polatuzumab vedotin and mosunetuzumab in a dosing regimen comprising at least a first dosing cycle and a second dosing cycle, wherein:

(a) the first dosing cycle comprises a first dose (C1D1) of the mosunetuzumab, a second dose (C1D2) of the mosunetuzumab, and a third dose (C1D3) of the mosunetuzumab, wherein the C1D1 of the mosunetuzumab is about 1 mg, the C1D2 of the mosunetuzumab is about 2 mg, and the C1D3 of the mosunetuzumab is about 9 mg, about 13.5 mg, about 20 mg, about 40 mg, about 45 mg, or about 60 mg; and (b) the second dosing cycle comprises a single dose (C2D1) of the mosunetuzumab, wherein the C2D1 of the mosunetuzumab is equal to or greater than the C1D3.

158. A method of treating a subject having an NHL comprising administering to the subject polatuzumab vedotin and mosunetuzumab in a dosing regimen comprising at least a first dosing cycle and a second dosing cycle, wherein:

(a) the first dosing cycle comprises:
  (i) a single dose (C1D1) of the polatuzumab vedotin; and
  (ii) a first dose (C1D1) of the mosunetuzumab and a second dose (C1D2) of the mosunetuzumab, wherein the C1D1 and the C1D2 of the mosunetuzumab are each administered to the subject after the C1D1 of the polatuzumab vedotin, wherein the C1D1 of the mosunetuzumab is about 1 mg, and the C1D2 of the mosunetuzumab is about 2 mg; and (b) the second dosing cycle comprises:
  (i) a single dose (C2D1) of the polatuzumab vedotin; and
  (ii) a single dose (C2D1) of the mosunetuzumab, wherein the C2D1 of the mosunetuzumab is about 9 mg, about 13.5 mg, about 20 mg, or about 40 mg, and the C1D1 and C2D2 of the polatuzumab vedotin are each about 1.8 mg/kg.

159. A method of treating a subject having an NHL comprising administering to the subject polatuzumab vedotin and mosunetuzumab in a dosing regimen comprising eight or more dosing cycles, wherein:

(a) the first dosing cycle comprises:
  (i) a first dose (C1D1) of the mosunetuzumab, a second dose (C1D2) of the mosunetuzumab, and a third dose (C1D3) of the mosunetuzumab, wherein the C1D1 of the mosunetuzumab is about 1 mg, the C1D2 of the mosunetuzumab is about 2 mg, and the C1D3 of the mosunetuzumab is about 9 mg, about 13.5 mg, about 20 mg, about 40 mg, about 45 mg, or about 60 mg; and (ii) a single dose (C1D1) of the polatuzumab vedotin;

(b) the second dosing cycle comprises a single dose (C2D1) of the mosunetuzumab and a single dose (C2D1) of the polatuzumab vedotin;

(c) the third dosing cycle comprises a single dose (C3D1) of the mosunetuzumab and a single dose (C3D1) of the polatuzumab vedotin;

(d) the fourth dosing cycle comprises a single dose (C4D1) of the mosunetuzumab and a single dose (C4D1) of the polatuzumab vedotin;

(e) the fifth dosing cycle comprises a single dose (C5D1) of the mosunetuzumab and a single dose (C5D1) of the polatuzumab vedotin;

(f) the sixth dosing cycle comprises a single dose (C6D1) of the mosunetuzumab and a single dose (C6D1) of the polatuzumab vedotin;

(g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C2D1-C8D1 of the mosunetuzumab is about equal to or less than the C1D3 and each single dose C1D1-C6D1 of the polatuzumab vedotin is about 1.8 mg/kg.

160. A method of treating a subject having an NHL comprising administering to the subject polatuzumab vedotin and mosunetuzumab in a dosing regimen comprising at least a first dosing cycle and a second dosing cycle, wherein:

(a) the first dosing cycle comprises a first dose (C1D1) of the mosunetuzumab, a second dose (C1D2) of the mosunetuzumab, and a third dose (C1D3) of the mosunetuzumab, wherein the C1D1 of the mosunetuzumab is about 5 mg, the C1D2 of the mosunetuzumab is about 15 mg, and the C1D3 of the mosunetuzumab is about 45 mg; and (b) the second dosing cycle comprises a single dose (C2D1) of the mosunetuzumab, wherein the C2D1 of the mosunetuzumab is equal to or greater than the C1D3. 161. A method of treating a subject having an NHL comprising administering to the subject polatuzumab vedotin and mosunetuzumab in a dosing regimen comprising eight or more dosing cycles, wherein:

(a) the first dosing cycle comprises:

(i) a first dose (C1D1) of the mosunetuzumab, a second dose (C1D2) of the mosunetuzumab, and a third dose (C1D3) of the mosunetuzumab, wherein the C1D1 of the mosunetuzumab is about 5 mg, the C1D2 of the mosunetuzumab is about 15 mg, and the C1D3 of the mosunetuzumab is about 45 mg; and (ii) a single dose (C1D1) of the polatuzumab vedotin;

(b) the second dosing cycle comprises a single dose (C2D1) of the mosunetuzumab and a single dose (C2D1) of the polatuzumab vedotin;

(c) the third dosing cycle comprises a single dose (C3D1) of the mosunetuzumab and a single dose (C3D1) of the polatuzumab vedotin;

(d) the fourth dosing cycle comprises a single dose (C4D1) of the mosunetuzumab and a single dose (C4D1) of the polatuzumab vedotin;

(e) the fifth dosing cycle comprises a single dose (C5D1) of the mosunetuzumab and a single dose (C5D1) of the polatuzumab vedotin;

(f) the sixth dosing cycle comprises a single dose (C6D1) of the mosunetuzumab and a single dose (C6D1) of the polatuzumab vedotin;

(g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C2D1-C8D1 of the mosunetuzumab is about equal to the C1 D3 and each single dose C1D1-C6D1 of the polatuzumab vedotin is about 1.8 mg/kg.

162. A method of treating a subject having an NHL comprising administering to the subject polatuzumab vedotin and mosunetuzumab in a dosing regimen comprising at least a first dosing cycle and a second dosing cycle, wherein:

(a) the first dosing cycle comprises a first dose (C1D1) of the mosunetuzumab, a second dose (C1D2) of the mosunetuzumab, and a third dose (C1D3) of the mosunetuzumab, wherein the C1D1 of the mosunetuzumab is about 5 mg, the C1D2 of the mosunetuzumab is about 45 mg, and the C1D3 of the mosunetuzumab is about 45 mg; and (b) the second dosing cycle comprises a single dose (C2D1) of the mosunetuzumab, wherein the C2D1 of the mosunetuzumab is equal to or greater than the C1D3. 163. A method of treating a subject having an NHL comprising administering to the subject polatuzumab vedotin and mosunetuzumab in a dosing regimen comprising eight or more dosing cycles, wherein:

(a) the first dosing cycle comprises:

(i) a first dose (C1D1) of the mosunetuzumab, a second dose (C1D2) of the mosunetuzumab, and a third dose (C1D3) of the mosunetuzumab, wherein the C1D1 of the mosunetuzumab is about 5 mg, the C1D2 of the mosunetuzumab is about 45 mg, and the C1D3 of the mosunetuzumab is about 45 mg; and (ii) a single dose (C1D1) of the polatuzumab vedotin;

(b) the second dosing cycle comprises a single dose (C2D1) of the mosunetuzumab and a single dose (C2D1) of the polatuzumab vedotin;

(c) the third dosing cycle comprises a single dose (C3D1) of the mosunetuzumab and a single dose (C3D1) of the polatuzumab vedotin;

(d) the fourth dosing cycle comprises a single dose (C4D1) of the mosunetuzumab and a single dose (C4D1) of the polatuzumab vedotin;

(e) the fifth dosing cycle comprises a single dose (C5D1) of the mosunetuzumab and a single dose (C5D1) of the polatuzumab vedotin;

(f) the sixth dosing cycle comprises a single dose (C6D1) of the mosunetuzumab and a single dose (C6D1) of the polatuzumab vedotin;

(g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C2D1-C8D1 of the mosunetuzumab is about equal to the C1 D3 and each single dose C1D1-C6D1 of the polatuzumab vedotin is about 1.8 mg/kg.

164. A method of treating a subject having an NHL comprising administering to the subject polatuzumab vedotin and mosunetuzumab in a dosing regimen comprising at least a first dosing cycle and a second dosing cycle, wherein:

(a) the first dosing cycle comprises a first dose (C1D1) of the mosunetuzumab, a second dose (C1D2) of the mosunetuzumab, and a third dose (C1D3) of the mosunetuzumab, wherein the C1D1 of the mosunetuzumab is about 1 mg, the C1D2 of the mosunetuzumab is about 2 mg, and the C1D3 of the mosunetuzumab is about 60 mg; and (b) the second dosing cycle comprises a single dose (C2D1) of the mosunetuzumab, wherein the C2D1 of the mosunetuzumab is about equal in amount to the C1D3.

165. A method of treating a subject having an NHL comprising administering to the subject polatuzumab vedotin and mosunetuzumab in a dosing regimen comprising eight or more dosing cycles, wherein:

(a) the first dosing cycle comprises:

(i) a first dose (C1D1) of the mosunetuzumab, a second dose (C1D2) of the mosunetuzumab, and a third dose (C1D3) of the mosunetuzumab, wherein the C1D1 of the mosunetuzumab is about 1 mg, the C1D2 of the mosunetuzumab is about 2 mg, and the C1D3 of the mosunetuzumab is about 9 mg, about 13.5 mg, about 20 mg, about 40 mg, about 45 mg, or about 60 mg; and (ii) a single dose (C1D1) of the polatuzumab vedotin;

(b) the second dosing cycle comprises a single dose (C2D1) of the mosunetuzumab and a single dose (C2D1) of the polatuzumab vedotin, wherein the C2D1 of the mosunetuzumab is about 60 mg;

(c) the third dosing cycle comprises a single dose (C3D1) of the mosunetuzumab and a single dose (C3D1) of the polatuzumab vedotin;

(d) the fourth dosing cycle comprises a single dose (C4D1) of the mosunetuzumab and a single dose (C4D1) of the polatuzumab vedotin;

(e) the fifth dosing cycle comprises a single dose (C5D1) of the mosunetuzumab and a single dose (C5D1) of the polatuzumab vedotin;

(f) the sixth dosing cycle comprises a single dose (C6D1) of the mosunetuzumab and a single dose (C6D1) of the polatuzumab vedotin;

(g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C3D1-C8D1 of the mosunetuzumab is about 30 mg and each single dose C1D1-C6D1 of the polatuzumab vedotin is about 1.8 mg/kg.

166. A method of treating a subject having an NHL comprising administering to the subject polatuzumab vedotin and mosunetuzumab in a dosing regimen comprising eight or more dosing cycles, wherein:

(a) the first dosing cycle comprises a first dose (C1D1) of the mosunetuzumab, a second dose (C1D2) of the mosunetuzumab, and a third dose of the mosunetuzumab, wherein the C1D1 of the mosunetuzumab is between about 0.02 mg to about 5.0 mg, the C1D2 is between about 0.05 mg to about 60 mg, and the C1D3 is about 9 mg, about 13.5 mg, about 20 mg, about 40, about 45 mg, or about 60 mg;

(b) the second dosing cycle comprises a single dose (C2D1) of the mosunetuzumab and a single dose (C2D1) of the polatuzumab vedotin;

(c) the third dosing cycle comprises a single dose (C3D1) of the mosunetuzumab and a single dose (C3D1) of the polatuzumab vedotin;

(d) the fourth dosing cycle comprises a single dose (C4D1) of the mosunetuzumab and a single dose (C4D1) of the polatuzumab vedotin;

(e) the fifth dosing cycle comprises a single dose (C5D1) of the mosunetuzumab and a single dose (C5D1) of the polatuzumab vedotin;

(f) the sixth dosing cycle comprises a single dose (C6D1) of the mosunetuzumab and a single dose (C6D1) of the polatuzumab vedotin;

(g) the seventh dosing cycle comprises a single dose (C7D1) of the mosunetuzumab and does not comprise administration of the polatuzumab vedotin; and (h) the eighth dosing cycle comprises a single dose (C8D1) of the mosunetuzumab and does not comprise administration of the polatuzumab vedotin, wherein each single dose C2D1-C8D1 of the mosunetuzumab is about equal to or less than the C1D3 and each single dose C2D1-C6D1 of the polatuzumab vedotin is about 1.8 mg/kg.

167. The method of any one of embodiments 153-166, wherein the NHL is an aggressive NHL.

168. The method of any one of embodiments 153-166, wherein the NHL is a DLBCL.

169. The method of any one of embodiments 153-166, wherein the NHL is a R/R MCL.

170. A method of treating a population of subjects having a CD20-positive cell proliferative disorder comprising administering to the subjects an anti-CD79b antibody drug conjugate and a bispecific antibody that binds to CD20 and CD3 in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C2D1) of the anti-CD79b antibody drug conjugate, wherein the C1D1 of the anti-CD79b antibody drug conjugate and the C2D1 of the anti-CD79b antibody drug conjugate are each about 1.8 mg/kg.

171. A bispecific antibody that binds to CD20 and CD3 for use in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C2D1) of the anti-CD79b antibody drug conjugate, wherein the C1D1 of the anti-CD79b antibody drug conjugate and the C2D1 of the anti-CD79b antibody drug conjugate are each about 1.8 mg/kg.

172. Use of a bispecific antibody that binds to CD20 and CD3 in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C2D1) of the anti-CD79b antibody drug conjugate, wherein the C1D1 of the anti-CD79b antibody drug conjugate and the C2D1 of the anti-CD79b antibody drug conjugate are each about 1.8 mg/kg.

173. Use of a bispecific antibody that binds to CD20 and CD3 in the manufacture of a medicament in combination with an anti-CD79b antibody drug conjugate for treating a population of subjects having a CD20-positive cell proliferative disorder, wherein the bispecific antibody and the anti-CD79b antibody drug conjugate are formulated for administration to the subjects in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C2D1) of the anti-CD79b antibody drug conjugate, wherein the C1D1 of the anti-CD79b antibody drug conjugate and the C2D1 of the anti-CD79b antibody drug conjugate are each about 1.8 mg/kg.

174. A method of treating a population of subjects having a CD20-positive cell proliferative disorder comprising administering to the subjects an anti-CD79b antibody drug conjugate and a bispecific antibody that binds to CD20 and CD3 in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is about 1 mg, the C1D2 of the bispecific antibody is about 2 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C1D1) of the anti-CD79b antibody drug conjugate, wherein the C1D1 of the anti-CD79b antibody drug conjugate and the C2D1 of the anti-CD79b antibody drug conjugate are each about 1.8 mg/kg.

175. A bispecific antibody that binds to CD20 and CD3 for use in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is about 1 mg, the C1D2 of the bispecific antibody is about 2 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C1D1) of the anti-CD79b antibody drug conjugate, wherein the C1D1 of the anti-CD79b antibody drug conjugate and the C2D1 of the anti-CD79b antibody drug conjugate are each about 1.8 mg/kg.

176. Use of a bispecific antibody that binds to CD20 and CD3 in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is about 1 mg, the C1D2 of the bispecific antibody is about 2 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C1D1) of the anti-CD79b antibody drug conjugate, wherein the C1D1 of the anti-CD79b antibody drug conjugate and the C2D1 of the anti-CD79b antibody drug conjugate are each about 1.8 mg/kg.

177. Use of a bispecific antibody that binds to CD20 and CD3 in the manufacture of a medicament in combination with an anti-CD79b antibody drug conjugate for treating a population of subjects having a CD20-positive cell proliferative disorder, wherein the bispecific antibody and the anti-CD79b antibody drug conjugate are formulated for administration to the subjects in a dosing regimen comprising at least a first dosing cycle and a second dosing cycle, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is about 1 mg, the C1D2 of the bispecific antibody is about 2 mg, and the C1D3 of the bispecific antibody is about 9 mg, about 13.5 mg, about 20 mg, or about 40 mg; and (ii) a single dose (C1D1) of the anti-CD79b antibody drug conjugate; and (b) the second dosing cycle comprises:

(i) a single dose (C2D1) of the bispecific antibody, wherein the C2D1 of the bispecific antibody is about equivalent in amount to the C1 D3; and (ii) a single dose (C1D1) of the anti-CD79b antibody drug conjugate, wherein the C1D1 of the anti-CD79b antibody drug conjugate and the C2D1 of the anti-CD79b antibody drug conjugate are each about 1.8 mg/kg.

178. A method of treating a population of subjects having a CD20-positive cell proliferative disorder comprising administering to the subjects an anti-CD79b antibody drug conjugate and a bispecific antibody that binds to CD20 and CD3 in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody about equivalent in amount to the C1D3, and wherein each single dose C1D1-C6D1 of the anti-CD79b antibody drug conjugate is about 1.8 mg/kg.

179. A bispecific antibody that binds to CD20 and CD3 for use in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody about equivalent in amount to the C1D3, and wherein each single dose C1D1-C6D1 of the anti-CD79b antibody drug conjugate is about 1.8 mg/kg.

180. Use of a bispecific antibody that binds to CD20 and CD3 in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody about equivalent in amount to the C1D3, and wherein each single dose C1D1-C6D1 of the anti-CD79b antibody drug conjugate is about 1.8 mg/kg.

181. Use of a bispecific antibody that binds to CD20 and CD3 in the manufacture of a medicament in combination with an anti-CD79b antibody drug conjugate for treating a population of subjects having a CD20-positive cell proliferative disorder, wherein the bispecific antibody and the anti-CD79b antibody drug conjugate are formulated for administration to the subjects in a dosing regimencomprising eight or more dosing cycles, wherein:

(a) the first dosing cycle comprises:

(i) a first dose (C1D1) of the bispecific antibody, a second dose (C1D2) of the bispecific antibody, and a third dose (C1D3) of the bispecific antibody, wherein the C1D1 of the bispecific antibody is between about 0.02 mg to about 2.0 mg, the C1D2 of the bispecific antibody is between about 0.05 mg to about 5 mg, and the C1D3 of the bispecific antibody is about 9 mg, about 13.5 mg, about 20 mg, or about 40 mg; and (ii) a single dose (C1D1) of the anti-CD79b antibody drug conjugate;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody about equivalent in amount to the C1D3, and wherein each single dose C1D1-C6D1 of the anti-CD79b antibody drug conjugate is about 1.8 mg/kg.

182. A method of treating a population of subjects having a CD20-positive cell proliferative disorder comprising administering to the subjects an anti-CD79b antibody drug conjugate and a bispecific antibody that binds to CD20 and CD3 in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, or about 40 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is about equivalent in amount to the C1D3, and wherein each single dose C1D1-C6D1 of the anti-CD79b antibody drug conjugate is about 1.8 mg/kg.

183. A bispecific antibody that binds to CD20 and CD3 for use in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, or about 40 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is about equivalent in amount to the C1D3, and wherein each single dose C1D1-C6D1 of the anti-CD79b antibody drug conjugate is about 1.8 mg/kg.

184. Use of a bispecific antibody that binds to CD20 and CD3 in combination with an anti-CD79b antibody drug conjugate in treating a population of subjects having a CD20-positive cell proliferative disorder, wherein the bispecific antibody and the anti-CD79b antibody drug conjugate are formulated for administration to the subjects in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, or about 40 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is about equivalent in amount to the C1D3, and wherein each single dose C1D1-C6D1 of the anti-CD79b antibody drug conjugate is about 1.8 mg/kg.

185. Use of a bispecific antibody that binds to CD20 and CD3 in the manufacture of a medicament in combination with an anti-CD79b antibody drug conjugate for treating a population of subjects having a CD20-positive cell proliferative disorder, wherein the bispecific antibody and the anti-CD79b antibody drug conjugate are formulated for administration to the subjects in a dosing regimen comprising eight or more dosing cycles, wherein:

(a) the first dosing cycle comprises a first dose (C1D1) of the bispecific antibody, a second dose (C1D2) of the bispecific antibody, and a third dose of the bispecific antibody, wherein the C1D1 of the bispecific antibody is between about 0.02 mg to about 5.0 mg, the C1D2 is between about 0.05 mg to about 60 mg, and the C1D3 is about 9 mg, about 13.5 mg, about 20 mg, or about 40 mg;

(b) the second dosing cycle comprises a single dose (C2D1) of the bispecific antibody and a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is about equivalent in amount to the C1D3, and wherein each single dose C1D1-C6D1 of the anti-CD79b antibody drug conjugate is about 1.8 mg/kg.

186. The method, bispecific antibody for use, or use of any one of embodiments 170-185, wherein the CD20-positive cell proliferative disorder is an NHL.

187. The method, bispecific antibody for use, or use of embodiment 186, wherein the overall response rate is at least 55%.

188. The method, bispecific antibody for use, or use of embodiment 187, wherein the overall response rate is at least 65%.

189. The method, bispecific antibody for use, or use of embodiment 186, wherein the complete response rate is at least 45%.

190. The method, bispecific antibody for use, or use of embodiment 189, wherein the complete response rate is at least 55%.

191. The method, bispecific antibody for use, or use of any one of embodiments 170-185, wherein the CD20-positive cell proliferative disorder is an aggressive NHL.

192. The method, bispecific antibody for use, or use of embodiment 191, wherein the overall response rate is at least 50%.

193. The method, bispecific antibody for use, or use of embodiment 192, wherein the overall response rate is at least 60%.

194. The method, bispecific antibody for use, or use of embodiment 191, wherein the complete response rate is at least 35%.

195. The method, bispecific antibody for use, or use of embodiment 194, wherein the complete response rate is at least 45%.

196. The method, bispecific antibody for use, or use of any one of embodiments 170-185, wherein the CD20-positive cell proliferative disorder is an NHL, and wherein the subjects of the population are post-CAR-T subjects.

197. The method, bispecific antibody for use, or use of embodiment 196, wherein the overall response rate is at least 50%.

198. The method, bispecific antibody for use, or use of embodiment 197, wherein the overall response rate is at least 55%.

199. The method, bispecific antibody for use, or use of embodiment 196, wherein the complete response rate is at least 20%.

200. The method, bispecific antibody for use, or use of embodiment 199, wherein the complete response rate is at least 25%.

201. The method, bispecific antibody for use, or use of any one of embodiments 170-185, wherein the CD20-positive cell proliferative disorder is an FL.

202. The method, bispecific antibody for use, or use of embodiment 201, wherein the overall response rate is at least 80%.

203. The method, bispecific antibody for use, or use of embodiment 202, wherein the overall response rate is at least 90%.

204. The method, bispecific antibody for use, or use of embodiment 201, wherein the complete response rate is at least 80%.

205. The method, bispecific antibody for use, or use of embodiment 204, wherein the complete response rate is at least 90%.

206. The method, bispecific antibody for use, or use of any one of embodiments 170-205, wherein the bispecific antibody is mosunetuzumab.

207. The method, bispecific antibody for use, or use of any one of embodiments 170-205, wherein the anti-CD79b antibody drug conjugate is polatuzumab vedotin.

208. A method of treating a subject having a CD20-positive cell proliferative disorder comprising administering to the subject an anti-CD79b antibody drug conjugate and a bispecific antibody that binds to CD20 and CD3 in a dosing regimen comprising at least a first dosing cycle and a second dosing cycle, wherein:

(a) the first dosing cycle comprises:

(i) a single dose (C1D1) of the anti-CD79b antibody drug conjugate; and (ii) a first dose (C1D1) of the bispecific antibody and a second dose (C1D2) of the bispecific antibody, wherein the C1D1 and the C1D2 of the bispecific antibody are each administered to the subject after the C1D1 of the anti-CD79b antibody drug conjugate, wherein the C1D1 of the bispecific antibody is between about 0.02 mg to about 5.0 mg, and the C1D2 of the bispecific antibody is between about 0.05 mg to about 10.0 mg; and (b) the second dosing cycle comprises:

(i) a single dose (C2D1) of the anti-CD79b antibody drug conjugate; and (ii) a single dose (C2D1) of the bispecific antibody, wherein the C2D1 of the bispecific antibody is greater than the C1D2.

209. A bispecific antibody that binds to CD20 and CD3 for use in combination with an anti-CD79b antibody drug conjugate in treating a subjects having a CD20-positive cell proliferative disorder, wherein the bispecific antibody and the anti-CD79b antibody drug conjugate are formulated for administration to the subject in a dosing regimen comprising at least a first dosing cycle and a second dosing cycle, wherein:

(a) the first dosing cycle comprises:

(i) a single dose (C1D1) of the anti-CD79b antibody drug conjugate; and (ii) a first dose (C1D1) of the bispecific antibody and a second dose (C1D2) of the bispecific antibody, wherein the C1D1 and the C1D2 of the bispecific antibody are each administered to the subject after the C1D1 of the anti-CD79b antibody drug conjugate, wherein the C1D1 of the bispecific antibody is between about 0.02 mg to about 5.0 mg, and the C1D2 of the bispecific antibody is between about 0.05 mg to about 10.0 mg; and (b) the second dosing cycle comprises:

(i) a single dose (C2D1) of the anti-CD79b antibody drug conjugate; and (ii) a single dose (C2D1) of the bispecific antibody, wherein the C2D1 of the bispecific antibody is greater than the C1D2.

210. Use of a bispecific antibody that binds to CD20 and CD3 in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising at least a first dosing cycle and a second dosing cycle, wherein:

(a) the first dosing cycle comprises:

(i) a single dose (C1D1) of the anti-CD79b antibody drug conjugate; and (ii) a first dose (C1D1) of the bispecific antibody and a second dose (C1D2) of the bispecific antibody, wherein the C1D1 and the C1D2 of the bispecific antibody are each administered to the subject after the C1D1 of the anti-CD79b antibody drug conjugate, wherein the C1D1 of the bispecific antibody is between about 0.02 mg to about 5.0 mg, and the C1D2 of the bispecific antibody is between about 0.05 mg to about 10.0 mg; and (b) the second dosing cycle comprises:

(i) a single dose (C2D1) of the anti-CD79b antibody drug conjugate; and (ii) a single dose (C2D1) of the bispecific antibody, wherein the C2D1 of the bispecific antibody is greater than the C1D2.

211. Use of a bispecific antibody that binds to CD20 and CD3 in the manufacture of a medicament in combination with an anti-CD79b antibody drug conjugate for treating a subjects having a CD20-positive cell proliferative disorder, wherein the bispecific antibody and the anti-CD79b antibody drug conjugate are formulated for administration to the subject in a dosing regimen comprising at least a first dosing cycle and a second dosing cycle, wherein:

(a) the first dosing cycle comprises:

(i) a single dose (C1D1) of the anti-CD79b antibody drug conjugate; and (ii) a first dose (C1D1) of the bispecific antibody and a second dose (C1D2) of the bispecific antibody, wherein the C1D1 and the C1D2 of the bispecific antibody are each administered to the subject after the C1D1 of the anti-CD79b antibody drug conjugate, wherein the C1D1 of the bispecific antibody is between about 0.02 mg to about 5.0 mg, and the C1D2 of the bispecific antibody is between about 0.05 mg to about 10.0 mg; and (b) the second dosing cycle comprises:

(i) a single dose (C2D1) of the anti-CD79b antibody drug conjugate; and (ii) a single dose (C2D1) of the bispecific antibody, wherein the C2D1 of the bispecific antibody is greater than the C1D2.

212. The method, bispecific antibody for use, or use of any one of embodiments 208-211, wherein the C1D1 of the bispecific antibody is about 1 mg and the C1 D2 of the bispecific antibody is about 2 mg.

213. The method, bispecific antibody for use, or use of any one of embodiments 208-212, wherein the C2D1 of the bispecific antibody is about 9 mg, about 13.5 mg, about 20 mg, or about 40 mg.

214. The method, bispecific antibody for use, or use of any one of embodiments 208-213, wherein the first dosing cycle comprises a single dose C1D1 of the anti-CD79b antibody drug conjugate.

215. The method, bispecific antibody for use, or use of embodiment 214, wherein the single dose C1D1 of the anti-CD79b antibody drug conjugate is from about 0.5 mg/kg to about 10 mg/kg.

216. The method, bispecific antibody for use, or use of embodiment 215, wherein the single dose C1D1 of the anti-CD79b antibody drug conjugate is about 1.8 mg/kg.

217. The method, bispecific antibody for use, or use of any one of embodiments 208-216, wherein the second dosing cycle comprises a single dose C2D1 of the anti-CD79b antibody drug conjugate.

218. The method, bispecific antibody for use, or use of embodiment 217, wherein the single dose C2D1 of the anti-CD79b antibody drug conjugate is from about 0.5 mg/kg to about 10 mg/kg.

219. The method, bispecific antibody for use, or use of embodiment 218, wherein the single dose C2D1 of the anti-CD79b antibody drug conjugate is about 1.8 mg/kg.

220. The method, bispecific antibody for use, or use of any one of embodiments 208-219, wherein the C1D1 of the bispecific antibody and the C1D2 of the bispecific antibody are administered or are to be administered to the subject on or about Days 8 and 15, respectively, of the first dosing cycle.

221. The method, bispecific antibody for use, or use of any one of embodiments 208-220, wherein the C2D1 of the bispecific antibody is administered or is to be administered to the subject on Day 1 of the second dosing cycle.

222. The method, bispecific antibody for use, or use of any one of embodiments 208-221, wherein the C1D1 of the anti-CD79b antibody drug conjugate is administered or is to be administered to the subject on Day 1 of the first dosing cycle and the C2D1 of the anti-CD79b antibody drug conjugate is administered or is to be administered to the subject on Day 1 of the second dosing cycle.

223. The method, bispecific antibody for use, or use of any one of embodiments 208-222, wherein the first and second dosing cycles are 21-day dosing cycles.

224. The method, bispecific antibody for use, or use of any one of embodiments 208-223, wherein the dosing regimen comprises one or more additional dosing cycles.

225. The method, bispecific antibody for use, or use of embodiment 224, wherein the dosing regimen comprises six to 15 additional dosing cycles.

226. The method, bispecific antibody for use, or use of embodiment 224 or 225, wherein the additional dosing cycles are 21-day dosing cycles.

227. The method, bispecific antibody for use, or use of any one of embodiments 224-226, wherein one or more of the additional dosing cycles comprise an additional single dose of the bispecific antibody and an additional single dose of the anti-CD79b antibody drug conjugate.

228. The method, bispecific antibody for use, or use of embodiment 227, wherein the additional single dose of the anti-CD79b antibody drug conjugate is about equivalent in amount to the C2D1 of the bispecific antibody.

229. The method, bispecific antibody for use, or use of embodiment 227 or 228, wherein the additional single dose of the anti-CD79b antibody drug conjugate is administered or is to be administered to the subject on Day 1 of each additional dosing cycle comprising an additional dose of the anti-CD79b antibody drug conjugate.

230. The method, bispecific antibody for use, or use of any one of embodiments 224-229, wherein one or more of the additional dosing cycles comprise an additional single dose of the bispecific antibody and do not comprise administration of the anti-CD79b antibody drug conjugate.

231. The method, bispecific antibody for use, or use of any one of embodiments 227-230, wherein the additional single dose of the bispecific antibody is equivalent in amount to the C2D1 of the bispecific antibody.

232. The method, bispecific antibody for use, or use of any one of embodiments 227-231, wherein the additional single dose of the bispecific antibody is administered or is to be administered to the subject on Day 1 of each additional dosing cycle comprising an additional dose of the bispecific antibody.

233. The method, bispecific antibody for use, or use of any one of embodiments 224-232, wherein the dosing regimen comprises six or more additional dosing cycles, wherein each of the six or more additional dosing cycles comprises a single dose of the bispecific antibody, and wherein no more than four of the eight or more additional dosing cycles comprises administration of the anti-CD79b antibody drug conjugate.

234. A method of treating a subject having a CD20-positive cell proliferative disorder comprising administering to the subject an anti-CD79b antibody drug conjugate and a bispecific antibody that binds to CD20 and CD3 in a dosing regimen comprising eight or more dosing cycles, wherein:

(a) the first dosing cycle comprises:
 (i) a first dose (C1D1) and a second dose (C1D2) of the bispecific antibody, wherein the C1D1 of the bispecific antibody is between about 0.02 mg to about 5.0 mg, and the C1D2 is between about 0.05 mg to about 60 mg; and
 (ii) a single dose (C1D1) of the anti-CD79b antibody drug conjugate;
(b) the second dosing cycle comprises:
 (i) a single dose (C2D1) of the bispecific antibody, wherein the C2D1 of the bispecific antibody is about 9 mg, about 13.5 mg, about 20 mg, about 40 mg, about 45 mg, or about 60 mg; and
 (ii) a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate, wherein each single dose C2D1-C8D1 of the bispecific antibody is greater than the C1 D2.

235. A bispecific antibody that binds to CD20 and CD3 for use in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:
 (i) a first dose (C1D1) and a second dose (C1D2) of the bispecific antibody, wherein the C1D1 of the bispecific antibody is between about 0.02 mg to about 5.0 mg, and the C1D2 is between about 0.05 mg to about 60 mg; and
 (ii) a single dose (C1D1) of the anti-CD79b antibody drug conjugate;
(b) the second dosing cycle comprises:
 (i) a single dose (C2D1) of the bispecific antibody, wherein the C2D1 of the bispecific antibody is about 9 mg, about 13.5 mg, about 20 mg, about 40 mg, about 45 mg, or about 60 mg; and
 (ii) a single dose (C2D1) of the anti-CD79b antibody drug conjugate;
(c) the third dosing cycle comprises a single dose (C3D1) of the bispecific antibody and a single dose (C3D1) of the anti-CD79b antibody drug conjugate;
(d) the fourth dosing cycle comprises a single dose (C4D1) of the bispecific antibody and a single dose (C4D1) of the anti-CD79b antibody drug conjugate;
(e) the fifth dosing cycle comprises a single dose (C5D1) of the bispecific antibody and a single dose (C5D1) of the anti-CD79b antibody drug conjugate;
(f) the sixth dosing cycle comprises a single dose (C6D1) of the bispecific antibody and a single dose (C6D1) of the anti-CD79b antibody drug conjugate;
(g) the seventh dosing cycle comprises a single dose (C7D1) of the bispecific antibody and does not comprise administration of the anti-CD79b antibody drug conjugate; and
(h) the eighth dosing cycle comprises a single dose (C8D1) of the bispecific antibody and does not comprise administration of the anti-CD79b antibody drug conjugate, wherein each single dose C2D1-C8D1 of the bispecific antibody is greater than the C1 D2.

236. Use of a bispecific antibody that binds to CD20 and CD3 in combination with an anti-CD79b antibody drug conjugate in treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:

(i) a first dose (C1D1) and a second dose (C1D2) of the bispecific antibody, wherein the C1D1 of the bispecific antibody is between about 0.02 mg to about 5.0 mg, and the C1D2 is between about 0.05 mg to about 60 mg; and (ii) a single dose (C1D1) of the anti-CD79b antibody drug conjugate;

(b) the second dosing cycle comprises:

(i) a single dose (C2D1) of the bispecific antibody, wherein the C2D1 of the bispecific antibody is about 9 mg, about 13.5 mg, about 20 mg, about 40 mg, about 45 mg, or about 60 mg; and (ii) a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is greater than the C1 D2.

237. Use of a bispecific antibody that binds to CD20 and CD3 in the manufacture of a medicament in combination with an anti-CD79b antibody drug conjugate for treating a subject having a CD20-positive cell proliferative disorder, wherein the bispecific antibody and the anti-CD79b antibody drug conjugate are formulated for administration to the subject in a dosing regimen comprising eight or more dosing cycles, wherein:

(a) the first dosing cycle comprises:

(i) a first dose (C1D1) and a second dose (C1D2) of the bispecific antibody, wherein the C1D1 of the bispecific antibody is between about 0.02 mg to about 5.0 mg, and the C1D2 is between about 0.05 mg to about 60 mg; and (ii) a single dose (C1D1) of the anti-CD79b antibody drug conjugate;

(b) the second dosing cycle comprises:

(i) a single dose (C2D1) of the bispecific antibody, wherein the C2D1 of the bispecific antibody is about 9 mg, about 13.5 mg, about 20 mg, about 40 mg, about 45 mg, or about 60 mg; and (ii) a single dose (C2D1) of the anti-CD79b antibody drug conjugate;

(c) the third dosing cycle comprises a single dose (C3D1) of the bispecific antibody and a single dose (C3D1) of the anti-CD79b antibody drug conjugate;

(d) the fourth dosing cycle comprises a single dose (C4D1) of the bispecific antibody and a single dose (C4D1) of the anti-CD79b antibody drug conjugate;

(e) the fifth dosing cycle comprises a single dose (C5D1) of the bispecific antibody and a single dose (C5D1) of the anti-CD79b antibody drug conjugate;

(f) the sixth dosing cycle comprises a single dose (C6D1) of the bispecific antibody and a single dose (C6D1) of the anti-CD79b antibody drug conjugate;

(g) the seventh dosing cycle comprises a single dose (C7D1) of the bispecific antibody and does not comprise administration of the anti-CD79b antibody drug conjugate; and (h) the eighth dosing cycle comprises a single dose (C8D1) of the bispecific antibody and does not comprise administration of the anti-CD79b antibody drug conjugate, wherein each single dose C2D1-C8D1 of the bispecific antibody is greater than the C1 D2.

238. The method, bispecific antibody for use, or use of any one of embodiments 234-237, wherein the C2D1-C8D1 of the bispecific antibody are about equivalent in amount.

239. The method, bispecific antibody for use, or use of any one of embodiments 234-238, wherein the C1D1-C6D1 of the anti-CD79b antibody drug conjugate are about equivalent in amount.

240. The method, bispecific antibody for use, or use of any one of embodiments 234-239, wherein each of the C1D1-C6D1 of the anti-CD79b antibody drug conjugate is from about 0.5 mg/kg to about 10 mg/kg.

241. The method, bispecific antibody for use, or use of embodiment 240, wherein each of the C1D1-C6D1 of the anti-CD79b antibody drug conjugate is about 1.8 mg/kg.

242. The method, bispecific antibody for use, or use of any one of embodiments 234-241, wherein the C1D1 of the bispecific antibody is administered after the C1 D1 of the anti-CD79b antibody drug conjugate.

243. The method, bispecific antibody for use, or use of embodiment 242, wherein the C1D1 of the bispecific antibody is administered or is to be administered about seven days after the C1D1 of the anti-CD79b antibody drug conjugate.

244. The method, bispecific antibody for use, or use of any one of embodiments 234-243, wherein the C1D1 of the bispecific antibody and the C1D2 of the bispecific antibody are administered or are to be administered to the subject on or about Days 8 and 15, respectively, of the first dosing cycle.

245. The method, bispecific antibody for use, or use of any one of embodiments 234-244, wherein the C2D1-C8D1 of the bispecific antibody are administered or are to be administered to the subject on Day 1 of each dosing cycle.

246. The method, bispecific antibody for use, or use of any one of embodiments 234-245, wherein the C1D1-C6D1 of the anti-CD79b antibody drug conjugate are administered or are to be administered to the subject on Day 1 of each dosing cycle.

247. The method, bispecific antibody for use, or use of any one of embodiments 234-246, wherein each dosing cycle is a 21-day dosing cycle.

248. The method, bispecific antibody for use, or use of any one of embodiments 1-247, wherein the subject is a human.

VIII. EXAMPLES

The following are examples of the methods of the invention. It is understood that various other embodiments may be practiced, given the general description provided above.

Example 1. In Vivo Efficacy of Anti-CD20/Anti-CD3 TDB in Combination with Anti-CD79b (SN8v28)-MC-Vc-PAB-MMAE, Vs WSU-DLCL2+/−PBMCs, in NSG Female Mice

Materials and Methods

All animal studies were performed in compliance with NIH guidelines for the care and use of laboratory animals and were approved by the Institutional Animal Care and Use Committee (IACUC) at Genentech, Inc. 10 million WSU-DLCL2 cells were inoculated into the right unilateral-thoracic flank of a total of 68 NSG female mice at 8-10 weeks of age (The Jackson Laboratory; stock no. 005557) in HBSS/Matrigel in a volume of 0.1 mL. One day later, 16 of the mice were given an intraperitoneal injection of $10\times10^6$human PBMCs cultured overnight in non-activating conditions.

When mean tumor size reached the desired volume (92-290 $mm^3$), animals were randomized into 9 groups of n=7-8, each with similar mean tumor size, and received a single intravenous dose of vehicle or anti-CD20/anti-CD3 TDB, or anti-CD79b (SN8v28)-MC-vc-PAB-MMAE or both antibodies, through the tail vein (referred to as Day 0). Both antibodies were formulated in vehicle solution (20 mM Histidine acetate, 240 mM sucrose, 0.02% Tween-20, pH 5.5 buffer). Anti-CD20/anti-CD3 TDB and vehicle were also administered on days 7 and 14.

Tumor sizes and mouse weights were recorded once or twice weekly over the course of the study. Changes in mouse body weights were reported as a percentage relative to the starting weight at Day 0.

Test Materials

Anti-CD20/anti-CD3 TDB antibody K&H (hu Anti-CD20 2H7v16) x (hu Anti-CD3 40G5c N297G), was produced at Genentech, Inc. (South San Francisco, CA) and was provided in a clear liquid form at a concentration of 1 mg/mL, and stored at 4-8° C.

Polatuzumab vedotin was provided as a clear liquid at a concentration of 10.6 mg/mL and was diluted in histidine buffer (20 mM histidine acetate, 240 mM sucrose, and 0.02% polysorbate-20, pH 5.5; Lot 21000-MP10) before administration to animals. Hu Anti-huCD79b SN8v28 MC vc PAB MMAE is a Human Anti-CD79B IgG1 antibody produced at Genentech, Inc. (South San Francisco, CA) and was provided in a clear liquid form at a concentration of 10.6 mg/mL, and stored at 4-8° C.

Vehicle

Histidine buffer 8 (20 mM his-acetate, 0.02% polysorbate 20, 240 mM sucrose, pH 5.5) was used as the vehicle and also as the diluent for both antibodies. The vehicle was stored in a refrigerator set to maintain a temperature range of 4° C. to 8° C.

Cell Line

The human diffuse large B-cell lymphoma cell line WSU-DLCL2 was obtained from DSMZ, the German Resource Center for Biological Material (Braunschweig, Germany). Cells were sub-cultured twice a week using RPMI 1640 medium supplemented with 10% FBS (fetal bovine serum) and 2 mM L-glutamine at 37° C. in a 5% $CO_2$ incubator. For in vivo experiments, the cells were collected, centrifuged, and resuspended in Hank's Balanced Salt Solution (HBSS; Thermo Fisher Scientific; Waltham, MA) at a concentration of 100 million cells/mL before inoculation into animals.

PBMC Preparation and Transfer to NSG Mice

Human peripheral mononuclear cells (PBMCs) were purified from the blood of healthy donors by using Lymphocyte Separation Medium (MP Biomedical, LLC; Salon, Ohio) and were cryopreserved at 80° C. Prior to transfer into tumor-bearing mice, PBMCs were thawed and cultured overnight in 10% FBS (fetal bovine serum) containing RPMI 1640 medium, 2 mM L-glutamine at 37° C., in a 5% $CO_2$ incubator. Mice were inoculated with PBMCs intraperitoneally, one day after tumor cell inoculation, at a concentration of $10\times10^6$ cells per mouse, in a volume of 100 μL Hank's Balanced Salt Solution (HBSS) buffer.

Species 120 female NOD.Cg-Prkdc$^{scid}$ Il2rg$^{tm1Wjl}$/SzJ (common name NOD scid gamma; NSG; JAX: 005557) mice were obtained from The Jackson Laboratory (Sacramento, CA).

Results

The activity of anti-CD20/anti-CD3 TDB was evaluated either as a single agent or in combination with anti-CD79b (SN8v28)-MC-vc-PAB-MMAE (polatuzumab vedotin), with or without the presence of PBMCs. Results are summarized in FIG. 1 and FIG. 2A-FIG. 2I. Mice with established WSU-DLCL2 tumors (average volume of 180.9 $mm^3$), were previously inoculated with PBMCs (except Groups 2 and 6). Group 1 served as a control, as the mice were inoculated with PBMCs and on Day 0 were treated with vehicle alone. Group 2 was an additional control, the animals treated with 5 mg/kg anti-CD20/anti-CD3 TDB, in the absence of PBMCs. None of the animals in Groups 1 and 2 showed signs of tumor regression, indicating that efficacy is dependent on the presence of both the PBMCs and the antibody. Group 6 also served as control, the animals treated with 2 mg/kg anti-CD79b (SN8v28)-MC-vc-PAB-MMAE but were not inoculated with PBMCs. It was verified that the presence of PBMCs did not affect activity of the anti-CD79b (SN8v28)-MC-vc-PAB-MMAE as expected. In Group 7, the animals were treated with 2 mg/kg anti-CD79b (SN8v28)-MC-vc-PAB-MMAE and were inoculated with PBMCs. Both groups 6 and 7 behaved similarly, having initial tumor regression on days 0-7 and full tumor regrowth by day 10. Groups 3 to 5 were treated with the anti-CD20/anti-CD3 TDB doses of 0.5-1 mg/kg with no tumor regression in all animals. Groups 8 and 9 were treated with both anti-CD79b (SN8v28)-MC-vc-PAB-MMAE at 2 mg/kg and anti-CD20/anti-CD3 TDB at 0.5 and 1 mg/kg, respectively. Both combinations resulted in clear inhibition of tumor growth in the WSU-DLCL2 tumor model, with a TTD of 18.5 days and a tumor growth inhibition (TGI) of 96% compared to the vehicle group (TTD of 24.5 and >27 days, respectively). No single agent efficacy was observed with the anti-CD20/anti-CD3 TDB at 0.5-5 mg/kg or with anti-CD79b (SN8v28)-MC-vc-PAB-MMAE at 2 mg/kg. Combination of anti-CD79b (SN8v28)-MC-vc-PAB-MMAE at 2 mg/kg and anti-CD20/anti-CD3 TDB at both 0.5 and 1 mg/kg resulted in clear tumor growth inhibition. Taken together, this study shows a significant in vivo benefit of combination treatment over mosunetuzumab and polatuzumab vedotin as single agents.

Example 2. An Open-Label, Randomized, Multicenter, Phase Ib/II Trial Evaluating the Safety, Tolerability, Pharmacokinetics, and Efficacy of Mosunetuzumab (BTCT4465A) in Combination with Polatuzumab Vedotin in Patients with B-Cell Non-Hodgkin Lymphoma This study evaluates the safety, tolerability, pharmacokinetics, and efficacy of mosunetuzumab in combination with polatuzumab vedotin in patients with B-cell NHL. Specific objectives and corresponding endpoints for the study are outlined in Table 5.

TABLE 5

| Objectives and Endpoints | |
|---|---|
| Objectives | Corresponding Endpoints |
| Safety Objective: | |
| To evaluate the safety and tolerability of mosunetuzumab plus polatuzumab vedotin in patients with R/R DLBCL or FL, including estimation of the MTD, determination of the RP2D, and characterization of DLTs (Phase 1b)<br>To evaluate the safety of mosunetuzumab plus polatuzumab vedotin (Group I) in patients with R/R FL (Phase II)<br>To evaluate the safety of mosunetuzumab plus polatuzumab vedotin (Group J) in patients with R/R DLBCL (Phase II)<br>To evaluate the safety of mosunetuzumab plus polatuzumab vedotin (Group F) compared with mosunetuzumab alone (Group E) and compared with polatuzumab vedotin plus bendamustine and rituximab (Group D) in patients with R/R DLBCL (Phase II) | Occurrence and severity of adverse events, including DLTs, with severity determined according to NCI CTCAE v5.0; for CRS, severity determined according to the ASTCT CRS Consensus Grading criteria<br>Change from baseline in targeted vital signs<br>Change from baseline in targeted clinical laboratory test results |
| Efficacy Objective: | |
| To make a preliminary assessment of the anti-tumor activity of mosunetuzumab plus polatuzumab vedotin (Phase 1b)<br>To evaluate the efficacy of mosunetuzumab plus polatuzumab vedotin (Group I) in patients with R/R FL (Phase II)<br>To evaluate the efficacy of mosunetuzumab plus polatuzumab vedotin (Group J) in patients with R/R DLBCL (Phase II)<br>To evaluate the efficacy of mosunetuzumab plus polatuzumab vedotin (Group F) compared with mosunetuzumab alone (Group E) and compared with polatuzumab vedotin plus bendamustine and rituximab in (Group D) patients with R/R DLBCL (Phase II) | CR rate at the time of PRA based on PET and/or CT scan, as determined by the investigator using Lugano 2014 criteria<br>ORR, defined as CR or PR, at PRA based on PET and/or CT scan, as determined by the investigator and IRC using Lugano 2014 criteria<br>Best ORR (CR or PR at any time) on study based on PET and/or CT scan, as determined by the investigator using Lugano 2014 criteria<br>DOR, defined as the time from the first occurrence of a documented objective response to disease progression or relapse, as determined by the investigator using Lugano 2014 criteria, or death from any cause, whichever occurs first<br>PFS, defined as the time from randomization to the first occurrence of disease progression or relapse, as determined by the investigator and IRC using Lugano 2014 criteria, or death from any cause, whichever occurs first<br>EFS, defined as the time from randomization to the first occurrence of disease progression or relapse, as determined by the investigator and IRC using Lugano 2014 criteria, initiation of NALT, or death from any cause, whichever occurs first<br>OS, defined as the time from randomization to death from any cause<br>Time to deterioration in EORTC QLQ-C30 physical functioning and fatigue and in the FACT Lym subscale<br>Proportion of patients who become eligible to undergo SCT while on study<br>Proportion of patients who undergo SCT after achieving a response on study<br>Proportion of patients achieving meaningful improvement in EORTC QLQ-C30 physical functioning and fatigue and in the FACT-Lym subscale<br>EORTC QLQ-C30 rate of treatment-related symptoms and FACT/GOG-Ntx peripheral neuropathy rate<br>All scales of the EORTC QLQ-C30, the FACT Lym subscale, and FACT/GOG-Ntx peripheral neuropathy |
| Pharmacokinetic Objective: | |
| To assess the pharmacokinetics of polatuzumab vedotin in combination with bendamustine and rituximab compared with historical data (Phase II)<br>To characterize the pharmacokinetics of mosunetuzumab as a single agent (Group E) and when administered in combination with polatuzumab (Groups A, B, and C; Groups I, J, and F) (Phase Ib and II)<br>To characterize the relationship between pharmacokinetics and safety, biomarkers, or efficacy (Phase Ib and II)<br>To assess potential PK interactions between mosunetuzumab and polatuzumab vedotin (Phase Ib and II) | For mosunetuzumab pharmacokinetics as a single agent (Phase Ib and II), polatuzumab vedotin as a single agent (Phase II), or mosunetuzumab in combination with polatuzumab vedotin (Phase Ib and II):<br>$C_{max}$<br>$C_{min}$<br>Total exposure (AUC), CL, and volume of distribution, as estimated by population PK modeling, as appropriate, and supported by data<br>Relationship between pharmacokinetics and safety, biomarkers, or efficacy endpoints, as appropriate<br>Concentrations of mosunetuzumab when administered in combination with polatuzumab vedotin compared with mosunetuzumab given as a single agent based on historical data<br>Concentrations of polatuzumab vedotin analytes when administered in combination with mosunetuzumab compared with polatuzumab vedotin as a single agent based on historical data |
| Immunogenicity Objective: | |
| To assess the incidence of ADAs to mosunetuzumab (Phase Ib and II)<br>To assess the incidence of ADAs to polatuzumab vedotin (Phase Ib and II) | Relationship between ADA status and efficacy, safety, pharmacokinetics, and biomarkers |
| Biomarker Objective: | |
| To identify biomarkers that are predictive of response to mosunetuzumab plus polatuzumab vedotin (i.e., predictive biomarkers), are associated with progression to a more severe disease state (i.e., prognostic biomarkers), are associated with acquired resistance to mosunetuzumab plus polatuzumab vedotin, are associated with susceptibility to developing adverse events, can provide evidence of mosunetuzumab plus polatuzumab vedotin activity, or can | Association between prognostic subtypes, exploratory biomarkers, and PET-CT CR rate, ORR, DOR, PFS, and EFS endpoints<br>Relationship over time between ctDNA and tumor burden as measured by imaging |

TABLE 5-continued

| Objectives and Endpoints | |
|---|---|
| Objectives | Corresponding Endpoints |
| increase the knowledge and understanding of disease biology (Phase Ib and II) | |
| To make a preliminary assessment of response to mosunetuzumab plus polatuzumab vedotin in different clinical and biologic prognostic subgroups of NHL (Phase 1b and II) | |
| To make a preliminary assessment of MRD status following mosunetuzumab treatment as a single agent (Group E) and in combination with polatuzumab vedotin (Groups A, B, and C; Groups I, J, and F) (Phase Ib and II) | |
| Health Status Utility Objective: | |
| To assess health status of patients | Health status (EQ-5D-5L) |

ADA = anti-drug antibody;
ASTCT = American Society for Transplantation and Cellular Therapy;
AUC = area under the concentration—time curve;
CL = clearance;
Cmax = maximum serum concentration;
Cmin = minimum serum concentration;
CR = complete response;
CRS = cytokine release syndrome;
CT = computed tomography (scan);
ctDNA = circulating tumor DNA;
DLBCL = diffuse large B-cell lymphoma;
DLT = dose-limiting toxicity;
DOR = duration of response;
EFS = event-free survival;
EORTC QLQ-C30 = European Organization for Research and Treatment of Cancer Quality of Life—Core 30 Questionnaire;
EQ-5D-5L = EuroQol 5-Dimension, 5-Level (questionnaire);
FACT/GOG-Ntx = Functional Assessment of Cancer Treatment/Gynecologic Oncology Group—Neurotoxicity;
FACT-Lym = Functional Assessment of Cancer Therapy—Lymphoma (subscale);
FL = follicular lymphoma;
IRC = Independent Review Committee;
MRD = minimal residual disease;
MTD = maximum tolerated dose;
NALT = new anti-lymphoma treatment;
NCI CTCAE v5.0 = National Cancer Institute Common Terminology Criteria for Adverse Events, Version 5.0;
NHL = non-Hodgkin lymphoma;
ORR = objective response rate;
OS = overall survival;
PET = positron emission tomography (scan);
PET-CR = complete response based on positron emission tomography scan;
PET-CT = positron emission tomography-computed tomography (scan);
PFS = progression-free survival;
PK = pharmacokinetic;
PR = partial response;
PRA = primary response assessment;
RP2D = recommended Phase II dose;
R/R = relapsed or refractory;
SCT = stem-cell transplantation.

Study Design

This Phase Ib/II open-label multicenter study is designed to evaluate the safety, tolerability, pharmacokinetics, pharmacodynamics, and efficacy of escalating doses of mosunetuzumab in combination with polatuzumab vedotin, in patients with R/R FL and DLBCL expected to express CD20; to determine a recommended Phase II dose (RP2D) and schedule of mosunetuzumab in combination with polatuzumab vedotin; and to evaluate the efficacy of mosunetuzumab in combination with polatuzumab vedotin.

Figure 3A:
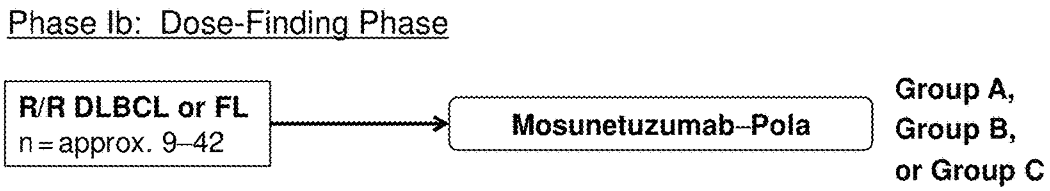
FIG. 3A-FIG. 3C are images depicting the overview of the study design as described in Example 2.
Figure 3B:
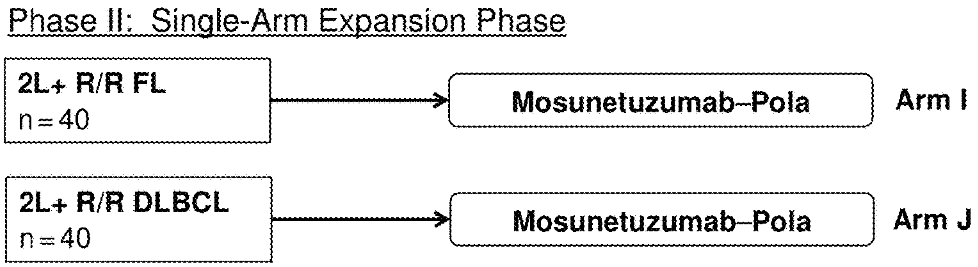
Figure 3C:
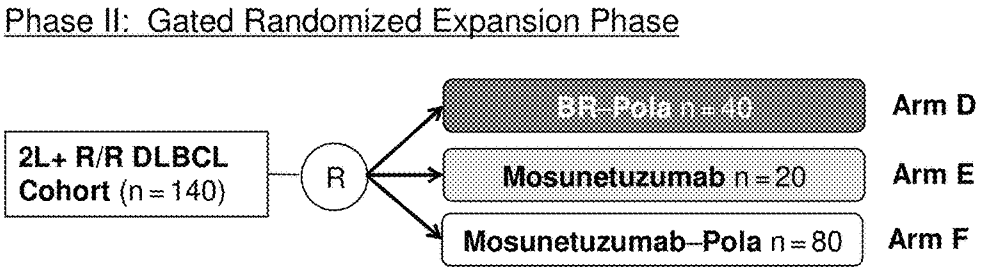

FIG. 3A-FIG. 3C are flow charts showing the Phase Ib dose escalation phase followed by the Phase II single-group expansion phase for second line or later (2L+) patients with R/R DLBCL and 2L+R/R FL. In addition, for patients with (2L+) R/R DLBCL in Phase II, a subsequent randomized expansion phase can be included based on data from the single-group expansion phase. Approximately 89-122 patients are expected to be enrolled in this study at approximately 40 investigative sites globally. If the subsequent randomized expansion phase is opened, then a total of 229-262 patients may be enrolled in this study.

All patients are closely monitored for adverse events throughout the study and for at least 90 days after the last dose of study treatment or until the initiation of another anti-cancer agent, whichever is earlier. Adverse events are graded according to the National Cancer Institute Common Terminology Criteria for Adverse Events, Version 5.0 (NCI CTCAE v5.0), except for CRS events, which are graded according to the ASTCT CRS Consensus Grading criteria. An Internal Monitoring Committee (IMC) is responsible for monitoring patient safety throughout the study.

Blood samples are taken at various time-points before and during study treatment administration for biomarker analyses and to characterize the PK properties of mosunetuzumab and polatuzumab vedotin, as well as the immunogenicity of mosunetuzumab and polatuzumab vedotin when given in combination.

Response in the Phase II portion of the study is determined by an IRC and investigators using the Lugano Response Criteria for Malignant Lymphoma (Cheson et al., *J Clin Oncol.* 2014. 32(27): 3059-3067), hereinafter referred to as the "Lugano 2014 criteria." Interim response is assessed between Day 15 of Cycle 4 and Day 21 of Cycle 4, prior to Cycle 5. Primary response assessment (PRA) for all cohorts treated with mosunetuzumab at the end of Cycle 8 (C8D21±1 week) for patients following either the Group A or C dosing schedule, or at the end of Cycle 9 (C9D21±1 week) for patients following the Group B dosing schedule. PRA is assessed for the cohort treated with polatuzumab plus bendamustine and rituximab at 5 to 7 weeks after Cycle 6.

Figure 4:
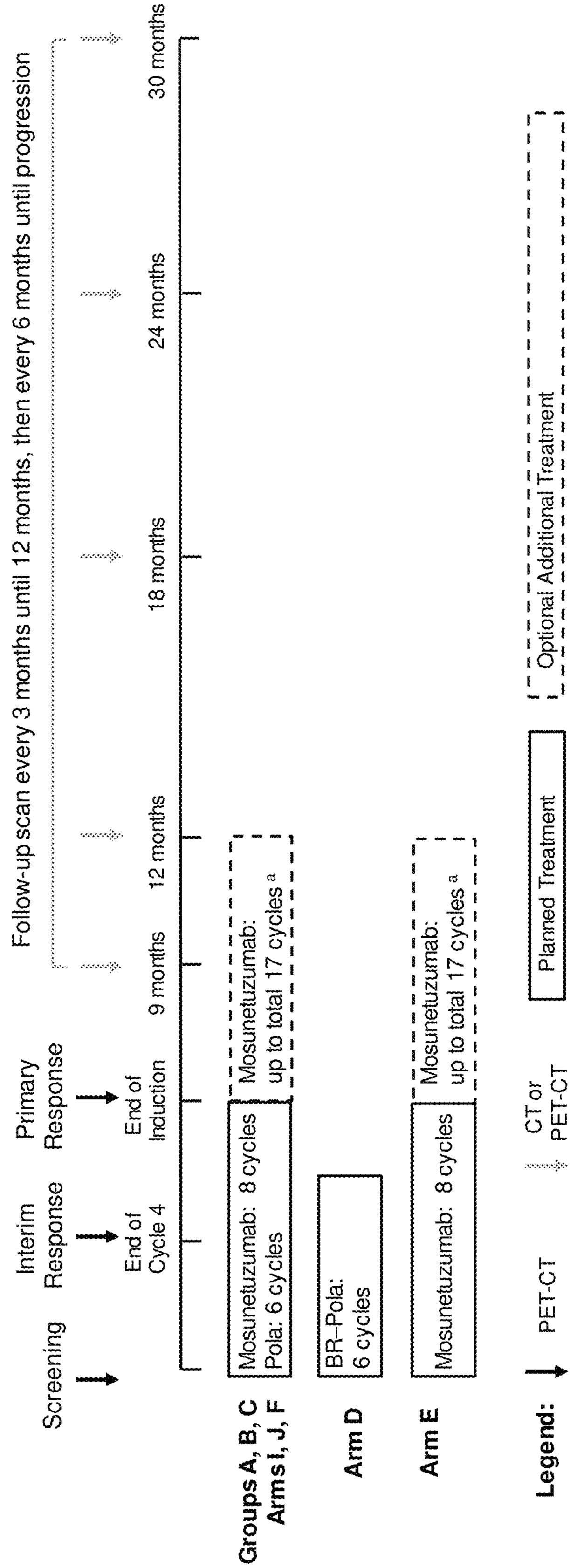
FIG. 4 is an image depicting the overview of the response assessments schedule as described in Example 2. BR=bendamustine plus rituximab; CT=computed tomography (scan); PET-CT=positron emission tomography-computed tomography (scan); Pola=polatuzumab vedotin.

Patients are evaluated every 3 months (±2 weeks) by computed tomography (CT) scan or positron emission tomography (PET)-CT for the first year after C1D1, and then every 6 months (±2 weeks) until disease progression, death, withdrawal of consent, or initiation of another anti-cancer therapy (FIG. 4). Tumor assessments are performed to confirm clinical suspicion of relapse or disease progression.

Study treatments are administered every 21 days, with each 21-day period comprising a cycle. Mosunetuzumab is administered for 8-17 cycles. Polatuzumab vedotin is administered for 6 cycles. Rituximab is administered on Day 1 of each cycle for 6 cycles. Bendamustine is administered on Day 2 and Day 3 of Cycle 1, and then Day 1 and Day 2 of each subsequent cycle for 6 cycles.

A schedule of the activities is outlined in Table 6.

TABLE 6

Schedule of Activities
Screening, Cycles 1-3, and Interim Response

| | Cycles 4-6 | | Interim Response (between C4D15 and | Cycle 7 | Cycle 8 | Primary | Cycle 9 and beyond | Study Drug Completion/ Early |
|---|---|---|---|---|---|---|---|---|
| | D1 | D2 | C4D21) | D1 | D1 | Response | D1 | Discontinuation |
| ECOG PS | x | | x | x | x | x | x | x |
| B symptoms | x | | x | x | x | x | x | x |
| Concomitant medications | x | x | x | x | x | x | x | x |
| Adverse events | x | x | x | x | x | x | x | x |
| Vital signs | x | | x | x | x | x | x | x |
| Height, BSA, and weight | x | | | x | x | x | x | x |
| Targeted physical examination | x | | x | x | x | x | x | x |
| Single 12-lead ECG | | | | | | | | x |
| PET-CT | | | x | | | x | | |
| PET-CT or CT only | | | | | | | At 9 months, 12 months, then every 6 months | |
| Bone marrow aspirate and biopsy | | | | | | x | | |
| Tumor biopsy for biomarkers | | | x | | | | | (x) |
| EORTC QLQ-C30, FACT-Lym subscale, FACT/GOG-Ntx, and EQ-5D-5L (Groups D, E, and F) | x | | | | x | | Every 3 months | x |
| Assessment of transplant eligibility status | | | | | | x | | x |
| Survival and new anti-cancer Therapy follow-up | | | | | | | | Every 3 months from completion/ Discontinuation of treatment |
| **Study Drug Administration** | | | | | | | | |
| **Group A** | | | | | | | | |
| Polatuzumab vedotin | x | | | | | | | |
| Mosunetuzumab | x | | | x | x | | x | |
| **Group B** | | | | | | | | |
| Polatuzumab vedotin | x | | | | | | | |
| Mosunetuzumab | x | | | x | x | | x | |

TABLE 6-continued

Schedule of Activities
Screening, Cycles 1-3, and Interim Response

| | Cycles 4-6 | | Interim Response (between C4D15 and | Cycle 7 | Cycle 8 | Primary | Cycle 9 and beyond | Study Drug Completion/ Early |
|---|---|---|---|---|---|---|---|---|
| | D1 | D2 | C4D21) | D1 | D1 | Response | D1 | Discontinuation |
| Group C | | | | | | | | |
| Polatuzumab vedotin | x | | | x | | | | |
| Mosunetuzumab | x | | | x | x | | x | |
| Group D | | | | | | | | |
| Rituximab | x | | | | | | | |
| Polatuzumab vedotin | x | | | | | | | |
| Bendamustine | x | x | | | | | | |
| Group E | | | | | | | | |
| Mosunetuzumab | x | | | x | x | | x | |
| Groups I, J, and F | | | | | | | | |
| Polatuzumab vedotin Mosunetuzumab | Follow schedule from either Group A, B, or C (selected from dose escalation phase) | | | | | | | |
| Local Labs | | | | | | | | |
| Hematology | x | | | x | x | x | x | x |
| Chemistry (serum)[v] | x | | | x | x | x | x | x |
| C-reactive protein and serum ferritin | x | | | x | x | x | x | x |
| Pregnancy test | x | | | x | x | | x | x |
| Total IgA, IgG, IgM | Every 6 months (collected at closest corresponding visit) | | | | | | | |
| Central Labs | | | | | | | | |
| Blood for viral infection test by Quantitative PCR | See below | | | | | | | |

Cycles 4-9 and Beyond Through Study Drug Completion/Early Discontinuation

| | Screening | Cycle 1 | | | | | | | | Cycle 2 | | | | Cycle 3 | |
|---|---|---|---|---|---|---|---|---|---|---|---|---|---|---|---|
| | (−14 days) | D1 | D2 | D3 | D4 | D8 | D9 | D11 | D15 | D1 | D2 | D8 | D15 | D1 | D2 |
| Informed consent | x | | | | | | | | | | | | | | |
| Demographic data | x | | | | | | | | | | | | | | |
| General medical history and baseline conditions | x | | | | | | | | | | | | | | |
| FLIPI, FLIPI2 (for FL) and IPI (for DLBCL) | x | | | | | | | | | | | | | | |
| Assessment of transplant eligibility status | x | | | | | | | | | | | | | | |
| ECOG PS | x | x | | | | | | | | x | | | | x | |
| B symptoms | x | x | | | | x | | | x | x | | x | x | x | |
| Concomitant medications | x | x | x | x | | x | | | x | x | x | x | x | x | x |
| Adverse events | x | x | x | x | | x | | | x | x | x | x | x | x | x |
| Vital signs | x | x | | | | x | | | x | x | | x | x | x | |
| Height, BSA, and weight | x | x | | | | | | | | x | | | | x | |
| Complete physical and neurologic examination | x | | | | | | | | | | | | | | |
| Targeted physical examination | | x | | | | x | | | x | x | | x | x | x | |
| Single 12-lead ECG | x | | | | | | | | | | | | | | |
| MRI of the brain | x | | | | | | | | | | | | | | |
| PET-CT | x | | | | | | | | | | | | | | |

TABLE 6-continued

Schedule of Activities
Screening, Cycles 1-3, and Interim Response

| | Cycles 4-6 D1 | Cycles 4-6 D2 | Interim Response (between C4D15 and C4D21) | Cycle 7 D1 | Cycle 8 D1 | Primary Response | Cycle 9 and beyond D1 | Study Drug Completion/ Early Discontinuation |
|---|---|---|---|---|---|---|---|---|
| Bone marrow aspirate and biopsy | x | | | | | | | |
| Tumor biopsy for biomarkers | x | | | | | | x | |
| Blood sample for RBR (optional) | | x | | | | | | |
| EORTC QLQ-C30, FACT-Lym subscale, FACT/GOG-Ntx, and EQ-5D-5L (Groups D, E, and F) | | x | | | x | | | |
| **Study Drug Administration** | | | | | | | | |
| Group A | | | | | | | | |
| Polatuzumab vedotin | | x | | | x | | | x |
| Mosunetuzumab | | x | x | x | x | | | x |
| Group B | | | | | | | | |
| Polatuzumab vedotin | | x | | | x | | | x |
| Mosunetuzumab | | | x | x | x | | | x |
| Group C | | | | | | | | |
| Polatuzumab vedotin | | | | | x | | | x |
| Mosunetuzumab | | x | x | x | x | | | x |
| Group D | | | | | | | | |
| Rituximab | | x | | | x | | | x |
| Polatuzumab vedotin | | x | | | x | | | x |
| Bendamustine | | x | x | | x | x | x | x |
| Group E | | | | | | | | |
| Mosunetuzumab | x | x | | x | x | | x | |
| Groups I, J, and F | | | | | | | | |
| Polatuzumab vedotin Mosunetuzumab | | | Follow schedule from either Group A, B, or C (selected from dose escalation phase) | | | | | |
| Local Labs | | | | | | | | |
| HBV, HCV, and HIV screening | x | | | | | | | |
| Blood for EBV and CMV titer by PCR | x | | | | x | | | |
| Hematology | x | x | x | x | x | x | x | x |
| Chemistry (serum) | x | x | x | x | x | x | x | x |
| Beta-2 microglobulin | x | | | | | | | |
| C-reactive protein and serum ferritin | x | x | x | x | x | x | x | x |
| Coagulation (aPTT, PT, INR) | x | x | x | x | x | x | x | |
| Pregnancy test | x | | | | x | | | x |
| Total IgA, IgG, IgM | x | | Every 6 months (collected at closest corresponding visit) | | | | | |

TABLE 6-continued

| Schedule of Activities Screening, Cycles 1-3, and Interim Response | | | | | | | | |
|---|---|---|---|---|---|---|---|---|
| | Cycles 4-6 | | Interim Response (between C4D15 and | Cycle 7 | Cycle 8 | Primary | Cycle 9 and beyond | Study Drug Completion/ Early |
| | D1 | D2 | C4D21) | D1 | D1 | Response | D1 | Discontinuation |
| Central Labs | | | | | | | | |
| Blood for viral infection test by quantitative PCR | x | | | | x | | | |

ADA = anti-drug antibody;
BSA = body surface area;
C = cycle;
CMV = cytomegalovirus;
CR = complete response;
CRu = complete response, unconfirmed;
CT = computed tomography (scan);
D = day;
DLBCL = diffuse large B-cell lymphoma;
EBV = Epstein-Barr virus;
ECOG PS = Eastern Cooperative Oncology Group Performance Status;
eCRF = electronic Case Report Form;
EORTC QLQ-C30 = European Organization for Research and Treatment of Cancer Quality of Life-Core 30 Questionnaire;
EQ-5D-5L = EuroQol 5-Dimension, 5-Level (questionnaire);
FACT/GOG-Ntx = Functional Assessment of Cancer Treatment/Gynecologic Oncology Group-Neurotoxicity;
FACT-Lym = Functional Assessment of Cancer Therapy-Lymphoma (subscale);
FL = follicular lymphoma;
FLIPI = Follicular Lymphoma International Prognostic Index;
GGT = gamma-glutamyl transferase;
HBcAb = hepatitis B core antibody;
HBsAb = hepatitis B surface antibody;
HBsAg = hepatitis B surface antigen;
HBV = hepatitis B virus;
HCV = hepatitis C virus;
IMC = Internal Monitoring Committee;
IPI = International Prognostic Index;
IRR = infusion-related reaction;
LDH = lactate dehydrogenase;
mo = month(s);
MRI = magnetic resonance imaging;
PCR = polymerase chain reaction;
PET = positron emission tomography (scan);
PET-CT = positron emission tomography-computed tomography (scan);
PK = pharmacokinetic;
PR = partial response;
PRO = patient-reported outcome;
RBR = Research Biosample Repository;
wk = week.
Visits/assessments denoted as "(x)" may be omitted with Medical Monitor approval for patients with no clinically significant toxicities after receiving at least two cycles of study treatment.
Assessments are to be taken prior to study drug infusion, unless otherwise specified. Pre-infusion laboratory samples are drawn 0-24 hours prior to study treatment infusion.

Mosunetuzumab is administered for up to a total of 17 cycles; polatuzumab vedotin (if applicable) is administered for up to 6 cycles. Screening assessments for re-treatment follow the same schedule as the initial screening assessments.

Screening and pretreatment tests and evaluations are performed within 14 days preceding the first dose of study treatment (except pretreatment biopsy, radiographic tumor assessment (including brain MRI), and bone marrow aspirate and biopsy (if applicable), which may be performed up to 28 days preceding the first dose of study drug, providing no anti-tumor therapy was administered in this period). In addition, a serum pregnancy test is performed within 7 days preceding the first dose of study treatment. Results of standard-of-care tests or examinations performed prior to obtaining informed consent and within the screening window specified above can be used; these tests are not repeated for screening.

Patients enrolled in Group A dose escalation are hospitalized for at least 72 hours after the completion of mosunetuzumab administration on C1D1 and for a minimum of 24 hours on C2D1. Patients enrolled in Group B dose escalation are hospitalized for at least 72 hours after the completion of mosunetuzumab administration on C1D8 and for a minimum of 24 hours on C2D1. Patients enrolled in Group C dose escalation are hospitalized for at least 72 hours after the completion of mosunetuzumab administration on C2D1.

For Group B, as well as Groups I, J, and F when using Group B dosing schedule: In Cycle 3 and beyond, study drug infusions occur on Day 1 of each 21-day cycle but may be given up to ±2 days from scheduled date (with a minimum of 19 days between doses) for logistic/scheduling reasons. Other study visits starting in Cycle 3 occur within ±2 days from the scheduled date, unless otherwise noted. For Groups A and C, Groups D and E, as well as Groups I, J, and F when using Group A or C dosing schedule: For Cycle 2, study drug infusion occurs on Day 1 of the cycle but may be given up to ±1 day from the scheduled date (with a minimum of 6 days after C1 D15 dosing). For Cycle 3 and beyond, study drug infusions occur on Day 1 of each 21-day cycle but can be given up to ±2 days from scheduled date (with a minimum of 19 days between doses) for logistic/scheduling reasons. Other study visits starting in Cycle 2 occur within ±2 days from the scheduled date, unless otherwise noted.

Concomitant medication (e.g., prescription drugs, over-the-counter drugs, vaccines, herbal or homeopathic remedies, nutritional supplements) are those used by a patient in addition to protocol-mandated treatment from 7 days prior to initiation of study drug until the study completion/discontinuation visit.

After informed consent has been obtained but prior to initiation of study drug, only serious adverse events caused by a protocol-mandated intervention are reported. After initiation of study drug, all adverse events are recorded until 90 days after the last dose of study treatment or the initiation of another anti-cancer agent, whichever is earlier. After this period, the Sponsor is notified if the investigator becomes aware of any serious adverse event (if believed to be related to prior study drug treatment) that occurs after the end of the adverse event reporting period. The investigator follows each adverse event until the event has resolved to baseline grade or better, the event is assessed as stable by the investigator, the patient is lost to follow-up, or the patient withdraws consent. Every effort is made to follow all serious adverse events considered to be related to study drug or trial-related procedures until a final outcome can be reported.

Vital signs include systolic and diastolic blood pressure, respiratory rate, pulse oximetry, pulse rate, and body temperature while the patient is in a sitting or semi-supine position. Observed abnormalities are recorded at baseline on the General Medical History and Baseline Conditions eCRF. During subsequent visits, new or worsened clinically significant abnormalities are recorded on the Adverse Event eCRF. Vital signs are recorded for mosunetuzumab infusions for which patients are hospitalized (Group A C1D1 and C2D1; Group B C1D8 and C2D1; Group C C2D1, or other times recommended by IMC): Vital signs are checked pre-infusion, every 30 (±10) minutes during the infusion, at the end of the infusion, and then every 60 (±10) minutes until 6 hours after the end of infusion. Thereafter, vital signs are checked every 4 hours until hospital or clinic discharge. For all other Cycle 1 and 2 mosunetuzumab infusions, vital signs are checked pre-infusion, every 30 (±10) minutes during the infusion, at the end of the infusion, and 2 hours after infusion. For patients who tolerated Cycle 1 and 2 mosunetuzumab infusions without the development of IRRs, in subsequent cycles, vital signs are assessed pre-infusion, every 60 (±15) minutes during the infusion and for 2 hours after the end of infusion. For patients who experienced an IRR in Cycle 1, vital signs are assessed pre-infusion, every 30 (±10) minutes during the infusion, and for 2 hours after the end of infusion. During the administration of polatuzumab vedotin, vital signs are assessed before the start of the infusion, every 15 (±5) minutes during the infusion, at the end of the infusion, and every 30 (±10) minutes for 90 minutes following completion of dosing at Cycle 1 and 30 (±10) minutes following completion of dosing in subsequent cycles. During the administration of rituximab in Cycle 1, vital signs are obtained before infusion of rituximab, then after the start of the infusion, approximately every 15 (±5) minutes for 90 minutes, and then every 30 (±10) minutes until 1 hour after the end of the infusion. During administration of rituximab in subsequent cycles, vital signs are recorded before infusion of rituximab, then after the start of infusion, and approximately every 30 (±10) minutes until 1 hour after the end of infusion.

Height and BSA are required at screening only, within 96 hours of C1D1, unless there has been a >10% change in body weight since the last BSA assessment, in which case BSA is recalculated and documented in the eCRF.

Complete physical examination includes an evaluation of the head, eyes, ears, nose, and throat, and the cardiovascular, dermatologic, musculoskeletal, respiratory, gastrointestinal, genitourinary, and neurologic systems. A complete neurologic examination, which includes an evaluation of mental status, cranial nerves, muscle strength, sensation, and coordination is performed and documented in the patient chart. Record abnormalities observed at baseline on the General Medical History and Baseline Conditions eCRF. At subsequent visits, record new or worsened clinically significant abnormalities on the Adverse Event eCRF.

Targeted physical examinations are limited to systems of primary relevance (i.e., cardiovascular, respiratory, neurologic, and any system that might be associated with tumor assessment, or potential drug-related toxicity [e.g., clinical assessment for peripheral neuropathy in patients receiving polatuzumab vedotin]). Record new or worsened clinically significant abnormalities on the Adverse Event eCRF. For pre-infusion time-points, targeted physical examinations may be performed within 96 hours preceding study treatment administration unless otherwise specified.

Single ECG recordings are obtained at screening and at end of treatment. ECGs are also performed when clinically indicated in any patient with evidence of, or suspicion for, clinically significant signs or symptoms of cardiac dysfunction. Post-screening ECGs are obtained as close as possible to scheduled serum and plasma PK samples. If a PK sample is not scheduled for that timepoint, an unscheduled PK sample is obtained.

Assessment of response using image-based evaluation is performed using standard Lugano 2014. PET and diagnostic-quality CT scans are required at screening, at the interim response assessment, and at the PRA visit. Perform CT scan with or without PET during follow-up at 9 months (±2 weeks) after C1D1, 12 months (±2 weeks) after C1D1, and then every 6 months (±2 weeks) until disease progression or study discontinuation, whichever is earlier. Before a metabolic complete response is achieved, it is recommended that PET scans continue in conjunction with diagnostic-quality CT scans. A full tumor assessment including radiographic assessment must be performed any time disease progression or relapse is suspected. If disease progression or relapse is suspected before the PRA, both PET and diagnostic-quality CT scans are performed for tumor assessment.

Bone marrow examinations include a biopsy for morphology and an aspirate for local hematology (flow studies are optional). Repeat bone marrow examinations are required to confirm a CR for CT-based response if there was bone marrow infiltration at screening, or if bone marrow involvement is suspected for disease relapse or transformation. Additional (unscheduled) bone marrow examinations can be performed at the discretion of the investigator. The associated hematopathology report are submitted when available. For patients with DLBCL, PET/CT scans can be utilized to assess bone marrow involvement; bone marrow examinations are not required unless clinically indicated.

Pretreatment, on-treatment, and re-treatment tumor tissue biopsies are mandatory. Fresh pretreatment biopsy is preferred but archival tissue is acceptable if the conditions for fresh biopsy cannot be met and approval is received from the Medical Monitor. For dose-escalation Groups A, B, and C on-treatment biopsy is obtained between C2D15 and C2D21. For expansion cohorts (Groups D-J) on-treatment biopsy is obtained at interim assessment. Patients proceeding to re-treatment following disease progression need to complete screening assessments to re-confirm eligibility, including undergoing a repeat tumor biopsy from a safely accessible site. Patients who have no lesion amenable for biopsy at disease progression can still be considered for study drug re-treatment following a discussion between the study investigator and the Medical Monitor. Additional tumor biopsies are optional and can be performed at the investigator's discretion (e.g., to confirm disease recurrence or progression or to confirm an alternate histologic diagnosis). All biopsies, whether fresh or archival, must be accompanied by the associated pathology report. Tumor tissue samples consist of representative tumor specimens in paraffin blocks (preferred) or at least 20 unstained slides.

Blood samples for RBR are not applicable for a site that has not been granted approval for RBR sampling. Sampling is performed only for patients at participating sites who have provided written informed consent to participate and obtained prior to study treatment.

HBsAg, HBsAb, HBcAb, HCV antibody, and HIV antibody serology are required. Patients whose hepatitis B serology results cannot rule out acute or chronic HBV infection must be negative for HBV by PCR to be eligible for study participation. Patients who are positive for HCV antibody must be negative for HCV by PCR to be eligible for study participation.

Quantitative PCR for detection of active EBV and CMV is performed at screening, C2D1, and when clinically indicated on a peripheral blood sample per local lab requirements. Blood samples are also collected for central laboratory assessments at the same time-points. If local laboratory assessments are not available for quantitative PCR detection of active EBV and CMV, local laboratory collections can be waived only if samples are collected for central laboratory assessments of viral infections. If EBV or CMV DNA levels are detected (positive), the Medical Monitor is contacted for additional recommendations, and quantitative PCR monitoring is repeated weekly until DNA levels decrease, and then continue to monitor by quantitative PCR at every cycle until two consecutive negative (undetectable) results.

Chemistry panel (serum) includes sodium, potassium, chloride, bicarbonate, glucose, BUN or urea, creatinine, calcium, magnesium, phosphorous, total and direct bilirubin, total protein, albumin, ALT, AST, ALP, GGT, LDH, and uric acid.

For quantitative PCR detection of viral infection, which may include, but is not limited to, EBV and CMV. At screening, C2D1 pre-dose and at other time-points when clinically indicated, blood samples are sent for central laboratory assessments, in addition to local laboratory assessments.

Primary response assessment is conducted at the end of Cycle 8 (C8D21±1 week) prior to C9D1 for Groups A and C, Group E (and Groups I, J, and F, if following the Group A or C dosing schedule); at the end of Cycle 9 (C9D21±1 week) prior to C10D1 for Group B (and Groups I, J, and F, if following Group B dosing schedule); or 5-7 weeks after the end of Cycle 6 (C6D21) for Group D, in order to inform the duration of study treatment. Primary response assessment is conducted at the end of Cycle 8 (C8D21±1 week) prior to C9D1 for Groups A and C, Group E (and Groups I, J, and F, if following the Group A or C dosing schedule); at the end of Cycle 9 (C9D21±1 week) prior to C10D1 for Group B (and Groups I, J, and F, if following Group B dosing schedule); or 5-7 weeks after the end of Cycle 6 (C6D21) for Group D, in order to inform the duration of study treatment.

Group B includes one scheduled dose of mosunetuzumab on C9D1. Patients who are eligible for extended treatment with mosunetuzumab can receive up to a total of 17 cycles of treatment with mosunetuzumab.

Patients who complete the treatment period return to the clinic for a treatment completion visit within 30 (±7) days after the last dose of study drug. Patients who discontinue study drug prematurely return to the clinic for a treatment discontinuation visit within 30 (±7) days after the last dose of study drug. The visit at which response assessment shows progressive disease can be used as the treatment discontinuation visit.

When completed/discontinued from treatment, patients are followed for survival follow-up and new anti-cancer therapy via telephone calls, patient medical records, and/or clinic visits approximately every 3 months until death (unless the patient withdraws consent, or the Sponsor terminates the study). If the patient withdraws from the study, the site's staff can only use a public information source (e.g., county records) to obtain information about survival status.

Dose Escalation

Figure 5A:
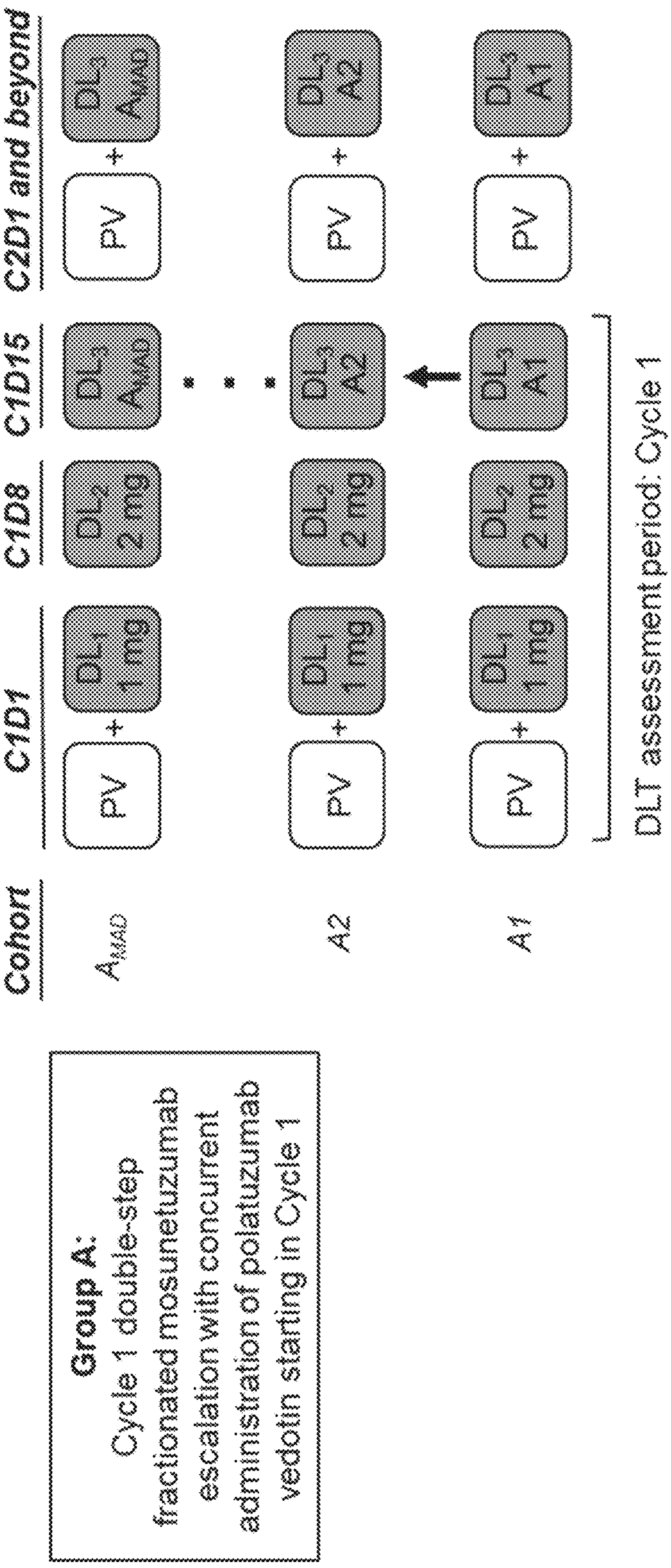
FIG. 5A-FIG. 5C are images depicting the dosing of mosunetuzumab and polatuzumab vedotin during the dose escalation phase of Groups A (FIG. 5A), B (FIG. 5B), and C (FIG. 5C), as described in Example 2. $DL_1$-$DL_3$ indicates mosunetuzumab double-step fractionation dose levels 1-3. C=cycle (except in reference to group/cohort “C”); D=day; DL=dose level; DLT=dose-limiting toxicity; PV=polatuzumab vedotin; MAD=maximal assessed dose.
Figure 5B:
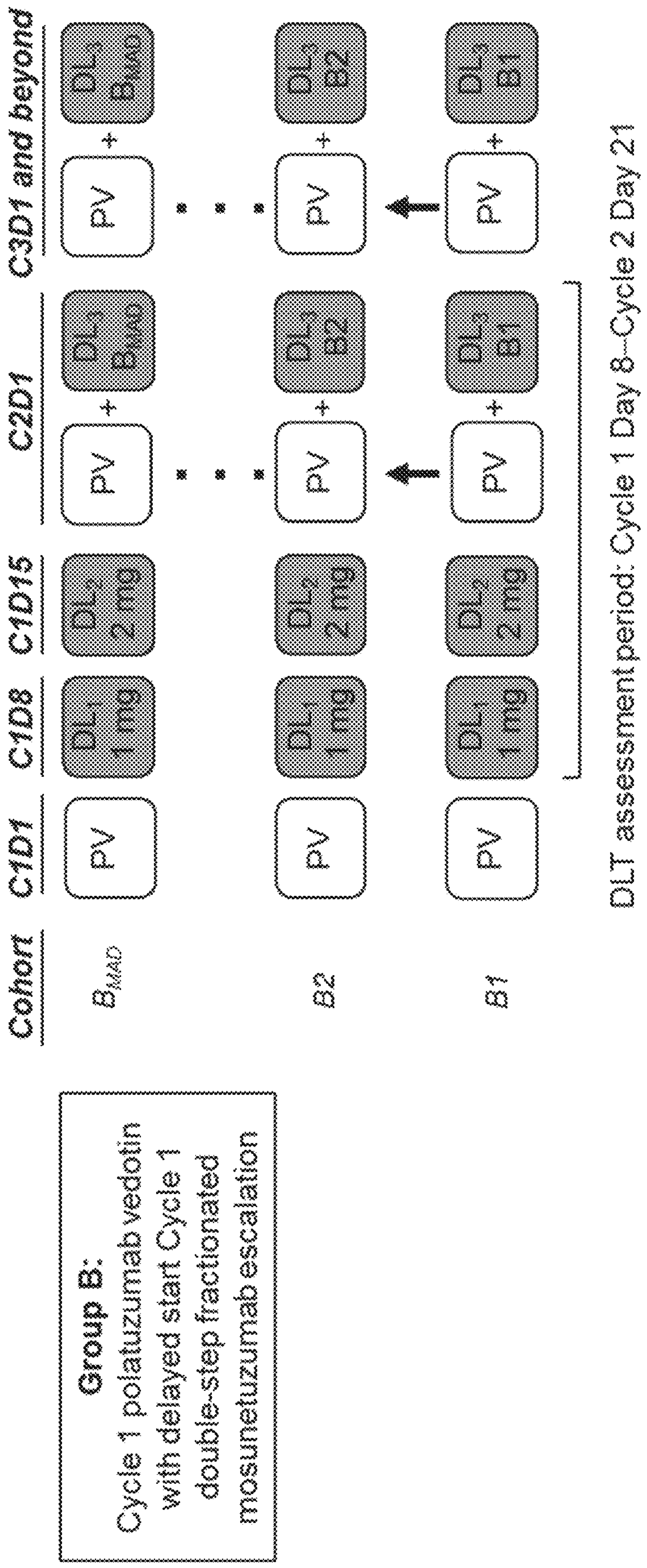
Figure 5C:
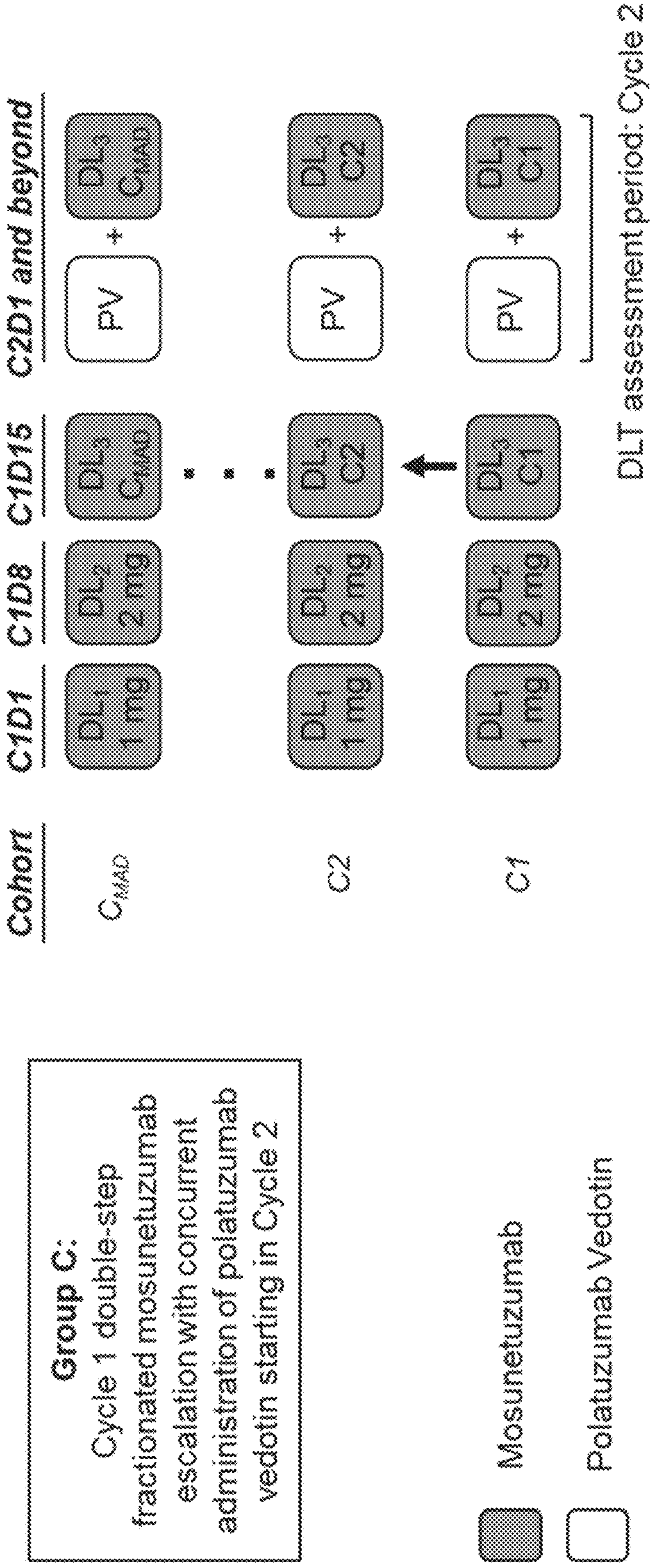

Approximately 9-42 patients with either R/R DLBCL or FL are enrolled in up to three dose-escalation treatment groups, as shown in FIG. 5A-FIG. 5C, to determine the RP2D and schedule for mosunetuzumab when given in combination with fixed doses of polatuzumab vedotin (1.8 mg/kg). Both mosunetuzumab and polatuzumab vedotin are administered by IV infusion. Dose escalation Groups A, B, and C may be run sequentially or in parallel, at the discretion of the Sponsor. Dose-escalation is performed based on a modified 3+3 design, and each group consists of at least 3 patients, unless DLTs are observed in the first 2 patients prior to the enrollment of a third patient. For each group, treatment is staggered such that the second patient enrolled receives the first dose of study treatment at least 72 hours after the first enrolled patient receives the first dose of study treatment, to assess for any sever or unexpected acute drug or infusion-related toxicities. Approximately 6-12 patients are treated at the RP2D and schedule of mosunetuzumab in combination with polatuzumab vedotin prior to the expansion phase. Any of dose escalation groups A, B, or C may be prioritized or suspended by the Sponsor based on the overall safety profile, in consultation with the IMC. Patients exhibiting acceptable safety and clinical benefit may continue to receive study treatment every 21 days up to 8-17 cycles for mosunetuzumab, and up to 6 cycles for polatuzumab vedotin, until confirmed objective disease progression or unacceptable toxicity, whichever occurs first.

Mosunetuzumab dose levels are independent of patient weight (flat-dosing). The starting dose level of double-step fractionated mosunetuzumab is 1 mg ($DL_1$, fixed for all schedules), 2 mg ($DL_2$, fixed for all schedules, given 7 days after $DL_1$), and 9 mg ($DL_3$, initial mosunetuzumab test dose, given 7 days after $DL_2$), for each initial cohort in Groups A, B, and C based on preliminary data from Study GO29781. Dose escalation Groups A, B, and C may be run sequentially or in parallel, at the discretion of the Sponsor.

During dose finding in Groups A, B, and C, only the $DL_3$ test dose may be escalated or de-escalate according to rules discussed below in detail. Mosunetuzumab dose levels may be rounded if the difference before and after the rounding is within 15% (e.g., 13.5 may be rounded to 14 mg, and 27 mg may be rounded to 30 mg). An example of dose escalation and de-escalation is shown in Table 7, though specific doses listed are for illustrative purposes only.

TABLE 7

Examples of Dose Escalation and De-Escalation for Groups A, B, and C

| Group | Cohort | $DL_1$ (mg) | $DL_2$ (mg) | $DL_3$ (mg) |
|---|---|---|---|---|
| A | Cohort A3 (escalation) | 1.0 | 2.0 | 40.0 |
| | Cohort A2 (escalation) | 1.0 | 2.0 | 20.0 |
| | Cohort A1 (initial cohort) | 1.0 | 2.0 | 9.0 |
| | Cohort A0 (de-escalation) | 1.0 | 2.0 | 6.0 |
| | | No $DL_1$ de-escalation allowed; assess alternate schedule. | No $DL_2$ de-escalation allowed; assess alternate schedule. | |
| B | Cohort B3 (escalation) | 1.0 | 2.0 | 40.0 |
| | Cohort B2 (escalation) | 1.0 | 2.0 | 20.0 |
| | Cohort B1 (initial cohort) | 1.0 | 2.0 | 9.0 |
| | Cohort B0 (de-escalation) | 1.0 | 2.0 | 6.0 |
| | | No $DL_1$ de-escalation allowed; assess alternate schedule. | No $DL_2$ de-escalation allowed; assess alternate schedule. | |
| C | Cohort C3 (escalation) | 1.0 | 2.0 | 40.0 |
| | Cohort C2 (escalation) | 1.0 | 2.0 | 20.0 |
| | Cohort C1 (initial cohort) | 1.0 | 2.0 | 9.0 |
| | Cohort C0 (de-escalation) | 1.0 | 2.0 | 6.0 |
| | | No $DL_1$ de-escalation allowed. | No $DL_2$ de-escalation allowed. | |

DL = dose level.

Group A—Cycle 1 Double-Step Fractionated Mosunetuzumab Escalation with Concurrent Administration of Polatuzumab Vedotin Starting in Cycle 1

Group A evaluates mosunetuzumab and polatuzumab vedotin given concurrently starting on C1D1. Patients enrolled in dose finding Group A receive mosunetuzumab 1 mg ($DL_1$) on C1D1, 2 mg ($DL_2$) on C1D8, and the first $DL_3$ test dose on C1D15 by IV infusion. In Cycle 2 and beyond (up to 8-17 cycles), the mosunetuzumab $DL_3$ dose is given on Day 1 of each 21-day cycle, with Day 1 of Cycle 2 being 7 days after the C1D15 dose.

Patients receive polatuzumab vedotin 1.8 mg/kg by IV infusion on Day 1 of each 21-day cycle for up to a maximum of 6 cycles, starting on C1D1.

Schedule and dose level of mosunetuzumab plus polatuzumab vedotin are found in Table 8.

the scheduled date for Cycle 3 and beyond (i.e., with a minimum of 19 days between doses) for logistic/scheduling reasons.

Figure 6:
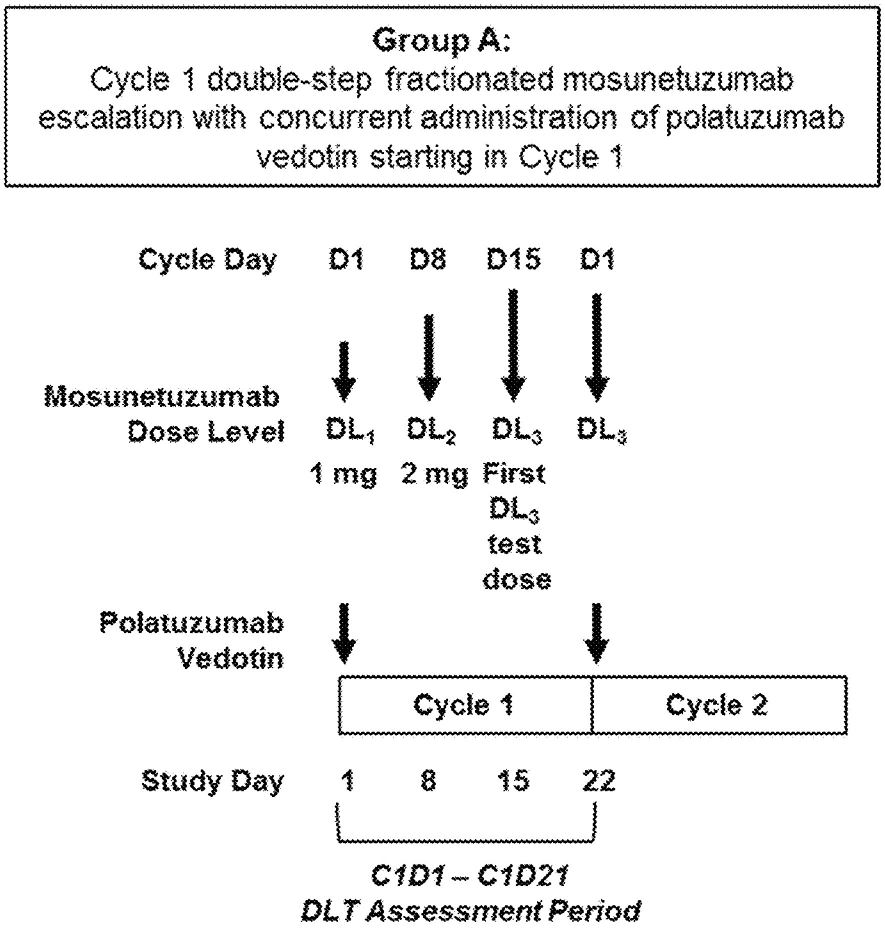
FIG. 6 is a flowchart depicting the dose-limiting toxicity (DLT) dosing and schedule of the assessment period for Group A, as described in Example 2.

Dose escalation in Group A uses a modified 3+3 design. The DLT assessment period for Group A is C1D1 through C1D21 (FIG. 6). Dose escalation of mosunetuzumab $DL_3$ alone is based on recommendations by the IMC for each successive cohort based on set escalation rules. A minimum of 3 patients are enrolled into each cohort, unless the first 2 enrolled patients experience a protocol-defined DLT, in which case enrollment into the cohort is terminated. If none of the first 3 DLT-evaluable patients experiences a DLT, enrollment of the next cohort at the next highest dose level may proceed. If 1 of the first 3 DLT-evaluable patients experiences a DLT, the cohort is expanded to 6 patients, and all 6 patients are evaluated for DLTs before any dose-escalation decision. If no additional patient experiences a DLT in the 6 DLT-evaluable patients, enrollment of the next cohort at the next highest dose level may proceed.

Otherwise, if the cohort has expanded to 6 patients, the cumulative MTD of a cohort may be exceeded under 2 scenarios. In the first scenario, because DL1 and DL2 are fixed for each cohort in each group and are evaluated with each cohort during dose escalation, the assessment of MTD associated with these two doses reviews all DLTs occurring prior to the administration of the first $DL_3$ test dose across all cohorts within a group. The MTD is exceeded if the number of DLTs prior to the administration of the first DL3 test dose across all applicable cohorts has ≥80% chance that the true DLT rate ≥20%, by the posterior probability approach (Thall and Simon Controlled Clinical Trials. 1994. 15(6): 463-81). For example, there is an ≥80% chance that true DLT rate ≥20% if DLTs observed in 2/4, 2/5, 2/6, 3/7, 3/8, 3/9, 3/10, 4/11, 4/12, 4/13, 4/14, or 5/15 patients. If the MTD has been exceeded based on DLTs occurring prior to the administration of the first $DL_3$ test dose, there are no dose reductions allowed for $DL_1$ or $DL_2$. Instead, an alternate schedule in other groups is tested. In the second scenario, if 2 or more out of 6 DLT-evaluable patients experience a DLT after the administration of the first $DL_3$ test dose, the MTD is deemed to have been exceeded and dose escalation stops. An additional 3 patients are evaluated for DLTs at the preceding dose level, unless 6 patients have already been evaluated at that level. However, if the dose level at which the MTD is exceeded is ≥25% higher than the preceding dose level, 6 patients may be evaluated at an intermediate dose level.

TABLE 8

Mosunetuzumab Plus Polatuzumab Vedotin Regimen (Group A)

| | | | Cycle 1 | | | Cycles 2-6 | Cycles 7-8 | Cycles 9-17[a] |
|---|---|---|---|---|---|---|---|---|
| Agent | Dose | Route | Day 1 | Day 8 | Day 15 | Day 1 | Day 1 | Day 1 |
| Polatuzumab vedotin | 1.8 mg/kg | IV | x | | | x | | |
| Mosunetuzumab | $DL_1$ | IV | x | | | | | |
| | $DL_2$ | IV | | x | | | | |
| | $DL_3$ | IV | | | x | x | x | x |

DL = dose level.

Mosunetuzumab and polatuzumab vedotin may be given up to ±1 day from the scheduled date for Cycle 2 (i.e., with a minimum of 6 days after C1D15 dosing), and ±2 days from If the MTD is exceeded at any dose level, the highest dose where fewer than 2 out of 6 DLT-evaluable patients (i.e., <33%) experience a DLT after the administration of the first $DL_3$ test dose is declared the MTD. If the MTD is not exceeded at any dose level, the highest dose administered in this group is declared the maximum assessed dose. In the event that the initial mosunetuzumab $DL_3$ test dose in combination with polatuzumab vedotin is above the MTD (i.e., ≥33% out of 6 DLT-evaluable patients experience a DLT after the administration of the first $DL_3$ test dose), a reduced $DL_3$ dose level that is at least 25% lower may be evaluated in an additional cohort of 3 to 6 patients. If this dose level is again above the MTD, further $DL_3$ dose reductions of >25% of the preceding $DL_3$ dose may be assessed in subsequent cohorts of 3-6 patients. The highest dose level where fewer than 2 out of 6 DLT-evaluable patients (i.e., <33%) experience DLTs is declared the MTD.

Group B—Cycle 1 Polatuzumab Vedotin with Delayed Start Cycle 1 Double-Step Fractionated Mosunetuzumab Escalation Group B evaluates an alternate schedule of polatuzumab vedotin and mosunetuzumab, with polatuzumab starting on C1D1 and mosunetuzumab double-step fractionated doses starting on C1D8. Patients enrolled in dose-escalation Group B receive polatuzumab vedotin 1.8 mg/kg by IV infusion on Day 1 of each 21-day cycle for up to a maximum of 6 cycles, starting on C1D1.

Patients receive mosunetuzumab 1 mg ($DL_1$) on C1D8, 2 mg ($DL_2$) on C1D15, and the first $DL_3$ test dose on C2D1 by IV infusion. In Cycle 3 and beyond (up to 9-17 cycles), the mosunetuzumab $DL_3$ dose is given on Day 1 of each cycle.

Schedule and dose level of mosunetuzumab plus polatuzumab vedotin are found in Table 9.

TABLE 9

Mosunetuzumab Plus Polatuzumab Vedotin Regimen (Group B)

| | | | Cycle 1 | | | Cycles 2-6 | Cycles 7-9 | Cycles 10-17 |
|---|---|---|---|---|---|---|---|---|
| Agent | Dose | Route | Day 1 | Day 8 | Day 15 | Day 1 | Day 1 | Day 1 |
| Polatuzumab vedotin | 1.8 mg/kg | IV | x | | | x | | |
| Mosunetuzumab | $DL_1$ | IV | | x | | | | |
| | $DL_2$ | IV | | | x | | | |
| | $DL_3$ | IV | | | | x | x | x |

DL = dose level.

Mosunetuzumab and polatuzumab vedotin may be given up to ±2 days from the scheduled date for Cycle 3 and beyond (i.e., with a minimum of 19 days between doses) for logistic/scheduling reasons.

Figure 7:
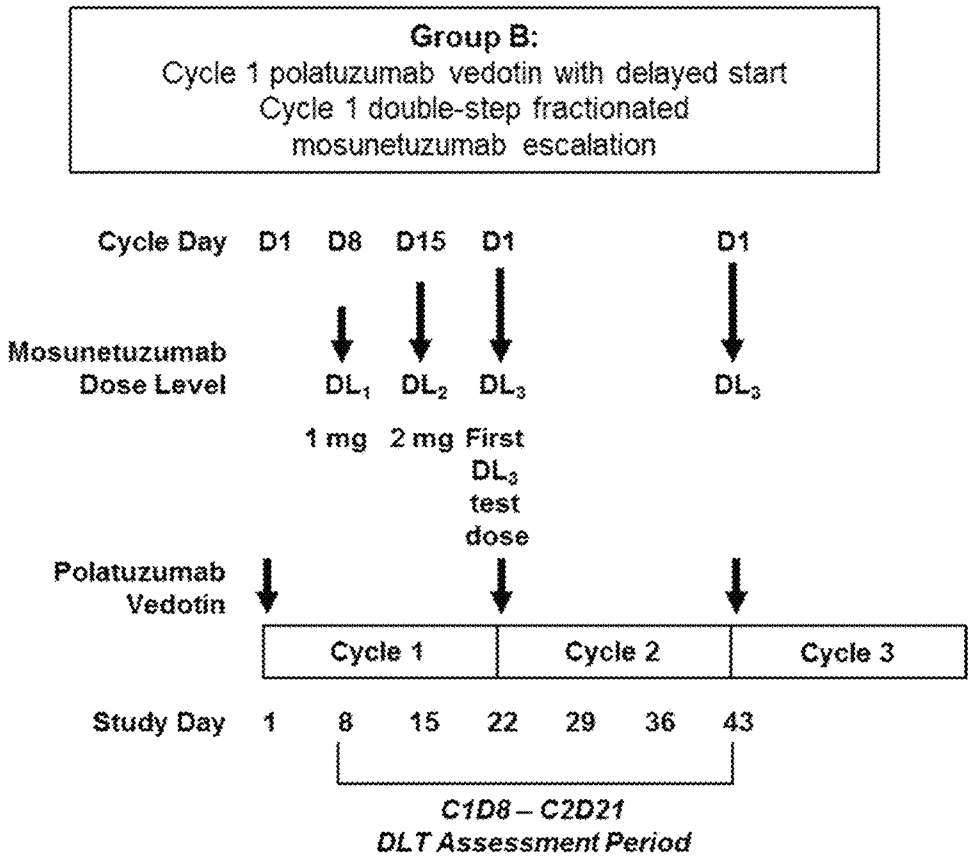
FIG. 7 is a flowchart depicting the DLT dosing and schedule of the assessment period for Group B, as described in Example 2.

Dose escalation in Group B uses the same modified 3+3 design and dose-escalation and de-escalation rules as Group A. The DLT assessment period for Group B is C1D8 through C2D21 (FIG. 7). The main difference between Group A and Group B dose-escalation rules is the timing of the administration of the first $DL_3$ test dose, which occurs on C2D1 for Group B.

Group C—Cycle 1 Double-Step Fractionated Mosunetuzumab Escalation with Concurrent Administration of Polatuzumab Vedotin Starting in Cycle 2

Group C evaluates an alternate schedule of polatuzumab vedotin and mosunetuzumab, with mosunetuzumab given on a double-step fractionated schedule starting on C1D1 and polatuzumab vedotin given starting on C2D1. Patients enrolled in Group C receive mosunetuzumab 1 mg ($DL_1$) on C1D1, 2 mg ($DL_2$) on C1D8, and $DL_3$ test dose on C1D15 by IV infusion. In Cycle 2 and beyond (up to 8-17 cycles) the mosunetuzumab $DL_3$ dose is given on Day 1 of each 21-day cycle.

Patients receive polatuzumab vedotin 1.8 mg/kg by IV infusion on Day 1 of each cycle up to a maximum of 6 cycles, starting on C2D1.

Schedule and dose level of mosunetuzumab plus polatuzumab vedotin are found in Table 10.

TABLE 10

| Mosunetuzumab Plus Polatuzumab Vedotin Regimen (Group C) | | | | | | | | |
|---|---|---|---|---|---|---|---|---|
| | | | Cycle 1 | | | Cycles 2-7 | Cycle 8 | Cycles 9-17 |
| Agent | Dose | Route | Day 1 | Day 8 | Day 15 | Day 1 | Day 1 | Day 1 |
| Polatuzumab vedotin | 1.8 mg/kg | IV | | | | x | | |
| Mosunetuzumab | $DL_1$ | IV | x | | | | | |
| | $DL_2$ | IV | | x | | | | |
| | $DL_3$ | IV | | | x | x | x | x |

DL = dose level.

For logistic/scheduling reasons, C2D1 administration of mosunetuzumab and polatuzumab vedotin may be given up to ±1 day from the scheduled date for Cycle 2 (i.e., with a minimum of 6 days after C1 D15 dosing), and ±2 days from the scheduled date for Cycle 3 and beyond (with a minimum of 19 days between doses).

Figure 8:
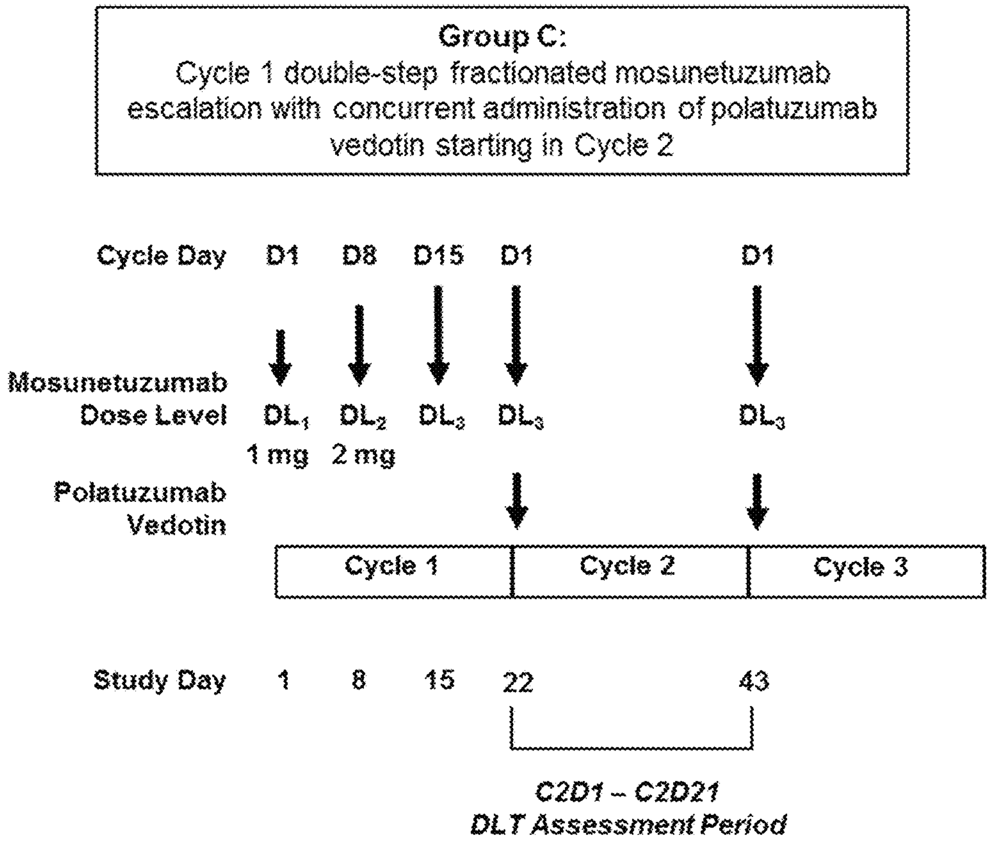
FIG. 8 is a flowchart depicting the DLT dosing and schedule of the assessment period for Group C, as described in Example 2.

Dose escalation in Group C uses a 3+3 design. The DLT assessment window in Group C is from C2D1 through C2D21 (FIG. 8), because polatuzumab vedotin is given in combination with mosunetuzumab starting on C2D1. Between C1D1 and C1 D21, if a patient experiences a treatment-emergent toxicity that does not completely resolve to baseline level by C2D1, the patient may be considered unevaluable for dose-escalation decisions and MTD determination and be replaced by an additional patient at that same dose level and schedule. Dose escalation of mosunetuzumab $DL_3$ alone is based on recommendations by the IMC for each successive cohort based on set escalation rules. A minimum of 3 patients are enrolled into each cohort, unless the first 2 enrolled patients experience a protocol-defined DLT, in which case enrollment into the cohort is terminated. If none of the first 3 DLT-evaluable patients experiences a DLT, enrollment of the next cohort at the next highest dose level may proceed. If 1 of the first 3 DLT-evaluable patients experiences a DLT, the cohort is expanded to 6 patients, and all 6 patients are evaluated for DLTs before any dose-escalation decision. If no additional patient experiences a DLT in the 6 DLT-evaluable patients, enrollment of the next cohort at the next highest dose level may proceed.

Otherwise, if the cohort has expanded to 6 patients, and 2 or more out of 6 DLT-evaluable patients experience a DLT after the administration of the first $DL_3$ test dose, the MTD is deemed to have been exceeded and dose escalation stops. An additional 3 patients are then evaluated for DLTs at the preceding dose level, unless 6 patients have already been evaluated at that level. However, if the dose level at which the MTD is exceeded is 2 25% higher than the preceding dose level, 6 patients may be evaluated at an intermediate dose level.

If the MTD is exceeded at any dose level, the highest dose where fewer than 2 out of 6 DLT-evaluable patients (i.e., <33%) experience a DLT after the administration of the first $DL_3$ test dose is declared the MTD. If the MTD is not exceeded at any dose level, the highest dose administered in this group is declared the maximum assessed dose. In the event that the initial mosunetuzumab $DL_3$ test dose in combination with polatuzumab vedotin is above the MTD (i.e., 2 33% out of 6 DLT-evaluable patients experience a DLT after the administration of the first $DL_3$ test dose), a reduced $DL_3$ dose level that is at least 25% lower may be evaluated in an additional cohort of 3 to 6 patients. If this dose level is again above the MTD, further $DL_3$ dose reductions of >25% of the preceding $DL_3$ dose may be assessed in subsequent cohorts of 3-6 patients. The highest dose level where fewer than 2 out of 6 DLT-evaluable patients (i.e., <33%) experience DLTs is declared the MTD. An example of dose escalation and de-escalation is shown in Table 7, though specific doses listed are for illustrative purposes only.

Continued Dosing Beyond the DLT Assessment Period

Patients are eligible to receive additional cycles of study treatment with mosunetuzumab given in combination with polatuzumab vedotin every 21 days (the day of infusion being Day 1 of each cycle) beyond the DLT assessment period if they have no clinical signs or symptoms of progressive disease, and have not experienced Grade 4 non-hematologic adverse events with the possible exception of Grade 4 TLS. Patients who experience Grade 4 TLS may be considered for continued study treatment provided TLS resolves completely within 14 days and with Medical Monitor approval. All other study treatment related adverse events from prior study treatment administration must have decreased to Grade ≤1 or baseline grade by the next administration. Exceptions on the basis of ongoing overall clinical benefit may be allowed after a careful assessment and discussion of benefit-risk with the patient by the study investigator and with approval from the Medical Monitor. Any treatment delay for toxicities not attributed to study treatment may not require study treatment discontinuation but must be approved by the Medical Monitor. Within each treatment group, a lower dose level on Day 1 of Cycle 3 or subsequent cycles may be administered to assess whether a lower dose than the mosunetuzumab $DL_3$ administered in the first two cycles is sufficient to maintain clinical efficacy during later cycles. Once an RP2D is declared, the IMC may permit patients receiving mosunetuzumab at doses below the RP2D to be dose escalated to the RP2D. A patient may be dose escalated to the RP2D provided that no prior DLTs or dose reductions have occurred, and provided that the treating physician views such dose escalation is in the patient's best interest. Patients who complete study treatment without disease progression are monitored according to the schedule for post-treatment follow-up, including regularly scheduled tumor assessments until discontinuation from the post-treatment follow-up (e.g., due to progression).

Expansion Phase

In the expansion phase (Phase II), approximately 80 patients are treated with mosunetuzumab plus polatuzumab vedotin in the single-group expansion phase, with approximately 40 R/R FL (Grade 1-3a) patients assigned to Group I, and approximately 40 R/R DLBCL, transformed FL, or Grade 3b FL patients assigned to Group J. Based on safety and efficacy data from the single-group expansion phase, a randomized expansion phase may be initiated, in which approximately 140 patients with R/R DLBCL, transformed FL, or Grade 3b FL are randomized to one of three treatment groups. The three treatment groups consist of Group D with approximately 40 patients who are treated with polatuzumab vedotin plus bendamustine and rituximab, Group E with approximately 20 patients who are treated with mosunetuzumab, and Group F with approximately 80 patients who are treated with mosunetuzumab and polatuzumab vedotin.

For Groups I, J, and F the dose level and schedule of mosunetuzumab follow the RP2D and schedule selected from one of Groups A, B, and C, and similarly the schedule for polatuzumab vedotin follows the schedule selected from Groups A, B, or C (see Tables 8, 9, and 10, respectively). For Group E, the dose level and schedule of single-agent mosunetuzumab follows the dose that is assessed to be safe and active based on results from all completed and ongoing clinical studies of mosunetuzumab as a single agent and the schedule of Table 11.

TABLE 11

Single-Agent Mosunetuzumab Regimen (Group E)

| | | | Cycle 1 | | | Cycles 2-8 | Cycles 9-17 |
|---|---|---|---|---|---|---|---|
| Agent | Dose | Route | Day 1 | Day 8 | Day 15 | Day 1 | Day 1 |
| Mosunetuzumab | $DL_1$ | IV | x | | | | |
| | $DL_2$ | IV | | x | | | |
| | $DL_3$ | IV | | | x | x | x |

DL = dose level. For mosunetuzumab treatment duration beyond Cycle 8, see below or Table 6.

For Group D, the dose level and schedule of polatuzumab vedotin in combination with bendamustine and rituximab follows the dose level and schedule of Table 12.

TABLE 12

Polatuzumab Vedotin Plus Bendamustine and Rituximab Regimen (Group D)

| | | | Cycle 1 | | | Cycles 2-6 | |
|---|---|---|---|---|---|---|---|
| Agent | Dose | Route | Day 1 | Day 2 | Day 3 | Day 1 | Day 2 |
| Rituximab | 375 mg/$m^2$ | IV | x | | | x | |
| Polatuzumab vedotin | 1.8 mg/kg | IV | | x | | x | |
| Bendamustine | 90 mg/$m^2$ | IV | | x | x | x | x |

Mosunetuzumab Treatment Duration and Re-Treatment Following Disease Progression Patients who initially respond or have SD to mosunetuzumab combined with polatuzumab vedotin or mosunetuzumab as a single agent may benefit from additional cycles beyond the initial 8 cycles of mosunetuzumab treatment, depending on anti-tumor responses to initial treatment.

Figure 9A:
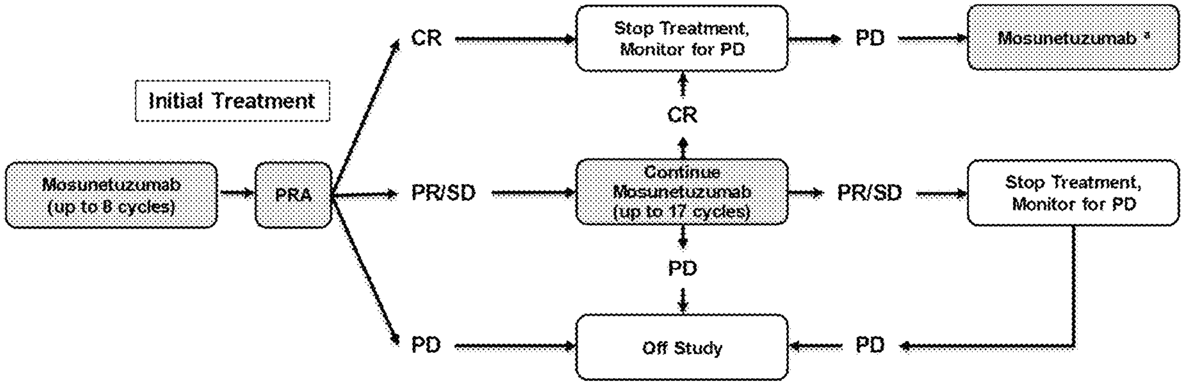
FIG. 9A and FIG. 9B are flowcharts depicting the schema for duration of initial study treatment and options for re-treatment or continued study treatment beyond the initial eight cycles of study treatment, as described in Example 2, with either mosunetuzumab alone (FIG. 9A) or mosunetuzumab plus polatuzumab vedotin (FIG. 9B).
Figure 9B:
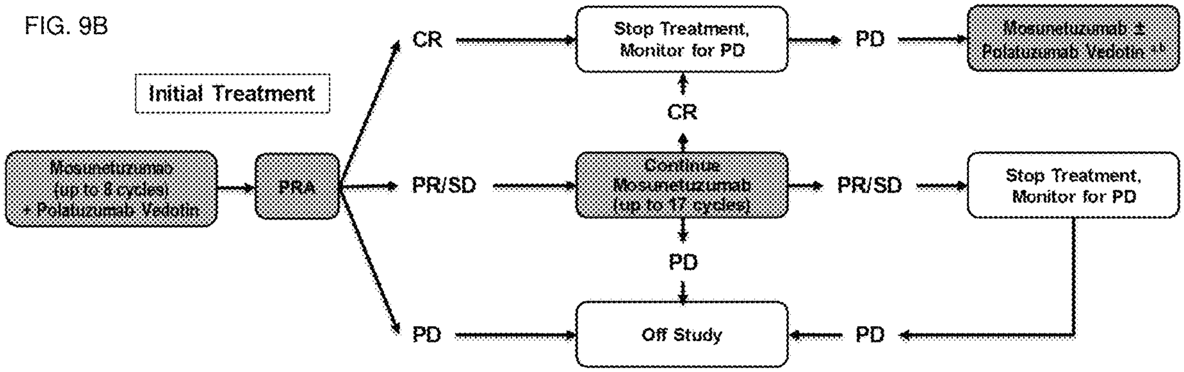
Figure 12A:
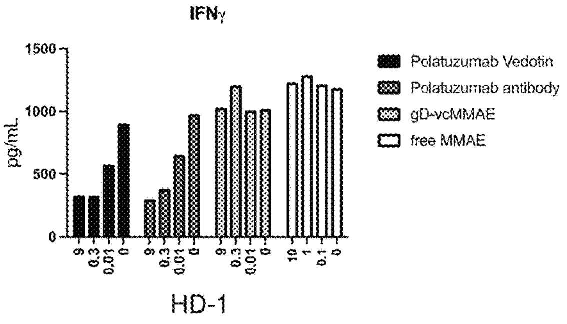
FIG. 12A-FIG. 12D are series of graphs depicting representative cytokine levels after anti-CD20/CD3 combination treatment.
Figure 12B:
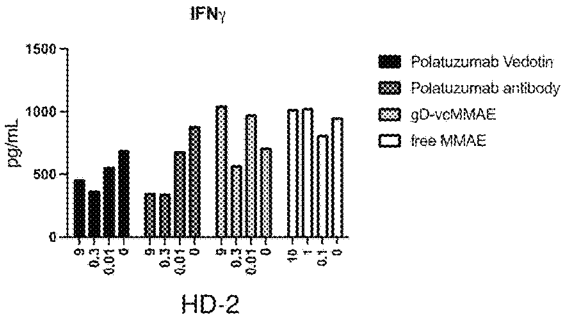
Figure 12C:
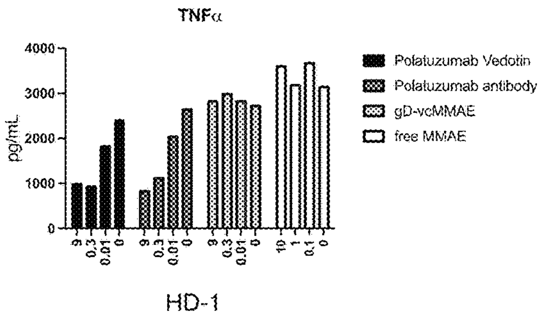
Figure 12D:
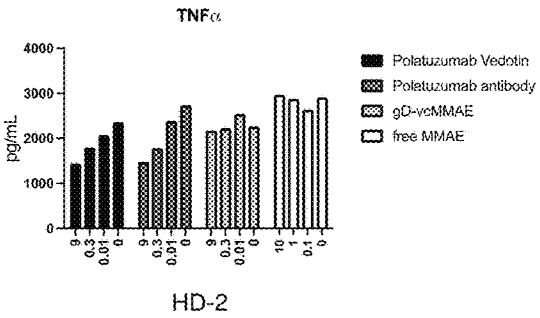

The dose and schedule of study treatment to be administered for patients receiving re-treatment is determined by the Medical Monitor and is a previously tested dose and schedule that has cleared the DLT assessment period. The schema of the duration of initial study treatment and options for re-treatment or continued study treatment beyond the initial 8 cycles of study treatment are described in FIG. 9A and FIG. 9B. The dose and schedule of administration of mosunetuzumab with or without polatuzumab vedotin based on the nature and timing of study treatment is described below.

For patients initially receiving mosunetuzumab combined with polatuzumab vedotin (Groups A, B, and C; Groups I, J and F), polatuzumab vedotin is given for 6 cycles during re-treatment, unless progressive disease or unacceptable toxicity is observed prior to completion of the 6 cycles. In addition, eight cycles of mosunetuzumab is given unless progressive disease or unacceptable toxicity is observed prior to completion of the 8 cycles, halting study treatment. Patients who achieve CR at PRA after 8 cycles of mosunetuzumab treatment do not receive any additional cycles of mosunetuzumab and are instead be monitored according to the post-treatment follow-up schedule. If progressive disease following completion of combination treatment is observed, and the patient has s Grade 1 peripheral neuropathy, mosunetuzumab combined with polatuzumab vedotin re-treatment may be initiated. If progressive disease following completion of combination treatment is observed and the patient has continued Grade >1 peripheral neuropathy or otherwise by physician choice, single-agent mosunetuzumab re-treatment may be initiated. Patients who achieve a PR or maintain SD at PRA after receiving 8 cycles of mosunetuzumab treatment may continue single-agent mosunetuzumab for up to a total of 17 cycles unless progressive disease or unacceptable toxicity is observed. PRA is conducted at the end of Cycle 8 (C8D21±1 week) prior to the C9D1 treatment for Groups A and C (and Groups I, J, and F, if following the Group A or C dosing schedule) or at the end of Cycle 9 (C9D21±1 week) prior to C10D1 treatment for Group B (and Groups I, J, and F, if following the Group B dosing schedule), in order to inform the duration of study treatment. If CR, PR, or SD is achieved by the completion of 17 total cycles, patients are monitored according to the post-treatment follow-up schedule. If progressive disease is observed on additional cycles of mosunetuzumab treatment, then study treatment is discontinued.

For patients initially receiving single-agent mosunetuzumab (Group E), initial treatment and re-treatment with single-agent mosunetuzumab is given for 8 cycles unless progressive disease or unacceptable toxicity is observed prior to completion of the 8 cycles. If progressive disease is observed, study treatment is discontinued. Patients who achieve a CR at PRA after 8 cycles of treatment do receive any additional cycles of mosunetuzumab and are monitored according to the post-treatment follow-up schedule. If progressive disease following completion of initial single-agent mosunetuzumab treatment is observed, single-agent mosunetuzumab re treatment may be initiated. Treatment may continue with mosunetuzumab for at least 8 additional cycles. Patients who achieve a PR or maintain SD at PRA after receiving 8 cycles of treatment may continue with single-agent mosunetuzumab for up to a total of 17 cycles unless progressive disease or unacceptable toxicity is observed. PRA is conducted at the end of Cycle 8 (C8D21±1 week) prior to the C9D1 treatment to inform the duration of study treatment. If CR, PR, or SD is achieved after 17 cycles of treatment, patients are monitored according to the post-treatment follow-up schedule. If progressive disease is observed, then study treatment is discontinued.

The post-treatment follow-up schedule is outlined below in Table 13:

TABLE 13

Schedule for Post-Treatment Follow-up

| Assessments/Procedures | Post-Treatment Follow-Up |
|---|---|
| EORTC QLQ-C30, FACT-Lym subscale, FACT/GOG-Ntx, and EQ-5D-5L (Groups D, E, F) | Every 3 months |
| Targeted physical examination | Every 3 months |
| Vital signs (blood pressure, pulse rate, and body temperature) | Every 3 months |
| ECOG PS | Every 3 months |
| B symptoms | Every 3 months |
| Tumor assessments | At 9 months, 12 months, then every 6 months |
| Total IgA, IgG, IgM | Every 6 months |
| Hematology | Every 3 months × 2 then every 6 months |
| Serum chemistry | Every 3 months × 2 then every 6 months |
| Bone marrow biopsy and aspirate | As needed to confirm relapse |
| Tumor biopsy for biomarkers (optional) | At disease progression |
| Serum PK sample and serum ADA sample for mosunetuzumab and polatuzumab vedotin | Once, ≤90 days after last study drug administration |

ADA = anti-drug antibody;
C = cycle;
CT = computed tomograph (scan);
ECOG PS = Eastern Cooperative Oncology Group Performance Status;
eCRF = electronic Case Report Form;
EORTC QLQ-C30 = European Organisation for Research and Treatment of Cancer Quality of Life—Core 30 Questionnaire;
EQ-5D-5L = EuroQol 5-Dimension, 5-Level (questionnaire);
FACT/GOG-Ntx = Functional Assessment of Cancer Treatment/Gynecologic Oncology Group—Neurotoxicity;
FACT-Lym = Functional Assessment of Cancer Therapy—Lymphoma (subscale);
GGT = gamma-glutamyl transferase;
LDH = lactate dehydrogenase;
NK = natural killer (cell);
PET = positron emission tomography (scan);
PK = pharmacokinetic.

Schedule corresponds to visit time-points only for patients who complete or discontinue the study treatment but remain on the study without disease progression. Patients are followed on this schedule timed from the study drug completion/early discontinuation visit. The first two visits occur within ±7 days from the scheduled date, while subsequent visits occur within ±14 days from the scheduled date. Other assessments/procedures can be performed at an earlier time-point to align with the tumor assessment visit. Assessments are performed until disease relapse/progression (assessments are performed for the last visit when disease relapse/progression occurs), start of new anti-cancer therapy, or withdrawal from study participation, whichever occurs first.

The questionnaires are completed by patients prior to any other study assessments (except laboratory blood collections).

Targeted physical examinations are limited to systems of primary relevance (i.e., cardiovascular, respiratory, neurologic, and any system that might be associated with tumor assessment [e.g., lymph nodes, liver, and spleen and those systems associated with symptoms], or potential drug related toxicity [e.g., clinical assessment for peripheral neuropathy in patients receiving polatuzumab vedotin]). Changes from baseline abnormalities are recorded in patient notes. New or worsened clinically significant abnormalities are recorded as adverse events on the Adverse Event eCRF.

B symptoms include unexplained weight loss of >10% over previous 6 months, fever (>38° C./100.4° F.), and/or drenching night sweats.

Response is assessed using image-based evaluation using standard Lugano 2014 criteria. Perform CT scan with or without PET during follow up at 9 months (±1 week) after C1D1, 12 months (±1 week) after C1D1, and then every 6 months until disease progression or study discontinuation, whichever is earlier. Before a metabolic complete response is achieved, it is recommended that PET scans continue in conjunction with diagnostic-quality CT scans. A full tumor assessment including radiographic assessment using CT scan with or without PET must be performed any time disease progression or relapse is suspected during follow up. Scans are performed according to the guidelines in the imaging manual provided to all sites.

Hematology includes CBC (including hemoglobin, hematocrit, RBC, WBC), platelet count, ANC, absolute lymphocyte count, and other cells.

Chemistry panel (serum) includes sodium, potassium, chloride, bicarbonate, glucose, BUN or urea, creatinine, calcium, magnesium, phosphorous, total and direct bilirubin, total protein, albumin, ALT, AST, ALP, GGT, LDH, and uric acid.

Bone marrow examination (biopsy and aspirate for morphology) is required only if there is a clinical suspicion of disease recurrence in the bone marrow. Unsuccessful attempts at marrow aspiration are not considered a protocol violation. For patients with DLBCL, PET/CT scans can be utilized to assess bone marrow involvement; bone marrow examinations are not required unless clinically indicated.

Optional tumor biopsies can be performed at disease progression and at the investigator's discretion (e.g., to confirm disease recurrence or progression or to confirm an alternate histologic diagnosis). Tumor tissue samples consist of representative tumor specimens in paraffin blocks (preferred) or at least 20 unstained slides.

Additional rounds of re-treatment with mosunetuzumab with or without polatuzumab vedotin are permitted, following the re-treatment rules described.

If the time between the last dose of initial treatment and first dose of re-treatment including step dose is ≥6 weeks, administer mosunetuzumab at previous schedule including Cycle 1 double-step fractionation. If the time between the last dose of initial treatment and first dose of re-treatment including step dose is <6 weeks, mosunetuzumab is administered at previous schedule Cycle 2 dose every 21 days; mosunetuzumab double-step fractionation is not needed.

Inclusion Criteria

Patients meet the following criteria:

Signed Informed Consent Form

Age ≥18 years at time of signing Informed Consent Form

- Able to comply with the study protocol and procedures in the investigator's judgment
- ECOG PS of 0, 1, or 2
- Life expectancy of at least 12 weeks
- Histologically confirmed FL or DLBCL from the following diagnoses by 2016 WHO classification of lymphoid neoplasms:
  - FL (including in situ follicular neoplasia and duodenal-type FL)
  - Pediatric-type FL
  - DLBCL, not otherwise specified (NOS) (including germinal center B-cell type and activated B-cell type)
  - T-cell/histiocyte-rich large B-cell lymphoma
  - High-grade B-cell lymphoma with MYC and BCL-2 and/or BCL-6 rearrangements
  - EBV+DLBCL, NOS
  - HHV8+DLBCL, NOS
  - High grade B-cell lymphoma, NOS
  - Anaplastic lymphoma kinase (ALK)+large B-cell lymphoma
- Must have received at least one prior systemic treatment regimen containing an anti-CD20-directed therapy for DLBCL or FL. Patients have either relapsed or have become refractory to a prior regimen as defined below:
  - R/R FL
    - Relapsed to prior regimen(s) after having a documented history of response (CR, CR unconfirmed [CRu], or PR) of ≥6 months in duration from completion of regimen(s)
    - Refractory to any prior regimen, defined as no response to the prior therapy, or progression within 6 months of completion of the last dose of therapy
    - Patients with Grade 3b FL are not eligible for enrollment into the FL expansion cohort.
  - R/R DLBCL
    - Relapsed to prior regimen(s) after having a documented history of response (CR, CRu, or PR) of ≥6 months in duration from completion of regimen(s)
    - Refractory to any prior regimen, defined as no response to the prior therapy, or progression within 6 months of completion of the last dose of therapy
    - Transformed FL is an eligible diagnosis for enrollment in the DLBCL cohort but must be R/R to standard therapies for transformed FL.
      - The Sponsor may retain the option to limit the number of transformed FL patients enrolled in the study.
    - Grade 3b FL is an eligible diagnosis for enrollment in the DLBCL cohort but must be R/R to standard therapies for aggressive NHL.
      - The Sponsor may retain the option to limit the number of Grade 3b FL patients enrolled in the study.
- Measurable disease, defined as at least one bi-dimensionally measurable nodal lesion, defined as >1.5 cm in its longest dimension, or at least one bi-dimensionally measurable extranodal lesion, defined as >1.0 cm in its longest dimension
- Pathology report for the initial histopathology diagnosis and the most recent histopathology diagnosis prior to study entry must be provided.
  - Patients with transformed FL must also provide the pathology report at the time of disease transformation.
  - The results of all tests conducted on the tissue at initial diagnosis, including, but not limited to, tests assessing cell of origin, BCL2 and MYC abnormalities, are provided if done.
- Tumor accessible for biopsy
- Adverse events from prior anti-cancer therapy resolved to ≤Grade 1
- Laboratory values as follows:
- Hepatic Function
  - AST and ALT ≤2.5×ULN
  - Total bilirubin ≤1.5×ULN
    - Patients with a documented history of Gilbert syndrome and in whom total bilirubin elevations are accompanied by elevated indirect bilirubin are eligible.
- Hematologic Function
  - Platelet count ≥75,000/$mm^3$ without transfusion within 14 days prior to first dose of study treatment
  - ANC ≥1000/$mm^3$
  - Total hemoglobin ≥10 g/dL without transfusion within 21 days prior to first dose of study treatment
  - INR ≤1.5×ULN in the absence of therapeutic anticoagulation
  - PTT or aPTT ≤1.5×ULN in the absence of lupus anticoagulant
  - Patients who do not meet criteria for hematologic function because of extensive marrow involvement of NHL and/or disease-related cytopenias (e.g., immune thrombocytopenia) may be enrolled into the study after discussion with and approval of the Medical Monitor
- Serum creatinine ≤ULN or estimated creatinine CL ≥60 mL/min by Cockroft-Gault method or other institutional standard methods, e.g., based on nuclear medicine renal scan
- For women of childbearing potential: agreement to remain abstinent (refrain from heterosexual intercourse) or use contraceptive measures, and agreement to refrain from donating eggs
- For men: agreement to remain abstinent (refrain from heterosexual intercourse) or use a condom, and agreement to refrain from donating sperm Exclusion Criteria

- Patients with any of the following criteria are excluded:
- Inability to comply with protocol-mandated hospitalization and activity restrictions
- Pregnant or breastfeeding, or intending to become pregnant during the study or within 3 months after the final dose of mosunetuzumab, 12 months after the final dose of polatuzumab vedotin, 12 months after the final dose of rituximab, 3 months after the final dose of bendamustine, and 3 months after the final dose of tocilizumab, as applicable.
  - Women of childbearing potential must have a negative serum pregnancy test result within 7 days prior to initiation of study treatment.
- Prior treatment with mosunetuzumab or other CD20-directed bispecific antibodies
- Prior treatment with polatuzumab vedotin
- Current >Grade 1 peripheral neuropathy
- Prior use of any monoclonal antibody, radioimmunoconjugate or ADC within 4 weeks before first dose of study treatment Treatment with any chemotherapeutic agent, or treatment with any other anti-cancer agent (investigational or otherwise) within 4 weeks or 5 half-lives of the drug, whichever is shorter, prior to first dose of study treatment Treatment with radiotherapy within 2 weeks prior to the first dose of study treatment If patients have received radiotherapy within 4 weeks prior to the first study treatment administration, patients must have at least one measurable lesion outside of the radiation field. Patients who have only one measurable lesion that was previously irradiated but subsequently progressed are eligible.

Autologous SCT within 100 days prior to first study treatment administration

Prior treatment with CAR-T therapy within 30 days before first study treatment administration Current eligibility for autologous SCT in patients with R/R DLBCL, R/R transformed FL, or R/R Grade 3b FL Prior allogeneic SCT Prior solid organ transplantation Patients with history of confirmed progressive multifocal leukoencephalopathy (PML)

History of severe allergic or anaphylactic reactions to monoclonal antibody therapy (or recombinant antibody-related fusion proteins)

History of other malignancy that could affect compliance with the protocol or interpretation of results Patients with a history of curatively treated basal or squamous cell carcinoma of the skin or in situ carcinoma of the cervix are allowed.

Patients with a malignancy that has been treated with curative intent will also be allowed if the malignancy has been in remission without treatment for 2 2 years prior to first study treatment administration.

Current or past history of CNS lymphoma

Current or past history of CNS disease, such as stroke, epilepsy, CNS vasculitis, or neurodegenerative disease Patients with a history of stroke who have not experienced a stroke or transient ischemic attack in the past 2 years and have no residual neurologic deficits as judged by the investigator are allowed.

Patients with a history of epilepsy who have had no seizures in the past 2 years while not receiving any anti-epileptic medications are allowed in the expansion cohorts only.

Significant cardiovascular disease such as New York Heart Association Class Ill or IV cardiac disease, myocardial infarction within the last 6 months, unstable arrhythmias, or unstable angina Significant active pulmonary disease (e.g., bronchospasm and/or obstructive pulmonary disease)

Known active bacterial, viral, fungal, mycobacterial, parasitic, or other infection (excluding fungal infections of nail beds) at study enrollment, or any major episode of infection requiring treatment with IV antibiotics or hospitalization (relating to the completion of the course of antibiotics) within 4 weeks prior to first study treatment administration Known or suspected chronic active EBV infection Recent major surgery within 4 weeks prior to first study treatment administration Protocol-mandated procedures (e.g., tumor biopsies and bone marrow biopsies) are permitted.

Positive test results for chronic hepatitis B infection (defined as positive hepatitis B surface antigen [HBsAg] serology)

Patients with occult or prior hepatitis B infection (defined as positive total hepatitis B core antibody and negative HBsAg) may be included if HBV DNA is undetectable at the time of screening. These patients must be willing to undergo monthly DNA testing and appropriate antiviral therapy as indicated.

Acute or chronic HCV infection

Patients who are positive for HCV antibody must be negative for HCV by PCR to be eligible for study participation.

Positive serologic test results for HIV infection

Administration of a live, attenuated vaccine within 4 weeks before first dose of study treatment administration or anticipation that such a live, attenuated vaccine will be required during the study Patients must not receive live, attenuated vaccines (e.g., FluMist®) while receiving study treatment and after the last dose until B-cell recovery to the normal ranges. Killed vaccines or toxoids should be given at least 4 weeks prior to the first dose of study treatment to allow development of sufficient immunity.

Inactivated influenza vaccination should be given during local influenza season only.

Investigators should review the vaccination status of potential study patients being considered for this study and follow the U.S. Centers for Disease Control and Prevention guidelines for adult vaccination with any other non-live vaccines intended to prevent infectious diseases prior to study.

History of autoimmune disease, including, but not limited to, myasthenia gravis, myositis, autoimmune hepatitis, systemic lupus erythematosus, rheumatoid arthritis, inflammatory bowel disease, vascular thrombosis associated with antiphospholipid syndrome, Wegener granulomatosis, Sjögren syndrome, Guillain-Barré syndrome, multiple sclerosis, vasculitis, or glomerulonephritis Patients with a history of autoimmune-related hypothyroidism on a stable dose of thyroid replacement hormone may be eligible.

Patients with controlled Type 1 diabetes mellitus who are on an insulin regimen are eligible for the study.

Patients with a history of disease-related immune thrombocytopenic purpura, autoimmune hemolytic anemia, or other stable autoimmune diseases may be eligible after review and approval by the Medical Monitor.

Received systemic immunosuppressive medications (including, but not limited to, cyclophosphamide, azathioprine, methotrexate, thalidomide, and anti-tumor necrosis factor agents) with the exception of corticosteroid treatments 10 mg/day prednisone or equivalent within 2 weeks prior to first dose of study treatment Patients who received acute, low-dose, systemic immunosuppressant medications (e.g., single dose of dexamethasone for nausea or B symptoms) may be enrolled in the study after discussion with and approval of the Medical Monitor.

The use of inhaled corticosteroids is permitted.

The use of mineralocorticoids for management of orthostatic hypotension is permitted.

The use of physiologic doses of corticosteroids for management of adrenal insufficiency is permitted.

Clinically significant history of liver disease, including viral or other hepatitis, current alcohol abuse, or cirrhosis Any serious medical condition or abnormality in clinical laboratory tests that, in the investigator's or Medical Monitor's judgment, precludes the patient's safe participation in and completion of the study, or which could affect compliance with the protocol or interpretation of results Method of Administration Mosunetuzumab is administered by IV infusion in combination with polatuzumab vedotin or as a single agent, depending on the assigned treatment regimen. Mosunetuzumab is administered to well-hydrated patients. Corticosteroid premedication consisting of dexamethasone 20 mg IV or methylprednisolone 80 mg IV are administered 1 hour prior to the administration of each mosunetuzumab dose. In addition, premedication with oral acetaminophen or paracetamol (e.g., 500-1000 mg) and/or 50-100 mg diphenhydramine may be administered per standard institutional practice prior to administration of mosunetuzumab. Initially, mosunetuzumab is infused over 4 hours ±15 minutes. The infusion may be slowed or interrupted for patients experiencing infusion-associated symptoms. Following each mosunetuzumab dose, patients are observed at least 90 minutes for fever, chills, rigors, hypotension, nausea, or other signs and symptoms of IRRs. In the absence of infusion-related adverse events, the infusion time of mosunetuzumab in Cycle 2 (Group A and Group E) or Cycle 3 (Groups B and C) and beyond may be reduced to 2 hours (±15 minutes), after consultation with the Medical Monitor.

Polatuzumab vedotin is administered by IV infusion in combination with mosunetuzumab or in combination with bendamustine and rituximab, depending on the assigned treatment regimen. The dose of polatuzumab vedotin for each patient is 1.8 mg/kg. The total dose of polatuzumab vedotin for each patient depends on the patient's weight on C1D1 (or within 96 hours before C1D1). If the patient's weight within 96 hours prior to Day 1 of a given treatment cycle increases or decreases >10% from the weight obtained during screening, the new weight is used to calculate the dose. The weight that triggered a dose adjustment is taken as the new reference weight for future dose adjustments. All subsequent doses are modified accordingly. The initial dose is administered over 90 (±10) minutes to patients who are well hydrated. Premedication (e.g., 500-1000 mg of oral acetaminophen or paracetamol and 50-100 mg diphenhydramine as per institutional standard practice) may be administered to an individual patient before administration of polatuzumab vedotin. Administration of corticosteroids is permitted at the discretion of the treating physician. Following the initial dose, patients are observed for 90 minutes for fever, chills, rigors, hypotension, nausea, or other infusion associated symptoms. If prior infusions have been well tolerated, subsequent doses of polatuzumab vedotin may be administered over 30 (±10) minutes, followed by a 30-minute observation period after the infusion. The time interval between the end of infusion of polatuzumab vedotin and the start of mosunetuzumab infusion is at least 60 minutes.

Rituximab is administered by IV infusion in combination with polatuzumab vedotin and bendamustine. Rituximab 375 mg/$m^2$ is administered by IV infusion. No dose modifications of rituximab are allowed. The rituximab administration is completed at least 30 minutes before administration of other study treatments. The infusion of rituximab can be split over two days if the patient is at increased risk for an IRR (high tumor burden, high peripheral lymphocyte count). Administration of rituximab can be continued on the following day, if needed, for patients who experience an adverse event during the rituximab infusion. If a dose of rituximab is split over 2 days, both infusions must occur with appropriate premedication and at the first infusion rate. All rituximab infusions are administered to patients after premedication with oral acetaminophen (e.g., 650-1000 mg) and an antihistamine such as diphenhydramine hydrochloride (50-100 mg) 30-60 minutes before starting each infusion (unless contraindicated). An additional glucocorticoid (e.g., 100 mg IV prednisone or prednisolone or equivalent) is allowed at the investigator's discretion. For patients who did not experience infusion-related symptoms with their previous infusion, premedication at subsequent infusions may be omitted at the investigator's discretion. During the treatment period, rituximab must be administered to patients in a setting where full emergency resuscitation facilities are immediately available. Rituximab is administered as a slow IV infusion through a dedicated line. IV infusion pumps (such as the Braun Infusomat Space) are used to control the infusion rate of rituximab. After the end of the first infusion, the IV line or central venous catheter remains in place for 2 2 hours in order to administer IV drugs if necessary.

Bendamustine is administered by IV infusion in combination with polatuzumab vedotin and rituximab. The bendamustine dose is 90 mg/$m^2$ IV over 60 minutes on two consecutive days. Administration of bendamustine follows any rituximab and polatuzumab vedotin administration. Premedication with anti-emetics can be administered as per institutional guidelines. Granulocyte colony-stimulating factor (G-CSF) can be administered as primary prophylaxis in each cycle of therapy, as per the American Society of Clinical Oncology guidelines or each site's institutional standards.

Tocilizumab is administered when necessary. Any overdose or incorrect administration of tocilizumab is noted on the Study Drug Administration eCRF. Adverse events associated with an overdose or incorrect administration of study drug is recorded on the Adverse Event eCRF.

Assessments and Monitoring

Patients are closely monitored for safety and tolerability throughout the study. FLIPI and FLIPI2 clinical factors obtained at diagnosis and at enrollment are collected for patients with FL. IPI clinical factors at diagnosis and at enrollment are collected for patients with DLBCL or transformed FL. All evaluable or measurable disease are documented at screening and re-assessed at each subsequent tumor evaluation. Response is assessed by the IRC and the investigator on the basis of physical examinations, CT scans, PET-CT scans, and bone marrow examinations (if applicable) using the Lugano 2014 criteria.

PET and diagnostic-quality CT scans are required at screening, at the interim response assessment, and at the PRA visit. Additionally, if disease progression or relapse is suspected before the PRA, both PET and diagnostic-quality CT scans are performed for tumor assessment using the Lugano 2014 criteria to assess overall response to study treatment. PET-CT scans include skull-base to mid-thigh. Full-body PET-CT scan is performed when clinically appropriate. CT scans with oral and IV contrast include chest, abdomen, and pelvic scans; CT scans of the neck are if clinically indicated. CT scans for response assessment may be limited to areas of prior involvement only if required by local regulatory authorities. A baseline brain MRI with gadolinium contrast is obtained in all patients unless medically contraindicated as part of the baseline neurologic assessment.

Bone marrow examinations are required at screening for staging purposes for patients with FL. For patients with DLBCL, screening PET/CT scans may be utilized to assess bone marrow involvement; bone marrow examinations are not required unless clinically indicated. The screening bone marrow may be obtained within 28 days before the start of study treatment. In addition, the definition of CR for CT-based response requires clearing of previously infiltrated bone marrow. Bone marrow examinations include a biopsy for morphology and an aspirate for local hematology (local flow studies are optional). Repeat bone marrow examination is required at the PRA visit for patients who achieve a CR for CT-based response if there was bone marrow infiltration at screening or at time of relapse or transformation if bone marrow involvement is suspected. In patients with a PR and continued bone marrow involvement, a subsequent bone marrow examination may be required to confirm a CR for CT-based response at a later timepoint. For patients with DLBCL, PET/CT scans may be utilized to assess bone marrow involvement, and repeat bone marrow examinations are not required unless clinically indicated.

Laboratory, Biomarker, and Other Biological Samples

Exploratory biomarker research in tumor tissue and blood may include, but is limited to, analysis of genes or gene signatures associated with tumor immunobiology, prognostic or predictive markers associated with response to mosunetuzumab and polatuzumab vedotin, markers associated with T-cell activation, localization, and activation status of immune cells and their subsets, and may involve extraction of DNA, circulating tumor DNA or RNA, analysis of somatic mutations, and use of next-generation sequencing (NGS). Assays for exploratory analysis include, but are not limited to, IHC, immunofluorescence, and RNA sequencing. Additional exploratory biomarkers may be assessed based on evolving clinical and nonclinical data.

Samples for the following laboratory tests are sent to the study site's local laboratory for analysis:

- Hematology: CBC (including hemoglobin, hematocrit, RBC, WBC), platelet count, ANC, absolute lymphocyte count, and other cells
- Coagulation: aPTT, PT, INR, and fibrinogen (e.g., collected when monitoring systemic immune activation events (e.g., MAS/HLH, severe CRS)
- Quantitative Igs (IgA, IgG, and IgM)
- Serum chemistry: sodium, potassium, chloride, bicarbonate, glucose, BUN or urea, creatinine, calcium, magnesium, phosphorous, total and direct bilirubin, total protein, albumin, ALT, AST, ALP, gamma-glutamyl transferase, LDH, and uric acid
- Beta-2 microglobulin
- C-reactive protein
- Serum ferritin
- Viral serology and detection (e.g., hepatitis B (HBsAg, hepatitis B surface antibody [HBsAb], and hepatitis B core antibody [HBcAb]; HBV DNA by PCR if acute or chronic HBV infection cannot be ruled out by serology results [cdc.gov]), HCV antibody; HCV RNA by PCR if the patient is HCV antibody positive, and/or EBV and CMV by quantitative PCR using peripheral blood samples, HIV serology)
- Pregnancy test
- All women of childbearing potential undertake a serum pregnancy test at screening (within 7 days prior to C1D1). Urine or serum pregnancy tests are performed at specified subsequent visits. If a urine pregnancy test is positive, it must be confirmed by a serum pregnancy test.
- Samples for the following laboratory tests are sent to one or several central laboratories or to the Sponsor or designee for analysis:
  - Whole blood samples for flow cytometry and PBMC isolation
  - Plasma (e.g., for cytokines, including but not limited to IL-6 and IFN-γ, circulating CD20) for assessment of minimal residual disease status (expansion cohorts only)
  - Serum samples for measurement of mosunetuzumab, polatuzumab vedotin, rituximab, obinutuzumab, and/or tocilizumab concentrations using validated PK assay
  - Lithium plasma for polatuzumab vedotin acMMAE and unconjugated MMAE using a validated PK assay
  - Blood samples are collected for viral infection test for quantitative PCR detection of viral infection that may include, but is not limited to, EBV and CMV
  - Serum samples for measurement of ADAs to mosunetuzumab, polatuzumab vedotin, and/or tocilizumab using validated assays
  - Tumor biopsies from safely accessible tumor sites (i.e., without unacceptable risk of a major procedural complication(s) per investigator assessment). Samples collected via resection, core-needle biopsy, or excisional, incisional, punch, or forceps biopsies are preferred. The specimen must contain adequate evaluable tumor cells (≥20% for excisional biopsy and ≥50% for core biopsy). Tumor biopsies are required at the following time-points: pretreatment, on-treatment, and re-treatment.

Statistics

Demographic and baseline characteristics, such as age, sex, race/ethnicity, duration of malignancy, and baseline ECOG PS are summarized by using means, standard deviations, medians, and ranges for continuous variables and proportions for categorical variables. All summaries are presented overall and by treatment group and dose level.

Efficacy Analysis

The primary efficacy endpoint is CR rate as determined by PET-CT scan at the PRA as assessed by IRC. The primary analysis is an estimation of CR rate in patients assigned to treatment with mosunetuzumab in combination with polatuzumab vedotin (Group J) in the R/R DLBCL cohort, and in patients assigned to treatment with mosunetuzumab in combination with polatuzumab vedotin (Group 1) in the R/R FL cohort.

For the DLBCL Phase II randomized expansion cohort, the primary analysis is an estimation of CR rate at PRA as assessed by the IRC in patients randomized to treatment with polatuzumab vedotin in combination with bendamustine and rituximab (Group D) and in patients randomized to treatment with mosunetuzumab in combination with polatuzumab vedotin (Group F). In order to isolate the individual contribution of mosunetuzumab, the secondary analysis is an estimation of CR rate at PRA in patients randomized to treatment with mosunetuzumab alone (Group E) in the R/R DLBCL cohort, as well as the difference in CR rates between Group E and Group F. With 20, 40, or 80 patients in a treatment group, the 95% exact Clopper-Pearson Confidence Intervals (Cis) for estimation of the true CR rate would have a margin of error not exceeding ±24.3%, ±16.7%, or ±11.6%, respectively. Detailed CIs for sample sizes of 20, 40, and 80 and observed CRs from 30% to 80% are outlined below in Table 14.

TABLE 14

Clopper-Pearson Exact 95% Confidence Intervals for Observed CR Rates based on Sample Size of 20, 40, and 80 Patients

| Observed | No. of Patients with CR (95% CI for rate) | | |
|---|---|---|---|
| CR Rates | N = 20 | N = 40 | N = 80 |
| 80% | 16 (56.3%, 94.3%) | 32 (64.4%, 90.9%) | 64 (69.6%, 88.1%) |
| 75% | 15 (50.9%, 91.3%) | 30 (58.8%, 87.3%) | 60 (64.1%, 84.0%) |
| 70% | 14 (45.7%, 88.1%) | 28 (53.5%, 83.4%) | 56 (58.7%, 79.7%) |
| 65% | 13 (40.8%, 84.6%) | 26 (48.3%, 79.4%) | 52 (53.5%, 75.3%) |
| 60% | 12 (36.1%, 80.9%) | 24 (43.3%, 75.1%) | 48 (48.4%, 70.8%) |
| 55% | 11 (31.5%, 76.9%) | 22 (38.5%, 70.7%) | 44 (43.5%, 66.2%) |
| 50% | 10 (27.2%, 72.8%) | 20 (33.8%, 66.2%) | 40 (38.6%, 61.4%) |
| 45% | 9 (23.1%, 68.5%) | 18 (29.3%, 61.5%) | 36 (33.8%, 56.5%) |
| 40% | 8 (19.1%, 63.9%) | 16 (24.9%, 56.7%) | 32 (29.2%, 51.6%) |
| 35% | 7 (15.4%, 59.2%) | 14 (20.6%, 51.7%) | 28 (24.7%, 46.5%) |
| 30% | 6 (11.9%, 54.3%) | 12 (16.6%, 46.5%) | 24 (20.3%, 41.3%) |

CR = complete response.

Safety Analysis

With respect to assessment of safety, point estimates are presented. Table 15 provides probabilities of seeing at least one adverse event among 20, 40, and 80 patients for true adverse event frequencies ranging from 1% to 20%/.

TABLE 15

Probability of Safety-Signal Detection based on Sample Size of 20, 40, and 80 Patients

| True Underlying Probability of an AE | Probability of Observing at Least 1 AE in 20 Patients | Probability of Observing at Least 1 AE in 40 Patients | Probability of Observing at Least 1 AE in 80 Patients |
|---|---|---|---|
| 1% | 18% | 33% | 55% |
| 5% | 64% | 87% | 98% |
| 10% | 88% | 99% | >99% |
| 15% | 96% | >99% | >99% |
| 20% | 99% | >99% | >99% |

AE = adverse event.

Pharmacokinetic Analysis

Individual and mean serum concentration of mosunetuzumab versus time data are tabulated and plotted by dose level. The $C_{max}$ and $C_{min}$, of mosunetuzumab and polatuzumab vedotin are summarized. For patients with dense PK sampling scheme, additional PK parameters are calculated including area AUC, CL, and $V_{ss}$, as appropriate for data collected. Estimates for these parameters are tabulated and summarized. Serum trough and maximum concentrations for rituximab, where applicable, are summarized, as appropriate and as data allow. Compartmental, non-compartmental, and/or population methods may be considered. Pre-dose rituximab and obinutuzumab concentrations are summarized for patients who received prior rituximab or obinutuzumab treatments. Additional PK analyses may be conducted as appropriate.

Immunogenicity Analysis

Validated screening, titering, and confirmatory assays are employed to assess ADAs before, during, and after treatment with mosunetuzumab and polatuzumab vedotin. The immunogenicity analysis population consists of all patients with at least one ADA assessment. Patients are considered to be negative for ADAs if they are ADA negative at all timepoints. Patients are considered to be treatment unaffected if they are ADA positive at baseline but do not have any postbaseline samples with a titer that is at least 4-fold greater than the titer of the baseline sample. Patients are considered to have treatment-induced ADA responses if they are ADA negative or missing data at baseline and then develop an ADA response following study drug administration. Patients are considered to have treatment-enhanced ADA responses if they are ADA positive at baseline and the titer of one or more postbaseline samples is at least 4-fold greater (i.e., at least 0.60 titer unit) than the titer of the baseline sample. The relationship between ADA status and safety, efficacy, PK, and biomarker endpoints may also be assessed as appropriate and reported in a descriptive manner via subgroup analyses.

Biomarker Analysis

Exploratory analyses of biomarkers related to tumor and disease biology as well as the mechanisms of action of polatuzumab vedotin and mosunetuzumab are conducted. The association between candidate biomarkers and PET-CT CR rate and other measures of efficacy and safety, with treatment and independent of treatment, are explored to assess potential predictive and prognostic value, respectively. The effects of baseline prognostic characteristics, including NHL subtypes and mutation profiles on efficacy, are evaluated using univariate and/or multivariate statistical methods such as Cox regression and logistic regression. Exploratory PD analyses may include assessments of cytokines, T-cell activation and proliferation, NK cells, B cells as well as other assessments of biomarkers in both tumor tissue and blood when available.

Example 3. Safety, Tolerability, Pharmacokinetics, and Efficacy of Mosunetuzumab (BTCT4465A) Dose Escalation Study in Combination with Polatuzumab Vedotin in Patients with B-Cell Non-Hodgkin Lymphoma (Group A)

Dose escalation is ongoing in Group A (described above) where the combination of mosunetuzumab and polatuzumab vedotin starts in Cycle 1, and mosunetuzumab is administered using a Cycle 1 step-up IV dosing schedule on C1D1 (1 mg), C1D8 (2 mg), and C1D15 (9 mg in cohort A1, 20 mg in cohort A2 and 40 mg in cohort A3) by IV infusion. Additionally, in cohort A4 mosunetuzumab is administered as Cycle 1 step-up doses on C1D1 (1 mg), C1D8 (2 mg), and C1 D15 (60 mg), followed by 60 mg on Day 1 of Cycle 2 and 30 mg on Day 1 of Cycle 3 and beyond. The maximal assessed dose (MAD) has been established for Group A (step-up Cycle 1 IV dosing) as 1/2/60/30 mg of mosunetuzumab; enrollment for this dosing cohort (cohort A4) was still ongoing at the time of clinical cutoff date (CCOD). The recommended Phase II dose (RP2D) has not been established. The maximum tolerated dose (MTD) has not been reached. Patient characteristics are summarized below in Table 16.

TABLE 16

| Patient characteristics in mosunetuzumab dose escalation study (Group A) | |
|---|---|
| Median age, years (range) | 70 (38-81) |
| Male sex, n (%) | 11 (50%) |
| ECOG score at baseline, n (%) | |
| 0 | 10 (45.5%) |
| 1 | 12 (54.5%) |
| 2 | 0 |
| NHL histology at study entry, n (%) | |
| De novo diffuse Large B-Cell Lymphoma | 12 (54.5%) |
| DLBCL arising from FL (trFL) | 4 (18.2%) |
| FL Grade 3B | 3 (13.6%) |

TABLE 16-continued

| Patient characteristics in mosunetuzumab dose escalation study (Group A) | |
|---|---|
| FL Grade 1-3A | 3 (13.6%) |
| Number of prior lines of therapy, median (range) | 3 (1-10) |
| Only 1 prior line, n (%) | 4 (18.2%) |
| Refractory Status to Latest Prior Regimen, n (%) | |
| Refractory | 17 (77.3%) |
| Relapsed | 5 (22.7%) |
| Refractory Status to Any Prior CD20 Regimen, n (%) | |
| Refractory | 19 (86.4%) |
| Relapsed | 3 (13.6%) |
| Prior CAR-T therapy, n (%) | 7 (31.8%) |
| Time since last therapy (months), median (range) | 6.3 (0.3-72) |
| <3 months, n (%) | 9 (40.9%) |
| Time since last CD20 therapy (months), median (range) | 8.8 (1.3-69) |
| Bulky Disease, at least one lesion, 10 cm, n (%) | 1 (4.5%) |
| Ann Arbor stage at study entry | |
| I | 1 (4.5%) |
| II | 3 (13.6%) |
| III | 9 (40.9%) |
| IV | 9 (40.9%) |

As of the CCOD, 1 dose-limiting toxicity (DLT) of Grade 3 new onset atrial fibrillation has been reported. All the 22 safety evaluable patients experienced at least 1 adverse event (AE) of any grade. A total number of 108 AEs assessed by the investigator as related to mosunetuzumab were reported in 18 patients (82%). Five patients (23%) experienced at least a severe adverse event (SAE). Three patients had an AE, each, with fatal outcome (Grade 5 malignant disease progression, Grade 5 sudden cardiac arrest, and Grade 5 respiratory failure), both unrelated to mosunetuzumab treatment. As of the CCOD, the most frequently observed AE considered related to mosunetuzumab was fatigue, occurring in eight (36%) safety evaluable patients, followed by neutrophil count decreased, occurring in 6 patients (27%), and then diarrhea, nausea, pruritus, and pyrexia, each occurring in four patients (18%). In addition, six patients (27%) experienced infections and two patients (9%) experienced CRS, both of which were Grade 1. The median time to first CRS onset was 2 days, and the median CRS duration was 1 day. All CRS was treated with antipyretics, and no tocilizumab was given. Furthermore, there was no occurrence of immune effector cell-associated neurotoxicity syndrome (ICANS) events in any of the 22 patients in the study. Details of all AEs related to mosunetuzumab can be found in FIG. 10.

A total number of 109 AEs assessed by the investigator as related to polatuzumab vedotin were reported in 19 patients (86.4%). As of the CCOD, the most frequently observed AE considered related to polatuzumab vedotin was fatigue, occurring in eight (36%) safety evaluable patients, followed by neutrophil count decreased, occurring in 7 patients (32%), then nausea, occurring in 6 patients (27%), followed by diarrhea and peripheral sensory neuropathy, both occurring in four patients (18%). Details of all AEs related to polatuzumab vedotin can be found in FIG. 11.

Efficacy of treatment with mosunetuzumab dose escalation in combination with polatuzumab vedotin (1.8 mg/kg IV) (Group A) is summarized below in Table 17. For determining response rates below, PET-CT result was used when available, and CT-only result was used if PET scan was unavailable. Aggressive NHL includes de novo DLBCL, transformed FL, and Grade 3b FL. Post-CAR-T patients are patients who were treated with CAR-T therapy at least 30 days prior to administration of the first study treatment (e.g., anti-CD20/anti-CD3 bispecific antibody and/or anti-CD79b antibody drug conjugate; e.g., mosunetuzumab and/or polatuzumab vedotin).

TABLE 17

Response rates of patients in mosunetuzumab dose escalation + polatuzumab vedotin study

| Response rate, n (%) | All Patients (n = 22) | All Aggressive NHL (aNHL) Patients (n = 19) | Post-CAR-T patients (n = 7) | All FL Patients (n = 3) |
|---|---|---|---|---|
| Overall Response Rate (95% CI) | 15 (68%) (45, 86) | 12 (63%) (38, 84) | 4 (57%) (18, 90) | 3 (100%) (29, 100) |
| Complete Response Rate (95% CI) | 12 (55%) (32, 76) | 9 (47%) (25, 71) | 2 (29%) (4, 71) | 3 (100%) (29, 100) |

Example 4. In Vitro Study of Anti-CD20/Anti-CD3 Bispecific Antibody in Combination with Anti-CD79b (SN8v28)-MC-Vc-PAB-MMAE (Polatuzumab Vedotin) Vs Anti-CD20/Anti-CD3 Bispecific Antibody Alone, Anti-CD20/Anti-CD3 Bispecific Antibody in Combination with Polatuzumab (Non-ADC Anti-CD79b Antibody), with gD-vcMMAE (Non-Targeted ADC with Same Linker and Payload as Polatuzumab Vedotin), or with Free Payload MMAE

Materials and Methods

Anti-CD20/anti-CD3 (2H7v16/38E4.v1), was provided as a liquid at 4.86 mg/mL concentration. Polatuzumab vedotin, Lot DCDS4501A, was provided as a liquid at 10 mg/mL concentration. Polatuzumab antibody, Lot PUR22571, was provided as a liquid at 20.4 mg/mL concentration. gD-vcMMAE, Lot CNJ4680, was provided as a liquid at 9.26 mg/mL concentration. Before use, all above materials were stored in a refrigerator set to maintain a temperature range of 4-8° C. MMAE, Lot G00060245.1-8, was provided as a liquid in DMSO at 1 mM concentration; before use, it was stored in a −20° C. freezer.

Human peripheral blood mononuclear cells (PBMCs) were prepared from whole blood of healthy donors by Ficoll® density gradient centrifugation (GE Healthcare Bio Sciences; Pittsburgh, PA). After isolation, PBMCs were resuspended in the assay medium (RPMI 1640 supplemented with 10% heat inactivated fetal bovine serum) and dispensed into 96 well, U bottom tissue culture plates at $3.0\times10^5$ cells/well in a volume of 50 µL. After 1-hour incubation, 50 µL of serial dilutions of each treatment was added to the plates and incubated for another 20 hours at 37° C. After this incubation, culture supernatants were set aside to be analyzed using human cytokine MILLIPLEX® Assays with Luminex® technology (MilliporeSigma; Burlington, MA). Remaining cells were stained with anti-CD4-APC/Fire750 (clone RPA-T4), anti-CD8a-BV421 (clone RPA-T8), anti-CD14-FITC (cloneHCD14), anti-CD25-APC (clone BC96), and anti-CD69-PE (clone FN50) from BioLegend (San Diego, CA) for 30 minutes. After two wash steps, cells were resuspended in phosphate buffered saline (PBS) containing 7-amino-actinomycin D (7 AAD; BioLegend), 0.5% bovine serum albumin, and 0.05% sodium azide. Flow cytometry was performed on a BD FACSymphony® Flow Cytometer equipped with BD FACSDiva@Software for data acquisition (BD Biosciences; San Jose, CA). Acquired data were analyzed using FlowJo software (FlowJo, LLC; Ashland, OR). Activation of CD8+ T-cells was quantified by calculating the percentage of CD8+/CD69+/CD25+ cells among total CD8+ T cells.

Results

In phase I clinical trials, patients treated with polatuzumab vedotin and mosunetuzumab combination displayed less frequent cytokine release syndrome (CRS) compared with mosunetuzumab treatment alone. In order to gain insight of this interesting clinical observation, cell-based assays were conducted to see if similar findings could be recapitulated in vitro, and to determine what could be the contribution factors to it.

Figure 13A:
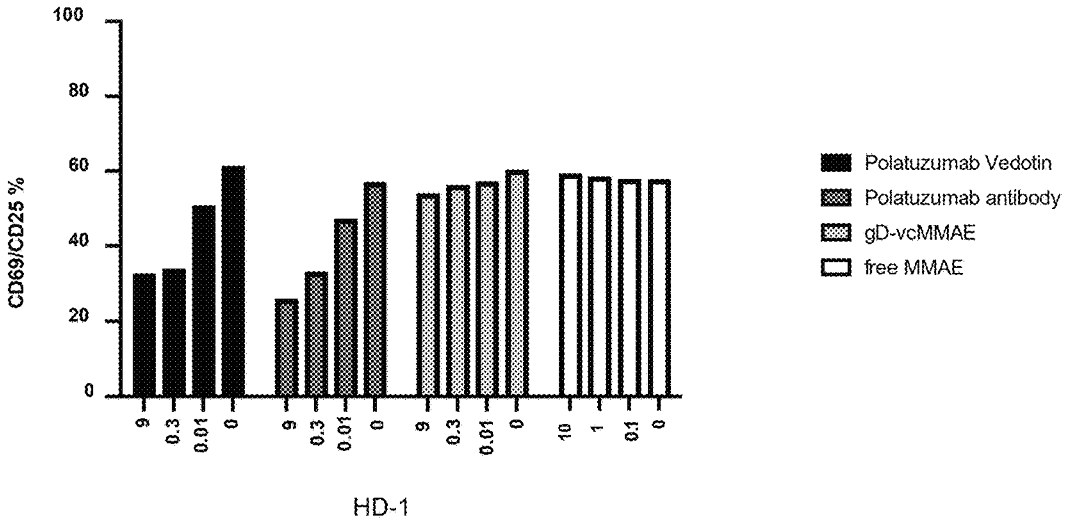
FIG. 13A and FIG. 13B are a series of graphs depicting T cell activation after anti-CD20/CD3 combination treatment. Purified PBMCs from two healthy donors (HD-1 [FIG. 13A] and HD-2 [FIG. 13B]) were treated with 100 ng/mL of anti-CD20/CD3 bispecific antibody and another test article as indicated. Polatuzumab vedotin, polatuzumab antibody or gD-vcMMAE was in μg/mL concentration, while free MMAE was in nM concentration. T-cell activation was quantified as the percentage of CD69+/CD25+ cells in total CD8+ T-cells. Assays were performed in duplicate; mean values were shown.
Figure 13B:
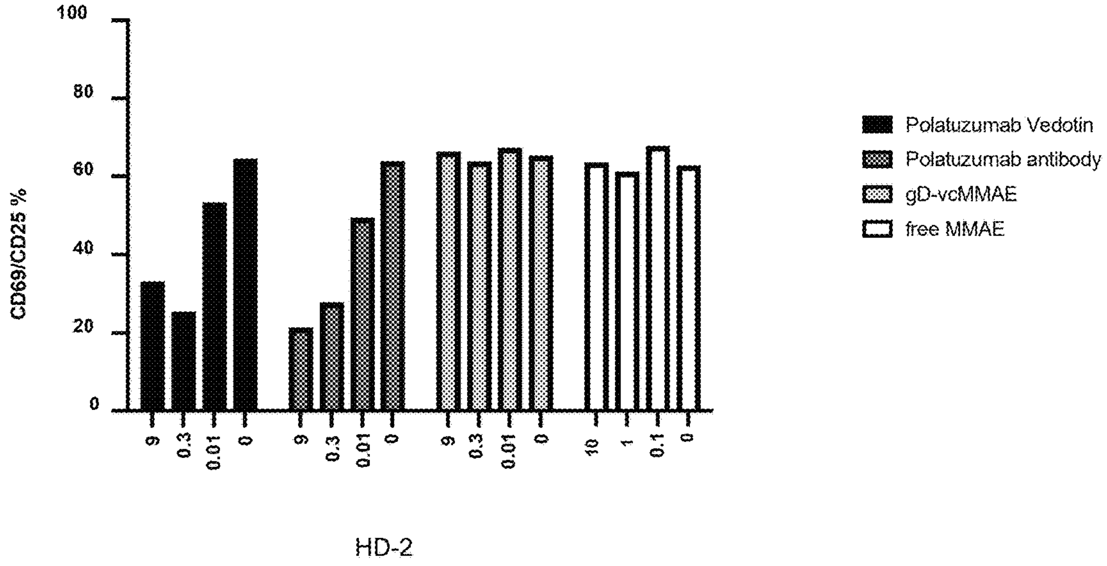

PBMCs from two healthy donors were either treated with single agent anti-CD20/anti-CD3 bispecific antibody at a concentration of 100 ng/mL, or co-treated with either polatuzumab vedotin, polatuzumab antibody (anti-CD79b antibody, polatuzumab vedotin without linker and payload), gD-vcMMAE (non-targeting ADC with same linker and payload as of polatuzumab vedotin), or free payload MMAE. Note that a bispecific antibody with the same anti-CD20 arm but a different anti-CD3 arm that has a higher binding affinity to CD3 was used as a surrogate for mosunetuzumab. After 20-hours incubation, T cell activation and levels of CRS-related cytokines were measured. Compared with single agent anti-CD20/anti-CD3 bispecific antibody treatment, dose-dependent reduction of major CRS-related cytokines levels, such as IFNγ and TNFα, were observed in combination treatments with the increasing concentration of either polatuzumab vedotin or polatuzumab antibody (see FIG. 12A-FIG. 12D). No marked difference was observed in combination treatment with either non-targeting gD-vcMMAE or free payload MMAE. In a similar fashion, reduction of T-cell activation was only observed in combination with either polatuzumab vedotin or polatuzumab antibody (see FIG. 13A and FIG. 13B). These results suggested that in cell-based conditions, the reduction of cytokine release and T-cell activation was likely associated with an anti-CD79b antibody-based mechanism, but not with the cytotoxic payload MMAE. In addition, reduced levels of two macrophage related cytokines, GM-CSF and MIP-1a, were also observed when treated with anti-CD20/anti-CD3 bispecific antibody in combination with polatuzumab vedotin or polatuzumab antibody, but not in combination with gD-vcMMAE or free MMAE (data not shown).

VII. OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a subject having a CD20-positive cell proliferative disorder comprising intravenously administering to the subject an anti-CD79b antibody drug conjugate and a bispecific antibody that binds to CD20 and CD3 in a dosing regimen comprising at least a first 21-day dosing cycle, a second 21-day dosing cycle, and a third 21-day dosing cycle, wherein:

(a) the first dosing cycle comprises;

(i) administering a first dose (C1D1) of the bispecific antibody, a second dose (C1D2) of the bispecific antibody, and a third dose (C1D3) of the bispecific antibody on Days 1, 8, and 15, respectively, wherein the C1D1 of the bispecific antibody is about 1 mg, the C1D2 of the bispecific antibody is about 2 mg, and the C1D3 of the bispecific antibody is about 60 mg; and (ii) administering a single dose (C1D1) of the anti-CD79b antibody drug conjugate on Day 1, wherein the single dose C1D1 of the anti-CD79b antibody drug conjugate is about 1.8 mg/kg, and wherein the C1D1 of the bispecific antibody is administered to the subject at least 60 minutes after administration of the C1D1 of the anti-CD79b antibody drug conjugate;

(b) the second dosing cycle comprises;

(i) administering a single dose (C2D1) of the bispecific antibody on Day 1, wherein the C2D1 of the bispecific antibody is about 60 mg; and (ii) administering a single dose (C2D1) of the anti-CD79b antibody drug conjugate on Day 1, wherein the C2D1 of the anti-CD79b antibody drug conjugate is about 1.8 mg/ka; and (c) the third dosing cycle comprises:

(i) administering a single dose (C3D1) of the bispecific antibody on Day 1, wherein the C3D1 of the bispecific antibody is about 30 mg; and (ii) administering a single dose (C3D1) of the anti-CD79b antibody drug conjugate on Day 1, wherein the C3D1 of the anti-CD79b antibody drug conjugate is about 1.8 mg/kg, wherein the bispecific antibody is a full-length antibody comprising:

an anti-CD20 arm comprising a first binding domain comprising the following six hypervariable regions (HVRs):

(a) an HVR-H1 comprising the amino acid sequence of GYTFTSYNMH (SEQ ID NO: 1);

(b) an HVR-H2 comprising the amino acid sequence of AIYPGNGDTSYNQKFKG (SEQ ID NO: 2):

(c) an HVR-H3 comprising the amino acid sequence of VVYYSNSYWYFDV (SEQ ID NO: 3);

(d) an HVR-L1 comprising the amino acid sequence of RASSSVSYMH (SEQ ID NO: 4):

(e) an HVR-L2 comprising the amino acid sequence of APSNLAS (SEQ ID NO: 5); and (f) an HVR-L3 comprising the amino acid sequence of QQWSFNPPT (SEQ ID NO: 6); and an anti-CD3 arm comprising a second binding domain comprising the following six HVRs;

(a) an HVR-H1 comprising the amino acid sequence of NYYIH (SEQ ID NO: 17):

(b) an HVR-H2 comprising the amino acid sequence of WIYPGDGNTKYNEKFKG (SEQ ID NO: 18);

(c) an HVR-H3 comprising the amino acid sequence of DSYSNYYFDY (SEQ ID NO: 19):

(d) an HVR-L1 comprising the amino acid sequence of KSSQSLLNSRTRKNYLA (SEQ ID NO: 20);

(e) an HVR-L2 comprising the amino acid sequence of WASTRES (SEQ ID NO: 21); and (f) an HVR-L3 comprising the amino acid sequence of TQSFILRT (SEQ ID NO: 22), wherein the anti-CD79b antibody drug conjugate comprises an anti-CD79b antibody conjugated to monomethyl auristatin E (MMAE), and wherein the anti-CD79b antibody comprises the following six HVRs;

(a) an HVR-H1 comprising the amino acid sequence of GYTFSSYWIE (SEQ ID NO: 65);

(b) an HVR-H2 comprising the amino acid sequence of GEILPGGGDTNYNEIFKG (SEQ ID NO: 66);

(c) an HVR-H3 comprising the amino acid sequence of TRRVPIRLDY (SEQ ID NO: 67);

(d) an HVR-L1 comprising the amino acid sequence of KASQSVDYEGDSFLN (SEQ ID NO: 68);

(e) an HVR-L2 comprising the amino acid sequence of AASNLES (SEQ ID NO: 69); and (f) an HVR-L3 comprising the amino acid sequence of QQSNEDPLT (SEQ ID NO: 70).

2. The method of claim 1, wherein the dosing regimen comprises one or more additional dosing cycles or the dosing regimen comprises three to fourteen additional dosing cycles.

3. The method of claim 2, wherein the additional dosing cycles are 21-day dosing cycles.

4. The method of claim 2, wherein:

(a) one or more of the additional dosing cycles comprise an additional single dose of the bispecific antibody and an additional single dose of the anti-CD79b antibody drug conjugate; or (b) one or more of the additional dosing cycles comprise an additional single dose of the bispecific antibody and do not comprise administration of the anti-CD79b antibody drug conjugate.

5. The method of claim 4, wherein:

(a) the additional single dose of the bispecific antibody is about 30 mg; and/or (b) the additional single dose of the bispecific antibody is administered to the subject on Day 1 of each additional dosing cycle comprising an additional dose of the bispecific antibody.

6. The method of claim 2, wherein:

(a) the dosing regimen comprises five additional dosing cycles, wherein each of the five additional dosing cycles comprises a single dose of the bispecific antibody, and wherein three of the five additional dosing cycles comprises administration of the anti-CD79b antibody drug conjugate; or (b) the dosing regimen comprises fourteen additional dosing cycles, wherein each of the fourteen additional dosing cycles comprises a single dose of the bispecific antibody, and wherein three of the fourteen additional dosing cycles comprises administration of the anti-CD79b antibody drug conjugate.

7. A method of treating a subject having a CD20-positive cell proliferative disorder comprising administering to the subject an anti-CD79b antibody drug conjugate and intravenously administering a bispecific antibody that binds to CD20 and CD3 in a dosing regimen comprising eight e-ere dosing cycles, wherein:

(a) the first dosing cycle comprises:

(i) administering a first dose (C1D1) of the bispecific antibody, a second dose (C1D2) of the bispecific antibody, and a third dose (C1D3) of the bispecific antibody on Days 1, 8, and 15, respectively, wherein the C1D1 of the bispecific antibody is about 1 mg, the C1D2 of the bispecific antibody is about 2 mg, and the C1D3 of the bispecific antibody is about 60 mg; and (ii) administering a single dose (C1D1) of the anti-CD79b antibody drug conjugate, wherein the C1D1 of the anti-CD79b antibody drug conjugate is about 1.8 ma/kg, and wherein the C1D1 of the bispecific antibody is administered to the subject at least 60 minutes after administration of the C1D1 of the anti-CD79b antibody drug conjugate;

(b) the second dosing cycle comprises administering a single dose (C2D1) of the bispecific antibody on Day 1 and a single dose (C2D1) of the anti-CD79b antibody drug conjugate on Day 1, wherein the C2D1 of the bispecific antibody is about 60 ma and the C2D1 of the anti-CD79b antibody drug conjugate is about 1.8 mg/kg;

(c) the third to sixth dosing cycles each comprises administering a single dose (C3D1-C6D1) of the bispecific antibody on Day 1 and a single dose (C3D1-C6D1) of the anti-CD79b antibody drug conjugate on Day 1; and (d) the seventh and eighth dosing cycles each comprises administering a single dose (C7D1-C8D1) of the bispecific antibody on Day 1 and do not comprise administration of the anti-CD79b antibody drug conjugate, and wherein each single dose C3D1-C8D1 of the bispecific antibody is about 30 mg and each single dose C1D1-C6D1 of the anti-CD79b antibody drug conjugate is about 1.8 mg/kg, wherein the bispecific antibody is a full-length antibody comprising:

an anti-CD20 arm comprising a first binding domain comprising the following six hypervariable regions (HVRs):

(a) an HVR-H1 comprising the amino acid sequence of GYTFTSYNMH (SEQ ID NO: 1);

(b) an HVR-H2 comprising the amino acid sequence of AIYPGNGDTSYNQKFKG (SEQ ID NO: 2);

(c) an HVR-H3 comprising the amino acid sequence of VVYYSNSYWYFDV (SEQ ID NO: 3):

(d) an HVR-L1 comprising the amino acid sequence of RASSSVSYMH (SEQ ID NO: 4);

(e) an HVR-L2 comprising the amino acid sequence of APSNLAS (SEQ ID NO: 5); and (f) an HVR-L3 comprising the amino acid sequence of QQWSFNPPT (SEQ ID NO: 6); and an anti-CD3 arm comprising a second binding domain comprising the following six HVRs;

(a) an HVR-H1 comprising the amino acid sequence of NYYIH (SEQ ID NO: 17);

(b) an HVR-H2 comprising the amino acid sequence of WIYPGDGNTKYNEKFKG (SEQ ID NO: 18);

(c) an HVR-H3 comprising the amino acid sequence of DSYSNYYFDY (SEQ ID NO: 19);

(d) an HVR-L1 comprising the amino acid sequence of KSSQSLLNSRTRKNYLA (SEQ ID NO: 20);

(e) an HVR-L2 comprising the amino acid sequence of WASTRES (SEQ ID NO: 21); and (f) an HVR-L3 comprising the amino acid sequence of TQSFILRT (SEQ ID NO: 22), wherein the anti-CD79b antibody drug conjugate comprises an anti-CD79b antibody conjugated to monomethyl auristatin E (MMAE), and wherein the anti-CD79b antibody comprises the following six HVRs:

(a) an HVR-H1 comprising the amino acid sequence of GYTFSSYWIE (SEQ ID NO: 65);

(b) an HVR-H2 comprising the amino acid sequence of GEILPGGGDTNYNEIFKG (SEQ ID NO: 66):

(c) an HVR-H3 comprising the amino acid sequence of TRRVPIRLDY (SEQ ID NO: 67);

(d) an HVR-L1 comprising the amino acid sequence of KASQSVDYEGDSFLN (SEQ ID NO: 68);

(e) an HVR-L2 comprising the amino acid sequence of AASNLES (SEQ ID NO: 69); and (f) an HVR-L3 comprising the amino acid sequence of QQSNEDPLT (SEQ ID NO: 70).

8. The method of claim 7, wherein the dosing regimen comprises one or more additional dosing cycles comprising a single dose of the bispecific antibody.

9. The method of claim 8, wherein each of the additional dosing cycles does not comprise administration of the anti-CD79b antibody drug conjugate and/or each of the additional dosing cycles is a 21-day dosing cycle.

10. The method of claim 1, wherein the bispecific antibody and the anti-CD79b antibody drug conjugate have a synergistic effect in a mouse NSG:human WSU-DLCL2 model system when compared to either the bispecific antibody or the anti-CD79b antibody drug conjugate alone.

11. The method of claim 1, wherein the method further comprises administering to the subject one or more additional therapeutic agents, and wherein the one or more additional therapeutic agents is a corticosteroid, an IL-6R antagonist, or a chemotherapeutic agent.

12. A method of reducing the rate of cytokine release syndrome in a population of subjects having a CD20-positive cell proliferative disorder who are administered an anti-CD79b antibody drug conjugate and a bispecific antibody that binds to CD20 and CD3, wherein the method comprises administering to one or more subjects of the population an anti-CD79b antibody drug conjugate and a bispecific antibody that binds to CD20 and CD3 according to the method of claim 1.

13. The method of claim 12, wherein the population of subjects exhibits cytokine release syndrome after administering the bispecific antibody, wherein the rate of the cytokine release syndrome in the population of subjects is less than or equal to about 20%, less than or equal to about 20%, less than or equal to about 5%, or less than or equal to about 3%.

14. The method of claim 12, wherein the rate of cytokine release syndrome having a grade of 2 or greater (as defined by the American Society for Transplantation and Cellular Therapy, 2019; ASTCT) is less than or equal to about 20%, less than or equal to about 5%, or about 0%.

15. The method of claim 1, wherein the CD20-positive cell proliferative disorder is a B cell proliferative disorder.

16. The method of claim 15, wherein the B cell proliferative disorder is a non-Hodgkin's lymphoma (NHL), a chronic lymphoid leukemia (CLL), or a central nervous system lymphoma (CNSL).

17. The method of claim 16, wherein the NHL is a diffuse-large B cell lymphoma (DLBCL), a follicular lymphoma (FL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma.

18. The method of claim 15, wherein the B cell proliferative disorder is relapsed and/or refractory.

19. The method of claim 1, wherein the anti-CD79b antibody drug conjugate is polatuzumab vedotin or anti-CD79b-MC-vc-PAB-MMAE.

20. The method of claim 1, wherein the first binding domain of the bispecific antibody comprises (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b).

21. The method of claim 1, wherein the second binding domain of the bispecific antibody comprises (a) a VH domain comprising an amino acid sequence having at least 95% sequence identity to the amino acid sequence of SEQ ID NO: 23; (b) a VL domain comprising an amino acid sequence having at least 95% sequence identity to the amino acid sequence of SEQ ID NO: 24; or (c) a VH domain as in (a) and a VL domain as in (b).

22. The method of claim 1, wherein the bispecific antibody comprises (a) an anti-CD20 arm comprising (i) a heavy chain comprising an amino acid sequence having at least 95% sequence identity to the amino acid sequence of SEQ ID NO: 85, and (ii) a light chain comprising an amino acid sequence having at least 95% sequence identity to the amino acid sequence of SEQ ID NO: 86; and (b) an anti-CD3 arm comprising (i) a heavy chain comprising an amino acid sequence having at least 95% sequence identity to the amino acid sequence of SEQ ID NO: 83, and (ii) a light chain comprising an amino acid sequence having at least 95% sequence identity to the amino acid sequence of SEQ ID NO: 84.

23. The method of claim 1, wherein the bispecific antibody is mosunetuzumab.

24. The method of claim 1, wherein the bispecific antibody is an IgG antibody.

25. The method of claim 24, wherein the IgG antibody comprises a mutation at amino acid residue N297 (EU numbering) that results in the absence of glycosylation and/or a substitution mutation that reduces effector function.

26. The method of claim 25, wherein the mutation is an N297G or N297A mutation.

27. The method of claim 24, wherein the bispecific antibody comprises a mutation in the Fc region that reduces effector function and/or a substitution mutation at amino acid residue L234, L235, D265, and/or P329 (EU numbering).

28. The method of claim 27, wherein the substitution mutation is selected from the group consisting of L234A, L235A, D265A, and P329G.

29. The method of claim 1, wherein the bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, a second CH2 ($CH2_2$) domain, and a second CH3 ($CH3_2$) domain, wherein at least one of the one or more heavy chain constant domains is paired with another heavy chain constant domain and wherein:

(a) the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain and the $CH3_1$ and $CH3_2$domains meet at an interface between the protuberance and cavity; and/or (b) the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain and the $CH2_1$ and $CH2_2$domains meet at an interface between said protuberance and cavity.

30. The method of claim 1, wherein the anti-CD20 arm further comprises T366W and N297G substitution mutations (EU numbering).

31. The method of claim 1, wherein the anti-CD3 arm further comprises T366S, L368A, Y407V, and N297G substitution mutations (EU numbering).

32. The method of claim 1, wherein the anti-CD79b antibody drug conjugate comprises an anti-CD79b antibody comprising (a) a VH domain comprising an amino acid sequence having at least 95% sequence identity to the amino acid sequence of SEQ ID NO: 71; (b) a VL domain comprising an amino acid sequence having at least 95% sequence identity to the amino acid sequence of SEQ ID NO: 72; or (c) a VH domain as in (a) and a VL domain as in (b).

33. The method of claim 1, wherein the anti-CD79b antibody drug conjugate comprises an anti-CD79b antibody comprising (a) a heavy chain comprising an amino acid sequence having at least 95% sequence identity to the amino acid sequence of SEQ ID NO: 81; and (b) a light chain comprising an amino acid sequence having at least 95% sequence identity to the amino acid sequence of SEQ ID NO: 82.

34. A method of treating a subject having an NHL comprising intravenously administering to the subject polatuzumab vedotin and mosunetuzumab in a dosing regimen comprising eight or more 21-da dosing cycles, wherein:

(a) the first dosing cycle comprises:

(i) administering a first dose (C1D1) of the mosunetuzumab, a second dose (C1D2) of the mosunetuzumab, and a third dose (C1D3) of the mosunetuzumab on Days 1, 8, and 15, respectively wherein the C1D1 of the mosunetuzumab is about 1 mg, the C1D2 of the mosunetuzumab is about 2 mg, and the C1D3 of the mosunetuzumab is about 60 mg; and (ii) administering a single dose (C1D1) of the polatuzumab vedotin on Day 1, wherein the C1D1 of the bispecific antibody is administered to the subject at least 60 minutes after administration of the C1D1 of the anti-CD79b antibody drug conjugate;

(b) the second dosing cycle comprises administering a single dose (C2D1) of the mosunetuzumab on Day 1 and a single dose (C2D1) of the polatuzumab vedotin on Day 1, wherein the C2D1 of the mosunetuzumab is about 60 ma;

(c) the third to sixth dosing cycles each comprises administering a single dose (C3D1-C6D1) of the mosunetuzumab on Day 1 and a single dose (C3D1-C6D1) of the polatuzumab vedotin on Day 1; and (d) the seventh and eighth dosing cycles each comprises administering a single dose (C7D1-C8D1) of the mosunetuzumab on Day 1 and does not comprise administration of the polatuzumab vedotin, and wherein each single dose C3D1-C8D1 of the mosunetuzumab is about 30 mg and each single dose C1D1-C6D1 of the polatuzumab vedotin is about 1.8 mg/kg.

35. The method of claim 1, wherein the subject is a human.

36. A method of treating a population of subjects having a CD20-positive cell proliferative disorder comprising administering to the subjects comprising intravenously administering to the subjects polatuzumab vedotin and mosunetuzumab in a dosing regimen comprising eight or more 21-day dosing cycles, wherein:

(a) the first dosing cycle comprises:

(i) administering a first dose (C1D1) of the mosunetuzumab, a second dose (C1D2) of the mosunetuzumab, and a third dose (C1D3) of the mosunetuzumab on Days 1, 8, and 15, respectively, wherein the C1D1 of the mosunetuzumab is about 1 mg, the C1D2 of the mosunetuzumab is about 2 mg, and the C1D3 of the mosunetuzumab is about 60 mg; and (ii) administering a single dose (C1D1) of the polatuzumab vedotin on Day 1, wherein the C1D1 of the anti-CD79b antibody drug conjugate is about 1.8 mg/kg, wherein the C1D1 of the bispecific antibody is administered to the subject at least 60 minutes after administration of the C1D1 of the anti-CD79b antibody drug conjugate;

(b) the second dosing cycle comprises administering a single dose (C2D1) of the mosunetuzumab on Day 1 and a single dose (C2D1) of the polatuzumab vedotin on Day 1, wherein the C2D1 of the mosunetuzumab is about 60 mg and the C2D1 of the polatuzumab vedotin is about 1.8 mg/kg;

(c) the third to sixth dosing cycles each comprises administering a single dose (C3D1-C6D1) of the mosunetuzumab on Day 1 and a single dose (C3D1-C6D1) of the polatuzumab vedotin on Day 1; and (d) the seventh and eighth dosing cycles each comprises administering a single dose (C7D1-C8D1) of the mosunetuzumab on Day 1 and does not comprise administration of the polatuzumab vedotin, wherein each single dose C3D1-C8D1 of the mosunetuzumab is about 30 mg and each single dose C1D1-C6D1 of the polatuzumab vedotin is about 1.8 mg/kg, and wherein the overall response rate is at least 50% and/or the complete response rate is at least 20%.

37. The method of claim 36, wherein:

(a) the CD20-positive cell proliferative disorder is an NHL, an aggressive NHL, or an FL; or (b) the CD20-positive cell proliferative disorder is an NHL, and the subjects of the population are post-CAR-T subjects.

38. The method of claim 36, wherein the CD20-positive cell proliferative disorder is relapsed and/or refractory NHL.

39. The method of claim 7, wherein the method further comprises administering to the subject one or more additional therapeutic agents, and wherein the one or more additional therapeutic agents is a corticosteroid, an IL-6R antagonist, or a chemotherapeutic agent.

40. The method of claim 7, wherein the CD20-positive cell proliferative disorder is a B cell proliferative disorder.

41. The method of claim 40, wherein the B cell proliferative disorder is a non-Hodgkin's lymphoma (NHL), a chronic lymphoid leukemia (CLL), or a central nervous system lymphoma (CNSL).

42. The method of claim 41, wherein the NHL is a diffuse-large B cell lymphoma (DLBCL), a follicular lymphoma (FL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma.

43. The method of claim 40, wherein the B cell proliferative disorder is relapsed and/or refractory.

44. The method of claim 18, wherein the relapsed and/or refractory B cell proliferative disorder is a relapsed and/or refractory NHL.

45. The method of claim 43, wherein the relapsed and/or refractory B cell proliferative disorder is a relapsed and/or refractory NHL.

46. The method of claim 7, wherein the anti-CD79b antibody drug conjugate comprises an anti-CD79b antibody comprising (a) a VH domain comprising an amino acid sequence having at least 95% sequence identity to the amino acid sequence of SEQ ID NO: 71; (b) a VL domain comprising an amino acid sequence having at least 95% sequence identity to the amino acid sequence of SEQ ID NO: 72; or (c) a VH domain as in (a) and a VL domain as in (b).

47. The method of claim 7, wherein the anti-CD79b antibody drug conjugate comprises an anti-CD79b antibody comprising (a) a heavy chain comprising an amino acid sequence having at least 95% sequence identity to the amino acid sequence of SEQ ID NO: 81; and (b) a light chain comprising an amino acid sequence having at least 95% sequence identity to the amino acid sequence of SEQ ID NO: 82.

48. The method of claim 7, wherein the anti-CD79b antibody drug conjugate is polatuzumab vedotin or anti-CD79b-MC-vc-PAB-MMAE.

49. The method of claim 7, wherein:

(a) the first binding domain of the bispecific antibody comprises a VH domain comprising an amino acid sequence having at least 95% sequence identity to the amino acid sequence of SEQ ID NO: 7 and a VL domain comprising an amino acid sequence having at least 95% sequence identity to the amino acid sequence of SEQ ID NO: 8; and (b) the second binding domain of the bispecific antibody comprises a VH domain comprising an amino acid sequence having at least 95% sequence identity to the amino acid sequence of SEQ ID NO: 23 and a VL domain comprising an amino acid sequence having at least 95% sequence identity to the amino acid sequence of SEQ ID NO: 24.

50. The method of claim 7, wherein:

(a) the first binding domain of the bispecific antibody comprises a VH domain comprising the amino acid sequence of SEQ ID NO: 7 and a VL domain comprising the amino acid sequence of SEQ ID NO: 8; and (b) the second binding domain of the bispecific antibody comprises a VH domain comprising the amino acid sequence of SEQ ID NO: 23 and a VL domain comprising the amino acid sequence of SEQ ID NO: 24.

51. The method of claim 1, wherein:

(a) the first binding domain of the bispecific antibody comprises a VH domain comprising the amino acid sequence of SEQ ID NO: 7 and a VL domain comprising the amino acid sequence of SEQ ID NO: 8; and (b) the second binding domain of the bispecific antibody comprises a VH domain comprising the amino acid sequence of SEQ ID NO: 23 and a VL domain comprising the amino acid sequence of SEQ ID NO: 24.

52. The method of claim 7, wherein the bispecific antibody comprises (a) an anti-CD20 arm comprising (i) a heavy chain comprising an amino acid sequence having at least 95% sequence identity to the amino acid sequence of SEQ ID NO: 85, and (ii) a light chain comprising an amino acid sequence having at least 95% sequence identity to the amino acid sequence of SEQ ID NO: 86; and (b) an anti-CD3 arm comprising (i) a heavy chain comprising an amino acid sequence having at least 95% sequence identity to the amino acid sequence of SEQ ID NO: 83, and (ii) a light chain comprising an amino acid sequence having at least 95% sequence identity to the amino acid sequence of SEQ ID NO: 84.

53. The method of claim 7, wherein the bispecific antibody is mosunetuzumab.

54. The method of claim 1, wherein the C2D1 and C3D1 of the bispecific antibody are administered to the subject after administration of the C2D1 and C3D1 of the anti-CD79b antibody drug conjugate, respectively.

55. The method of claim 54, wherein the C2D1 and C3D1 of the bispecific antibody are administered to the subject at least 60 minutes after administration of the C2D1 and C3D1 of the anti-CD79b antibody drug conjugate, respectively.

56. The method of claim 7, wherein the C2D1-C6D1 of the bispecific antibody are administered to the subject after administration of the C2D1-C6D1 of the anti-CD79b antibody drug conjugate, respectively.

57. The method of claim 56, wherein the C2D1-C6D1 of the bispecific antibody are administered to the subject at least 60 minutes after administration of the C2D1-C6D1 of the anti-CD79b antibody drug conjugate, respectively.

58. The method of claim 34, wherein the C2D1-C6D1 of the mosunetuzumab are administered to the subject after administration of the C2D1-C6D1 of the polatuzumab vedotin, respectively.

59. The method of claim 58, wherein the C2D1-C6D1 of the mosunetuzumab are administered to the subject at least 60 minutes after administration of the C2D1-C6D1 of the polatuzumab vedotin, respectively.

60. The method of claim 36, wherein the C2D1-C6D1 of the mosunetuzumab are administered to the subjects after administration of the C2D1-C6D1 of the polatuzumab vedotin, respectively.

61. The method of claim 60, wherein the C2D1-C6D1 of the mosunetuzumab are administered to the subjects at least 60 minutes after administration of the C2D1-C6D1 of the polatuzumab vedotin, respectively.

62. The method of claim 34, wherein the dosing regimen comprises one to nine additional dosing cycles comprising a single dose of the mosunetuzumab.

63. The method of claim 62, wherein each of the additional dosing cycles does not comprise administration of the polatuzumab vedotin and/or each of the additional dosing cycles is a 21-day dosing cycle.

64. The method of claim 36, wherein the dosing regimen comprises one to nine additional dosing cycles comprising a single dose of the mosunetuzumab.

65. The method of claim 64, wherein each of the additional dosing cycles does not comprise administration of the polatuzumab vedotin and/or each of the additional dosing cycles is a 21-day dosing cycle.

* * * * *